(12) United States Patent
Adams et al.

(10) Patent No.: US 8,562,992 B2
(45) Date of Patent: Oct. 22, 2013

(54) IMMUNOGLOBULIN VARIANTS AND USES THEREOF

(75) Inventors: Camellia W. Adams, Mountain View, CA (US); Andrew C. Chan, Menlo Park, CA (US); Craig W. Crowley, Del Mar, CA (US); Henry B. Lowman, El Granada, CA (US); Gerald R. Nakamura, San Francisco, CA (US); Leonard G. Presta, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 643 days.

(21) Appl. No.: 12/256,349

(22) Filed: Oct. 22, 2008

(65) Prior Publication Data

US 2009/0155257 A1 Jun. 18, 2009

Related U.S. Application Data

(60) Division of application No. 11/147,780, filed on Jun. 7, 2005, now Pat. No. 7,799,900, which is a continuation of application No. PCT/US03/40426, filed on Dec. 16, 2003.

(60) Provisional application No. 60/526,163, filed on Dec. 1, 2003, provisional application No. 60/434,115, filed on Dec. 16, 2002.

(51) Int. Cl.
*B28B 17/00* (2006.01)

(52) U.S. Cl.
USPC ........... 424/144.1; 424/133.1; 424/141.1; 424/143.1

(58) Field of Classification Search
None
See application file for complete search history.

(56) References Cited

U.S. PATENT DOCUMENTS

| | | | |
|---|---|---|---|
| 4,861,579 A | 8/1989 | Meyer et al. | |
| 5,500,362 A | 3/1996 | Robinson et al. | |
| 5,576,195 A | 11/1996 | Robinson et al. | |
| 5,595,721 A | 1/1997 | Kaminski et al. | |
| 5,677,180 A | 10/1997 | Robinson et al. | |
| 5,721,108 A | 2/1998 | Robinson et al. | |
| 5,736,137 A | 4/1998 | Anderson et al. | |
| 5,776,456 A | 7/1998 | Anderson et al. | |
| 5,821,337 A | 10/1998 | Carter et al. | |
| 5,843,398 A | 12/1998 | Kaminski et al. | |
| 5,843,439 A | 12/1998 | Anderson et al. | |
| 5,846,818 A | 12/1998 | Robinson et al. | |
| 5,849,898 A | 12/1998 | Seed et al. | |
| 5,859,205 A | 1/1999 | Adair et al. | |
| 6,015,542 A | 1/2000 | Kaminski et al. | |
| 6,090,365 A | 7/2000 | Kaminski et al. | |
| 6,120,767 A | 9/2000 | Robinson et al. | |
| 6,171,586 B1 | 1/2001 | Lam et al. | |
| 6,194,551 B1 | 2/2001 | Idusogie et al. | |
| 6,204,023 B1 | 3/2001 | Robinson et al. | |
| 6,224,866 B1 | 5/2001 | Barbera-Guillem | |
| 6,242,195 B1 | 6/2001 | Idusogie et al. | |
| 6,267,958 B1 | 7/2001 | Andya et al. | |
| 6,287,537 B1 | 9/2001 | Kaminski et al. | |
| 6,306,393 B1 | 10/2001 | Goldenberg | |
| 6,368,596 B1 | 4/2002 | Ghetie et al. | |
| 6,399,061 B1 | 6/2002 | Anderson et al. | |
| 6,410,391 B1 | 6/2002 | Zelsacher | |
| 6,455,043 B1 | 9/2002 | Grillo-Lopez | |
| 6,528,624 B1 | 3/2003 | Idusogie et al. | |
| 6,538,124 B1 | 3/2003 | Idusogie et al. | |
| 6,565,827 B1 | 5/2003 | Kaminski et al. | |
| 6,652,852 B1 | 11/2003 | Robinson et al. | |
| 6,682,734 B1 | 1/2004 | Anderson et al. | |
| 6,737,056 B1 | 5/2004 | Presta | |
| 7,416,727 B2 | 8/2008 | Presta | |
| 7,601,335 B2 * | 10/2009 | McCutcheon et al. | 424/9.2 |
| 7,708,994 B2 * | 5/2010 | Benyunes | 424/130.1 |
| 7,820,161 B1 | 10/2010 | Curd et al. | |
| 7,976,838 B2 * | 7/2011 | Benyunes | 424/130.1 |
| 2001/0018041 A1 | 8/2001 | Hanna et al. | |
| 2001/0056066 A1 | 12/2001 | Bugelski et al. | |
| 2002/0004587 A1 | 1/2002 | Miller et al. | |
| 2002/0006404 A1 | 1/2002 | Hanna et al. | |
| 2002/0009427 A1 | 1/2002 | Wolin et al. | |
| 2002/0009444 A1 | 1/2002 | Grillo-Lopez | |
| 2002/0012665 A1 | 1/2002 | Hanna | |
| 2002/0041847 A1 | 4/2002 | Goldenberg | |
| 2002/0058029 A1 | 5/2002 | Hanna | |
| 2002/0128448 A1 | 9/2002 | Reff | |
| 2002/0128488 A1 | 9/2002 | Yamakawa et al. | |
| 2002/0136719 A1 | 9/2002 | Shenoy et al. | |
| 2002/0197255 A1 | 12/2002 | Anderson et al. | |
| 2002/0197256 A1 | 12/2002 | Grewal | |
| 2003/0021781 A1 | 1/2003 | Anderson et al. | |

(Continued)

FOREIGN PATENT DOCUMENTS

CA 2 476 166 A1 8/2003
EP 0 274 394 A2 7/1988

(Continued)

OTHER PUBLICATIONS

Shan et al, Blood, 91,1644-1652, 1998.*
Freshney (Culture of Animal Cells, A Manual of Basic Technique, Alan R. Liss, Inc., 1983, New York, p. 4).*
Dermer (Bio/Technology, 1994, vol. 12 p. 320).*
de Haji et al (Can. Res., 70(8):3209-317, 2010).*
Weinberg et al (Mol. Med. Today, 4(2):76-83, 1998).*
Ewing et al (Immun. Cell Bio., 76-47-54).*
Helliwell et al (Ther Adv Neurol Dis, 2(4):195-203, 2009) attached as pp. 1-10.*

(Continued)

*Primary Examiner* — Brad Duffy
(74) *Attorney, Agent, or Firm* — Morrison & Foerster LLP

(57) ABSTRACT

The invention provides humanized and chimeric anti-CD20 antibodies for treatment of CD20 positive malignancies and autoimmune diseases.

6 Claims, 25 Drawing Sheets

(56) References Cited

U.S. PATENT DOCUMENTS

| | | |
|---|---|---|
| 2003/0026801 A1 | 2/2003 | Weiner et al. |
| 2003/0068664 A1 | 4/2003 | Albitar et al. |
| 2003/0082172 A1 | 5/2003 | Anderson et al. |
| 2003/0095963 A1 | 5/2003 | Anderson et al. |
| 2003/0103971 A1 | 6/2003 | Hariharan et al. |
| 2003/0133930 A1 | 7/2003 | Goldenberg et al. |
| 2003/0147885 A1 | 8/2003 | Anderson et al. |
| 2003/0157108 A1 | 8/2003 | Presta |
| 2003/0180292 A1 | 9/2003 | Hanna et al. |
| 2003/0185796 A1 | 10/2003 | Wolin et al. |
| 2003/0219433 A1 | 11/2003 | Hansen et al. |
| 2003/0219818 A1 | 11/2003 | Bohen et al. |
| 2004/0093621 A1 | 5/2004 | Shitara et al. |
| 2004/0191244 A1 | 9/2004 | Presta |
| 2004/0228856 A1 | 11/2004 | Presta |
| 2005/0025764 A1 | 2/2005 | Watkins et al. |
| 2005/0118174 A1 | 6/2005 | Presta |
| 2005/0233382 A1 | 10/2005 | Presta |
| 2006/0034835 A1 | 2/2006 | Adams et al. |
| 2006/0051345 A1 | 3/2006 | Frohna |
| 2010/0158903 A1 | 6/2010 | Smith et al. |
| 2010/0233121 A1 | 9/2010 | Frohna |
| 2011/0008250 A1 | 1/2011 | Curd et al. |
| 2011/0008337 A1 | 1/2011 | Curd et al. |
| 2011/0008338 A1 | 1/2011 | Curd et al. |
| 2012/0199516 A1 | 8/2012 | Frohna |
| 2012/0225070 A1 | 9/2012 | Smith et al. |

FOREIGN PATENT DOCUMENTS

| | | |
|---|---|---|
| EP | 0 274 394 A3 | 7/1988 |
| EP | 0 330 191 B1 | 8/1989 |
| EP | 0 332 865 A2 | 9/1989 |
| SG | 150888 | 8/2006 |
| WO | WO-88/04936 A1 | 7/1988 |
| WO | WO-90/07861 A1 | 7/1990 |
| WO | WO-95/03770 A1 | 2/1995 |
| WO | WO-98/56418 A1 | 12/1998 |
| WO | WO-98/58964 A1 | 12/1998 |
| WO | WO-99/22764 A1 | 5/1999 |
| WO | WO-99/51642 A1 | 10/1999 |
| WO | WO-00/09160 A1 | 2/2000 |
| WO | WO-00/20864 A1 | 4/2000 |
| WO | WO-00/27428 A1 | 5/2000 |
| WO | WO-00/27433 A1 | 5/2000 |
| WO | WO-00/42072 A2 | 7/2000 |
| WO | WO-00/44788 A1 | 8/2000 |
| WO | WO-00/67795 A1 | 11/2000 |
| WO | WO-00/67796 A1 | 11/2000 |
| WO | WO-00/74718 A1 | 12/2000 |
| WO | WO-00/76542 A1 | 12/2000 |
| WO | WO-01/03734 A1 | 1/2001 |
| WO | WO-01/10460 A1 | 2/2001 |
| WO | WO-01/10461 A1 | 2/2001 |
| WO | WO-01/10462 A1 | 2/2001 |
| WO | WO-01/13945 A1 | 3/2001 |
| WO | WO-01/34194 | 5/2001 |
| WO | WO-01/72333 | 10/2001 |
| WO | WO-01/74388 | 10/2001 |
| WO | WO-01/77342 | 10/2001 |
| WO | WO-01/80884 | 11/2001 |
| WO | WO-01/97858 | 12/2001 |
| WO | WO-02/04021 | 1/2002 |
| WO | WO-02/22212 | 3/2002 |
| WO | WO-02/34790 | 5/2002 |
| WO | WO-02/060955 | 8/2002 |
| WO | WO-02/079255 | 10/2002 |
| WO | WO-02/096948 | 12/2002 |
| WO | WO-02/102312 | 12/2002 |
| WO | WO-03/002607 | 1/2003 |
| WO | WO-03/049694 | 6/2003 |
| WO | WO-03/061694 | 7/2003 |
| WO | WO-03/068821 | 8/2003 |
| WO | WO-2004/032828 | 4/2004 |
| WO | WO-2004/035607 | 4/2004 |
| WO | WO-2004/056312 | 7/2004 |
| WO | WO-2004/103404 | 12/2004 |
| WO | WO-2005/117978 A2 | 12/2005 |
| WO | WO-2005/117978 A3 | 12/2005 |
| WO | WO-2010/033587 A2 | 3/2010 |
| WO | WO-2010/033587 A3 | 3/2010 |

OTHER PUBLICATIONS

Townsend et al (Immun. Rev.,237(1):264-83, 2010).*
Anderson, D.R. et al. (May 1997). "Targeted Anti-Cancer Therapy Using Rituximab, a Chimaeric Anti-CD20 Antibody (IDEC-C2B8) in the Treatment of Non-Hodgkin's B-cell Lymphoma," *Biochem. Soc. Trans.* 25(2):705-708.
Arzoo et al. (2002). "Treatment of Refractory Antibody Mediated Autoimmune Disorders with an Anti-CD20 Monoclonal Antibody (Rituximab)," *Annals of the Rheumatic Diseases* 61(10):922-924.
Auner et al. (Mar. 2002). "Restoration of Erythropoiesis by Rituximab in an Adult Patient with Primary Acquired Pure Red Cell Aplasia Refractory to Conventional Treatment," *Br. J. Haematol.* 116(3):727-728.
Bauduer (Mar. 2001). "Rituximab: A Very Efficient Therapy in Cold Agglutinins and Refractory Autoimmune Haemolytic Anaemia Associated with CD20-Positive, Low-Grade Non-Hodgkin's Lymphoma," *Br. J. Haematol.* 112(4):1085-1086.
Berenstein et al. (Apr. 15, 2004). "Rituximab for Primary Chronic Cold Agglutinin Disease: A Prospective Study of 37 Courses of Therapy in 27 Patients," *Blood* 103(8):2925-2928.
Berenstein et al. (Oct. 2001). "Favourable Response to Therapy with the Anti-CD20 Monoclonal Antibody Rituximab in Primary Chronic Cold Agglutinin Disease," *Br. J. Haematol.* 115(1):79-83.
Binder, M. et al. (Sep. 15, 2006). "The Epitope Recognized by Rituximab," *Blood* 108(6):1975-1978.
Caldas, C. et al. (May 2003). "Humanization of the Anti-CD18 Antibody 6.7: An Unexpected Effect of a Framework Residue in Binding to Antigen," *Mol. Immunol.* 39(15):941-952.
Cambridge et al. (2002). "B Lymphocyte Depletion in Patients with Rheumatoid Arthritis: Serial Studies of Immunological Parameters," *Arthritis and Rheumatism*, (#1350) 46:S506.
Campbell, P. et al. (Sep. 2003). "Monoclonal Antibody Therapy for Lymphoma," *Blood Reviews* 17(3):143-152.
Capra, J.D. et al. (Mar. 1974). "Variable Region Sequences of Five Human Immunoglobulin Heavy Chains of the $V_H$III Subgroup: Definitive Identification of Four Heavy Chain Hypervariable Regions," *Proc. Natl. Acad. Sci. USA* 71(3):845-848.
Carter et al. (May 1992). "Humanization of an Anti-p185$^{HER2}$ Antibody for Human Cancer Therapy," *Proc. Natl. Acad. Sci. USA* 89(10):4285-4289.
Chien, N.C. et al. (Jul. 1989). "Significant Structural and Functional Change of an Antigen-Binding Site by a Distant Amino Acid Substitution: Proposal of a Structural Mechanism," *Proc. Natl. Acad. Sci. USA* 86(14):5532-5526.
Clynes et al. (Apr. 2000). "Inhibitory Fc Recptors Modulate in Vivo Cytotoxicity Against Tumor Targets," *Nature Med.* 6(4):443-446.
Coll et al. (Jan. 15, 2004). "Rituximab Therapy for the Type B Syndrome of Severe Insulin Resistance," *N. Eng. J. Med.* 350(3):310-311.
Cragg et al. (Feb. 1, 2003). "Complement-Mediated Lysis by Anti-CD20 mAB Correlates with Segregation into Lipid Rafts," *Blood* 101(3):1045-1052.
Cragg, M.S. et al. (Apr. 1, 2004). "Antibody Specificity Controls in vivo Effector Mechanisms of Anti-CD20 Reagents," *Blood* 103(7):2738-2743.
Cross et al. (Oct. 19, 2003). "Preliminary Results from a Phase II Trial of Rituximab in MS," Abstract, *Eighth Annual Meeting of the Americas Committees for Research and Treatment in Multiple Sclerosis*, pp. 20-21.
Cunningham et al. (Jun. 2, 1989). "High-Resolution Epitope Mapping of hGH-Receptor Interactions by Alanine-Scanning Mutagenesis," *Science* 244:1081-1085.
D'Arena et al. (Mar. 2003). "Late and Long-lasting Response in an Adult Chronic Idiopathic Thrombocytopenic Purpura After Extended Course of Rituximab," *Leuk. Lymphoma* 44(3):561-562.

(56) References Cited

OTHER PUBLICATIONS

De Vita et al. (2002). "Efficacy and Safety of Rituximab Treatment in Type II Mixed Cryoglobulinemia," *Arthritis and Rheumatism* (ACR Concurrent Session Vaculitis: Novel Treatment and Pathogenesis # 469), 46:S206.
De Vita et al. (Aug. 2002). "Efficacy of Selective B Cell Blockade in the Treatment of Pheumatoid Arthritis," *Arthritis and Rheumatism* 46(8):2029-2033.
Dupuy et al. (Jan. 2004). "Treatment of Refractory Pemphigus Vulgaris with Rituximab (Anti CD20 Monoclonal Antibody)," *Arch. Dermatol.* 140(1):91-96.
Edwards et al. (2001). "Sustained Improvement in Rheumatoid Arthritis Following a Protocol Designed to Deplete B Lymphocytes," *Rheumatology* 40:205-211.
Edwards, J.C.W. et al. (2002). "B-Lymphocyte Depletion Therapy in Rheumatoid Arthritis and Other Autoimmune Disorders," *Biochemical Society Transactions* 30(part 4):824-828.
Edwards et al. (2002). "Efficacy and Safety of Rituximab, a B-Cell Targeted Chimeric Monoclonal Antibody: A Randomized, Placebo-Controlled Trial in Patients with Rheumatoid Arthritis," *Arthritis and Rheumatism* 46(9):S197, Abstract No. 446.
Eisenberg, R. (2003). "SLE—Rituximab in Lupus," *Arthritis Res. Ther.* 5(4):157-159.
Emery et al. (2003). "Sustained Efficacy at 48 Weeks After Single Treatment Course of Rituximab in Patients with Rheumatoid Arthritis," *Arthritis Rheumatology* 48(9):5439, Abstract No. 1095.
Eriksson (2003). "Short-Term Outcome and Safety in 5 Patients with ANCA-Positive Vasculities Treated with Rituximab," *Kidney and Blood Pressure Research* (P87) 26:294.
Final Office Action mailed Dec. 5, 2008, for U.S. Appl. No. 11/147,780, filed Dec. 16, 2003, 11 pages.
Final Office Action mailed Mar. 13, 2009, for U.S. Appl. No. 11/147,780, filed Dec. 16, 2003, 37 pages.
Genbank Accession No. P01781, created Jul. 21, 1986, (last updated Nov. 4, 2008), located at <http://www.ncbi.nlm.nih.gov/entrez/viewer.fcgi?db=protein&id=123860>, last visited Nov. 14, 2008, two pages.
Giusti, A.M. et al. (May 1987). "Somatic Diversification of S107 from an Antiphosphocholine to an Anti-DNA Autoantibody is due to a Single Base Change in its Heavy Chain Variable Region," *Proc. Natl. Acad. Sci. USA* 84(9):2926-2930.
Glennie et al. (Jun. 1, 2003). "Renaissance of Cancer Therapeutic Antibodies," *Drug Discov. Today* 8(11):503-510.
Gorman et al. (2004). "Does B Cell Depletion Have a Role to Play in the Treatment of Systemic Lupus Erythematosus," *Lupus* 13(5):312-316.
Gussow, D. et al. (1991). "Humanization of Monoclonal Antibodies," Chapter 5 *in Methods in Enzymology* 203:99-121.
Hong, K. et al. (2004, e-pub. Oct. 6, 2004). "Simple Quantitative Live Cell and Anti-Idiotypic Antibody Based ELSIA for Humanized Antibody Directed to Cell Surface Protein CD20," *Journal of Immunological Methods* 294:189-197.
Idusogie et al. (2000). "Mapping of the C1q Binding Site on Rituxan, A Chimeric Antibody with a Human IgG1 Fc," *J. Immunol.* 164(8):4178-4184.
Idusogie, E.E. et al. (Feb. 15, 2001). "Engineered Antibodies with Increased Activity to Recruit Complement," *J. Immun.* 166(4):2571-2575.
International Search Report mailed Apr. 7, 2005, for PCT Application No. PCT/US03/40426, filed Dec. 16, 2003, three pages.
Jiang, B. et al. (Feb. 11, 2005). "A Novel Peptide Isolated from a Phage Display Peptide Library with Trastuzumab Can Mimic Antigen Epitope of HER-2," *J. Biol. Chem.* 280(6):4656-4662.
Jayne et al. (2003). "B-Cell Depletion with Rituximab for Refractory Vasculitis," *Kidney and Blood Pressure Research* (P88) 26:294-295.
Jones et al. (May 29, 1986). "Replacing the Complementarity-Determining Regions in a Human Antibody with Those From a Mouse," *Nature* 321:522-525.

Kazkaz et al. (2004). "Anti B Cell Therapy (Rituximab) in the Treatment of Autoimmune Diseases," *Current Opinion in Pharmacology* 4:398-402.
Keogh et al. "Rituximab for Remission Induction in Severe ANCA-Associated Vasculities: Report of a Prospective Open-Label Pilto Trial in 10 Patients," *American College of Rheumatology, Session Title: Vasculitis, Session Type: ACR Concurrent Session, Primary Category: 28 Vasculitis* (Abstract 605).
Kipps, T.J. et al. (Jan. 1, 1985). "Importance of Immunoglobulin Isotype in Human Antibody-Dependent, Cell-Mediated Cytotoxicity Directed by Murine Monoclonal Antibodies," *J. Exp. Med.* 161(1):1-17.
Klemmer et al. (2003). "Treatment of Antibody Mediated Autoimmune Disorders with a AntiCD20 Monoclonal Antibody Rituximab," *Arthritis and Rheumatism* (#1623), 48(Suppl. 9):S624.
Kneitz et al. (2002). "Effective B Cell Depletion with Rituximab in the Treatment of Autoimmune Diseases," *Immunobiology* 206:519-527.
Lake et al. (2003). "Future Strategies in Immunotherapy," Chapter 6 *in Burger's Medicinal Chemistry and Drug Discovery (Part 2: Antibody-Directed Immunotherapy)*, Sixth Edition, Abraham, ed., John Wiley & Sons, Inc.: Hoboken, NJ, pp. 226-235.
Layios et al. (Jan. 2001). "Remission of Severe Cold Agulation Disease After Rituximab Therapy," *Leukemia* 15(1):187-188.
Leandro et al. (2001). "B Lymphocyte Depletion in Rheumatoid Arthritis: Early Evidence for Safety, Efficacy and Dose Response," *Arthritis and Rheumatism* (#1905) 44:9):S370.
Leandro, M.J. et al. (2002). "Clinical Outcome in 22 Patients with Rheumatoid Arthritis Treated with B Lympocyte Depletion," *Annals of the Rheumatic Diseases* 61(10):883-888.
Leandro et al. (Oct. 2002). "An Open Study of B Lymphocyte Depletion in Systemic Lupus Erythematosus," *Arthritis and Rheumatism* 46(10):2673-2677.
Leandro et al. (Oct. 27, 2003). "B Cell Repopulation Occurs Mainly From Naive B Cells in Patient with Rheumatoid Arthritis and Systemic Lupus Erythematousus," *Arthritis and Rheumatism* (#1160) 48(Suppl. 9):S464.
Levine (2002). "A Pilot Study of Rituximab Therapy for Refractory Dermatomyositis," *Arthritis Rheum.* 46(Suppl. 9): S488-S489, Abstract #1299.
Levine et al. (May 12, 1999). "IgM Antibody-Related Polyneuropathies: B-Cell Depletion Chemotherapy Using Rituximab," Neurology 52(8):1701-1704.
Liang et al. (Jan. 15, 2002). "CD20 as an Immunotheray Target," *in CD20 Wiley Encyclopedia of Molecular Medicine*, pp. 562-564.
Liu, A.Y. et al. (Nov. 15, 1987). "Production of a Mouse-Human Chimeric Monoclonal Antibody to CD20 with Potent Fc-Dependent Biologic Activity," *J. Immunol.* 139(10):3521-3526.
Looney (2002). "Treating Human Autoimmune Disease by Depleting B Cells," *Annals of the Rheumatic Diseases* 61:863-866.
Mariuzza, R.A. et al. (1987). "The Structural Basis of Antigen-Antibody Recognition," *Annu. Rev. Biophys. Biophys. Chem.* 16:139-159.
Martin et al. (May 2004). "Pathogenic Roles of B Cells in Human Autoimmunity: Insights from the Clinic," *Immunity* 20(5):517-527.
McKeever, K. et al. (Mar. 22, 2004). "A Toxicity Evaluation of Humanized Anti-CD20 Antibody PRO70769," Poster, *presented at Society of Toxicology Annual Meeting*, Baltimore, MD, 78:S-1:15, Poster No. 75.
Non-Final Office Action mailed Feb. 20, 2007, for U.S. Appl. No. 11/147,780, filed Dec. 16, 2003, 35 pages.
Paul, W.E. ed. (1993). *Fundamental Immunology*, Third Edition, p. 242.
Penichet et al. (2002). "Antibody Engineering," in *Wiley Encyclopedia of Molecular Medicine (Section: Chimeric, Humanized and Human Antobodies)* 214-216.
Perosa, F. et al. (Feb. 1, 2006). "Generation of Biologically Active Linear and Cyclic Peptides has Revealed a Unique Fine Specificity of Rituximab and its Possible Cross-Reactivity with Acid Sphingomyelinase-Like Phosphodiesterase 3b Precursor," *Blood* 107(3):1070-1077.

(56) References Cited

OTHER PUBLICATIONS

Perotta et al. (1998). "Response of Chronic Relapsing ITP of 10 Years Duration to Rituximab," *Blood* 10(1—part 1-2):88b, Abstract No. 3360.
Perotta et al. (1999). "Rituxan in the Treatment of Chronic Idiopathic Thrombocytopenic," *Blood* 94:4a, Abstract No. 49.
Pestronk et al. (Apr. 2003). "Treatment of IgM Antibody Associated Polyneuropathies Using Rituximab," *J. Neurol. Neurosurg. Psychiatry* 74(4):485-489.
Pranzatelli et al. (Mar. 2003). "CSF B-Cell Over-Expansion in Paraneoplastic Opsoclonus-Myoclonus: Effects of Rituximab, and Anti-B-Cell Monoclonal Antibody," *Neurology* 60(5):A395, Abstract #P05.128.
Press et al. (Feb. 1987). "Monoclonal Antibody IF5 (Anti-CD20) Serotherapy of Human B Cell Lymphomas," *Blood* 69(2):584-591.
Presta et al. (Sep. 1, 1993). "Humanization of an Antibody Directed Against IgE," *J. Immunol.* 151(5):2623-2632.
Ratanatharathorn et al. (Aug. 15, 2000). "Anti-CD20 Chimeric Monoclonal antibody Treatment of Refractory Immune-Mediated Thrombocytopenia in a Patient with Chronic Graft-Versus-Host Disease," *Ann. Intern. Med.* 133(4):275-279.
Riechman et al. (Mar. 24, 1988). "Reshaping Human Antibodies for Therapy," *Nature* 332(6162):323-327.
Rudikoff, S. et al. (Mar. 1982). "Single Amino Acid Substitution Altering Antigen-Binding Specificity," *Proc. Natl. Acad. Sci. USA* 79(6):1979-1983.
Saleh et al. (Dec. 2000). "A Pilot Study of the Anti-CD20 Monoclonal Antibody Rituximab in Patients with Refractory Immune Thrombocytopenia," *Semin. Oncol.* 27(6 Supp. 12):99-103.
Shields, R.L. et al. (Mar. 2, 2001). "High Resolution Mapping of the Binding Site on Human IgG1 for FcγRI, FcγRII, FcγRIII, and FcRn and Design of IgG1 Variants with Improved Binding to the FcγR," *Journal of Biological Chemistry* 276(9):6591-6604.
Silverman et al. (Jun. 2003). "Rituximab Therapy and Autoimmune Disorders, Prospects for Anti-B Cell Therapy," *Arthritis and Rheumatism* 48(6):1484-1492.
Somer et al. (Jun. 15, 2003). "Improvement in Sjogren's Syndrome Following Therapy with Rituximab for Marginal Zone Lymphoma," *Arthritis Rheum.* 49(3):394-398.
Specks et al. (Dec. 2001). "Response of Wegener's Granulomatosis to Anti-CD20 Chimeric Monoclonal Antibody Therapy," *Arthritis and Rheumatism* 44(12):2836-2840.
Stahl et al. (2003). "Rituximab in RA: Efficacy and Safety from a Randomised, Controlled Trial," *Ann. Rheum. Dis.* (OP004) 62(Suppl. 1).
Stahl et al. (Aug. 15, 2001). "Rituximab Chimeric Anti-CD20 Monoclonal Antibody Treatment for Adults with Chronic Idiopathic Thrombocytopenic Purpura," *Blood* 98(4):952-957.
Stancovski, I. et al. (Oct. 1, 1991). "Mechanistic Aspects of the Opposing Effects of Monoclonal Antibodies to the ERBB2 Receptor on Tumor Growth," *Proc. Natl. Acad. Sci. USA* 88:8691-8695.
Stockinger et al. (Feb. 2003). "Monoclonal Antibodies to Human Cell Surface Antigens," in *Current Protocols in Immunology*, Coligan et al., eds. John Wiley & Sons, Inc., Appendix A.
Stone et al. "Rituximab Therapy for the Induction of Remission and Tolerance in ANCA-Associated Vasculitis," *Clinical Trial Research Summary of the 2002-2003 Immune Tolerance Network*.
Szczepanski et al. (2003). "Safety Data from 48 Weeks Follow-Up of a Randomised Controlled Trial of Rituximab in Patients with Rheumatoid Arthritis," *Arthritis Rheumatology* 48(9):S121, Abstract No. 204.
Tedder, T.F. et al. (Jan. 1988). "Isolation and Structure of a cDNA Encoding the B1 (CD20) Cell-Surface Antigen of Human B Lymphocytes," *Proc. Natl. Acad. Sci. USA* 85:208-212.
Teeling et al. (Sep. 14, 2004). "Characteristics of New Human CD20 Monoclonal Antibodies with Potent Cytolytic Activity Against Non-Hodgkin's Lymphomas," *Blood* 104(6):1793-1800.
Tuscano et al. (Oct. 2002). "Successful Treatment of Infliximab-Refractory Rheumatoid Arthritis with Rituximab," Presentation No. LB11, Annual Scientific Meeting of the American College of Rheumatology, New Orleans, LA, Oct. 24-29, 2002, Poster No. 444.
Valentine et al. (1987). "Structure and Function of the B-Cell Specific 35-37 kDa CD20 Protein," *Leukocyte Typing III*, McMichael, ed., Oxford University Press, pp. 440-443.
Virgolini et al. (2004). "Rituximab in Autoimmune Diseases," *Biomedicine & Pharmacotherapy* 58:299-309.
Weide et al. (2003). "Successful Long-Term Treatment of Systemic Lupus Erythematosus with Rituximab Maintenance Therapy," *Lupus* 12:779-782.
Wylam et al. (Nov. 2003). "Successful Treatment of Refractory Myasthenia Gravis Using Rituximab: A Pediatric Case Report," *J. Pediatr.* 143(5):674-677.
Zaja et al. (Feb. 2002). "B-Cell Depletion with Rituximab as Treatment for Immune Hemolytic Anemia and Chronic Thrombocytopenia," *Haematologica* 87(2):189-195.
Zaja et al. (Mar. 3, 2002). "B-Cell Depletion with Rituximab as Treatment for Immune Hemolytic Anemia and Chronic Thrombocytopenia," Erratum, *Haematologica* 87:336.
Zaja et al. (May 15, 2003). "Efficacy and Safety of Rituximab in Type II Mixed Cryoglobulinemia," *Blood* 101(10):3827-3824.
Zaja et al. (Oct. 10, 2000). "Rituximab for Myasthenia Gravis Developing After Bone Marrow Transplant," *Neurology* 55(7):1062-1063.
Genovese, M.C. et al. (Sep. 2008). "Ocrelizumab, a Humanized Anti-CD20 Monoclonal Antibody, in the Treatment of Patients with Rheumatoid Arthritis: A Phase I/II Randomized, Blinded, Placebo-Controlled, Dose-Ranging Study," *Arthritis Rheum.* 58(9):2652-2661.
Rituxan.Com (2008). "Targeted B-Cell Therapy," located at < http://www.rituxan.com/>, last visited on May 13, 2009, 2 pages.
Borrecaeck, ed. (1995). Antibody Engineering, Second Edition, pp. 179-180.
Albelda, S.M. et al. (Aug. 1990). "Integrins and Other Cell Adhesion Molecules," *FASEB J.* 4(11):2868-2880.
Anonymous. (Dec. 2008). "Novel Anti-CD20 Monoclonal Antibody Shows Promise as Therapy for RA," *Nature Clinical Practice Rheumatology* 4(12):623.
Anonymous. (Jun. 11, 2009). "New Data Demonstrate the Ability of MabThera to Reduce the Progression of Joint Damage when used as a First-Line Biologic Treatment in Rheumatoid Arthritis," *Roche Media Release*, located at <http://www.roche.com/media/media_releases/med-cor-2009-06-11.htm>, last visited Dec. 14, 2009, four pages.
Anonymous. (Jun. 26, 2009). "Roche Files MabThera as a First-line Biologic Treatment for Rheumatoid Arthritis in Europe," *Roche Investor Update*, located at <http://www.roche.com/investors/ir_update/inv-update-2009-06-26.html>, last visited Dec. 28, 2009, four pages.
Anonymous. (Oct. 17, 2009). "Genentech and Biogen Idec Receive a Complete Response from FDA for Earlier Use of Rituxan for Rheumatoid Arthritis," *Genentech Press Release* located at <http://www.gene.com/gene/news/press-releases/display.do?method=print&id=12407>, last visited Dec. 28, 2009, four pages.
Anonymous. (Dec. 10, 2009). "Genentech and Biogen Idec Announce Positive Results from First Phase III Trial of Ocrelizumab in Rheumatoid Arthritis," *Genentech Press Release*, located at <http://gwiz4.gene.com/gene/news/press-releases/display.do?mehtod=print&id=12487>, last visited Dec. 14, 2009, two pages.
Anonymous. (Dec. 11, 2009). "First Phase III Study Evaluating Roche's Ocrelizumabin in Patients with Rheumatoid Arthritis Meets Primary Endpoint," Ejones on FierceBiotech, located at <http://www.fiercebiotech.com/node/71104/print>, last visited Dec. 11, 2009, three pages.
Anonymous. (Dec. 11, 2009). "Roche's RA Drug Posts Blockbuster Results in Phase III," John on FierceBiotech, located at <http://www.fiercebiotech.com/node/71100/print>, last visited Dec. 11, 2009, one page.
Carter, P.J. (May 2006). "Potent Antibody Therapeutics by Design," *Nature Reviews—Immunology* 6:343-357.
Cartron, G. et al. (Nov. 1, 2004, e-pub. Jun. 29, 2004). "From the Bench to the Bedsie: Ways to Improve Rituximab Efficacy," *Blood* 104(9):2635-2642.

(56) References Cited

OTHER PUBLICATIONS

Edwards, J.C.W. et al. (Jun. 17, 2004). "Efficacy of B-Cell_Targeted Therapy with Rituximab in Patients with Rheumatoid Arthritis," *The New England Journal of Medicine* 350(25):2572-2581.

Grogan, K. (Dec. 11, 2009). "Roche's Ocrelizumab Impresses in Phase III RA Study," *Pharma Times* located at <http://www.pharmatimes.com/WorldNews/article.aspx?id=17068&src=WorldNewsRSS>, last visited Dec. 11, 2009, two pages.

Hernandez, L.A. et al. (Sep. 1987). "Role of Neutrophils in Ischemia-Reperfusion-Induced Microvascular Injury," *J. Physiol.* 253(3-pt. 2):H699-H703.

Hynes, R.O. (Apr. 3, 1992). "Integrins: Versatility, Modulation, and Signaling in Cell Adhesion," *Cell* 69(1):11-25.

Jutila, M.A. (Nov. 1989). "Inflammation-induced Endothelial Cell Adhesion to Lymphocytes, Neutrophils, and Monocytes. Role of Homing Receptors and Other Adhesion Molecules," *Transplantation* 48(5):727-731.

Kennedy, A.D. et al. (2004). "Rituximab Infusion Promotes Rapid Complement Depletion and Acute CD20 Loss in Chronic Lymphocytic Leukemia," *The Journal of Immunology* 172:3280-3288.

Manches, O. et al. (Feb. 1, 2003). "In Vitro Mechanisms of Action of Rituximab on Primary Non-Hodgkin Lymphomas," *Blood* 101(3):949-954.

Mileski, W.J. et al. (Aug. 1990). "Inhibition of CD18-dependent Neutrophil Adherence Reduces Organ Injury After Hemorrhagic Shock in Primates," *Surgery* 108(2):206-212.

Morrison, S.L. et al. (Nov. 1984). "Chimeric Human Antibody Molecules: Mouse Antigen-binding Domains with Human Constant Region Domains," *Proc. Natl. Acad. Sci. USA* 81:6851-6855.

Power, B. et al. (2003). "Keystone Symposia: Antibody-based Therapeutics for Cancer," *Expert Opinion Biol. Ther.* 3(2):385-389.

Springer, T.A. (Aug. 2, 1990). "Adhesion Receptors of the Immune System," *Nature* 346(6283):425-434.

Stoolman, L.M. (Mar. 24, 1989). "Adhesion Molecules Controlling Lymphocyte Migration," *Cell* 56(6):907-910.

Van Der Kolk, L.E. et al. (2001). "Complement Activation Plays a Key Role in the Side-Effects of Rituximab Treatment," *British Journal of Haematology* 115:807-811.

Vedder, N.B. et al. Mar. 1988). "A Moncolonal Antibody to the Adherence-promoting Leukocyte Glycoprotein, CD18, Reduces Organ Injury and Improves Survival from Hemorrhagic Shock and Resuscitation in Rabbits," *J. Clin. Invest.* 81:939-944.

Wilkinson, I. et al. (Jul. 15, 1987). "Tolerance Induction in Mice by Conjugates of Monoclonal Immunoglobulins and Monomethoxypolyethylene Glycol. Transfer of Tolerance by T Cells and by T Cell Extracts," *J. Immunology* 139(2):326-331.

Einfeld, D.A. et al. (1988). "Molecular Cloning of the Human B Cell CD20 Receptor Predicts a Hydrophobic Protein With Multiple Transmembrane Domains," *EMBO J* 7(3):711-717.

Kappos, L. et al. (Nov. 19, 2011). "Ocrekuzynab ub Relapsing-Remitting Multiple Sclerosis: A Phase 2, Randomised, Placebo-Controlled, Multicentre Trial," *The Lancet* 378:1779-1787, Supplemenary Webappendix 1 p., Notable Adverse Event 1 page, Full List of Investigators pp. 2-3.

Carton, G. et al. (Feb. 1, 2002). "Therapeutic Activity of Humanized Anti-CD20 Monoclonal Antibody and Polymorphism in IgG Fc Receptor FcγRIIIa Gene," *Blood* 99(3):754-758.

Du, J. et al. (May 2008, e-pub. Mar. 17, 2008). "Crystal Structure of Chimeric Antibody C2H7 Fab in Complex With a CD20 Peptide," *Mol Immunol* 45(10):2861-2868.

Kettleborough, C.A. (Oct. 1991). "Humanization of a Mouse Monoclonal Antibody by CDR-Grafting: the Importance of Framework Residues on Loop Conformation," *Protein Eng* 4(7):773-783.

Shinkawa, T. et al. (Jan. 31, 2003, e-pub. Oct. 18, 2002). "The Absence of Fucose but not the Presence of Galactose or Bisecting N-Acetylglucosamine of Human IgG1 Complex-Type Oligosaccharides Shows the Critical Role of Enhancing Antibody-Dependent Cellular Cytotoxicity," *J Biol Chem* 278(5):3466-3473.

Tempest, P.R. et al. (Feb. 1995). "Identification of Framework Residues Required to Restore Antigen Binding During Reshaping of a Monoclonal Antibody Against the Glycoprotein gB of Human Cytomegalovirus," *Int. J. Biol. Macromol.* 17(1):37-42.

Ying, G. et al. (2002). Advances in the Studies of Humanization Monoclonal Antibody, reviewed by Gu Ying, proofread by Zhang Jun and Xia Ning, Foreign Medical Sciences, Section of Biologics for Phrophylaxis, Diagnosis and Therapy, vol. 25, No. 3, p. 117. (English Translation 3 pages).

\* cited by examiner

```
            |————FRI————|    CDRI       |——
              10        20       30         40
2H7      QIVLSQSPAILSASPGEKVTMTC [RASSSVS-YMH] WYQQKP
          *  ***   **    *  **   *
hu2H7.v16 DIQMTQSPSSLSASVGDRVTITC [RASSSVS-YMH] WYQQKP
                                  * * * **
hum kI   DIQMTQSPSSLSASVGDRVTITC [RASQSISNYLA] WYQQKP

|—FR2—|   CDR2    |————FR3————
                   50       60       70        80
2H7      GSSPKPWIY [APSNLAS] GVPARFSGSGSGTSYSLTISRVEA
          **    *                *       ***    ****
hu2H7.v16 GKAPKPLIY [APSNLAS] GVPSRFSGSGSGTDFTLTISSLQP
              *      * *  *
hum kI   GKAPKLLIY [AASSLES] GVPSRFSGSGSGTDFTLTISSLQP

|————|   CDR3   |——FR4——|
                           90     100
2H7      EDAATYYC [QQWSFNPPT] FGAGTKLELKR
          *                    *   * *
hu2H7.v16 EDFATYYC [QQWSFNPPT] FGQGTKVEIKR
                   ****  *
hum kI   EDFATYYC [QQYNSLPWT] FGQGTKVEIKR
```

FIG._1A

```
            |————FRI————|    CDRI       |——
              10        20       30         40
2H7      QAYLQQSGAELVRPGASVKMSCKAS [GYTFTSYNMH] WVKQT
          *** **   **    *  * *** *                * *
hu2H7.v16 EVQLVESGGGLVQPGGSLRLSCAAS [GYTFTSYNMH] WVRQA
                                     *   *  *  **
hum III  EVQLVESGGGLVQPGGSLRLSCAAS [GFTFSSYAMS] WVRQA

|—FR2—|      CDR2         |————FR3————
                    50    a      60          70        80
2H7      PRQGLEWIG [AIYPGNGDTSYNQKFKG] KATLTVDKSSSTAYM
          **    *                       ** **    ** * *
hu2H7.v16 PGKGLEWVG [AIYPGNGDTSYNQKFKG] RFTISVDKSKNTLYL
              *       * ****  * * ****                * *
hum III  PGKGLEWVA [VISGDGGSTYYADSVKG] RFTISRDNSKNTLYL

|—————|    CDR3    |——FR4——|
                       abc       90     100abcde     110
2H7      QLSSLTSEDSAVYFCAR [VVYYSNSYWYFDV] WGTGTTVTVSS
          **   **   *  *                    *   *
hu2H7.v16 QMNSLRAEDTAVYYCAR [VVYYSNSYWYFDV] WGQGTLVTVSS
                              ******* *** *
hum III  QMNSLRAEDTAVYYCAR [GRVGYSLY---DY] WGQGTLVTVSS
```

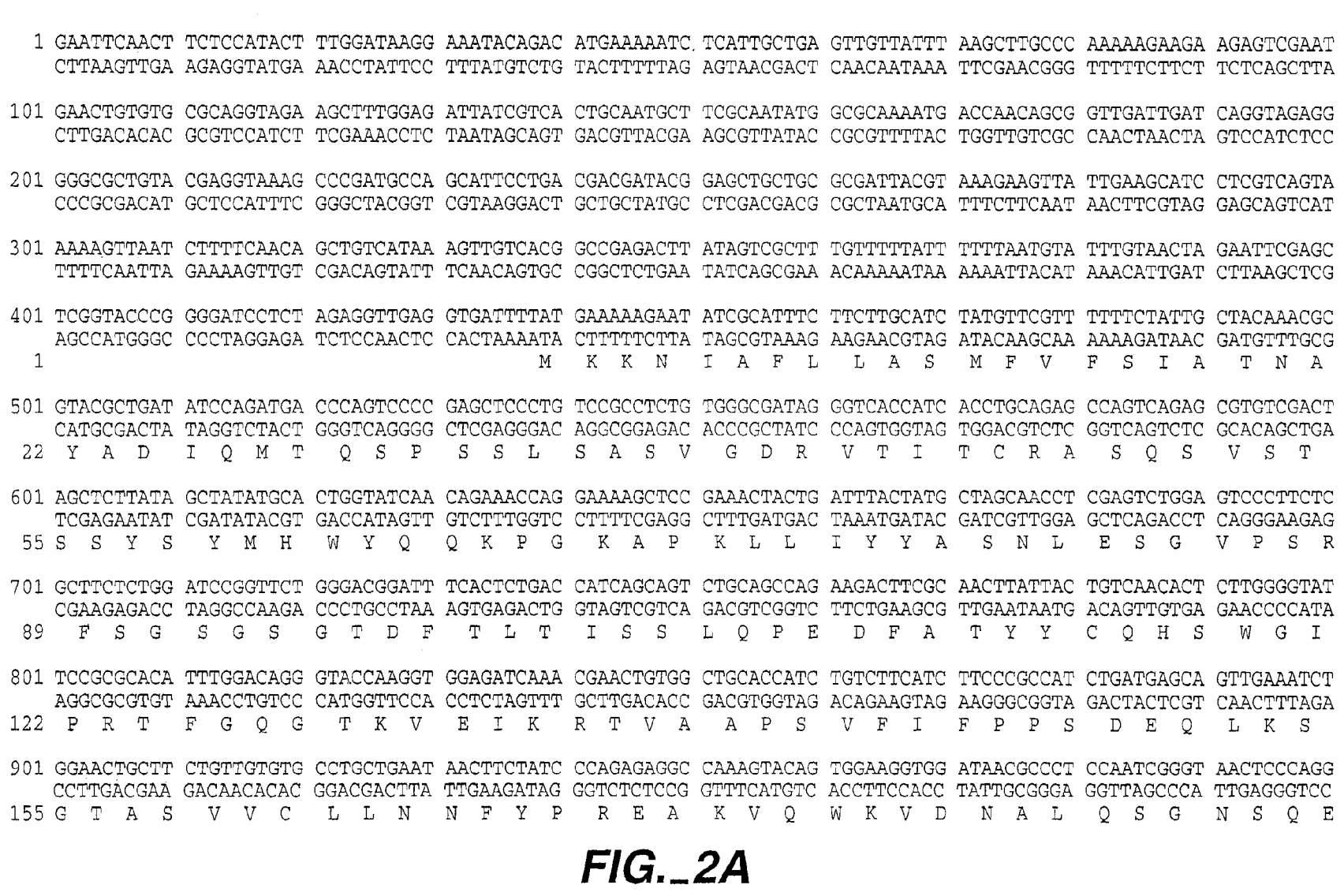

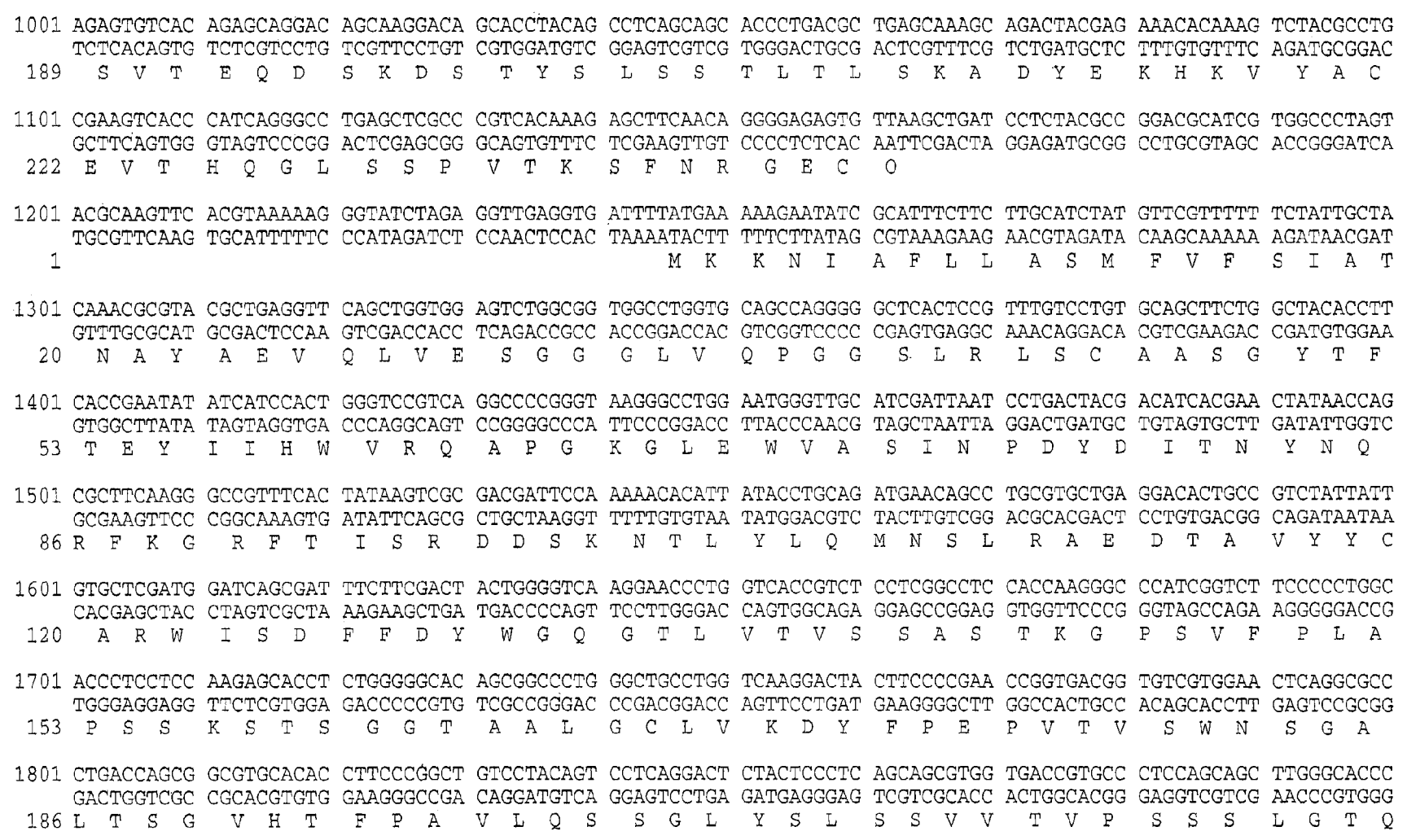

```
1901 AGACCTACAT CTGCAACGTG AATCACAAGC CCAGCAACAC CAAGGTGGAC AAGAAAGTTG AGCCCAAAATC TTGTGACAAA ACTCACACAT GACCACGCA
     TCTGGATGTA GACGTTGCAC TTAGTGTTCG GGTCGTTGTG GTTCCACCTG TTCTTTCAAC TCGGGTTTAG AACACTGTT TGAGTGTGTA CTGGTGGCGT
 220   T  Y  I   C  N  V    N  H  K  P   S  N  T    K  V  D    K  K  V  E   P  K  S    C  D  K    T  H  T  O

2001 TGCACCAGTA TCGTCCATTC CGACAGCATC GCCAGTCACT ATGGCGTGCT CCCTATACCT TGTCTGCCTC CCCGCGTTGC GTCGCGGTGC
     ACGTGGTCAT AGCAGGTAAG GCTGTCGTAG CGGTCAGTGA TACCGCACGA GGGATATGGA ACAGACGGAG GGGCGCAACG CAGCGCCACG

2101 ATGGAGCCGG GCCACCTCGA CCTGAATGGA AGCCGGCGGC ACCTCGCTAA ACTCCAAGAA TTGGAGCCAA TCAATTCTTG CGGAGAACTG
     TACCTCGGCC CGGTGGAGCT GGACTTACCT TCGGCCGCCG TGGAGCGATT TGAGGTTCTT AACCTCGGTT AGTTAAGAAC GCCTCTTGAC

2201 TGAATGCGCA AACCAAACCT TGGCAGAACA TATCCATCGC GTCCGCCATC TCCAGCAGCC GCACGCGGCG AGCGTTGGGT CCTGGCCACG
     ACTTACGCGT TTGGTTGGGA ACCGTCTTGT ATAGGTAGCG CAGGCGGTAG AGGTCGTCGG CGTGCGCCGC TCGCAACCCA GGACCGGTGC

2301 GGTGCGCATG ATCGTGCTCC TGTCGTTGAG GACCCGGCTA GTTGCCTTAC TGGTTAGCAG CATCTCGGGC GCACGCGGGA GCGAACGTGA
     CCACGCGTAC TAGCACGAGG ACAGCAACTC CTGGGCCGAT CAACGGAATG ACCAATCGTC GTAGAGCCCG CGTGCGCCCT CGCTTGCACT

2401 AGCGACTGCT GCTGCAAAAC GTCTGCGACC TGAGCAACAA CATGAATGGT CTTCGGTTTC CGTGTTTCGT AAAGTCTGGA AACGCGGAAG TCAGCGCCCT
     TCGCTGACGA CGACGTTTTG CAGACGCTGG ACTCGTTGTT GTACTTACCA GAAGCCAAAG GCACAAAGCA TTTCAGACCT TTGCGCCTTC AGTCGCGGGA

2501 GCACCATTAT GTTCCGGATC TGCATCGCAG GATGCTGCTG GCTACCCTGT CATCTGTATT GGAACACCTA CATCATCATCAG CCTGAGTGAT
     CGTGGTAATA CAAGGCCTAG ACGTAGCGTC CTACGACGAC CGATGGGACA CCTTGTGGAT GTAGACATAA GGTAGTAGTC GGACTCACTA

2601 TTTTCTCTGG TCCCGCCGCA TCCATAACGC CAGTTGTTTA CCCTCACAAC GTTCCAGTAA CGGGCCATGT TCATCATCAG CGTGAGCATC
     AAAAGAGACC AGGGCGGCGT AGGTATGGCG GTCAACAAAT GGGAGTGTTG CAAGGTCATT GCCCGGTACA AGTAGTAGTC GCACTCGTAG

2701 CTCTCTCGTT TCATCGGTAT CATTACCCCC ATGAACAGAA ATTCCCCCTT ACACGGAGGC ATCAAGTGAC TAACCCGTAT TTAACATGGC
     GAGAGAGCAA AGTAGCCATA GTAATGGGGG TACTTGTCTT TAAGGGGGAA TGTGCCTCCG TAGTTCACTG ATTGGGCATA AATTGTACCG

2801 CCGCTTTATC AGAAGCCAGA TCATTAACGCT TCTGGAGAAA CTCAACGAGC TGAACAGGCA GACATCGTG CGACCACGCT
     GGCGAAATAG TCTTCGGTCT AGTTAACCGA AGACCTCTTT GAGTTGCTCG ACTTGTGCCT CTGTAGACAC GCTGGTGCGA

2901 GATGAGCTTT ACCGCAGCAT CGGAAATTG TAAACGTTAA TATTTTGTTA AAATTCGCGT TTAAATTTTTG TCATTTTTTA ACCAATAGGC
     CTACTCGAAA TGGCGTCGTA GCCTTTAAC ATTTGCAATT ATAAAACAAT TTTAAGCGCA AATTTAAAAAC AGTAAAAAAT TGGTTATCCG

3001 CGAAATCGGC AAAATCCCTT ATAAATCAAA AGAATAGACC GAGATAGGGT TGAGTGTTGT TCCAGTTTGG AACAAGAGTC CACTATTAAA GAACGTGGAC
     GCTTTAGCCG TTTTAGGGAA TATTTAGTTT TCTTATCTGG CTCTATCCCA ACTCACAACA AGGTCAAACC TTGTTCTCAG GTGATAATTT CTTGCACCTG
```

FIG._2C

```
3101  TCCAACGTCA AAGGGCGAAA AACCGTCTAT CAGGGCTATG GCCCACTACG TGAACCATCA CCCTAATCAA GTTTTTGGG GTCGAGGTGC CGTAAAGCAC
      AGGTTGCAGT TTCCCGCTTT TTGGCAGATA GTCCCGATAC CGGGTGATGC ACTTGGTAGT GGGATTAGTT CAAAAAACCC CAGCTCCACG GCATTTCGTG

3201  TAAATCGGAA CCCTAAAGGG AGCCCCCGAT TTAGAGCTTG ACGGGGAAAG CCGGCGAACG TGGCGAGAAA GGAAGGGAAG AAAGCGAAAG GAGCGGGCGC
      ATTTAGCCTT GGGATTTCCC TCGGGGGCTA AATCTCGAAC TGCCCCTTTC GGCCGCTTGC ACCGCTCTTT CCTTCCCTTC TTTCGCTTTC CTCGCCCGCG

3301  TAGGGCGCTG GCAAGTGTAG CGGTCACGCT GCCGGTAACC ACCACACCCG CCGCGCTTAA TGCGCCGCTA CAGGGCGCGT CCGCATCCTG CCTCGCGCGT
      ATCCCGCGAC CGTTCACATC GCCAGTGCGA CGGCGCATTG TGGTGTGGGC GGCGCGAATT ACGCGGCGAT GTCCCGCGCA GGCGTAGGAC GGAGCGGCA

3401  TTCGGTGATG ACGTGAAAA CCTCTGACAC ATGCAGCTCC CGGAGACGGT CACAGTTGT CTGTAAGCGG ATGCCGGGAG CAGACAAGCC CGTCAGGGCG
      AAGCCACTAC TGCCACTTTT GGAGACTGTG TACGTCGAGG GCCTCTGCCA GTGTCAGCGG GACATTCGCC TACGGCCCTC GTCGTTCGG GCAGTCCGC

3501  CGTCAGCGGG TGTTGGCGGG CAGCCATGAC CCAGTCACGT AGCGATAGCC GAGTGTATAC TGGCTTAACT ATGCGGCATC AGAGCAGATT
      GCAGTCGCCC ACAACCGCCC GTCGGTACTG GGTCAGTGCA TCGCTATCGC CTCACATATG ACCGAATTGA TACGCCGTAG TCTCGTCTAA

3601  GTACTGAGAG TGCACCATAT GCGGTGTGAA ATACCGCACA GATGCGTAAG GAGAAAATAC CGCATCAGGC TTCCTCGCTC ACTGACTCGC
      CATGACTCTC ACGTGGTATA CGCCACACTT TATGGCGTGT CTACGCATTC CTCTTTTATG GCGTAGTCCG AAGGAGCGAG TGACTGAGCG

3701  TGCGCTCGGT CGTTCGGCTG CGGCGAGCTG CTCAAAGGCG GTAATACGGT TATCCACAGA AACGCAGGAA AGAACATGTG
      ACGCGAGCCA GCAAGCCGAC GCCGCTCGAC GAGTTTCCGC CATTATGCCA ATAGTGTCT TTGCGTCCTT TCTTGTACAC

3801  AGCAAAAGGC CAGCAAAACCG TAAAAAGGCC CGCGTTGCTG GCGTTTTTCCA CCCCCTGACG AGCATCACAA AAATCGACGC
      TCGTTTTCCG GTCGTTTTGGC ATTTTTCCGG GCGCAACGAC CGCAAAAGGT GGGGGACTGC TCGTAGTGTT TTTAGCTGCG

3901  TCAAGTCAGA GGTGGCGAAA CCCGACAGGA CTATAAAGAT ACCAGGCGTT TCCCCCCTGGA AGCTCCCTCG TGTTCCGACC CTGCCGCTTA
      AGTTCAGTCT CCACCGCTTT GGGCTGTCCT GATATTTCTA TGGTCCGCAA AGGGGGACCT TCGAGGGAGC ACAAGGCTGG GACGGCGAAT

4001  CCGGATACCT GTCCGCCTTT CTCCCTTCCG GAAGCGTGGC GCTTTCTCAT AGCTCACGCT GTAGGTATCT CAGTTCGGTG GCTCCAAGCT
      GGCCTATGGA CAGGCGGAAA GAGGGAAGGC CTTCGCACCG CGAAAGAGTA TCGAGTGCGA CATCCATAGA GTCAAGCCAC CGAGGTTCGA

4101  GGGCTGTGTG CACGAACCCC CCGTTCAGCC CGACCGCTGC GCCTTATCCG GTAACTATCG TCTTGAGTCC AACCCGGTAA ATCGCCACTG
      CCCGACACAC GTGCTTGGGG GGCAAGTCGG GCTGGCGACG CGGAATAGGC CATTGATAGC AGAACTCAGG TTGGGCCATT TAGCGGTGAC

4201  GCAGCAGCCA CTGGTAACAG GATTAGCAGA GCGAGGTATG TAGGCGGTGC TACAGAGTTC TTGAAGTGGT GGCCTAACTA AGAAGGACAG
      CGTCGTCGGT GACCATTGTC CTAATCGTCT CGCTCCATAC ATCCGCCACG ATGTCTCAAG AACTTCACCA CCGGATTGAT TCTTCCTGTC

4301  TATTTGGTAT CTGCGCTCTG CTGAAGCCAG TTACCTTCGG AAAAAGAGTT GGTAGCTCTT GATCCGGCAA ACAAACCACC GCTGGTAGCG GTGGTTTTTT
      ATAAACCATA GACGCGAGAC GACTTCGGTC AATGGAAGCC TTTTTCTCAA CCATCGAGAA CTAGGCCGTT TGTTTGGTGG CGACCATCGC CACCAAAAAA
```

FIG._2D

```
4401 TGTTTGCAAG CAGCAGATTA CGCGCAGAAA AAAAGGATCT CAAGAAGATC CTTTGATCTT TTCTACGGGG TCTGACGCTC AGTGGAACGA AAACTCACGT
     ACAAACGTTC GTCGTCTAAT GCGCGTCTTT TTTTCCTAGA GTTCTTCTAG GAATCTAGAA AAGATGCCCC AGACTGCGAG TCACCTTGCT TTTGAGTGCA

4501 TAAGGGATTT TGGTCATGAG ATTATCAAAA AGGATCTTCA CCTAGATCCT TTTAAATTAA AAATGAAGTT TTAAATCAAT CTAAAGTATA TATGAGTAAA
     ATTCCCTAAA ACCAGTACTC TAATAGTTTT TCCTAGAAGT GGATCTAGGA AAATTTAATT TTTACTTCAA AATTTAGTTA GATTTCATAT ATACTCATTT

4601 CTTGGTCTGA CAGTTACCAA TGCTTAATCA GTGAGGCACC TATCTCAGCG ATCTGTCTAT TTCGTTCATC CATAGTTGCC TGACTCCCCG TCGTGTAGAT
     GAACCAGACT GTCAATGGTT ACGAATTAGT CACTCCGTGG ATAGAGTCGC TAGACAGATA AAGCAAGTAG GTATCAACGG ACTGAGGGGC AGCACATCTA

4701 AACTACGATA CGGGAGGGCT TACCATCTGG CCCCAGTGCT GCAATGATAC CGCGAGACCC ACGCTCACCG GCTCCAGATT TATCAGCAAT AAACCAGCCA
     TTGATGCTAT GCCCTCCCGA ATGGTAGACC GGGGTCACGA CGTTACTATG GCGCTCTGGG TGCGAGTGGC CGAGGTCTAA ATAGTCGTTA TTTGGTCGGT

4801 GCCGAAGGG CCGAGCGCAG AAGTGGTCCT GCAACTTTAT CCGCCTCCAT AATTGTTGCC GGGAAGCTAG AGTAAGTAGT TCGCCAGTTA
     CGGCCTTCCC GGCTCGCGTC TTCACCAGGA CGTTGAAATA GGCGGAGGTA TTAACAACGG CCCTTCGATC TCATTCATCA AGCGGTCAAT

4901 ATAGTTTGCG CAACGTTGTT GCCATTGCTG CAGGCATCGT GGTGTCACGC TCGTCGTTTG GTATGGCTTC ATTCAGCTCC GGTTCCCAAC GATCAAGGCG
     TATCAAACGC GTTGCAACAA CGGTAACGAC GTCCGTAGCA AGCAGTGCG CCACAGTGCG AGCAGCAAAC CATACCGAAG TAAGTCGAGG CCAAGGGTTG CTAGTTCCGC

5001 AGTTACATGA TCCCCCATGT TGTGCAAAAA AGCGGTTAGC TCCTTCGGTC CTCCCGATCG TGTCAGAAGT AAGTTGGCCG CAGTGTTATC ACTCATGGTT
     TCAATGTACT AGGGGTACA ACACGTTTTT TCGCCAATCG AGGAAGCCAG GAGGCTAGCA ACAGTCTTCA TTCAACCGGC GTCACAATAG TGAGTACCAA

5101 ATGGCAGCAC TGCATAATTC TCTTACTGTC ATGCCATCCG TAAGATGCTT TTCTGTGACT GGTGAGTACT CAACCAAGTC ATTCTGAGAA TAGTGTATGC
     TACCGTCGTG ACGTATTAAG AGAATGACAG TACGGTAGGC ATTCTACGAA AAGACACTGA CCACTCATGA GTTGGTTCAG TAAGACTCTT ATCACATACG

5201 GGCGACCGAG TTGCTCCTTGC CCGGCGTCAA CACGGGGATAA TACCGCGCCA CATAGCAGAA CTTTAAAAGT GCTCATCATT GGAAACGTT CTTCGGGGCG
     CCGCTGGCTC AACGAGAACG GGCCGCAGTT GGCCCCTATT ATGGCGCGGT GTATCGTCTT GAAATTTCA CGAGTAGTAA CCTTTGCAA GAAGCCCGC

5301 AAAACTCTCA AGGATCTTAC CGCTGTTGAG ATCCAGTTCG ATGTAACCCA CTCGTGCACC CAACTGATCT TCAGCATCTT TTACTTTCAC CAGCGTTTCT
     TTTTGAGAGT TCCTAGAATG GCGACAACTC TAGGTCAAGC TACATTGGGT GAGCACGTGG GTTGACTAGA AGTCGTAGAA AATGAAGTG GTCGCAAAGA

5401 GGGTGAGCAA AAACAGGAAG GCAAAAATGCC GCAAAAAAGG GAATAAGGGC GACACGGAAA TGTTGAATAC TCATACTCTT CCTTTTTCAA TATTATTGAA
     CCCACTCGTT TTTGTCCTTC CGTTTTACGG CGTTTTTTCC CTTATTCCCG CTGTGCCTTT ACAACTTATG AGTATGAGAA GGAAAAAGTT ATAATAACTT

5501 GCATTATCA GGGTTATTGT CTCATGAGCG GATACATATT TGAATGTATT TAGAAAAATA ACAAATAGG GGTTCCGCGC ACATTTCCCC GAAAAGTGCC
     CGTAAATAGT CCCAATAACA GAGTACTCGC CTATGTATAA ACTTACATAA ATCTTTTTAT TGTTTATCC CCAAGGCGCG TGTAAAGGGG CTTTTCACGG

5601 ACCTGACGTC TAAGAAACCA TTATTATCAT GACATTAACC TATAAAAATA GGCGTATCAC GAGGCCCTTT CGTCTTCAA
     TGGACTGCAG ATTCTTTGGT AATAATAGTA CTGTAATTGG ATATTTTTAT CCGCATAGTG CTCCGGGAAA GCAGAAGTT
```

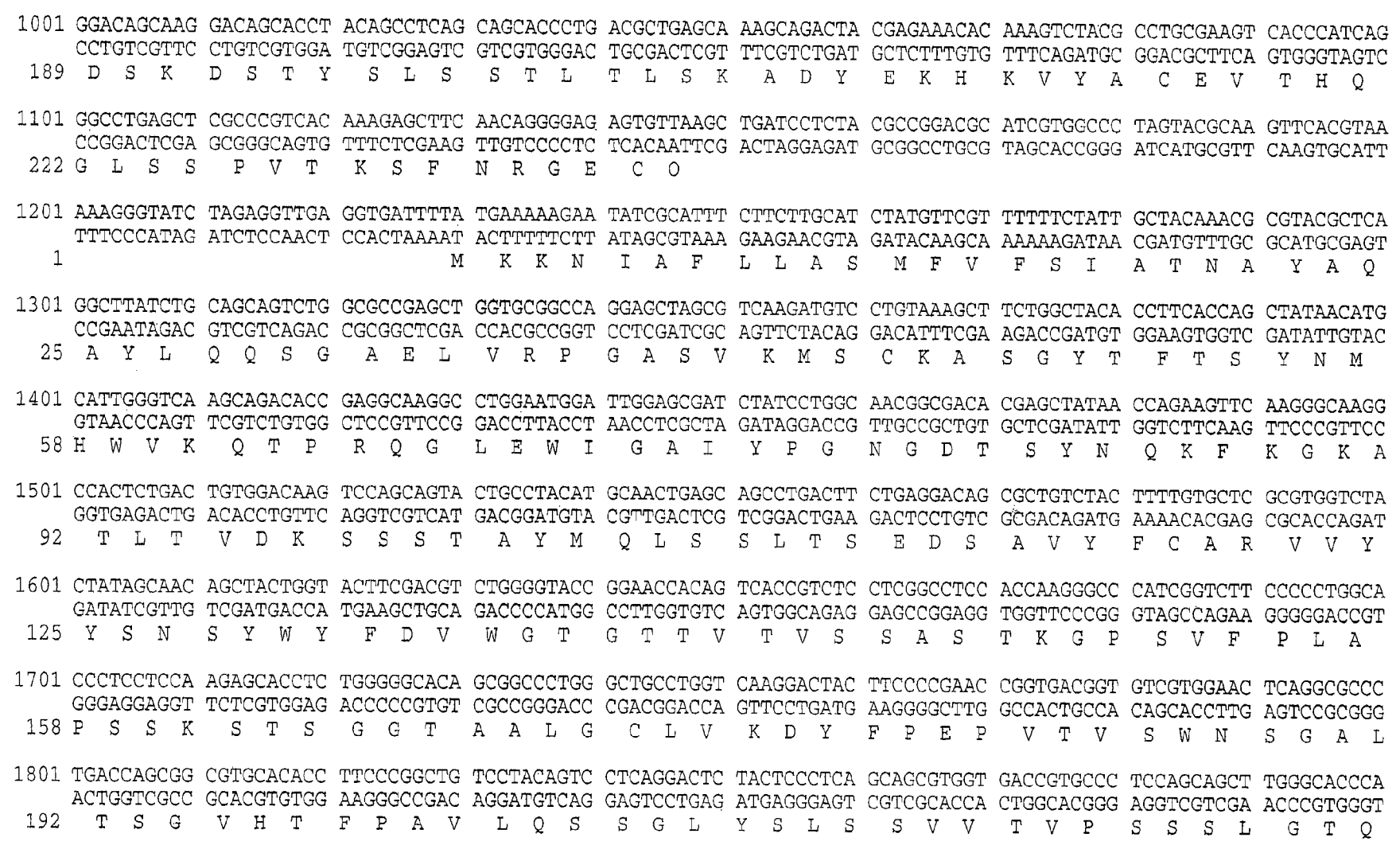

```
1901 GACCTACATC TGCAACGTGA ATCACAAGCC CAGCAACACC AAGGTGGACA AGAAAGTTGA GCCCAAATCT TGTGACAAAA CTTCACACATG ACCACCGCAT
     CTGGATGTAG ACGTTGCACT TAGTGTTCGG GTCGTTGTGG TTCCACCTGT TCTTTCAACT CGGGTTTAGA ACACTGTTTT GAGTGTGTAC TGGTGGCGTA
225   T  Y  I    C  N  V  N    H  K  P     S  N  T      K  V  D  K    K  V  E     P  K  S      C  D  K  T    H  T  O

2001 GCACCAGTAT CGTCCATTCC GACAGCATCG CCAGTCACTA TGGCGTGCTG CTAGCGCCGC CCTATACCTT GTCTGCCTCC CCGCGTTGCG TCGCGGTGCA
     CGTGGTCATA GCAGGTAAGG CTGTCGTAGC GGTCAGTGAT ACCGCACGAC GATCGCGGCG GGATATGGAA CAGACGGAGG GGCGCAACGC AGCGCCACGT

2101 TGGAGCCGGG CCACCTCGAC CTGAATGGAA GCCGGCGGCA CCTCGCTAAC GGATTCACCA CTCCAAGAAT TGGAGCCAAT CAATTCTTGC GGAGAACTGT
     ACCTCGGCCC GGTGGAGCTG GACTTACCTT CGGCCGCCGT GGAGCGATTG CCTAAGTGGT GAGGTTCTTA ACCTCGGTTA GTTAAGAACG CCTCTTGACA

2201 GAATGCGCAA ACCAACCCTT GGCAGAACAT ATCCATCGCG TCCGCCATCT CCAGCAGCCG CACGCGGGCA GCCGTTGGTC CGCAACCCAG CTTGGCCACGG
     CTTACGCGTT TGGTTGGGAA CCGTCTTGTA TAGGTAGCGC AGGCGGTAGA GGTCGTCGGC GTGCGCCCGT CGGCAACCAG GCGTTGGGTC GACCGGTGCC

2301 GTGCGCATGA TCGTGCTCCT GTCGTTGAGG ACCCGGCTAG GCTAGCAGCA TTGCCTTACT GTTTTCGTA ATCTCGGGCA GATACGCGAG CGAACGTGAA
     CACGCGTACT AGCACGAGGA CAGCAACTCC TGGGCCGATC CGACCGTCGT AACGGAATGA CACAAAGCAT TAGAGCCCGT CTATGCGCTC GCTTGCACTT

2401 GCGACTGCTG CTGCAAAACG TCTGCGGACT GAGCAACAAC ATGAATGGTC TTCGGTTTCC AAGTCTGAAA ACGAAGCGCT GGCATTGACC CAGCGCCCTG
     CGCTGACGAC GACGTTTTGC AGACGCCTGA CTCGTTGTTG TACTTACCAG AAGCCAAAGG TTCAGACCTT TGCTTCGCGA CCGTAACTGG GTCGCGGGAC

2501 CACCATTATG TTCCGGATCT GCATCGCAGG CTACCCTGTG CCCTCACAAG TTCCAGTAAC CACGGAGGCA ACGAAGCGCT GGCATTGACC CTGAGTGATT
     GTGGTAATAC AAGGCCTAGA CGTAGCGTCC GATGGGACAC GGAGTGTTGC AAGGTCATTG TGCCTCCCGT CCGTAACTGG CCGTAACTGG GACTCACTAA

2601 TTTTCTCTGT CCCGCCGCAT CCATACCGCC ATTACCCCCA TTCCCCCTTA CCCTCACAAG TTCCAGTAAC CACGGAGGCA TCAAGTGACC GTGAGCATCC
     AAAGAGACCA GGGCGGCGTA GGTATGGCGG TAATGGGGGT AAGGGGGAAT AGGTGTTGAC AAGGTCATTG GTGCCTCCGT AGTTCACTGG CACTCGTAGG

2701 TCTCTCGTTT CATCGGTATC ATTACCCCCA TGAACAGAAA CTGGAGAAAC TCAACTGTGA GAACAGGCAG GACGCGGAT AAACCGGAAA TAACATGGCC
     AGAGAGCAAA GTAGCCATAG TAATGGGGGT ACTTGTCTTT GACCTCTTTG AGTTGACACT CTTGTCCGTC CCTGCGCCTA TTTGGCGGGA ATTGTACCGG

2801 CGCTTTATCA GAAGCCAGAC CTTCGGTCTG CTGGAGAAAC ATTTGTTAA ACATCTGTGA GACGCGAGCT GGACGCGGAT ATCGCTTCAC GACCACGCTG
     GCGAAATAGT CTTCGGTCTG GAAGCCAGAC GACCCTCTTG TAAACAATT TGTAGACACT CTGCGCTCGA TAGCGAAGTG CTGGTGCGAC

2901 ATGAGCTTTA CCGCAGCATC CGGAAATTGT ATTTAGTGTT AAAGTTAAT ATTTGTTAA TAAATCAGCT CATTTTTTAA CCAATAGGCC AACGTGGACT
     TACTCGAAAT GGCGTCGTAG GCCTTTAACA TAAACCAATT TTCAATTA TTTAAAAACA ATTTAGTCGA GTAAAAAATT GGTTATCCGG TTGCACCTGA

3001 GAAATCGGCA AAATCCCTTA TAAATCAAAA GAATAGACCG GAGTGTGTT ACAAGAGTCC ACTATTAAAG AACGTGGACT
     CTTTAGCCGT TTTAGGGAAT ATTTAGTTTT CTTATCTGGC CTCACACAA TGTTCTCAGG TGATAATTTC TTGCACCTGA
```

FIG._3C

```
3101  CCAACGCTCAA AGGGCGAAAA ACCGTCTATC AGGGCTATGG CCCACTACGT GAACCATCAC CCTAATCAAG TTTTTTGGGG TCGAGGTGCC GTAAAGCACT
      GGTTGCAGTT TCCCGCTTTT TGGCAGATAG TCCCGATACC GGGTGATGCA CTTGGTAGTG GGATTAGTTC AAAAAACCCC AGCTCCACGG CATTTCGTGA

3201  AAATCGGAAC CCTAAAGGGA GCCCCCGATT TAGAGCTTGA CGGCGAAAGC CGGCGAACGT GGCGAGAAAG GAAGGGAAGA AAGGCGAAGG AGCGGGCGCT
      TTTAGCCTTG GGATTTCCCT CGGGGGCTAA ATCTCGAACT GCCGCTTTCG GCCGCTTTGCA CCGCTCTTTC CTTCCCTTCT TTCGCTTCC TCGCCCGCGA

3301  AGGGGCGCTGG CAAGTGTAGC GGTCACGCTG CGCGTAACCA CCACACCCGC CGCCGCTAAT GCGCCGCTAC AGGGGCGCGTC CGCATCCTGC CTCGCGCGTT
      TCCCGCGACC GTTCACATCG CCAGTGCGAC GGTGTGGGCG GCGCATTGGT GCGCGAATTA CGCGGCGATG TCCCGCGCAG GCGTAGGACG GAGCGCGCAA

3401  TCGGTGATGA CGGTGAAAAC CTCTGACACA TGCAGCTCCC GGAGACGGTC ACAGCTTGTC TGTAAGCGGA TGCCGGGAGC AGACAAGCCC GTCAGGGCGC
      AGCCACTACT GCCACTTTTG GAGACTGTGT ACGTCGAGGG CCTCTGCCAG TGTCGAACAG ACATTCGCCT ACGGCCCCTCG TCTGTTCGGG CAGTCCCGCG

3501  GTCAGCGGGT GTTGGCGGGT GTCGGGGCGC AGCCATGACC CAGTCACGTA GCGATAGCGG ACAGCTTACT GGCTTAACTA TGCGGCATCA GAGCAGATTG
      CAGTCGCCCA CAACCGCCCA CAGCCCCGCG TCGGTACTGG GTCATGCAT CGCTATCGCC AGTGTATACT CCGAATTGAT ACGCCGTAGT CTCGTCTAAC

3601  TACTGAGAGT GCACCATATG CGGTGTGAAA TACCGCACAG ATGGCGTAAGG AGAAAATACC TCTTTTATGG TCCTTCGCCT CTGACTCGCT
      ATGACTCTCA CGTGGTATAC GCCACACTTT ATGGCGTGTC TACGCATTCC TCTTTTATGG CGTAGTCGCG GAGAAGCGAGT GACTGAGCGA

3701  GCGCTCGGTC GTTGGCTGC GGCGAGCGGT ATCAGCTCAC TCAAAGGCGG TAATACGGTT ATCCACAGAA TCAGGGGATA ACGCAGGAAA GAACATGTGA
      CGCGAGCCAG CAAGCCGACG CCGCTCGCCA TAGTCGAGTG AGTTTCCGCC ATTATGCCAA AGGTGTCTT AGTCCCTAT TGCGTCCTTT CTTGTACACT

3801  GCAAAAAGGCC AGCAAAAGGC CAGGAACCGT AAAAAGGCCG CGTTGCTGGC GTTTTTCCAT AGGCTCCGCC CCCCCTGACGA GCATCACAAA AATCGACGCT
      CGTTTTCCGG TCGTTTTCCG GTCCTTGGCA TTTTTCCGGC CAAACGACCG CAAAAAGGTA TCCGAGGGCG GGGGGACTGCT CGTAGTGTTT TTAGCTGCGA

3901  CAAGTCAGAG GTGGCGAAAC CCGACAGGAC TATAAAGATA CCAGGCGTTT CCCCCTGGAA GCTCCCTCGT GCGCTCTCCT GTTCCGACCC TGCCGCTTAC
      GTTCAGTCTC CACCGCTTTG GGCTGTCCTG ATATTTCTAT GGTCCGCAAA GGGGGACCTT CGAGGGAGCA CGCGAGAGGA CAAGGCTGGG ACGGCGAATG

4001  CGGATACCTG TCCCTCCGGG AAGCGTGGCG CTTTCTCATA GCTCACGCTG TAGGTATCTC AGTTCGGTGT AGGTCGTTCG CTCCAAGCTG
      GCCTATGGAC AGGGAGAAAG TTCGCACCGC GAAAGAGTAT CGAGTGCGAC ATCCATAGAG TCAACCACA TCCAGCAAGC GAGGTTCGAC

4101  GGCTGTGTGC ACGAACCCCC CGTTCAGCCC GACCGCTGCG CCTTATATCGT TAACTATCGT CTTGAGTCCA ACCCGGTAAG ACACGACTTA TCGCCACTGG
      CCGACACACG TGCTTGGGGG GCAAGTCGGG CTGGCGACGC GGAATAGGCC ATTGATAGCA GAACTCAGGT TGGGCCATTC TGTGCTGAAT AGCGGTGACC

4201  CAGCAGCCAC TGGTAACAGG ATTAGCAGAG CGAGGTATGT AGGCGGTGCT ACAGAGTTCT TGAAGTGGTG GCCTAACTAC GGCTACACTA GAAGGACAGT
      GTCGTCGGTG ACCATTGTCC TAATCGTCTC GCTCCATACA TCCGCCACGA TGTCTCAAGA ACTTCACCAC CGGATTGATG CCGATGTGAT CTTCCTGTCA

4301  ATTTGGTATC TGCGCTCTGC TGAAGCCAGT TACCTTCGGA AAAAGAGTTG GTAGCTCTTG ATCCGGCAAA CAAACCACCG CTGGTAGCGG TGTTTTTTT
      TAAACCATAG ACGCGAGACG ACTTCGGTCA ATGGAAGCCT TTTCTCAAC CATCGAGAAC TAGGCCGTTT GTTTGGTGGC GACCATCGCC ACCAAAAAAA

FIG._3D
```

```
4401 GTTTGCAAGC AGCAGATTAC GCGCAGAAAA AAGAAGATCC TTTGATCTTT TCTACGGGGT CTGACGCTCA GTGGAACGAA AACTCACGTT
     CAAACGTTCG TCGTCTAATG CGCGTCTTTT TTCTTCTAGG AAACTAGAAA AGATGCCCCA GACTGCGAGT CACCTTGCTT TTGAGTGCAA

4501 AAGGGATTTT GGTCATGAGA TTATCAAAAA GGATCTTCAC CTAGATCCTT TTAAATTAAA AATGAAGTTT TAAAGTATAT ATGAGTAAAC
     TTCCCTAAAA CCAGTACTCT AATAGTTTTT CCTAGAAGTG GATCTAGGAA AATTTAATTT TTACTTCAAA ATTTCATATA TACTCATTTG

4601 TTGGTCTGAC AGTTACCAAT GCTTAATCAG TGAGGCACCT ATCTCAGCGA TCTGTCTATT TCGTTCATCC ATAGTTGCCT GACTCCCCGT CGTGTAGATA
     AACCAGACTG TCAATGGTTA CGAATTAGTC ACTCCGTGGA TAGAGTCGCT AGACAGATAA AGCAAGTAGG TATCAACGGA CTGAGGGGCA GCACATCTAT

4701 ACTACGATAC GGGAGGGCTT ACCATCTGGC CCCAGTGCTG CAATGATACC GCGAGACCCA CGCTCACCGG CTCCAGATTT ATCAGCAATA AACCAGCCAG
     TGATGCTATG CCCTCCCGAA TGGTAGACCG GGGTCACGAC GTTACTATGG CGCTCTGGGT GCGAGTGGCC GAGGTCTAAA TAGTCGTTAT TTGGTCGGTC

4801 CCGGAAGGGC CGAGCGCAGA AGTGGTCCTG CAACTTTATC CGCCTCCATC CAGTCTATTA ATTGTTGCCG GGAAGCTAGA GTAAGTAGTT CGCCAGTTAA
     GGCCTTCCCG GCTCGCGTCT TCACCAGGAC GTTGAAATAG GCGGAGGTAG GTCAGATAAT TAACAACGGC CCTTCGATCT CATTCATCAA GCGGTCAATT

4901 TAGTTTGCGC AACGTTGTTG CCATTGCTGC AGGCATCGTG GTGTCACGCT CGTCGTTTGG TATGGCTTCA TTCAGCTCCG GTTCCAACG ATCAAGGCGA
     ATCAAACGCG TTGCAACAAC GGTAACGACG TCCGTAGCAC CACAGTGCGA GCAGCAAACC ATACCGAAGT AAGTCGAGGC CAAGGGTTGC TAGTTCCGCT

5001 GTTACATGAT CCCCCATGTT GTGCAAAAAA GCGGTTAGCT CCTTCGGTCC GTCAGAAGTA AGTTGGCCGC AGTGTTATCA CTCATGGTTA
     CAATGTACTA GGGGGTACAA CACGTTTTTT CGCCAATCGA GGAAGCCAGG CAGTCTTCAT TCAACCGGCG TCACAATAGT GAGTACCAAT

5101 TGGCAGCACT GCATAATTCT CTTACTGTCA TGCCATCCGT AAGATGCTTT TCTGTGACTG GTGAGTACTC AACCAAGTCA TTCTGAGAAT AGTGTATGCG
     ACCGTCGTGA CGTATTAAGA GAATGACAGT ACGGTAGGCA TTCTACGAAA AGACACTGAC CACTCATGAG TTGGTTCAGT AAGACTCTTA TCACATACGC

5201 GCGACCGAGT TGCTCTTGCC CGGCGTCAAC ACGGGGATAAT ACCGCGCCAC ATAGCAGAAC TTTAAAAGTG CTCATCATTG GAAAACGTTC TTCGGGGCGA
     CGCTGGCTCA ACGAGAACGG GCCGCAGTTG TGCCCTATTA TGGCGCGGTG TATCGTCTTG AAATTTTCAC GAGTAGTAAC CTTTTGCAAG AAGCCCCGCT

5301 AAACTCTCAA GGATCTTACC GCTGTTGAGA TCCAGTTCGA TGTAACCCAC TCGTGCACCC AACTGATCTT CAGCATCTTT TACTTTCACC AGCGTTTCTG
     TTTGAGAGTT CCTAGAATGG CGACAACTCT AGGTCAAGCT ACATTGGGTG AGCACGTGGG TTGACTAGAA GTCGTAGAAA ATGAAAGTGG TCGCAAAGAC

5401 GGTGAGCAAA AACAGGAAGG CAAAATGCCG CAAAAAAGGG AATAAGGGCG ACACGGAAAT GTTGAATACT CATACTCTTC CTTTTTCAAT ATTATTGAAG
     CCACTCGTTT TTGTCCTTCC GTTTTACGGC GTTTTTTCCC TTATTCCCGC TGTGCCTTTA CAACTTATGA GTATGAGAAG GAAAAAGTTA TAATAACTTC

5501 CATTTATCAG GGTTATTGTC TCATGAGCGG ATACATATTT GAATGTATTT AGAAAAATAA ACAAATAGGG GTTCCGCGCA CATTTCCCCG AAAAGTGCCA
     GTAAATAGTC CCAATAACAG AGTACTCGCC TATGTATAAA CTTACATAAA TCTTTTTATT TGTTTATCCC CAAGGCGCGT GTAAAGGGGC TTTTCACGGT

5601 CCTGACGTCT AAGAAACCAT TATTATCATG ACATTAACCT ATAAAAATAG GCGTATCACG AGGCCCTTTC GTCTTCAA
     GGACTGCAGA TTCTTTGGTA ATAATAGTAC TGTAATTGGA TATTTTTATC CGCATAGTGC TCCGGGAAAG CAGAAGTT
```

FIG._3E

```
TTCGAGCTCGCCCGACATTGATTATTGACTAGTTATTAATAGTAATCAATTACGGGGTCA
TTAGTTCATAGCCCATATATGGAGTTCCGCGTTACATAACTTACGGTAAATGGCCCGCCT
GGCTGACCGCCCAACGACCCCCGCCCATTGACGTCAATAATGACGTATGTTCCCATAGTA
ACGCCAATAGGGACTTTCCATTGACGTCAATGGGTGGAGTATTTACGGTAAACTGCCCAC
TTGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCAG
TACATCTACGTATTAGTCATCGCTATTACCATGGTGATGCGGTTTTGGCAGTACATCAAT
GGGCGTGGATAGCGGTTTGACTCACGGGGATTTCCAAGTCTCCACCCCATTGACGTCAAT
GGGAGTTTGTTTTGGCACCAAAATCAACGGGACTTTCCAAAATGTCGTAACAACTCCGCC
CCATTGACGCAAATGGGCGGTAGGCGTGTACGGTGGGAGGTCTATATAAGCAGAGCTCGT
TTAGTGAACCGTCAGATCGCCTGGAGACGCCATCCACGCTGTTTTGACCTCCATAGAAGA
CACCGGGACCGATCCAGCCTCCGCGGCCGGGAACGGTGCATTGGAACGCGGATTCCCCGT
GCCAAGAGTGACGTAAGTACCGCCTATAGAGTCTATAGGCCCACCCCCTTGGCTTCGTTA
GAACGCGGCTACAATTAATACATAACCTTATGTATCATACACATACGATTTAGGTGACAC
TATAGAATAACATCCACTTTGCCTTTCTCTCCACAGGTGTCCACTCCCAGGTCCAACTGC
ACCTCGGTTCTATCGATTGAATTCCACCATGGGATGGTCATGTATCATCCTTTTTCTAGT
AGCAACTGCAACTGGAGTACATTCAGATATCCAGATGACCCAGTCCCCGAGCTCCCTGTC
CGCCTCTGTGGGCGATAGGGTCACCATCACCTGCCGTGCCAGTCAGGACATCCGTAATTA
TTTGAACTGGTATCAACAGAAACCAGGAAAAGCTCCGAAACTACTGATTTACTATACCTC
CCGCCTGGAGTCTGGAGTCCCTTCTCGCTTCTCTGGTTCTGGTTCTGGGACGGATTACAC
TCTGACCATCAGTAGTCTGCAACCGGAGGACTTCGCAACTTATTACTGTCAGCAAGGTAA
TACTCTGCCGTGGACGTTCGGACAGGGCACCAAGGTGGAGATCAAACGAACTGTGGCTGC
ACCATCTGTCTTCATCTTCCCGCCATCTGATGAGCAGTTGAAATCTGGAACTGCCTCTGT
TGTGTGCCTGCTGAATAACTTCTATCCCAGAGAGGCCAAAGTACAGTGGAAGGTGGATAA
CGCCCTCCAATCGGGTAACTCCCAGGAGAGTGTCACAGAGCAGGACAGCAAGGACAGCAC
CTACAGCCTCAGCAGCACCCTGACGCTGAGCAAAGCAGACTACGAGAAACACAAAGTCTA
CGCCTGCGAAGTCACCCATCAGGGCCTGAGCTCGCCCGTCACAAAGAGCTTCAACAGGGG
AGAGTGTTAAGCTTGGCCGCCATGGCCCAACTTGTTTATTGCAGCTTATAATGGTTACAA
ATAAAGCAATAGCATCACAAATTTCACAAATAAAGCATTTTTTTCACTGCATTCTAGTTG
TGGTTTGTCCAAACTCATCAATGTATCTTATCATGTCTGGATCGATCGGGAATTAATTCG
GCGCAGCACCATGGCCTGAAATAACCTCTGAAAGAGGAACTTGGTTAGGTACCTTCTGAG
GCGGAAAGAACCAGCTGTGGAATGTGTGTCAGTTAGGGTGTGGAAAGTCCCCAGGCTCCC
CAGCAGGCAGAAGTATGCAAAGCATGCATCTCAATTAGTCAGCAACCAGGTGTGGAAAGT
CCCCAGGCTCCCCAGCAGGCAGAAGTATGCAAAGCATGCATCTCAATTAGTCAGCAACCA
TAGTCCCGCCCCTAACTCCGCCCATCCCGCCCCTAACTCCGCCCAGTTCCGCCCATTCTC
CGCCCCATGGCTGACTAATTTTTTTTATTTATGCAGAGGCCGAGGCCGCCTCGGCCTCTG
AGCTATTCCAGAAGTAGTGAGGAGGCTTTTTTGGAGGCCTAGGCTTTTGCAAAAAGCTGT
TAACAGCTTGGCACTGGCCGTCGTTTTACAACGTCGTGACTGGGAAAACCCTGGCGTTAC
CCAACTTAATCGCCTTGCAGCACATCCCCCCTTCGCCAGCTGGCGTAATAGCGAAGAGGC
CCGCACCGATCGCCCTTCCCAACAGTTGCGTAGCCTGAATGGCGAATGGCGCCTGATGCG
GTATTTTCTCCTTACGCATCTGTGCGGTATTTCACACCGCATACGTCAAAGCAACCATAG
TACGCGCCCTGTAGCGGCGCATTAAGCGCGGCGGGTGTGGTGGTTACGCGCAGCGTGACC
GCTACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCCGATTT
AGTGCTTTACGGCACCTCGACCCCAAAAAACTTGATTTGGGTGATGGTTCACGTAGTGGG
CCATCGCCCTGATAGACGGTTTTTCGCCCTTTGACGTTGGAGTCCACGTTCTTTAATAGT
GGACTCTTGTTCCAAACTGGAACAACACTCAACCCTATCTCGGGCTATTCTTTTGATTTA
TAAGGGATTTTGCCGATTTCGGCCTATTGGTTAAAAAATGAGCTGATTTAACAAAAATTT
AACGCGAATTTTAACAAAATATTAACGTTTACAATTTTATGGTGCACTCTCAGTACAATC
TGCTCTGATGCCGCATAGTTAAGCCAACTCCGCTATCGCTACGTGACTGGGTCATGGCTG
CGCCCCGACACCCGCCAACACCCGCTGACGCGCCCTGACGGGCTTGTCTGCTCCCGGCAT
```

FIG._4A

```
CCGCTTACAGACAAGCTGTGACCGTCTCCGGGAGCTGCATGTGTCAGAGGTTTTCACCGT
CATCACCGAAACGCGCGAGGCAGTATTCTTGAAGACGAAAGGGCCTCGTGATACGCCTAT
TTTTATAGGTTAATGTCATGATAATAATGGTTTCTTAGACGTCAGGTGGCACTTTTCGGG
GAAATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATGAGTA
TTCAACATTTCCGTGTCGCCCTTATTCCCTTTTTTGCGGCATTTTGCCTTCCTGTTTTTG
CTCACCCAGAAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGTGATG
ACGCCGGGCAAGAGCAACTCGGTCGCCGCATACACTATTCTCAGAATGACTTGGTTGAGT
ACTCACCAGTCACAGAAAAGCATCTTACGGATGGCATGACAGTAAGAGAATTATGCAGTG
CTGCCATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATCGTT
GGGAACCGGAGCTGAATGAAGCCATACCAAACGACGAGCGTGACACCACGATGCCAGCAG
CAATGGCAACAACGTTGCGCAAACTATTAACTGGCGAACTACTTACTCTAGCTTCCCGGC
AACAATTAATAGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGGTCTCGCGGTA
TCATTGCAGCACTGGGGCCAGATGGTAAGCCCTCCCGTATCGTAGTTATCTACACGACGG
GGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAAC
TTCATTTTTAATTTAAAAGGATCTAGGTGAAGATCCTTTTTGATAATCTCATGACCAAAA
TCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGGTAACTG
GCTTCAGCAGAGCGCAGATACCAAATACTGTCCTTCTAGTGTAGCCGTAGTTAGGCCACC
ACTTCAAGAACTCTGTAGCACCGCCTACATACCTCGCTCTGCTAATCCTGTTACCAGTGG
CTGCTGCCAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTTGGAGCGAA
CGACCTACACCGAACTGAGATACCTACAGCGTGAGCATTGAGAAAGCGCCACGCTTCCCG
AAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCT
GACTTGAGCGTCGATTTTTGTGATGCTCGTCAGGGGGCGGAGCCTATGGAAAAACGCCA
GCAACGCGGCCTTTTTACGGTTCCTGGCCTTTTGCTGGCCTTTTGCTCACATGTTCTTTC
CTGCGTTATCCCCTGATTCTGTGGATAACCGTATTACCGCCTTTGAGTGAGCTGATACCG
CTCGCCGCAGCCGAACGACCGAGCGCAGCGAGTCAGTGAGCGAGGAAGCGGAAGAGCGCC
CAATACGCAAACCGCCTCTCCCCGCGCGTTGGCCGATTCATTAATCCAGCTGGCACGACA
GGTTTCCCGACTGGAAAGCGGGCAGTGAGCGCAACGCAATTAATGTGAGTTACCTCACTC
ATTAGGCACCCCAGGCTTTACACTTTATGCTTCCGGCTCGTATGTTGTGTGGAATTGTGA
GCGGATAACAATTTCACACAGGAAACAGCTATGACCATGATTACGAATTAA
```

FIG._4B

```
ATTCGAGCTCGCCCGACATTGATTATTGACTAGTTATTAATAGTAATCAATTACGGGGTC
ATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGT
AACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTGGCA
GTACATCTACGTATTAGTCATCGCTATTACCATGGTGATGCGGTTTTGGCAGTACATCAA
TGGGCGTGGATAGCGGTTTGACTCACGGGGATTTCCAAGTCTCCACCCCATTGACGTCAA
TGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTCG
TTTAGTGAACCGTCAGATCGCCTGGAGACGCCATCCACGCTGTTTTGACCTCCATAGAAG
ACACCGGGACCGATCCAGCCTCCGCGGCCGGGAACGGTGCATTGGAACGCGGATTCCCCG
TGCCAAGAGTGACGTAAGTACCGCCTATAGAGTCTATAGGCCCACCCCCTTGGCTTCGTT
AGAACGCGGCTACAATTAATACATAACCTTATGTATCATACACATACGATTTAGGTGACA
CTATAGAATAACATCCACTTTGCCTTTCTCTCCACAGGTGTCCACTCCCAGGTCCAACTG
CACCTCGGTTCTATCGATTGAATTCCACCATGGATGGTCATGTATCATCCTTTTCTAG
TAGCAACTGCAACTGGAGTACATTCAGAAGTTCAGCTGGTGGAGTCTGGCGGTGGCCTGG
TGCAGCCAGGGGGCTCACTCCGTTTGTCCTGTGCAGCTTCTGGCTACTCCTTTACCGGCT
ACACTATGAACTGGGTGCGTCAGGCCCCAGGTAAGGGCCTGGAATGGGTTGCACTGATTA
ATCCTTATAAAGGTGTTACTACCTATGCCGATAGCGTCAAGGGCCGTTTCACTATAAGCG
TAGATAAATCCAAAAACACAGCCTACCTGCAAATGAACAGCCTGCGTGCTGAGGACACTG
CCGTCTATTATTGTGCTAGAAGCGGATACTACGGCGATAGCGACTGGTATTTTGACGTCT
GGGGTCAAGGAACCCTGGTCACCGTCTCCTCGGCCTCCACCAAGGGCCCATCGGTCTTCC
CCCTGGCACCCTCCTCCAAGAGCACCTCTGGGGGCACAGCGGCCCTGGGCTGCCTGGTCA
AGGACTACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTGGTGA
CTGTGCCCTCTAGCAGCTTGGGCACCCAGACCTACATCTGCAACGTGAATCACAAGCCCA
GCAACACCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCCAAAAC
CCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATG
CCAAGACAAAGCCGCGGGAGGAGCAGTACAACAGCACGTACCGTGTGGTCAGCGTCCTCA
CCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGGCAGCCCCGAGAACCAC
AGGTGTACACCCTGCCCCCATCCCGGGAAGAGATGACCAAGAACCAGGTCAGCCTGACCT
GCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCT
ACAGCAAGCTCACCGTGGACAAGAGCAGGTGGCAGCAGGGGAACGTCTTCTCATGCTCCG
TGATGCATGAGGCTCTGCACAACCACTACACGCAGAAGAGCCTCTCCCTGTCTCCGGGTA
AATGAGTGCGACGGCCCTAGAGTCGACCTGCAGAAGCTTGGCCGCCATGGCCCAACTTGT
TTATTGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCATG
TCTGGATCGATCGGGAATTAATTCGGCGCAGCACCATGGCCTGAAATAACCTCTGAAAGA
GGAACTTGGTTAGGTACCTTCTGAGGCGGAAAGAACCATCTGTGGAATGTGTGTCAGTTA
GGGTGTGGAAAGTCCCCAGGCTCCCCAGCAGGCAGAAGTATGCAAAGCATGCATCTCAAT
TAGTCAGCAACCAGGTGTGGAAAGTCCCCAGGCTCCCCAGCAGGCAGAAGTATGCAAAGC
ATGCATCTCAATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTTTATTTATGCA
GAGGCCGAGGCCGCCTCGGCCTCTGAGCTATTCCAGAAGTAGTGAGGAGGCTTTTTTGGA
GGCCTAGGCTTTTGCAAAAAGCTGTTAACAGCTTGGCACTGGCCGTCGTTTTACAACGTC
GTGACTGGGAAAACCCTGGCGTTACCCAACTTAATCGCCTTGCAGCACATCCCCCCTTCG
```

FIG._5A

```
CCAGTTGGCGTAATAGCGAAGAGGCCCGCACCGATCGCCCTTCCCAACAGTTGCGTAGCC
TGAATGGCGAATGGCGCCTGATGCGGTATTTTCTCCTTACGCATCTGTGCGGTATTTCAC
ACCGCATACGTCAAAGCAACCATAGTACGCGCCCTGTAGCGGCGCATTAAGCGCGGCGGG
TGTGGTGGTTACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAACTTGA
TTTGGGTGATGGTTCACGTAGTGGGCCATCGCCCTGATAGACGGTTTTTCGCCCTTTGAC
GTTGGAGTCCACGTTCTTTAATAGTGGACTCTTGTTCCAAACTGGAACAACACTCAACCC
TATCTCGGGCTATTCTTTTGATTTATAAGGGATTTTGCCGATTTCGGCCTATTGGTTAAA
AAATGAGCTGATTTAACAAAAATTTAACGCGAATTTTAACAAAATATTAACGTTTACAAT
TTTATGGTGCACTCTCAGTACAATCTGCTCTGATGCCGCATAGTTAAGCCAACTCCGCTA
TCGCTACGTGACTGGGTCATGGCTGCGCCCCGACACCCGCCAACACCCGCTGACGCGCCC
TGACGGGCTTGTCTGCTCCCGGCATCCGCTTACAGACAAGCTGTGACCGTCTCCGGGAGC
TGCATGTGTCAGAGGTTTTCACCGTCATCACCGAAACGCGCGAGGCAGTATTCTTGAAGA
CGAAAGGGCCTCGTGATACGCCTATTTTTATAGGTTAATGTCATGATAATAATGGTTTCT
TAGACGTCAGGTGGCACTTTTCGGGGAAATGTGCGCGGAACCCCTATTTGTTTATTTTTC
TAAATACATTCAAATATGTATCCGCTCATGAGACAATAACCCTGATAAATGCTTCAATAA
TATTGAAAAAGGAAGAGTATGAGTATTCAACATTTCCGTGTCGCCCTTATTCCCTTTTTT
GCGGCATTTTGCCTTCCTGTTTTTGCTCACCCAGAAACGCTGGTGAAAGTAAAAGATGCT
GAAGATCAGTTGGGTGCACGAGTGGGTTACATCGAACTGGATCTCAACAGCGGTAAGATC
CTTGAGAGTTTTCGCCCCGAAGAACGTTTTCCAATGATGAGCACTTTTAAAGTTCTGCTA
TGTGGCGCGGTATTATCCCGTGATGACGCCGGGCAAGAGCAACTCGGTCGCCGCATACAC
TATTCTCAGAATGACTTGGTTGAGTACTCACCAGTCACAGAAAAGCATCTTACGGATGGC
ATGACAGTAAGAGAATTATGCAGTGCTGCCATAACCATGAGTGATAACACTGCGGCCAAC
TTACTTCTGACAACGATCGGAGGACCGAAGGAGCTAACCGCTTTTTTGCACAACATGGGG
GATCATGTAACTCGCCTTGATCGTTGGGAACCGGAGCTGAATGAAGCCATACCAAACGAC
GAGCGTGACACCACGATGCCAGCAGCAATGGCAACAACGTTGCGCAAACTATTAACTGGC
GAACTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCTGGA
GCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAG
ATCGCTGAGATAGGTGCCTCACTGATTAAGCATTGGTAACTGTCAGACCAAGTTTACTCA
TATATACTTTAGATTGATTTAAAACTTCATTTTTAATTTAAAAGGATCTAGGTGAAGATC
CTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGC
TGCTTGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTCCTT
CTAGTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGGGGTTCG
TGCACACAGCCCAGCTTGGAGCGAACGACCTACACCGAACTGAGATACCTACAGCGTGAG
CATTGAGAAAGCGCCACGCTTCCCGAAGGGAGAAAGGCGGACAGGTATCCGGTAAGCGGC
AGGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCCTTTTGC
TGGCCTTTTGCTCACATGTTCTTTCCTGCGTTATCCCCTGATTCTGTGGATAACCGTATT
ACCGCCTTTGAGTGAGCTGATACCGCTCGCCGCAGCCGAACGACCGAGCGCAGCGAGTCA
GTGAGCGAGGAAGCGGAAGAGCGCCCAATACGCAAACCGCCTCTCCCCGCGCGTTGGCCG
ATTCATTAATCCAACTGGCACGACAGGTTTCCCGACTGGAAAGCGGGCAGTGAGCGCAAC
GCAATTAATGTGAGTTACCTCACTCATTAGGCACCCCAGGCTTTACACTTTATGCTTCCG
GCTCGTATGTTGTGTGGAATTGTGAGCGGATAACAATTTCACACAGGAAACAGCTATGAC
CATGATTACGAATTA
```

FIG._5B

MGWSCIILFLVATATGVHSDIQMTQSPSSLSASVGDRVTITCRASSSVSYMHWYQQKPGK
APKPLIYAPSNLASGVPSRFSGSGSGTDFTLTISSLQPEDFATYYCQQWSFNPPTFGQGT
KVEIKRTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC

FIG._6

MGWSCIILFLVATATGVHSEVQLVESGGGLVQPGGSLRLSCAASGYTFTSYNMHWVRQAP
GKGLEWVGAIYPGNGDTSYNQKFKGRFTISVDKSKNTLYLQMNSLRAEDTAVYYCARVVY
YSNSYWYFDVWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK

FIG._7

MGWSCIILFLVATATGVHSEVQLVESGGGLVQPGGSLRLSCAASGYTFTSYNMHWVRQAP
GKGLEWVGAIYPGNGDTSYNQKFKGRFTISVDKSKNTLYLQMNSLRAEDTAVYYCARVVY
YSNSYWYFDVWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEVKFN
WYVDGVEVHNAKTKPREEQYNATYRVVSVLTVLHQDWLNGKEYKCKVSNKALPAPIAATI
SKAKGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK

FIG._8

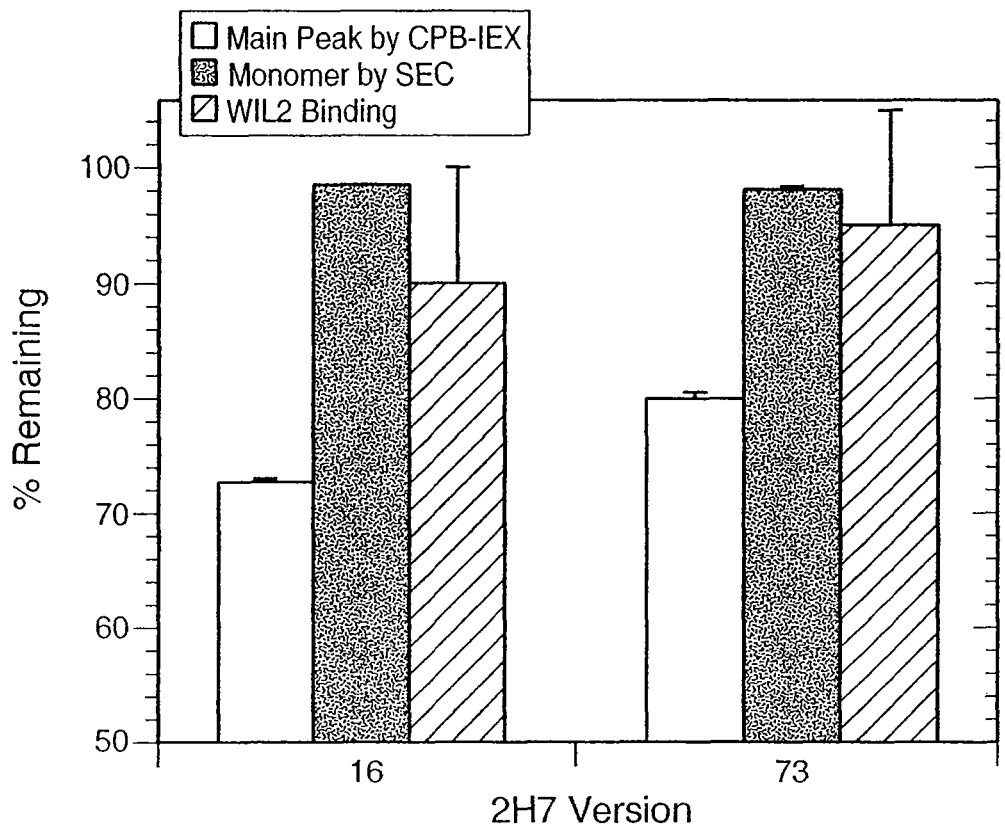
FIG._9
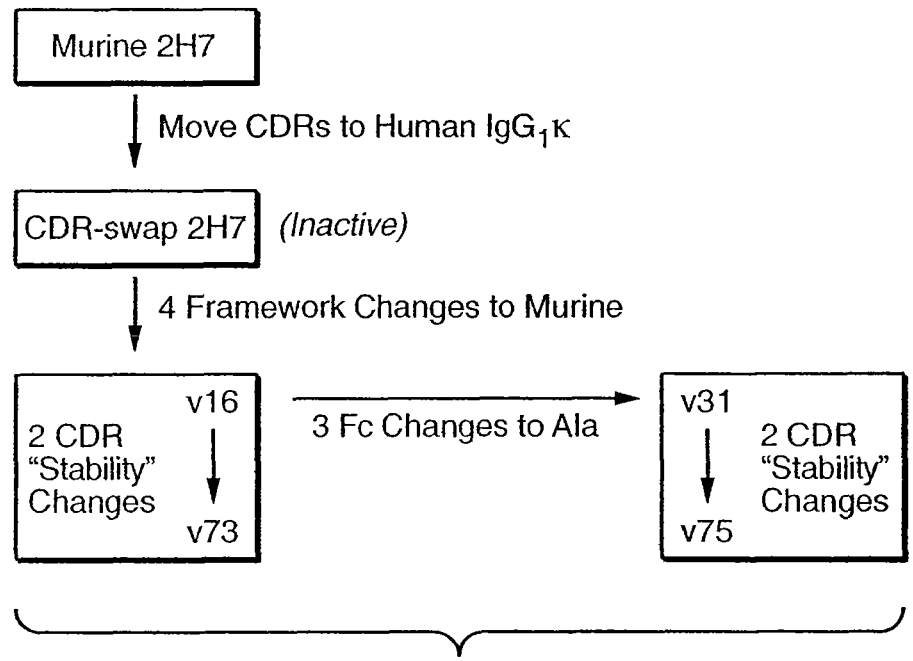
FIG._10

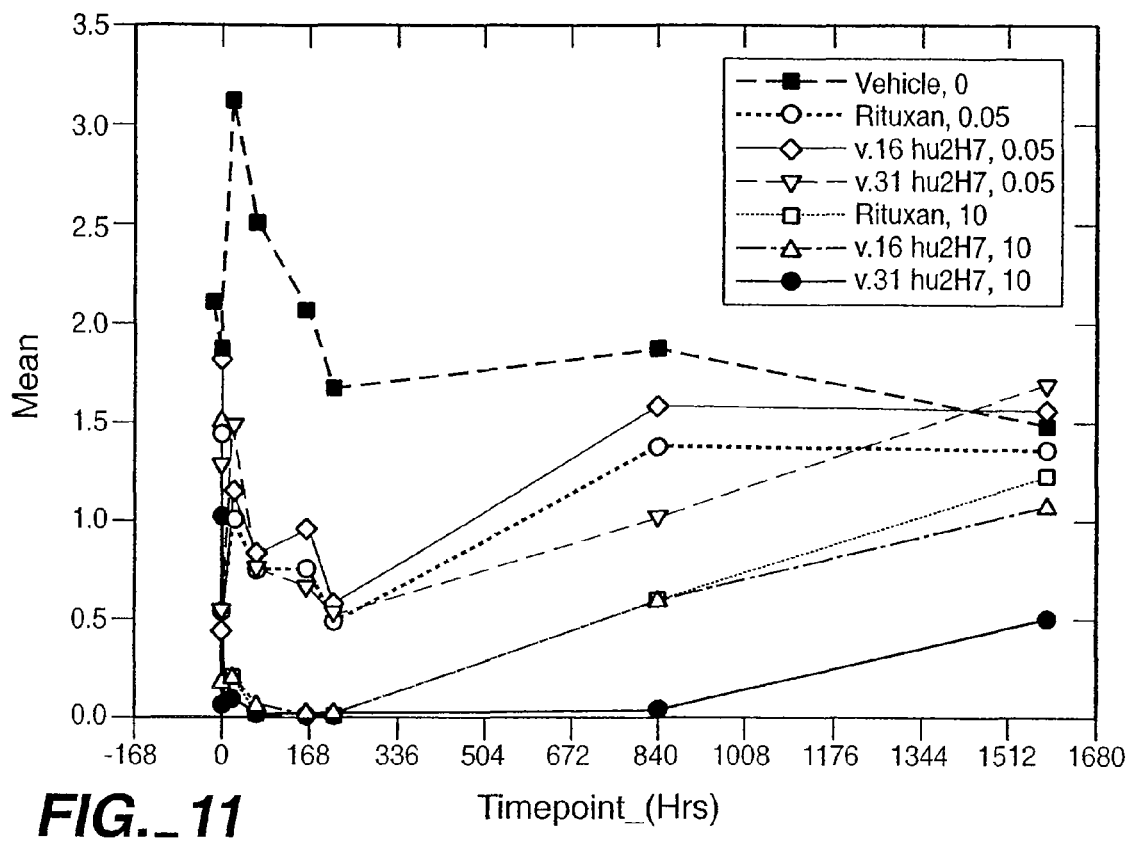
FIG._11
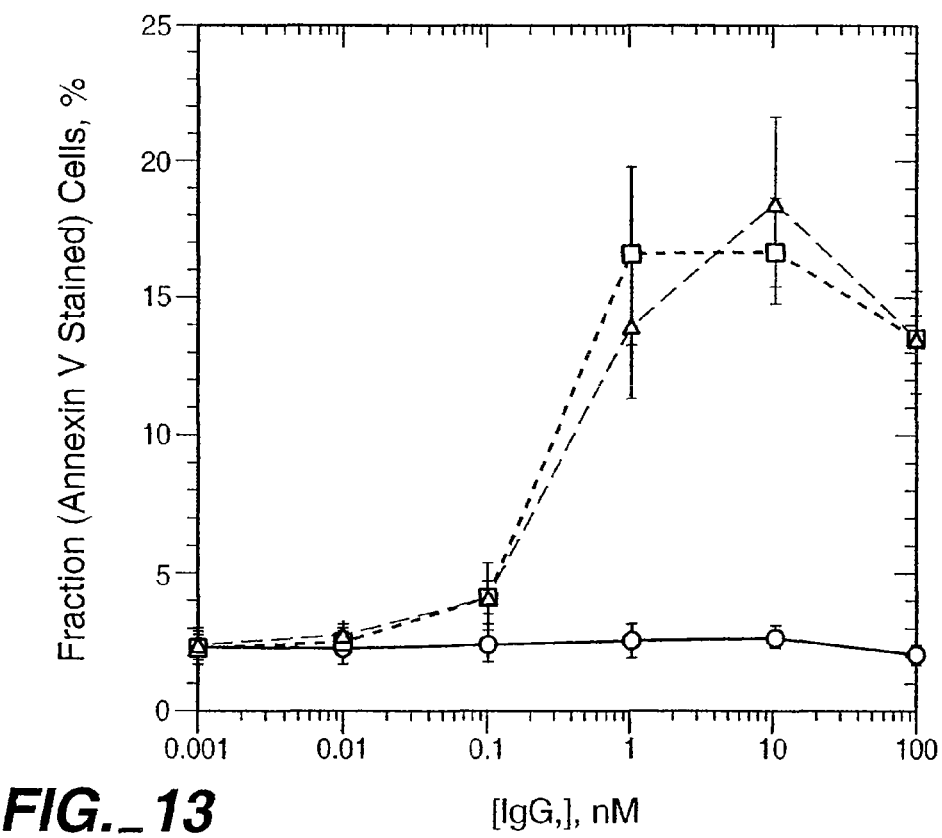
FIG._13

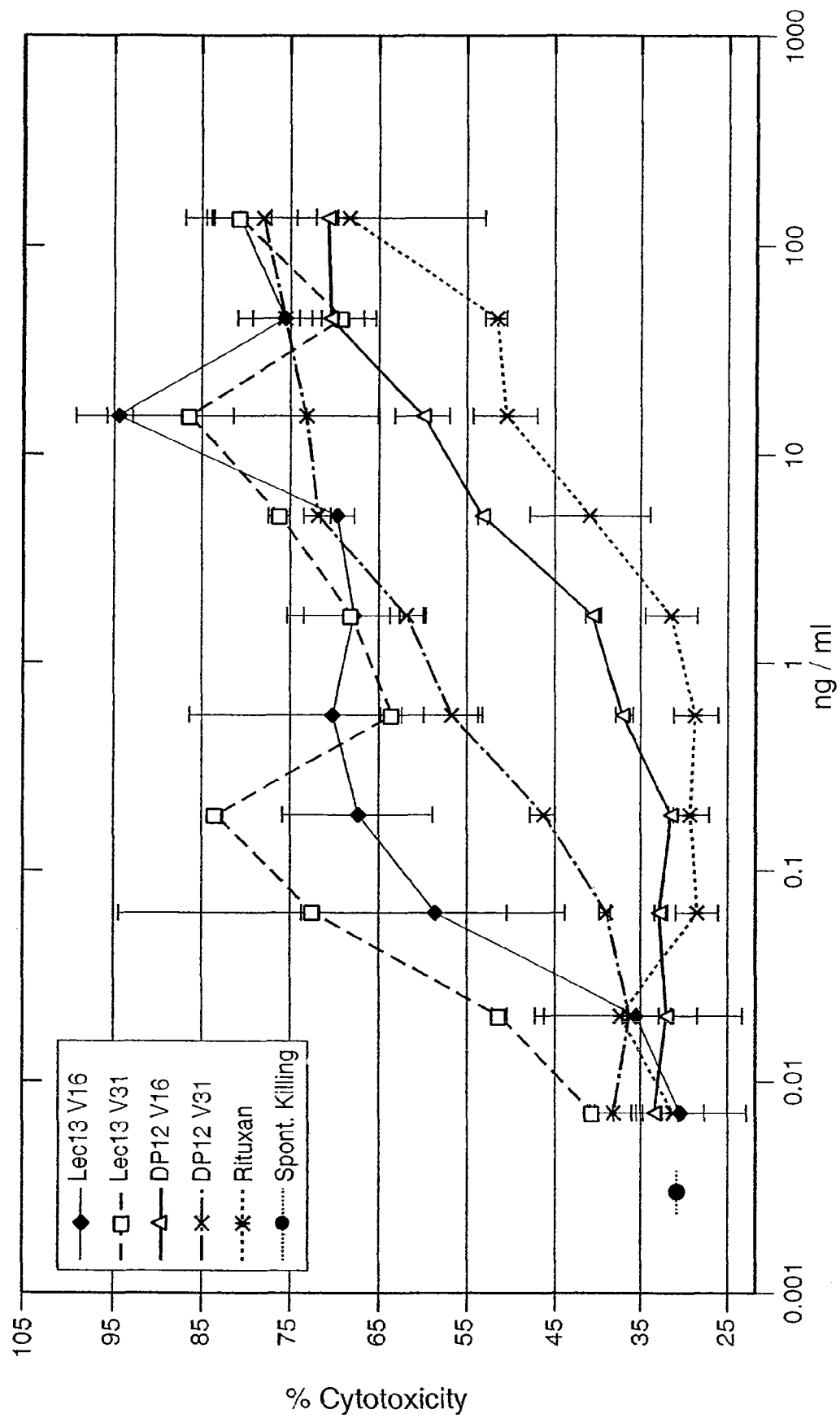
FIG._12

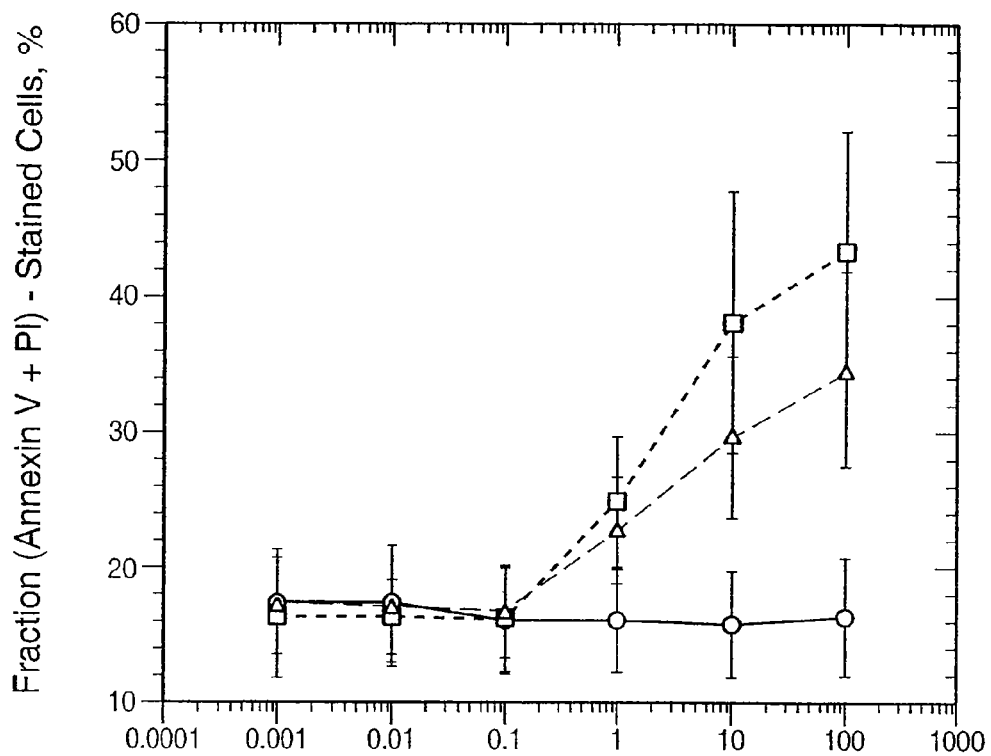
FIG._14
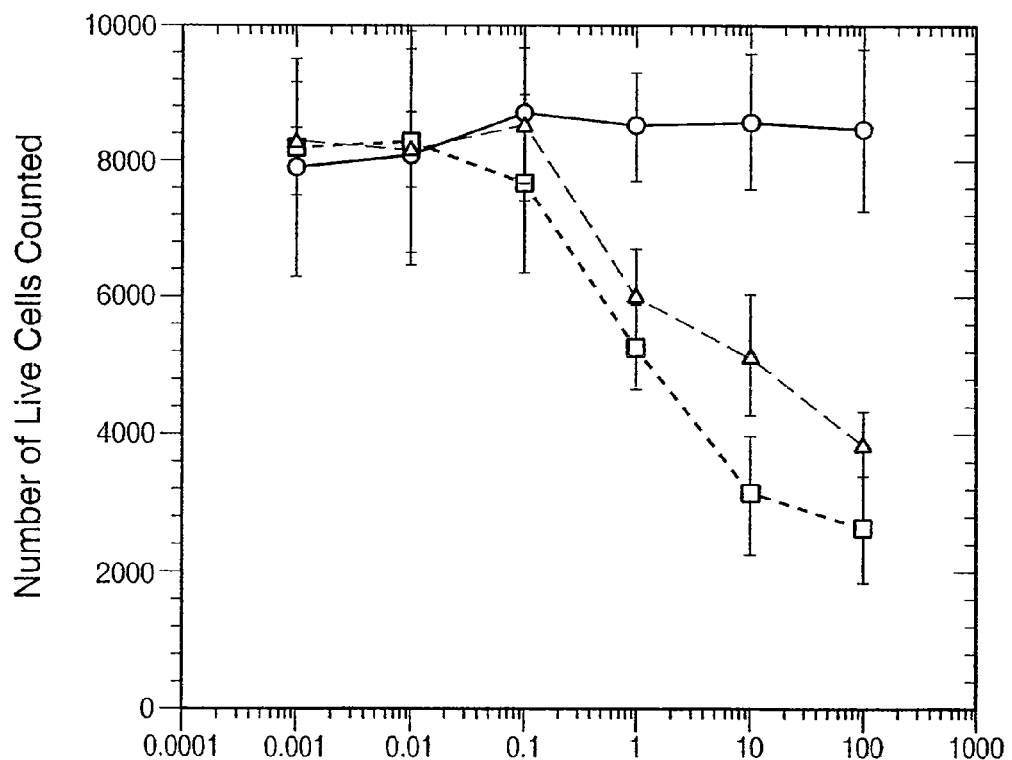
FIG._15

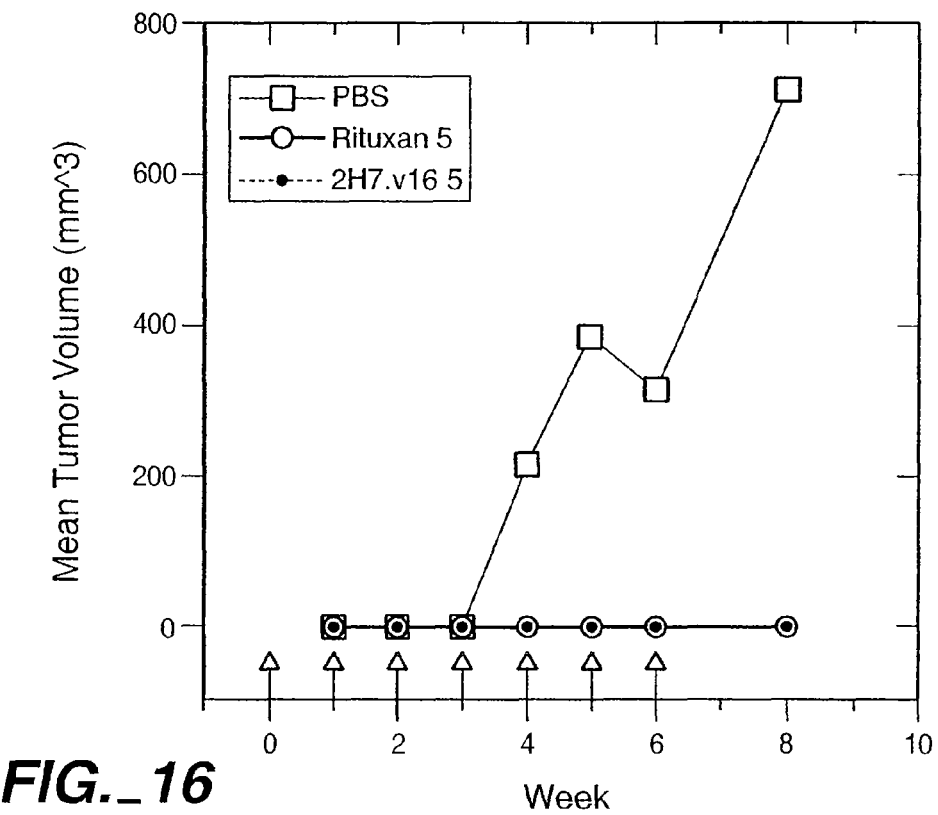
FIG._16
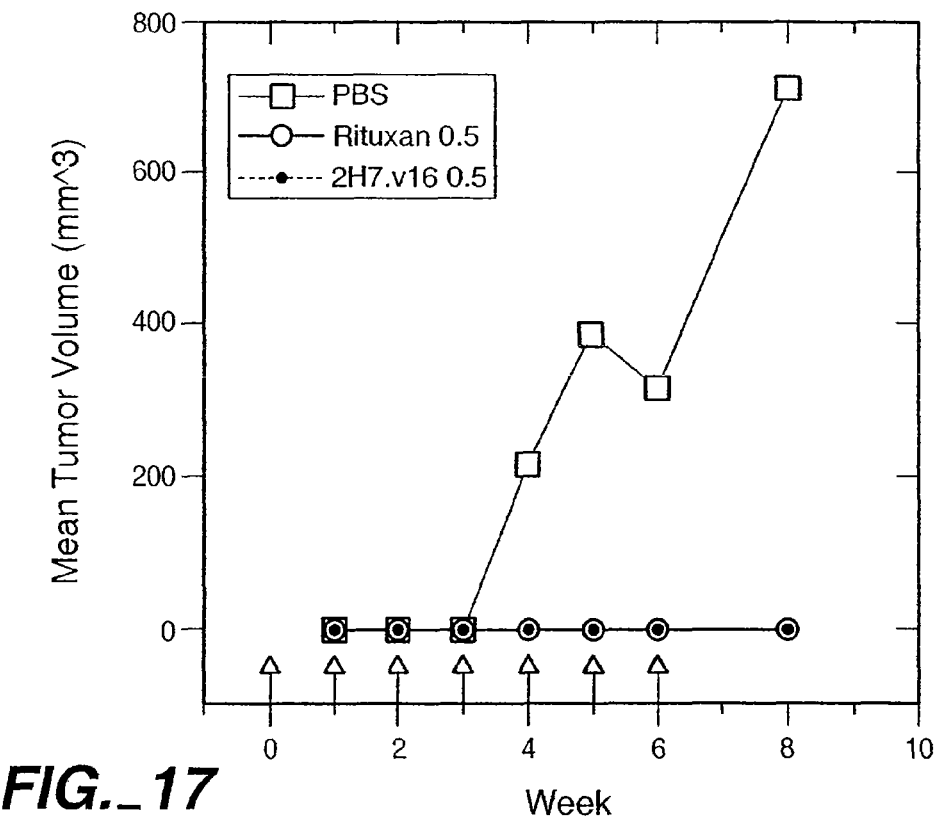
FIG._17

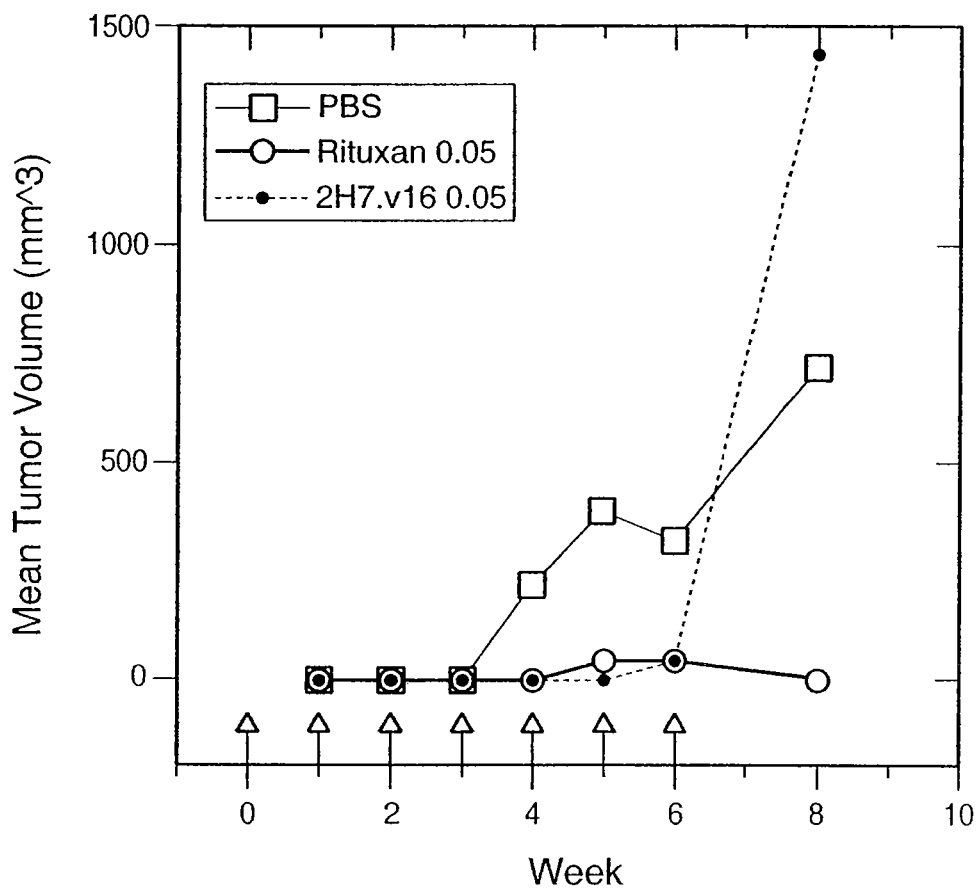

FIG._18

MTTPRNSVNGTFPAEPMKGPIAMQPGPKPLLRRMSSLVGPTQSFFMR
                       S      F
ESKALGAVQIMNGLFHIALGGLLMIPAGIYAPICVTVWYPLWGGIMYII

SGSLLAATEKNSRKCLVKGKMIMNSLSLFAAISGMILSIMDILNIKISH

FLKMESLNFIRVHTPYINIYNCEPANPSEKNSPSTQYCYSIQSLFLGILS
            A
VMLIFAFFQELVIAGIVENEWRRTCSRPKSSVVLLSAEEKKEQVIEIKE
                       K       NI            T
EVVGLTETSSQPKNEEAIEIIPIQEEEEETETNFPEPPQDQESSPIENDS
                 D
SP

FIG._20

```
  1  ATGACAACAC CCAGAAATTC AGTAAATGGG ACTTTCCCAG CAGAGCCAAT GAAAGGCCCT
     METThrThrPro ArgAsnSer ValAsnGly ThrPheProAla GluProMET LysGlyPro
 61  ATTGCTATGC AACCTGGTCC AAAACCACTC CTCAGGAGGA TGTCTTCACT GGTGGGTCCC
     IleAlaMETGln ProGlyPro LysProLeu LeuArgArgMET SerSerLeu ValGlyPro
121  ACGCAAAGCT TCTTCATGAG GGAATCTAAG GCTTTGGGGG CTGTCCAGAT TATGAATGGG
     ThrGlnSerPhe PheMETArg GluSerLys AlaLeuGlyAla ValGlnIle METAsnGly
181  CTCTTCCACA TTGCCCTGGG GGGTCTTCTG ATGATCCCAG CAGGGATCTA TGCACCCATC
     LeuPheHisIle AlaLeuGly GlyLeuLeu METIleProAla GlyIleTyr AlaProIle
241  TGTGTGACTG TGTGGTACCC TCTGTGGGGA GGCATTATGT ATATTATTTC CGGATCACTC
     CysValThrVal TrpTyrPro LeuTrpGly GlyIleMETTyr IleIleSer GlySerLeu
301  CTGGCAGCAA CGGAGAAAAA CTCCAGGAAG TGTTTGGTCA AAGGAAAAAT GATAATGAAT
     LeuAlaAlaThr GluLysAsn SerArgLys CysLeuValLys GlyLysMET IleMETAsn
361  TCATTGAGCC TCTTTGCTGC CATTTCTGGA ATGATTCTTT CAATCATGGA CATACTTAAT
     SerLeuSerLeu PheAlaAla IleSerGly METIleLeuSer IleMETAsp IleLeuAsn
421  ATTAAAATTT CCCATTTTTT AAAAATGGAG AGTCTGAATT TTATCAGAGT TCACACACCA
     IleLysIleSer HisPheLeu LysMETGlu SerLeuAsnPhe IleArgVal HisThrPro
481  TATATTAACA TATACAACTG TGAACCAGCT AATCCCTCTG AGAAAAACTC TCCATCTACT
     TyrIleAsnIle TyrAsnCys GluProAla AsnProSerGlu LysAsnSer ProSerThr
541  CAATACTGTT ACAGCATACA ATCTCTGTTC CTGGGCATTT TGTCAGTGAT GCTGATCTTT
     GlnTyrCysTyr SerIleGln SerLeuPhe LeuGlyIleLeu SerValMET LeuIlePhe
601  GCCTTCTTCC AGGAACTTGT AATAGCTGGC ATCGTTGAGA ATGAATGGAG AAGAACATGC
     AlaPhePheGln GluLeuVal IleAlaGly IleValGluAsn GluTrpArg ArgThrCys
661  TCCAGACCCA AATCTAGCGT AGTTCTCCTG TCAGCTGAAG AAAAAAAAGA ACAAGTCATT
     SerArgProLys SerSerVal ValLeuLeu SerAlaGluGlu LysLysGlu GlnValIle
721  GAAATAAAAG AAGAAGTGGT TGGGCTAACT GAAACATCTT CCCAACCAAA GAATGAAGAA
     GluIleLysGlu GluValVal GlyLeuThr GluThrSerSer GlnProLys AsnGluGlu
781  GCCATTGAAA TTATTCCAAT CCAAGAAGAG GAAGAAGAAG AAACAGAGAC AAACTTTCCA
     AlaIleGluIle IleProIle GlnGluGlu GluGluGluGlu ThrGluThr AsnPhePro
841  GAACCTCCCC AAGATCAGGA ATCTTCACCA ATAGAAAATG ACAGCTCTCC T
     GluProProGln AspGlnGlu SerSerPro IleGluAsnAsp SerSerPro
```

FIG. 19

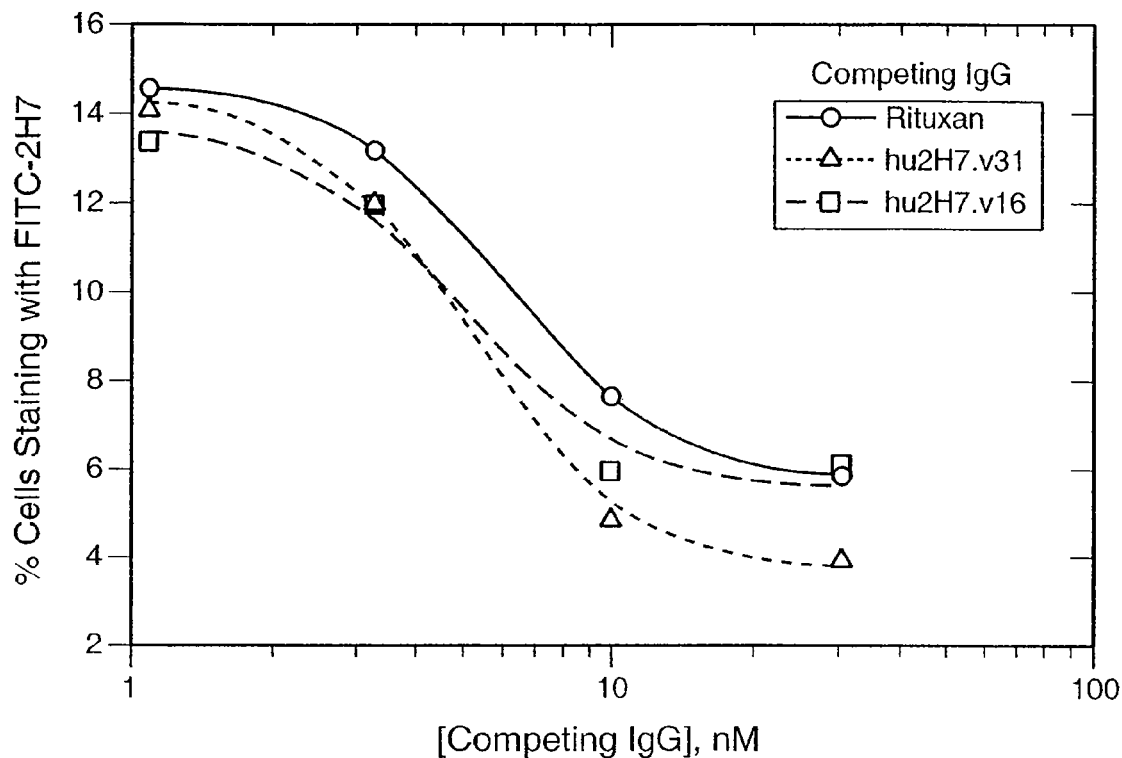
FIG._21
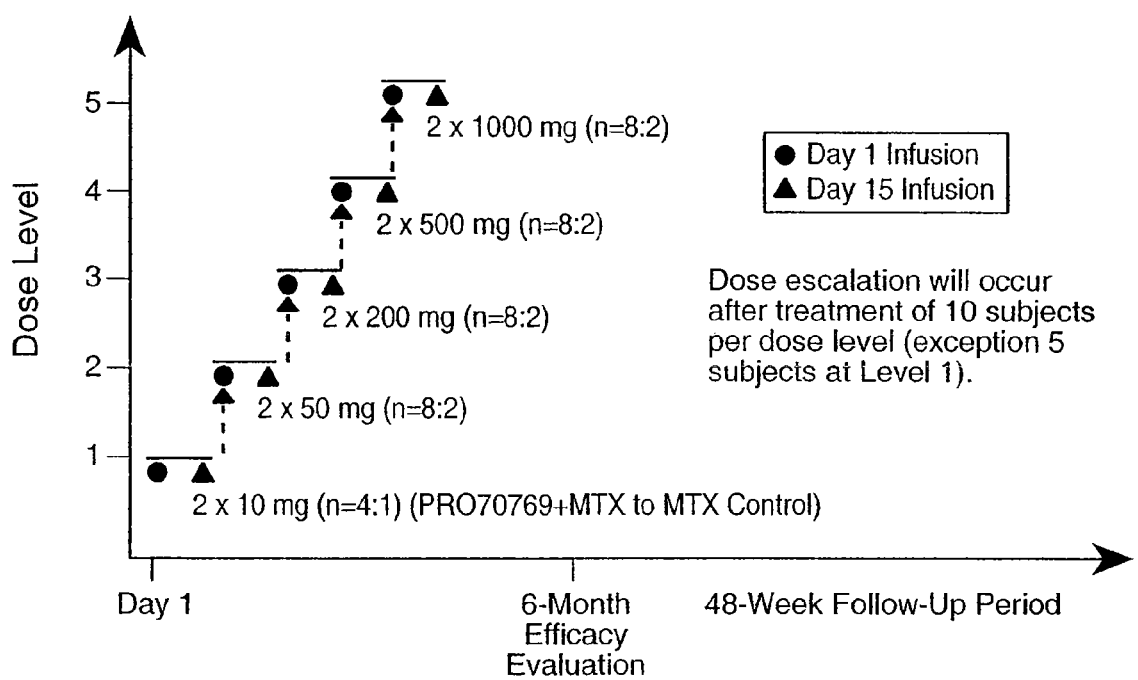
FIG._22

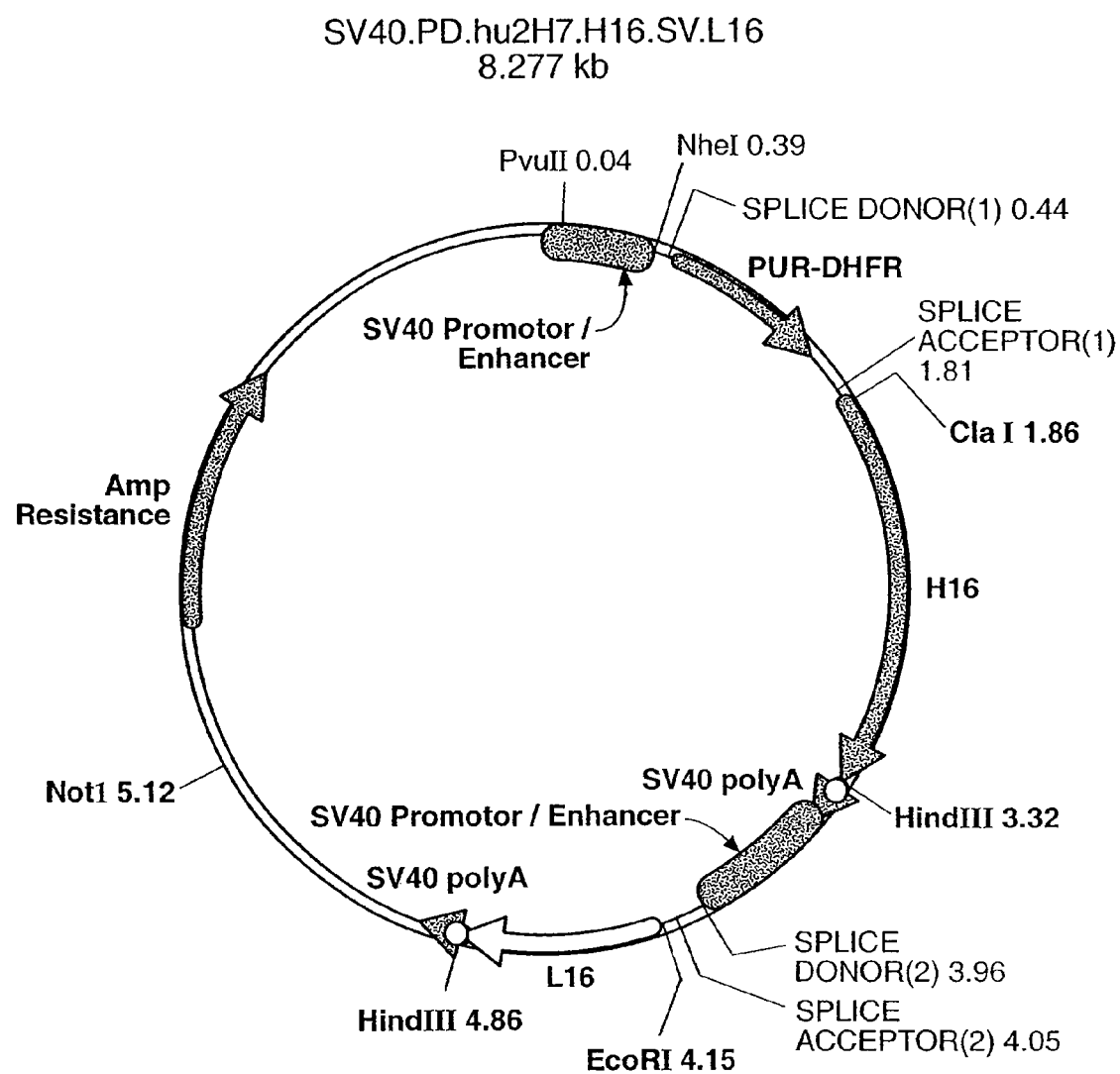
FIG._23

IMMUNOGLOBULIN VARIANTS AND USES THEREOF

RELATED APPLICATIONS

This is a divisional application of U.S. patent application Ser. No. 11/147,780, filed Jun. 7, 2005, which is a continuation application of international patent application number PCT/US03/40426, filed Dec. 16, 2003, which claims benefit of provisional application Ser. No. 60/526,163, filed on Dec. 1, 2003 and provisional application Ser. No. 60/434,115, filed on Dec. 16, 2002, which applications are incorporated herein by reference in their entirety.

FIELD OF THE INVENTION

The invention relates to anti-CD20 antibodies and their use in the treatment of B-cell related diseases.

BACKGROUND OF THE INVENTION

Lymphocytes are one of several populations of white blood cells; they specifically recognize and respond to foreign antigen. The three major classes of lymphocytes are B lymphocytes (B cells), T lymphocytes (T cells) and natural killer (NK) cells. B lymphocytes are the cells responsible for antibody production and provide humoral immunity. B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody but instead produce secreted form of the antibody. Secreted antibodies are the major effector molecules of humoral immunity.

The CD20 antigen (also called human B-lymphocyte-restricted differentiation antigen, Bp35) is a hydrophobic transmembrane protein with a molecular weight of approximately 35 kD located on pre-B and mature B lymphocytes (Valentine et al. *J. Biol. Chem.* 264(19):11282-11287 (1989); and Einfeld et al. *EMBO J.* 7(3):711-717 (1988)). The antigen is also expressed on greater than 90% of B cell non-Hodgkin's lymphomas (NHL) (Anderson et al. *Blood* 63(6):1424-1433 (1984)), but is not found on hematopoietic stem cells, pro-B cells, normal plasma cells or other normal tissues (Tedder et al. *J. Immunol.* 135(2):973-979 (1985)). CD20 is thought to regulate an early step(s) in the activation process for cell cycle initiation and differentiation (Tedder et al., supra) and possibly functions as a calcium ion channel (Tedder et al. *J. Cell. Biochem.* 14D:195 (1990)).

Given the expression of CD20 in B cell lymphomas, this antigen has been a useful therapeutic target to treat such lymphomas. There are more than 300,000 people in the United States with B-cell NHL and more than 56,000 new cases are diagnosed each year. For example, the rituximab (RITUXAN®) antibody which is a genetically engineered chimeric murine/human monoclonal antibody directed against human CD20 antigen (commercially available from Genentech, Inc., South San Francisco, Calif., U.S.) is used for the treatment of patients with relapsed or refractory low-grade or follicular, CD20 positive, B cell non-Hodgkin's lymphoma. Rituximab is the antibody referred to as "C2B8" in U.S. Pat. No. 5,736,137 issued Apr. 7, 1998 (Anderson et al.) and in U.S. Pat. No. 5,776,456. In vitro mechanism of action studies have demonstrated that RITUXAN® binds human complement and lyses lymphoid B cell lines through complement-dependent cytotoxicity (CDC) (Reff et al. *Blood* 83(2):435-445 (1994)). Additionally, it has significant activity in assays for antibody-dependent cellular cytotoxicity (ADCC). In vivo preclinical studies have shown that RITUXAN® depletes B cells from the peripheral blood, lymph nodes, and bone marrow of cynomolgus monkeys, presumably through complement and cell-mediated processes (Reff et al. *Blood* 83(2):435-445 (1994)). Other anti-CD20 antibodies indicated for the treatment of NHL include the murine antibody Zevalin™ which is linked to the radioisotope, Yttrium-90 (IDEC Pharmaceuticals, San Diego, Calif.), Bexxar™ which is a another fully murine antibody conjugated to I-131 (Corixa, Wash.).

A major limitation in the use of murine antibodies in human therapy is the human anti-mouse antibody (HAMA) response (see, e.g., Miller, R. A. et al. "Monoclonal antibody therapeutic trials in seven patients with T-cell lymphoma" Blood, 62:988-995, 1983; and Schroff, R. W., et al. "Human anti-murine immunoglobulin response in patients receiving monoclonal antibody therapy" Cancer Res., 45:879-885, 1985). Even chimeric molecules, where the variable (V) domains of rodent antibodies are fused to human constant (C) regions, are still capable of eliciting a significant immune response (HACA, human anti-chimeric antibody) (Neuberger et al. Nature (Lond.), 314:268-270, 1985). A powerful approach to overcome these limitations in the clinical use of monoclonal antibodies is "humanization" of the murine antibody or antibody from a non-human species (Jones et al. Nature (Lond), 321:522-525, 1986; Riechman et al., Nature (Lond), 332:323-327, 1988).

Thus, it is beneficial to produce therapeutic antibodies to the CD20 antigen that create minimal or no antigenicity when administered to patients, especially for chronic treatment. The present invention satisfies this and other needs. The present invention provides anti-CD20 antibodies that overcome the limitations of current therapeutic compositions as well as offer additional advantages that will be apparent from the detailed description below.

SUMMARY OF THE INVENTION

The present invention provides CD20 binding antibodies or functional fragments thereof, and their use in the treatment of B-cell associated diseases. These antibodies are monoclonal antibodies. In specific embodiments, the antibodies that bind CD20 are humanized or chimeric. The humanized 2H7 variants include those that have amino acid substitutions in the FR and affinity maturation variants with changes in the grafted CDRs. The substituted amino acids in the CDR or FR are not limited to those present in the donor or recipient antibody. In other embodiments, the anti-CD20 antibodies of the invention further comprise changes in amino acid residues in the Fc region that lead to improved effector function including enhanced CDC and/or ADCC function and B-cell killing (also referred to herein as B-cell depletion). Other anti-CD20 antibodies of the invention include those having specific changes that improve stability. In a specific embodiment, the humanized 2H7 variants with increased stability are as described in example 6 below. Fucose deficient variants having improved ADCC function in vivo are also provided. In one embodiment, the chimeric anti-CD20 antibody has murine V regions and human C region. One such specific chimeric anti-CD20 antibody is Rituxan® (Rituximab®; Genentech, Inc.).

In a preferred embodiment of all of the antibody compositions and methods of use of this invention, the humanized CD20 binding antibody is 2H7.v16 having the light and heavy chain amino acid sequence of SEQ ID NO. 21 and 22, respectively, as shown in FIG. 6 and FIG. 7. When referring to the polypeptide sequences in FIGS. 6, 7 and 8, it should be understood that the first 19 or so amino acids that form the secretory signal sequence are not present in the mature polypeptide. The V region of all other variants based on version 16 will have the amino acid sequences of v16 except at the positions of amino acid substitutions which are indicated in the disclosure. Unless otherwise indicated, the 2H7 variants will have the same L chain as that of v16.

The invention provides a humanized antibody that binds human CD20, or an antigen-binding fragment thereof, wherein the antibody is effective to deplete primate B cells in vivo, the antibody comprising in the H chain Variable region ($V_H$) at least a CDR3 sequence of SEQ ID NO. 12 from an anti-human CD20 antibody and substantially the human consensus framework (FR) residues of human heavy chain subgroup III ($V_H$III). In one embodiment, the primate B cells are from human and Cynomolgus monkey. In one embodiment, the antibody further comprises the H chain CDR1 sequence of SEQ ID NO. 10 and CDR2 sequence of SEQ ID NO. 11. In another embodiment, the preceding antibody comprises the L chain CDR1 sequence of SEQ ID NO. 4, CDR2 sequence of SEQ ID NO. 5, CDR3 sequence of SEQ ID NO. 6 with substantially the human consensus framework (FR) residues of human light chain κ subgroup I (VκI). In a preferred embodiment, the FR region in $V_L$ has a donor antibody residue at position 46; in a specific embodiment, FR2 in $V_L$ has an amino acid substitution of leuL46pro (Leu in the human κI consensus sequence changed to pro which is present in the corresponding position in m2H7).

The VH region further comprises a donor antibody residue at least amino acid positions 49, 71 and 73 in the framework. In one embodiment, in the $V_H$, the following FR positions in the human heavy chain subgroup III are substituted: AlaH49Gly in FR2; ArgH71Val and AsnH73Lys in FR3. In other embodiments, the CDR regions in the humanized antibody further comprise amino acid substitutions where the residues are neither from donor nor recipient antibody.

The antibody of the preceding embodiments can comprise the $V_H$ sequence of SEQ ID NO.8 of v16, as shown in FIG. 1B. In a further embodiment of the preceding, the antibody further comprises the $V_L$ sequence of SEQ ID NO.2 of v16, as shown in FIG. 1A.

In other embodiments, the humanized antibody is 2H7.v31 having the light and heavy chain amino acid sequence of SEQ ID NO. 21 and 23, respectively, as shown in FIG. 6 and FIG. 8; 2H7.v31 having the heavy chain amino acid sequence of SEQ ID NO. 23 as shown in FIG. 8; 2H7.v96 with the amino acid substitutions of D56A and N100A in the H chain and S92A in the L chain of v16.

In separate embodiments, the antibody of any of the preceding embodiments further comprises at least one amino acid substitution in the Fc region that improves ADCC and/or CDC activity over the original or parent antibody from which it was derived, v.16 being the parent antibody being compared to in most cases, and Rituxan in other cases. One such antibody with improved activity comprises the triple Alanine substitution of S298A/E333A/K334A in the Fc region. One antibody having S298A/E333A/K334A substitution is 2H7.v31 having the heavy chain amino acid sequence of SEQ ID NO. 23. Antibody 2H7.v114 and 2H7.v115 show at least 10-fold improved ADCC activity as compared to Rituxan.

In another embodiment, the antibody further comprises at least one amino acid substitution in the Fc region that decreases CDC activity as compared to the parent antibody from which it was derived which is v16 in most cases. One such antibody with decreased CDC activity as compared to v16 comprises at least the substitution K322A in the H chain. The comparison of ADCC and CDC activity can be assayed as described in the examples.

In a preferred embodiment, the antibodies of the invention are full length antibodies wherein the $V_H$ region is joined to a human IgG heavy chain constant region. In preferred embodiments, the IgG is human IgG1 or IgG3.

In one embodiment, the CD20 binding antibody is conjugated to a cytotoxic agent. In preferred embodiments the cytotoxic agent is a toxin or a radioactive isotope.

In one embodiment, the antibodies of the invention for use in therapeutic or diagnostic purposes are produced in CHO cells.

Also provided is a composition comprising an antibody of any one of the preceding embodiments, and a carrier. In one embodiment, the carrier is a pharmaceutically acceptable carrier. These compositions can be provided in an article of manufacture or a kit.

The invention also provided a liquid formulation comprising a humanized 2H7 antibody at 20 mg/mL antibody, 10 mM histidine sulfate pH5.8, 60 mg/ml sucrose (6%), 0.2 mg/ml polysorbate 20 (0.02%).

The invention also provides an isolated nucleic acid that encodes any of the antibodies disclosed herein, including an expression vector for expressing the antibody.

Another aspect of the invention are host cells comprising the preceding nucleic acids, and host cells that produce the antibody. In a preferred embodiment of the latter, the host cell is a CHO cell. A method of producing these antibodies is provided, the method comprising culturing the host cell that produces the antibody and recovering the antibody from the cell culture.

Yet another aspect of the invention is an article of manufacture comprising a container and a composition contained therein, wherein the composition comprises an antibody of any of the preceding embodiments. For use in treating NHL, the article of manufacture further comprises a package insert indicating that the composition is used to treat non-Hodgkin's lymphoma.

A further aspect of the invention is a method of inducing apoptosis in B cells in vivo, comprising contacting B cells with the antibody of any of the preceding, thereby killing the B cells.

The invention also provides methods of treating the diseases disclosed herein by administration of a CD20 binding antibody or functional fragment thereof, to a mammal such as a human patient suffering from the disease. In any of the methods for treating an autoimmune disease or a CD20 positive cancer, in one embodiment, the antibody is 2H7.v16 having the light and heavy chain amino acid sequence of SEQ ID NO. 21 and 22, respectively, as shown in FIG. 6 and FIG. 7. Thus, one embodiment is a method of treating a CD20 positive cancer, comprising administering to a patient suffering from the cancer, a therapeutically effective amount of a humanized CD20 binding antibody of the invention. In preferred embodiments, the CD20 positive cancer is a B cell lymphoma or leukemia including non-Hodgkin's lymphoma (NHL) or lymphocyte predominant Hodgkin's disease (LPHD), chronic lymphocytic leukemia (CLL) or SLL. In one embodiment of the method of treating a B cell lymphoma or leukemia, the antibody is administered at a dosage range of about 275-375 mg/m². In additional embodiments, the treatment method further comprises administering to the patient at least one chemotherapeutic agent, wherein for non-Hodgkin's lymphoma (NHL), the chemotherapeutic agent is selected from the group consisting of doxorubicin, cyclophosphamide, vincristine and prednisolone.

Also provided is a method of treating an autoimmune disease, comprising administering to a patient suffering from the autoimmune disease, a therapeutically effective amount of the humanized CD20 binding antibody of any one of the preceding claims. The autoimmune disease is selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. Where the autoimmune disease is rheumatoid arthritis, the antibody can be administered in conjunction with a second therapeutic agent which is preferably methotrexate.

In these treatment methods, the CD20 binding antibodies can be administered alone or in conjunction with a second therapeutic agent such as a second antibody, or a chemotherapeutic agent or an immunosuppressive agent. The second antibody can be one that binds CD20 or a different B cell antigen, or a NK or T cell antigen. In one embodiment, the second antibody is a radiolabeled anti-CD20 antibody. In other embodiments, the CD20 binding antibody is conjugated to a cytotoxic agent including a toxin or a radioactive isotope.

In another aspect, the invention provides a method of treating an autoimmune disease selected from the group consisting of Dermatomyositis, Wegner's granulomatosis, ANCA, Aplastic anemia, Autoimmune hemolytic anemia (AIHA), factor VIII deficiency, hemophilia A, Autoimmune neutropenia, Castleman's syndrome, Goodpasture's syndrome, solid organ transplant rejection, graft versus host disease (GVHD), IgM mediated, thrombotic thrombocytopenic purpura (TTP), Hashimoto's Thyroiditis, autoimmune hepatitis, lymphoid interstitial pneumonitis (HIV), bronchiolitis obliterans (non-transplant) vs. NSIP, Guillain-Barre Syndrome, large vessel vasculitis, giant cell (Takayasu's) arteritis, medium vessel vasculitis, Kawasaki's Disease, polyarteritis nodosa, comprising administering to a patient suffering from the disease, a therapeutically effective amount of a CD20 binding antibody. In one embodiment of this method, the CD20 binding antibody is Rituxan®.

The invention also provides an isolated nucleic acid comprising the nucleotide sequence of SEQ ID NO.: 24 of the Cynomolgus monkey CD20 (shown in FIG. 19), or a degenerate variant of this sequence. One embodiment is an isolated nucleic acid comprising a sequence that encodes a polypeptide with the amino acid sequence of SEQ ID NO. 25 (shown FIG. 20), or SEQ ID NO. 25 (FIG. 20) with conservative amino acid substitutions. Another embodiment is a vector comprising the preceding nucleic acid, including an expression vector for expression in a host cell. Included as well is a host cell comprising the vector. Also provided is an isolated polypeptide comprising the amino acid sequence [SEQ ID NO. 25; FIG. 20] of the Cynomolgus monkey CD20.

BRIEF DESCRIPTION OF THE FIGURES

FIG. 1A is a sequence alignment comparing the amino acid sequences of the light chain variable domain ($V_L$) of each of murine 2H7 (SEQ ID NO. 1), humanized 2H7.v16 variant (SEQ ID NO. 2), and human kappa light chain subgroup I (SEQ ID NO. 3). The CDRs of $V_L$ of 2H7 and hu2H7.v16 are as follows: CDR1 (SEQ ID NO.4), CDR2 (SEQ ID NO.5), and CDR3 (SEQ ID NO.6).

FIG. 1B is a sequence alignment which compares the $V_H$ sequences of murine 2H7 (SEQ ID NO. 7), humanized 2H7.v16 variant (SEQ ID NO. 8), and the human consensus sequence of heavy chain subgroup III (SEQ ID NO. 9). The CDRs of $V_H$ of 2H7 and hu2H7.v16 are as follow: CDR1 (SEQ ID NO.10), CDR2 (SEQ ID NO.11), and CDR3 (SEQ ID NO.12).

In FIG. 1A and FIG. 1B, the CDR1, CDR2 and CDR3 in each chain are enclosed within brackets, flanked by the framework regions, FR1-FR4, as indicated. 2H7 refers to the murine 2H7 antibody. The asterisks in between two rows of sequences indicate the positions that are different between the two sequences. Residue numbering is according to Kabat et al., Sequences of Immunological Interest. 5th Ed. Public Health Service, National Institutes of Health, Bethesda, Md. (1991), with insertions shown as a, b, c, d, and e.

FIG. 2 shows the sequence of phagemid pVX4 (SEQ ID NO.13) used for construction of 2H7 Fab plasmids (see Example 1) as well as the amino acid sequences of the L chain (SEQ ID NO.14) and H chain (SEQ ID NO.15) of the Fab for the CDR-grafted anti-IFN-α humanized antibody.

FIG. 3 shows the sequence of the expression plasmid which encodes the chimeric 2H7.v6.8 Fab (SEQ ID NO.16). The amino acid sequences of the L chain (SEQ ID NO.17) and H chain (SEQ ID NO.18) are shown.

FIG. 4 shows the sequence of the plasmid pDR1 (SEQ ID NO.19; 5391 bp) for expression of immunoglobulin light chains as described in Example 1. pDR1 contains sequences encoding an irrelevant antibody, the light chain of a humanized anti-CD3 antibody (Shalaby et al., J. Exp. Med. 175: 217-225 (1992)), the start and stop codons for which are indicated in bold and underlined.

FIG. 5 shows the sequence of plasmid pDR2 (SEQ ID NO.20; 6135 bp) for expression of immunoglobulin heavy chains as described in Example 1. pDR2 contains sequences encoding an irrelevant antibody, the heavy chain of a humanized anti-CD3 antibody (Shalaby et al., supra), the start and stop codons for which are indicated in bold and underlined.

FIG. 6 shows the amino acid sequence of the 2H7.v16 complete L chain (SEQ ID NO.21). The first 19 amino acids before DIQ are the secretory signal sequence not present in the mature polypeptide chain.

FIG. 7 shows the amino acid sequence of the 2H7.v16 complete H chain (SEQ ID NO.22). The first 19 amino acids before EVQ before are the secretory signal sequence not present in the mature polypeptide chain. Aligning the $V_H$ sequence in FIG. 1B (SEQ ID NO. 8) with the complete H chain sequence, the human γ1 constant region is from amino acid position 114-471 in SEQ ID NO. 22.

FIG. 8 shows the amino acid sequence of the 2H7.v31 complete H chain (SEQ ID NO.23). The first 19 amino acids before EVQ before are the secretory signal sequence not present in the mature polypeptide chain. The L chain is the same as for 2H7.v16 (see FIG. 6).

FIG. 9 shows the relative stability of 2H7.v16 and 2H7.v73 IgG variants as described in Example 6. Assay results were normalized to the values prior to incubation and reported as percent remaining after incubation.

FIG. 10 is a flow chart summarizing the amino acid changes from the murine 2H7 to a subset of humanized versions up to v75.

FIG. 11 is a summary of mean absolute B-cell count [CD3−/CD40+] in all groups (2H7 study and Rituxan study combined), as described in Example 10.

FIG. 12 shows the results of a representative ADCC assay on fucose deficient 2H7 variants as described in Example 11.

FIG. 13 shows the results of the Annexin V staining plotted as a function of antibody concentration. Ramos cells were treated with an irrelevant IgG1 control antibody (Herceptin®; circles), Rituximab (squares), or rhuMAb 2H7.v16 (triangles) in the presence of a crosslinking secondary antibody and were analyzed by FACS. FIGS. 13-15 are described in Example 13.

FIG. 14 shows the results of the Annexin V and propidium iodide double-staining are plotted as a function of antibody concentration. Ramos cells were treated with an irrelevant IgG1 control antibody (Herceptin®; circles), Rituximab (squares), or rhuMAb 2H7.v16 (triangles) in the presence of a crosslinking secondary antibody and were analyzed by FACS.

FIG. 15 shows the counts (per 10 s) of live, unstained cells are plotted as a function of antibody concentration. Ramos cells were treated with an irrelevant IgG1 control antibody (Herceptin®; circles), Rituximab (squares), or rhuMAb 2H7.v16 (triangles) in the presence of a crosslinking secondary antibody and were analyzed by FACS.

FIGS. 16, 17, 18 show inhibition of Raji cell tumor growth in nude mice, as described in Example 14. Animals were treated weekly (as indicated by vertical arrows; n=8 mice per group) for 6 weeks with PBS (control) or with Rituxan® or rhuMAb 2H7.v16 at 5 mg/kg (FIG. 16), 0.5 mg/kg (FIG. 17), or 0.05 mg/kg (FIG. 18).

FIG. 19 shows the nucleotide (SEQ ID NO.24) and amino acid (SEQ ID NO. 25) sequences of Cynomolgus monkey CD20, as described in Example 15.

FIG. 20 shows the amino acid sequence for cynomolgus monkey CD20 (SEQ ID NO. 25). Residues that differ from human CD20 are underlined and the human residues (SEQ ID NO. 26) are indicated directly below the monkey residue. The putative extracellular domain of the monkey CD20 is in bold type.

FIG. 21 shows the results of Cynomolgus monkey cells expressing CD20 binding to hu2H7.v16, .v31, and Rituxan, as described in Example 15. The antibodies were assayed for the ability to bind and displace FITC-conjugated murine 2H7 binding to cynomolgus CD20.

FIG. 22 shows dose escalation schema for rheumatoid arthritis phase I/II clinical trial.

FIG. 23 shows the vector for expression of 2H7.v16 in CHO cells.

DETAILED DESCRIPTION OF THE PREFERRED EMBODIMENTS

The "CD20" antigen is a non-glycosylated, transmembrane phosphoprotein with a molecular weight of approximately 35 kD that is found on the surface of greater than 90% of B cells from peripheral blood or lymphoid organs. CD20 is expressed during early pre-B cell development and remains until plasma cell differentiation; it is not found on human stem cells, lymphoid progenitor cells or normal plasma cells. CD20 is present on both normal B cells as well as malignant B cells. Other names for CD20 in the literature include "B-lymphocyte-restricted differentiation antigen" and "Bp35". The CD20 antigen is described in, for example, Clark and Ledbetter, *Adv. Can Res.* 52:81-149 (1989) and Valentine et al. *J. Biol. Chem.* 264(19):11282-11287 (1989).

The term "antibody" is used in the broadest sense and specifically covets monoclonal antibodies (including full length monoclonal antibodies), multispecific antibodies (e.g. bispecific antibodies), and antibody fragments so long as they exhibit the desired biological activity or function.

The biological activity of the CD20 binding and humanized CD20 binding antibodies of the invention will include at least binding of the antibody to human CD20, more preferably binding to human and other primate CD20 (including cynomolgus monkey, rhesus monkey, chimpanzees). The antibodies would bind CD20 with a $K_d$ value of no higher than $1 \times 10^{-8}$, preferably a $K_d$ value no higher than about $1 \times 10^{-9}$, and be able to kill or deplete B cells in vivo, preferably by at least 20% when compared to the appropriate negative control which is not treated with such an antibody. B cell depletion can be a result of one or more of ADCC, CDC, apoptosis, or other mechanism. In some embodiments of disease treatment herein, specific effector functions or mechanisms may be desired over others and certain variants of the humanized 2H7 are preferred to achieve those biological functions, such as ADCC.

"Antibody fragments" comprise a portion of a full length antibody, generally the antigen binding or variable region thereof. Examples of antibody fragments include Fab, Fab', $F(ab')_2$, and Fv fragments; diabodies; linear antibodies; single-chain antibody molecules; and multispecific antibodies formed from antibody fragments.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

"Functional fragments" of the CD20 binding antibodies of the invention are those fragments that retain binding to CD20 with substantially the same affinity as the intact full length molecule from which they are derived and show biological activity including depleting B cells as measured by in vitro or in vivo assays such as those described herein.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196: 901-917 (1987)).

As referred to herein, the "consensus sequence" or consensus V domain sequence is an artificial sequence derived from a comparison of the amino acid sequences of known human immunoglobulin variable region sequences. Based on these comparisons, recombinant nucleic acid sequences encoding the V domain amino acids that are a consensus of the sequences derived from the human κ and the human H chain subgroup III V domains were prepared. The consensus V sequence does not have any known antibody binding specificity or affinity.

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR is typically no more than 6 in the H chain, and in the L chain, no more than 3. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

WO00/42072 (Presta) describes antibody variants with improved or diminished binding to FcRs. The content of that patent publication is specifically incorporated herein by reference. See, also, Shields et al. *J. Biol. Chem.* 9(2): 6591-6604 (2001).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

The N-glycosylation site in IgG is at Asn297 in the CH2 domain. The present invention also provides compositions of a CD20-binding, humanized antibody having a Fc region, wherein about 80-100% (and preferably about 90-99%) of the antibody in the composition comprises a mature core carbohydrate structure which lacks fucose, attached to the Fc region of the glycoprotein. Such compositions were demonstrated herein to exhibit a surprising improvement in binding to FcγRIIIA (F158), which is not as effective as FcγRIIIA (V158) in interacting with human IgG. Thus, the compositions herein are anticipated to be superior to previously described anti-CD20 antibody compositions, especially for therapy of human patients who express FcγRIIIA (F158). FcγRIIIA (F58) is more common than FcγRIIIA (V158) in normal, healthy African Americans and Caucasians. See Lehrnbecher et al. *Blood* 94:4220 (1999). The present application further demonstrates the synergistic increase in FcγRIII binding and/or ADCC function that results from combining the glycosylation variations herein with amino acid sequence modification(s) in the Fc region of the glycoprotein.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Vector" includes shuttle and expression vectors. Typically, the plasmid construct will also include an origin of replication (e.g., the CoIE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

The cell that produces a humanized CD20 binding antibody of the invention will include the bacterial and eukaryotic host cells into which nucleic acid encoding the antibodies have been introduced. Suitable host cells are disclosed below.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

An "autoimmune disease" herein is a non-malignant disease or disorder arising from and directed against an individual's own (self) antigens and/or tissues.

As used herein, "B cell depletion" refers to a reduction in B cell levels in an animal or human after drug or antibody treatment, as compared to the B cell level before treatment. B cell levels are measurable using well known assays such as those described in the Experimental Examples. B cell depletion can be complete or partial. In one embodiment, the depletion of CD20 expressing B cells is at least 25%. Not to be limited by any one mechanism, possible mechanisms of B-cell depletion include ADCC, CDC, apoptosis, modulation of calcium flux or a combination of two or more of the preceding.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkalyzing or alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin (Adriamycin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; platinum; etoposide (VP-16); ifosfamide; mitomycin C; mitoxantrone; vincristine; vinblastine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); anti-androgens such as flutamide, nilutamide, bicalutamide, leuprolide, and goserelin; other chemotherapeutic agents such as prednisolone. Pharmaceutically acceptable salts, acids or derivatives of any of the above are included.

"Treating" or "treatment" or "alleviation" refers to both therapeutic treatment and prophylactic or preventative measures, wherein the object is to prevent or slow down (lessen) the targeted pathologic condition or disorder. A subject is successfully "treated" for a CD20 positive cancer or an autoimmune disease if, after receiving a therapeutic amount of a CD20 binding antibody of the invention according to the methods of the present invention, the subject shows observable and/or measurable reduction in or absence of one or more signs and symptoms of the particular disease. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. In a preferred embodiment, the cancer patients are still progression-free in the cancer after one year, preferably after 15 months. These parameters for assessing successful treatment and improvement in the disease are readily measurable by routine procedures familiar to a physician of appropriate skill in the art.

A "therapeutically effective amount" refers to an amount of an antibody or a drug effective to "treat" a disease or disorder in a subject. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating".

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Compositions and Methods of the Invention

The invention provides humanized antibodies that bind human CD20, and preferably other primate CD20 as well, comprising a H chain having at least one, preferably two or all of the H chain CDRs of a non-human species anti-human CD20 antibody (donor antibody), and substantially all of the framework residues of a human consensus antibody as the recipient antibody. The donor antibody can be from various non-human species including mouse, rat, guinea pig, goat, rabbit, horse, primate but most frequently will be a murine antibody. "Substantially all" in this context is meant that the recipient FR regions in the humanized antibody may include one or more amino acid substitutions not originally present in the human consensus FR sequence. These FR changes may comprise residues not found in the recipient or the donor antibody.

In one embodiment, the donor antibody is the murine 2H7 antibody, the V region including the CDR and FR sequences of each of the H and L chains of which are shown in FIGS. 1A and 1B. In a specific embodiment, the residues for the human Fab framework correspond to the consensus sequence of human Vκ subgroup I and of $V_H$ subgroup III, these consensus sequences are shown in FIG. 1A and FIG. 1B, respectively. The humanized 2H7 antibody of the invention will have at least one of the CDRs in the H chain of the murine donor antibody. In one embodiment, the humanized 2H7 antibody that binds human CD20 comprises the CDRs of both the H and L chains of the donor antibody.

In a full length antibody, the humanized CD20 binding antibody of the invention will comprise a humanized V domain joined to a C domain of a human immunoglobulin. In a preferred embodiment, the H chain C region is from human IgG, preferably IgG1 or IgG3. The L chain C domain is preferably from human κ chain.

Unless indicated otherwise, a humanized 2H7 antibody version herein will have the V and C domain sequences of 2H7.v16 L chain (FIG. 6, SEQ ID NO. 21) and H chain (FIG. 7, SEQ ID NO. 22) except at the positions of amino acid substitutions or changes indicated in the experimental examples below.

The humanized CD20 binding antibodies will bind at least human CD20 and preferably bind other primate CD20 such as that of monkeys including cynomolgus and rhesus monkeys, and chimpanzees. The sequence of the cynomolgus monkey CD20 is disclosed in Example 15 and FIG. 19

The biological activity of the CD20 binding antibodies and humanized CD20 binding antibodies of the invention will include at least binding of the antibody to human CD20, more preferably binding to human and primate CD20 (including cynomolgus monkey, rhesus monkey, chimpanzees), with a $K_d$ value of no higher than $1\times10^{-8}$, preferably a $K_d$ value no higher than about $1\times10^{-9}$, even more preferably a $K_d$ value no higher than about $1\times10^{-10}$, and be able to kill or deplete B cells in vitro or in vivo, preferably by at least 20% when compared to the baseline level or appropriate negative control which is not treated with such an antibody.

The desired level of B cell depletion will depend on the disease. For the treatment of a CD20 positive cancer, it may be desirable to maximize the depletion of the B cells which are the target of the anti-CD20 antibodies of the invention. Thus, for the treatment of a CD20 positive B cell neoplasm, it is desirable that the B cell depletion be sufficient to at least prevent progression of the disease which can be assessed by the physician of skill in the art, e.g., by monitoring tumor growth (size), proliferation of the cancerous cell type, metastasis, other signs and symptoms of the particular cancer. Preferably, the B cell depletion is sufficient to prevent progression of disease for at least 2 months, more preferably 3 months, even more preferably 4 months, more preferably 5 months, even more preferably 6 or more months. In even more preferred embodiments, the B cell depletion is sufficient to increase the time in remission by at least 6 months, more preferably 9 months, more preferably one year, more preferably 2 years, more preferably 3 years, even more preferably 5 or more years. In a most preferred embodiment, the B cell depletion is sufficient to cure the disease. In preferred embodiments, the B cell depletion in a cancer patient is at least about 75% and more preferably, 80%, 85%, 90%, 95%, 99% and even 100% of the baseline level before treatment.

For treatment of an autoimmune disease, it may be desirable to modulate the extent of B cell depletion depending on the disease and/or the severity of the condition in the individual patient, by adjusting the dosage of CD20 binding antibody. Thus, B cell depletion can but does not have to be complete. Or, total B cell depletion may be desired in initial treatment but in subsequent treatments, the dosage may be adjusted to achieve only partial depletion. In one embodiment, the B cell depletion is at least 20%, i.e., 80% or less of CD20 positive B cells remain as compared to the baseline level before treatment. In other embodiments, B cell depletion is 25%, 30%, 40%, 50%, 60%, 70% or greater. Preferably, the B cell depletion is sufficient to halt progression of the disease, more preferably to alleviate the signs and symptoms of the particular disease under treatment, even more preferably to cure the disease.

The invention also provides bispecific CD20 binding antibodies wherein one arm of the antibody has a humanized H and L chain of the humanized CD20 binding antibody of the invention, and the other arm has V region binding specificity for a second antigen. In specific embodiments, the second antigen is selected from the group consisting of CD3, CD64, CD32A, CD16, NKG2D or other NK activating ligands.

In comparison with Rituxan (rituximab), v16 exhibits about 2 to 5 fold increased ADCC potency, ~3-4 fold decreased CDC than Rituxan.

Antibody Production

Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Reichmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The humanized antibody may be an antibody fragment, such as a Fab, which is optionally conjugated with one or more cytotoxic agent(s) in order to generate an immunoconjugate. Alternatively, the humanized antibody may be an full length antibody, such as an full length IgG1 antibody.

Human Antibodies and Phage Display Methodology

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; and WO 97/17852.

Alternatively, phage display technology (McCafferty et al., Nature 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of antioxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the CD20 protein. Other such antibodies may combine a CD20 binding site with a binding site for another protein. Alternatively, an anti-CD20 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), or NKG2D or other NK cell activating ligand, so as to focus and localize cellular defense mechanisms to the CD20-expressing cell. Bispecific antibodies may also be used to localize cytotoxic agents to cells which express CD20. These antibodies possess a CD20-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J. Exp. Med.,* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the CD20 binding antibodies described herein are contemplated. For example, it may be desirable to improve the binding affinity and/or other biological properties of the antibody. Amino acid sequence variants of the anti-CD20 antibody are prepared by introducing appropriate nucleotide changes into the anti-CD20 antibody nucleic acid, or by peptide synthesis. Such modifications include, for example, deletions from, and/or insertions into and/or substitutions of, residues within the amino acid sequences of the anti-CD20 antibody. Any combination of deletion, insertion, and substitution is made to arrive at the final construct, provided that the final construct possesses the desired characteristics. The amino acid changes also may alter post-translational processes of the anti-CD20 antibody, such as changing the number or position of glycosylation sites.

A useful method for identification of certain residues or regions of the anti-CD20 antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with CD20 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-CD20 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-CD20 antibody with an N-terminal methionyl residue or the antibody fused to a cytotoxic polypeptide. Other insertional variants of the anti-CD20 antibody molecule include the fusion to the N- or C-terminus of the anti-CD20 antibody to an enzyme (e.g. for ADEPT) or a polypeptide which increases the serum half-life of the antibody.

Another type of variant is an amino acid substitution variant. These variants have at least one amino acid residue in the anti-CD20 antibody molecule replaced by a different residue. The sites of greatest interest for substitutional mutagenesis include the hypervariable regions, but FR alterations are also contemplated. Conservative substitutions are shown in the Table below under the heading of "preferred substitutions". If such substitutions result in a change in biological activity, then more substantial changes, denominated "exemplary substitutions" in the Table, or as further described below in reference to amino acid classes, may be introduced and the products screened.

TABLE of Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the anti-CD20 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human CD20. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-CD20 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-CD20 antibody.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement mediated lysis and ADCC capabilities. See Stevenson et al. *Anti-Cancer Drug Design* 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

Screening for Antibodies with the Desired Properties

Antibodies with certain biological characteristics may be selected as described in the Experimental Examples.

The growth inhibitory effects of an anti-CD20 antibody of the invention may be assessed by methods known in the art, e.g., using cells which express CD20 either endogenously or following transfection with the CD20 gene. For example, tumor cell lines and CD20-transfected cells may treated with an anti-CD20 monoclonal antibody of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-CD20 antibody of the invention. After antibody treatment, the cells are harvested and the amount of radioactivity incorporated into the DNA quantitated in a scintillation counter. Appropriate positive controls include treatment of a selected cell line with a growth inhibitory antibody known to inhibit growth of that cell line.

To select for antibodies which induce cell death, loss of membrane integrity as indicated by, e.g., propidium iodide (PI), trypan blue or 7AAD uptake may be assessed relative to control. A PI uptake assay can be performed in the absence of complement and immune effector cells. CD20-expressing tumor cells are incubated with medium alone or medium containing of the appropriate monoclonal antibody at e.g., about 10 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

To screen for antibodies which bind to an epitope on CD20 bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody binds the same site or epitope as an anti-CD20 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of CD20 can be used in competition assays with the test antibodies or with a test antibody and an antibody with a characterized or known epitope.

Vectors, Host Cells and Recombinant Methods

The invention also provides an isolated nucleic acid encoding a humanized CD20 binding antibody, vectors and host cells comprising the nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The CD20 binding antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native CD20 binding antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the CD20 binding antibody.

(ii) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the CD20 binding antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding CD20 binding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(iv) Promoter Component

Expression and cloning vectors usually contain a promoter that is recognized by the host organism and is operably linked to the nucleic acid encoding the CD20 binding antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the CD20 binding antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

CD20 binding antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of a DNA encoding the CD20 binding antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the CD20 binding antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding CD20 binding antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for CD20 binding antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244, 234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated CD20 binding antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for CD20 binding antibody production and cultured in conventional nutrient media modified as appropriate for inducing promoters, selecting transformants, or amplifying the genes encoding the desired sequences.

(viii) Culturing the Host Cells

The host cells used to produce the CD20 binding antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Antibody Conjugates

The antibody may be conjugated to a cytotoxic agent such as a toxin or a radioactive isotope. In certain embodiments, the toxin is calicheamicin, a maytansinoid, a dolastatin, auristatin E and analogs or derivatives thereof, are preferable.

Preferred drugs/toxins include DNA damaging agents, inhibitors of microtubule polymerization or depolymerization and antimetabolites. Preferred classes of cytotoxic agents include, for example, the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins and differentiation inducers. Particularly useful members of those classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, N-(5,5-diacetoxypentyl)doxorubicin, morpholino-doxorubicin, 1-(2-choroehthyl)-1,2-dimethanesulfonyl hydrazide, Ns-acetyl spermidine, aminopterin methopterin, esperamicin, mitomycin C, mitomycin A, actinomycin, bleomycin, caminomycin, aminopterin, tallysomycin, podophyllotoxin and podophyllotoxin derivatives such as etoposide or etoposide phosphate, vinblastine, vincristine, vindesine, taxol, taxotere, retinoic acid, butyric acid, $N^8$-acetyl spermidine, camptothecin, calicheamicin, bryostatins, cephalostatins, ansamitocin, actosin, maytansinoids such as DM-1, maytansine, maytansinol, N-desmethyl-4,5-desepoxymaytansinol, C-19-dechloromaytansinol, C-20-hydroxymaytansinol, C-20-demethoxymaytansinol, C-9-SH maytansinol, C-14-alkoxymethylmaytansinol, C-14-hydroxy or acetyloxymethlmaytansinol, C-15-hydroxy/acetyloxymaytansinol, C-15-methoxymaytansinol, C-18-N-demethylmaytansinol and 4,5-deoxymaytansinol, auristatins such as auristatin E, M, PHE and PE; dolostatins such as dolostatin A, dolostatin B, dolostatin C, dolostatin D, dolostatin E (20-epi and 11-epi), dolostatin G, dolostatin H, dolostatin I, dolostatin 1, dolostatin 2, dolostatin 3, dolostatin 4, dolostatin 5, dolostatin 6, dolostatin 7, dolostatin 8, dolostatin 9, dolostatin 10, deodolostatin 10, dolostatin 11, dolostatin 12, dolostatin 13, dolostatin 14, dolostatin 15, dolostatin 16, dolostatin 17, and dolostatin 18; cephalostatins such as cephalostatin 1, cephalostatin 2, cephalostatin 3, cephalostatin 4, cephalostatin 5, cephalostatin 6, cephalostatin 7, 25'-epi-cephalostatin 7, 20-epi-cephalostatin 7, cephalostatin 8, cephalostatin 9, cephalostatin 10, cephalostatin 11, cephalostatin 12, cephalostatin 13, cephalostatin 14, cephalostatin 15, cephalostatin 16, cephalostatin 17, cephalostatin 18, and cephalostatin 19.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al. *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene.

There are many linking groups known in the art for making antibody-maytansinoid conjugates, including, for example, those disclosed in U.S. Pat. No. 5,208,020 or EP Patent 0 425 235 B1, and Chari et al. *Cancer Research* 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an CD20 binding antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ ((Hinman et al. *Cancer Research* 53: 3336-3342 (1993), Lode et al. *Cancer Research* 58: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Radioactive Isotopes

For selective destruction of the tumor, the antibody may comprise a highly radioactive atom. A variety of radioactive isotopes are available for the production of radioconjugated anti-CD20 antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-1, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. *Cancer Research* 52: 127-131 (1992); U.S. Pat. No. 5,208,020) may be used.

Therapeutic Uses of the CD20 Binding Antibodies

The CD20 binding antibodies of the invention are useful to treat a number of malignant and non-malignant diseases including autoimmune diseases and related conditions, and CD20 positive cancers including B cell lymphomas and leukemias. Stem cells (B-cell progenitors) in bone marrow lack the CD20 antigen, allowing healthy B-cells to regenerate after treatment and return to normal levels within several months.

Autoimmune diseases or autoimmune related conditions include arthritis (rheumatoid arthritis, juvenile rheumatoid arthritis, osteoarthritis, psoriatic arthritis), psoriasis, dermatitis including atopic dermatitis; chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), respiratory distress syndrome, adult respiratory distress syndrome (ARDS), meningitis, allergic rhinitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), lupus (including nephritis, non-renal, discoid, alopecia), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, etc), graft versus host disease (GVHD), pemphigoid bullous, pemphigus (all including vulgaris, foliaceus), autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic thrombocytopenic purpura (TTP), autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, Lymphoid interstitial pneumonitis (HIV), bronchiolitis obliterans (non-transplant) vs NSIP, Guillain-Barre' Syndrome, Large Vessel Vasculitis (including Polymyalgia Rheumatica and Giant Cell (Takayasu's) Arteritis), Medium Vessel Vasculitis (including Kawasaki's Disease and Polyarteritis Nodosa), ankylosing spondylitis, Berger's Disease (IgA nephropathy), Rapidly Progressive Glomerulonephritis, Primary biliary cirrhosis, Celiac sprue (gluten enteropathy), Cryoglobulinemia, ALS, coronary artery disease.

CD20 positive cancers are those comprising abnormal proliferation of cells that express CD20 on the cell surface. The CD20 positive B cell neoplasms include CD20-positive Hodgkin's disease including lymphocyte predominant Hodgkin's disease (LPHD); non-Hodgkin's lymphoma (NHL); follicular center cell (FCC) lymphomas; acute lymphocytic leukemia (ALL); chronic lymphocytic leukemia (CLL); Hairy cell leukemia. The non-Hodgkins lymphoma include low grade/follicular non-Hodgkin's lymphoma (NHL), small lymphocytic lymphoma (SLL), intermediate grade/follicular NHL, intermediate grade diffuse NHL, high grade immunoblastic NHL, high grade lymphoblastic NHL, high grade small non-cleaved cell NHL, bulky disease NHL, plasmacytoid lymphocytic lymphoma, mantle cell lymphoma, AIDS-related lymphoma and Waldenstrom's macroglobulinemia. Treatment of relapses of these cancers are also contemplated. LPHD is a type of Hodgkin's disease that tends to relapse frequently despite radiation or chemotherapy treatment and is characterized by CD20-positive malignant cells. CLL is one of four major types of leukemia. A cancer of mature B-cells called lymphocytes, CLL is manifested by progressive accumulation of cells in blood, bone marrow and lymphatic tissues.

In specific embodiments, the humanized CD20 binding antibodies and functional fragments thereof are used to treat non-Hodgkin's lymphoma (NHL), lymphocyte predominant Hodgkin's disease (LPHD), small lymphocytic lymphoma (SLL), chronic lymphocytic leukemia, rheumatoid arthritis and juvenile rheumatoid arthritis, systemic lupus erythematosus (SLE) including lupus nephritis, Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis.

The humanized CD20 binding antibodies or functional fragments thereof are useful as a single-agent treatment in, e.g., for relapsed or refractory low-grade or follicular, CD20-positive, B-cell NHL, or can be administered to patients in conjunction with other drugs in a multi drug regimen.

Indolent lymphoma is a slow-growing, incurable disease in which the average patient survives between six and 10 years following numerous periods of remission and relapse. In one embodiment, the humanized CD20 binding antibodies or functional fragments thereof are used to treat indolent NHL.

The parameters for assessing efficacy or success of treatment of the neoplasm will be known to the physician of skill in the appropriate disease. Generally, the physician of skill will look for reduction in the signs and symptoms of the specific disease. Parameters can include median time to disease progression, time in remission, stable disease.

The following references describe lymphomas and CLL, their diagnoses, treatment and standard medical procedures for measuring treatment efficacy. Canellos G P, Lister, T A, Sklar J L: *The Lymphomas*. W.B. Saunders Company, Philadelphia, 1998; van Besien K and Cabanillas, F: Clinical Manifestations, Staging and Treatment of Non-Hodgkin's Lymphoma, Chap. 70, pp 1293-1338, in: *Hematology, Basic Principles and Practice,* 3rd ed. Hoffman et al. (editors). Churchill Livingstone, Philadelphia, 2000; and Rai, K and Patel, D: Chronic Lymphocytic Leukemia, Chap. 72, pp 1350-1362, in: *Hematology, Basic Principles and Practice,* 3rd ed. Hoffman et al. (editors). Churchill Livingstone, Philadelphia, 2000.

The parameters for assessing efficacy or success of treatment of an autoimmune or autoimmune related disease will be known to the physician of skill in the appropriate disease. Generally, the physician of skill will look for reduction in the signs and symptoms of the specific disease. The following are by way of examples.

In one embodiment, the antibodies of the invention are useful to treat rheumatoid arthritis. RA is characterized by inflammation of multiple joints, cartilage loss and bone erosion that leads to joint destruction and ultimately reduced joint function. Additionally, since RA is a systemic disease, it can have effects in other tissues such as the lungs, eyes and bone marrow. Fewer than 50 percent of patients who have had RA for more than 10 years can continue to work or function normally on a day-to-day basis.

The antibodies can be used as first-line therapy in patients with early RA (i.e., methotrexate (MTX) naive) and as monotherapy, or in combination with, e.g., MTX or cyclophosphamide. Or, the antibodies can be used in treatment as second-line therapy for patients who were DMARD and/or MTX refractory, and as monotherapy or in combination with, e.g., MTX. The humanized CD20 binding antibodies are useful to prevent and control joint damage, delay structural damage, decrease pain associated with inflammation in RA, and generally reduce the signs and symptoms in moderate to severe RA. The RA patient can be treated with the humanized CD20 antibody prior to, after or together with treatment with other drugs used in treating RA (see combination therapy below). In one embodiment, patients who had previously failed disease-modifying antirheumatic drugs and/or had an inadequate response to methotrexate alone are treated with a humanized CD20 binding antibody of the invention. In one embodiment of this treatment, the patients are in a 17-day treatment regimen receiving humanized CD20 binding antibody alone (Ig iv infusions on days 1 and 15); CD20 binding antibody plus cyclophosphamide (750 mg iv infusion days 3 and 17); or CD20 binding antibody plus methotrexate.

One method of evaluating treatment efficacy in RA is based on American College of Rheumatology (ACR) criteria, which measures the percentage of improvement in tender and swollen joints, among other things. The RA patient can be scored at for example, ACR 20 (20 percent improvement) compared with no antibody treatment (e.g., baseline before treatment) or treatment with placebo. Other ways of evaluating the efficacy of antibody treatment include X-ray scoring such as the Sharp X-ray score used to score structural damage such as bone erosion and joint space narrowing. Patients can also be evaluated for the prevention of or improvement in disability based on Health Assessment Questionnaire [HAQ] score, AIMS score, SF-36 at time periods during or after treatment. The ACR 20 criteria may include 20% improvement in both tender (painful) joint count and swollen joint count plus a 20% improvement in at least 3 of 5 additional measures:
   1. patient's pain assessment by visual analog scale (VAS),
   2. patient's global assessment of disease activity (VAS),
   3. physician's global assessment of disease activity (VAS),
   4. patient's self-assessed disability measured by the Health Assessment Questionnaire, and
   5. acute phase reactants, CRP or ESR.

The ACR 50 and 70 are defined analogously. Preferably, the patient is administered an amount of a CD20 binding antibody of the invention effective to achieve at least a score of ACR 20, preferably at least ACR 30, more preferably at least ACR50, even more preferably at least ACR70, most preferably at least ACR 75 and higher.

Psoriatic arthritis has unique and distinct radiographic features. For psoriatic arthritis, joint erosion and joint space narrowing can be evaluated by the Sharp score as well. The humanized CD20 binding antibodies of the invention can be used to prevent the joint damage as well as reduce disease signs and symptoms of the disorder.

Yet another aspect of the invention is a method of treating Lupus or SLE by administering to the patient suffering from SLE, a therapeutically effective amount of a humanized CD20 binding antibody of the invention. SLEDAI scores provide a numerical quantitation of disease activity. The SLEDAI is a weighted index of 24 clinical and laboratory parameters known to correlate with disease activity, with a numerical range of 0-103. see Bryan Gescuk & John Davis, "Novel therapeutic agent for systemic lupus erythematosus" in Current Opinion in Rheumatology 2002, 14:515-521. Antibodies to double-stranded DNA are believed to cause renal flares and other manifestations of lupus. Patients undergoing antibody treatment can be monitored for time to renal flare, which is defined as a significant, reproducible increase in serum creatinine, urine protein or blood in the urine. Alternatively or in addition, patients can be monitored for levels of antinuclear antibodies and antibodies to double-stranded DNA. Treatments for SLE include high-dose corticosteroids and/or cyclophosphamide (HDCC).

Spondyloarthropathies are a group of disorders of the joints, including ankylosing spondylitis, psoriatic arthritis and Crohn's disease. Treatment success can be determined by validated patient and physician global assessment measuring tools.

Various medications are used to treat psoriasis; treatment differs directly in relation to disease severity. Patients with a more mild form of psoriasis typically utilize topical treatments, such as topical steroids, anthralin, calcipotriene, clobetasol, and tazarotene, to manage the disease while patients with moderate and severe psoriasis are more likely to employ systemic (methotrexate, retinoids, cyclosporine, PUVA and UVB) therapies. Tars are also used. These therapies have a combination of safety concerns, time consuming regimens, or inconvenient processes of treatment. Furthermore, some require expensive equipment and dedicated space in the office setting. Systemic medications can produce serious side effects, including hypertension, hyperlipidemia, bone marrow suppression, liver disease, kidney disease and gastrointestinal upset. Also, the use of phototherapy can increase the incidence of skin cancers. In addition to the inconvenience and discomfort associated with the use of topical therapies, phototherapy and systemic treatments require cycling patients on and off therapy and monitoring lifetime exposure due to their side effects.

Treatment efficacy for psoriasis is assessed by monitoring changes in clinical signs and symptoms of the disease including Physician's Global Assessment (PGA) changes and Psoriasis Area and Severity Index (PASI) scores, Psoriasis Symptom Assessment (PSA), compared with the baseline condition. The patient can be measured periodically throughout treatment on the Visual analog scale used to indicate the degree of itching experienced at specific time points.

Patients may experience an infusion reaction or infusion-related symptoms with their first infusion of a therapeutic antibody. These symptoms vary in severity and generally are reversible with medical intervention. These symptoms include but are not limited to, flu-like fever, chills/rigors, nausea, urticaria, headache, bronchospasm, angioedema. It would be desirable for the disease treatment methods of the present invention to minimize infusion reactions. Thus, another aspect of the invention is a method of treating the diseases disclosed by administering a humanized CD20 binding antibody wherein the antibody has reduced or no complement dependent cytotoxicity and results in reduced infusion related symptoms as compared to treatment with Rituxan®. In one embodiment, the humanized CD20 binding antibody is 2H7.v116.

Dosage

Depending on the indication to be treated and factors relevant to the dosing that a physician of skill in the field would be familiar with, the antibodies of the invention will be administered at a dosage that is efficacious for the treatment of that indication while minimizing toxicity and side effects. For the treatment of a CD20 positive cancer or an autoimmune disease, the therapeutically effective dosage will be in the range of about 250 mg/m$^2$ to about 400 mg/m$^2$ or 500 mg/m$^2$, preferably about 250-375 mg/m$^2$. In one embodiment, the dosage range is 275-375 mg/m$^2$. In one embodiment of the treatment of a CD20 positive B cell neoplasm, the antibody is administered at a range of 300-375 mg/m$^2$. For the treatment of patients suffering from B-cell lymphoma such as non-Hodgkins lymphoma, in a specific embodiment, the anti-CD20 antibodies and humanized anti-CD20 antibodies of the invention will be administered to a human patient at a dosage of 10 mg/kg or 375 mg/m$^2$. For treating NHL, one dosing regimen would be to administer one dose of the antibody composition a dosage of 10 mg/kg in the first week of treatment, followed by a 2 week interval, then a second dose of the same amount of antibody is administered. Generally, NHL patients receive such treatment once during a year but upon recurrence of the lymphoma, such treatment can be repeated. In another dosing regimen, patients treated with low-grade NHL receive four weeks of a version of humanized 2H7, preferably v16 (375 mg/m2 weekly) followed at week five by three additional courses of the antibody plus standard CHOP (cyclophosphamide, doxorubicin, vincristine and prednisone) or CVP (cyclophosphamide, vincristine, prednisone) chemotherapy, which was given every three weeks for three cycles.

For treating rheumatoid arthritis, in one embodiment, the dosage range for the humanized antibody is 125 mg/m$^2$ (equivalent to about 200 mg/dose) to 600 mg/m$^2$, given in two doses, e.g., the first dose of 200 mg is administered on day one followed by a second dose of 200 mg on day 15. In different embodiments, the dosage is 250 mg/dose, 275 mg, 300 mg, 325 mg, 350 mg, 375 mg, 400 mg, 425 mg, 450 mg, 475 mg, 500 mg, 525 mg, 550 mg, 575 mg, 600 mg.

In treating disease, the CD20 binding antibodies of the invention can be administered to the patient chronically or intermittently, as determined by the physician of skill in the disease.

A patient administered a drug by intravenous infusion or subcutaneously may experience adverse events such as fever, chills, burning sensation, asthenia and headache. To alleviate or minimize such adverse events, the patient may receive an initial conditioning dose(s) of the antibody followed by a therapeutic dose. The conditioning dose(s) will be lower than the therapeutic dose to condition the patient to tolerate higher dosages.

Route of Administration

The CD20 binding antibodies are administered to a human patient in accord with known methods, such as by intravenous administration, e.g., as a bolus or by continuous infusion over a period of time, by subcutaneous, intramuscular, intraperitoneal, intracerobrospinal, intra-articular, intrasynovial, intrathecal, or inhalation routes, generally by intravenous or subcutaneous administration.

In on embodiment, the humanized 2H7 antibody is administered by intravenous infusion with 0.9% sodium chloride solution as an infusion vehicle.

Combination Therapy

In treating the B cell neoplasms described above, the patient can be treated with the CD20 binding antibodies of the present invention in conjunction with one or more therapeutic agents such as a chemotherapeutic agent in a multidrug regimen. The CD20 binding antibody can be administered concurrently, sequentially, or alternating with the chemotherapeutic agent, or after non-responsiveness with other therapy. Standard chemotherapy for lymphoma treatment may include cyclophosphamide, cytarabine, melphalan and mitoxantrone plus melphalan. CHOP is one of the most common chemotherapy regimens for treating Non-Hodgkin's lymphoma. The following are the drugs used in the CHOP regimen: cyclophosphamide (brand names cytoxan, neosar); adriamycin (doxorubicin/hydroxydoxorubicin); vincristine (Oncovin); and prednisolone (sometimes called Deltasone or Orasone). In particular embodiments, the CD20 binding antibody is administered to a patient in need thereof in combination with one or more of the following chemotherapeutic agents of doxorubicin, cyclophosphamide, vincristine and prednisolone. In a specific embodiment, a patient suffering from a lymphoma (such as a non-Hodgkin's lymphoma) is treated with an anti-CD20 antibody of the present invention in conjunction with CHOP (cyclophosphamide, doxorubicin, vincristine and prednisone) therapy. In another embodiment, the cancer patient can be treated with a humanized CD20 binding antibody of the invention in combination with CVP (cyclophosphamide, vincristine, and prednisone) chemotherapy. In a specific embodiment, the patient suffering from CD20-positive NHL is treated with humanized 2H7.v16 in conjunction with CVP. In a specific embodiment of the treatment of CLL, the CD20 binding antibody is administered in conjunction with chemotherapy with one or both of fludarabine and cytoxan.

In treating the autoimmune diseases or autoimmune related conditions described above, the patient can be treated with the CD20 binding antibodies of the present invention in conjunction with a second therapeutic agent, such as an immunosuppressive agent, such as in a multi drug regimen. The CD20 binding antibody can be administered concurrently, sequentially or alternating with the immunosuppressive agent or upon non-responsiveness with other therapy. The immunosuppressive agent can be administered at the same or lesser dosages than as set forth in the art. The preferred adjunct immunosuppressive agent will depend on many factors, including the type of disorder being treated as well as the patient's history.

"Immunosuppressive agent" as used herein for adjunct therapy refers to substances that act to suppress or mask the immune system of a patient. Such agents would include substances that suppress cytokine production, down regulate or suppress self-antigen expression, or mask the MHC antigens. Examples of such agents include steroids such as glucocorticosteroids, e.g., prednisone, methylprednisolone, and dexamethasone; 2-amino-6-aryl-5-substituted pyrimidines (see U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; cytokine or cytokine receptor antagonists including anti-interferon-$\gamma$, -$\beta$, or -$\alpha$ antibodies; anti-tumor necrosis factor-$\alpha$ antibodies; anti-tumor necrosis factor-$\beta$ antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-$\beta$; streptodornase; RNA or DNA from the host; FK506; RS-61443; deoxyspergualin; rapamycin; T-cell receptor (U.S. Pat No. 5,114,721); T-cell receptor fragments (Offner et al., Science 251:430-432 (1991); WO 90/11294; and WO 91/01133); and T cell receptor antibodies (EP 340, 109) such as T10B9.

For the treatment of rheumatoid arthritis, the patient can be treated with a CD20 antibody of the invention in conjunction with any one or more of the following drugs: DMARDS (disease-modifying anti-rheumatic drugs (e.g., methotrexate), NSAI or NSAID (non-steroidal anti-inflammatory drugs), HUMIRA™ (adalimumab; Abbott Laboratories), ARAVA® (leflunomide), REMICADE® (infliximab; Centocor Inc., of Malvern, Pa.), ENBREL (etanercept; Immunex, Wash.), COX-2 inhibitors. DMARDs commonly used in RA are hydroxycloroquine, sulfasalazine, methotrexate, leflunomide, etanercept, infliximab, azathioprine, D-penicillamine, Gold (oral), Gold (intramuscular), minocycline, cyclosporine, Staphylococcal protein A immunoadsorption. Adalimumab is a human monoclonal antibody that binds to TNF$\alpha$. Infliximab is a chimeric monoclonal antibody that binds to TNF$\alpha$. Etanercept is an "immunoadhesin" fusion protein consisting of the extracellular ligand binding portion of the human 75 kD (p75) tumor necrosis factor receptor (TNFR) linked to the Fc portion of a human IgG1. For conventional treatment of RA, see, e.g., "Guidelines for the management of rheumatoid arthritis" Arthritis & Rheumatism 46(2): 328-346 (February, 2002). In a specific embodiment, the RA patient is treated with a CD20 antibody of the invention in conjunction with methotrexate (MTX). An exemplary dosage of MTX is about 7.5-25 mg/kg/wk. MTX can be administered orally and subcutaneously.

For the treatment of ankylosing spondylitis, psoriatic arthritis and Crohn's disease, the patient can be treated with a CD20 binding antibody of the invention in conjunction with, for example, Remicade® (infliximab; from Centocor Inc., of Malvern, Pa.), ENBREL (etanercept; Immunex, Wash.).

Treatments for SLE include high-dose corticosteroids and/or cyclophosphamide (HDCC).

For the treatment of psoriasis, patients can be administered a CD20 binding antibody in conjunction with topical treatments, such as topical steroids, anthralin, calcipotriene, clobetasol, and tazarotene, or with methotrexate, retinoids, cyclosporine, PUVA and UVB therapies. In one embodiment, the psoriasis patient is treated with the CD20 binding antibody sequentially or concurrently with cyclosporine.

Pharmaceutical Formulations

Therapeutic formulations of the CD20-binding antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Exemplary anti-CD20 antibody formulations are described in WO98/56418, expressly incorporated herein by reference. Another formulation is a liquid multidose formulation comprising the anti-CD20 antibody at 40 mg/mL, 25 mM acetate, 150 mM trehalose, 0.9% benzyl alcohol, 0.02% polysorbate 20 at pH 5.0 that has a minimum shelf life of two years storage at 2-8° C. Another anti-CD20 formulation of interest comprises 10 mg/mL antibody in 9.0 mg/mL sodium chloride, 7.35 mg/mL sodium citrate dihydrate, 0.7 mg/mL polysorbate 80, and Sterile Water for Injection, pH 6.5. Yet another aqueous pharmaceutical formulation comprises 10-30 mM sodium acetate from about pH 4.8 to about pH 5.5, preferably at pH5.5, polysorbate as a surfactant in a an amount of about 0.01-0.1% v/v, trehalose at an amount of about 2-10% w/v, and benzyl alcohol as a preservative (U.S. Pat. No. 6,171,586). Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

One formulation for the humanized 2H7 variants is antibody at 12-14 mg/mL in 10 mM histidine, 6% sucrose, 0.02% polysorbate 20, pH 5.8.

In a specific embodiment, 2H7 variants and in particular 2H7.v16 is formulated at 20 mg/mL antibody in 10 mM histidine sulfate, 60 mg/ml sucrose, 0.2 mg/ml polysorbate 20, and Sterile Water for Injection, at pH5.8.

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g. one which binds LFA-1). The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semi-permeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

Articles of Manufacture and Kits

Another embodiment of the invention is an article of manufacture containing materials useful for the treatment of autoimmune diseases and related conditions and CD20 positive cancers such as non-Hodgkin's lymphoma. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a CD20 binding antibody of the invention. The label or package insert indicates that the composition is used for treating the particular condition. The label or package insert will further comprise instructions for administering the antibody composition to the patient. Package insert refers to instructions customarily included in commercial packages of therapeutic products, that contain information about the indications, usage, dosage, administration, contraindications and/or warnings concerning the use of such therapeutic products. In one embodiment, the package insert indicates that the composition is used for treating non-Hodgkins' lymphoma.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for B-cell killing assays, as a positive control for apoptosis assays, for purification or immunoprecipitation of CD20 from cells. For isolation and purification of CD20, the kit can contain an anti-CD20 antibody coupled to beads (e.g., sepharose beads). Kits can be provided which contain the antibodies for detection and quantitation of CD20 in vitro, e.g. in an ELISA or a Western blot. As with the article of manufacture, the kit comprises a container and a label or package insert on or associated with the container. The container holds a composition comprising at least one anti-CD20 antibody of the invention. Additional containers may be included that contain, e.g., diluents and buffers, control antibodies. The label or package insert may provide a description of the composition as well as instructions for the intended in vitro or diagnostic use.

Cynomolgus Monkey CD20

The invention also provides an isolated nucleic acid comprising the nucleotide sequence of SEQ ID NO.: 24 of the Cynomolgus monkey CD20 as shown in FIG. 19. In one embodiment, the nucleic acid is a cDNA. In one embodiment, the nucleic acid encoding the monkey CD20 is in an expression vector for expression in a host cell. The nucleotide sequence of SEQ ID NO.: 24 in the expression vector is operably linked to an expression control sequence such as a promoter or promoter and enhancer. The expression control sequence can be can be the native sequence normally associated with the Cynomolgus CD20 gene, or heterologous to the gene. Also provided is an isolated polypeptide comprising the amino acid sequence [SEQ ID NO. 25; FIGS. 19 & 20] of the Cynomolgus monkey CD20, as well as host cells containing the Cynomolgus CD20 nucleic acid. In one aspect the host cells are eukaryotic cells, e.g., CHO cells. Fusion proteins comprising the Cynomolgus CD20 amino acid sequence or fragments of the sequence are also contemplated.

EXPERIMENTAL EXAMPLES

Example 1

Humanization of 2H7 Anti-CD20 Murine Monoclonal Antibody

Humanization of the murine anti-human CD20 antibody, 2H7 (also referred to herein as m2H7, m for murine), was carried out in a series of site-directed mutagenesis steps. The murine 2H7 antibody variable region sequences and the chimeric 2H7 with the mouse V and human C have been described, see, e.g., U.S. Pat. Nos. 5,846,818 and 6,204,023. The CDR residues of 2H7 were identified by comparing the amino acid sequence of the murine 2H7 variable domains (disclosed in U.S. Pat. No. 5,846,818) with the sequences of known antibodies (Kabat et al., Sequences of proteins of immunological interest, Ed. 5. Public Health Service, National Institutes of Health, Bethesda, Md. (1991)). The CDR regions for the light and heavy chains were defined based on sequence hypervariability (Kabat et al., supra) and are shown in FIG. 1A and FIG. 1B, respectively. Using synthetic oligonucleotides (Table 1), site-directed mutagenesis (Kunkel, Proc. Natl. Acad. Sci. 82:488-492 (1985)) was used to introduce all six of the murine 2H7 CDR regions into a complete human Fab framework corresponding to a consensus sequence $V_\kappa I, V_H III$ ($V_L$ kappa subgroup I, $V_H$ subgroup III) contained on plasmid pVX4 (FIG. 2).

The phagemid pVX4 (FIG. 2) was used for mutagenesis as well as for expression of F(ab)s in E. coli. Based on the phagemid pb0720, a derivative of pB0475 (Cunningham et al., Science 243: 1330-1336 (1989)), pVX4 contains a DNA fragment encoding a humanized consensus κ-subgroup I light chain ($V_L\kappa I$-$C_L$) and a humanized consensus subgroup III heavy chain ($V_H III$-$C_H 1$) anti-IFN-α (interferon α) antibody. pVX4 also has an alkaline phosphatase promotor and Shine-Dalgamo sequence both derived from another previously described pUC119-based plasmid, pAK2 (Carter et al., Proc. Natl. Acad. Sci. USA 89: 4285 (1992)). A unique SpeI restriction site was introduced between the DNA encoding for the F(ab) light and heavy chains. The first 23 amino acids in both anti-IFN-α heavy and light chains are the StII secretion signal sequence (Chang et al., Gene 55: 189-196 (1987)).

To construct the CDR-swap version of 2H7 (2H7.v2), site-directed mutagenesis was performed on a deoxyuridine-containing template of pVX4; all six CDRs of anti-IFN-α were changed to the murine 2H7 CDRs. The resulting molecule is referred to as humanized 2H7 version 2 (2H7.v2), or the "CDR-swap version" of 2H7; it has the m2H7 CDR residues with the consensus human FR residues shown in FIGS. 1A and 1B. Humanized 2H7.v2 was used for further humanization.

Table 1 shows the oligonucleotide sequence used to create each of the murine 2H7 (m2H7) CDRs in the H and L chain. For example, the CDR-H1 oligonucleotide was used to recreate the m2H7 H chain CDR1. CDR-H1, CDR-H2 and CDR-H3 refers to the H chain CDR1, CDR2 and CDR3, respectively; similarly, CDR-L1, CDR-L2 and CDR-L3 refers to each of the L chain CDRs. The substitutions in CDR-H2 were done in two steps with two oligonucleotides, CDR-H2A and CDR-H2B.

TABLE 1

Oligonucleotide sequences used for construction of the CDR-swap of murine 2H7 CDRs into a human framework in pVX4.

| Substitution | Oligonucleotide sequence |
|---|---|
| CDR-H1 | C TAC ACC TTC ACG <u>ACG</u> TAT <u>AAC</u> <u>ATG</u> CAC TGG GTC CG (SEQ ID NO. 27) |
| CDR-H2A | G ATT AAT CCT GAC <u>AAC</u> <u>GGC</u> <u>GAC</u> ACG <u>AGC</u> TAT AAC CAG <u>AAG</u> TTC AAG GGC CG (SEQ ID NO. 28) |
| CDR-H2B | GAA TGG GTT GCA <u>GCG</u> ATC <u>TAT</u> CCT <u>GGC</u> AAC GGC GAC AC (SEQ ID NO. 29) |

TABLE 1-continued

Oligonucleotide sequences used for construction of the CDR-swap of murine 2H7 CDRs into a human framework in pVX4.

| Substitution | Oligonucleotide sequence |
|---|---|
| CDR-H3 | AT TAT TGT GCT CGA GTG <u>GTC</u> <u>TAC</u> <u>TAT</u> <u>AGC</u> <u>AAC</u> <u>AGC</u> <u>TAC</u> <u>TGG</u> <u>TAC</u> <u>TTC</u> GAC <u>GTC</u> TGG GGT CAA GGA (SEQ ID NO. 30) |
| CDR-L1 | C TGC ACA GCC AGC <u>TCT</u> TCT <u>GTC</u> AGC TAT ATG CAT TG (SEQ ID NO. 31) |
| CDR-L2 | AA CTA CTG ATT TAC <u>GCT</u> <u>CCA</u> <u>TCG</u> AAC CTC <u>GCG</u> TCT GGA GTC C (SEQ ID NO. 32) |
| CDR-L3 | TAT TAC TGT CAA CAG <u>TGG</u> <u>AGC</u> <u>TTC</u> <u>AAT</u> CCG <u>CCC</u> ACA TTT GGA CAG (SEQ ID NO. 33) |

Residues changed by each oligonucleotide are underlined.

For comparison with humanized constructs, a plasmid expressing a chimeric 2H7 Fab (containing murine $V_L$ and $V_H$ domains, and human $C_L$ and $CH_1$ domains) was constructed by site-directed mutagenesis (Kunkel, supra) using synthetic oligonucleotides to introduce the murine framework residues into 2H7.v2. The sequence of the resulting plasmid construct for expression of the chimeric Fab known as 2H7.v6.8, is shown in FIG. 3. Each encoded chain of the Fab has a 23 amino acid StII secretion signal sequence as described for pVX4 (FIG. 2) above.

Based on a sequence comparison of the murine 2H7 framework residues with the human $V_\kappa I, V_H III$ consensus framework (FIGS. 1A and 1B) and previously humanized antibodies (Carter et al., Proc. Natl. Acad. Sci. USA 89:4285-4289 (1992)), several framework mutations were introduced into the 2H7.v2 Fab construct by site-directed mutagenesis. These mutations result in a change of certain human consensus framework residues to those found in the murine 2H7 framework, at sites that might affect CDR conformations or antigen contacts. Version 3 contained $V_H$(R71V, N73K), version 4 contained $V_H$(R71V), version 5 contained $V_H$(R71V, N73K) and $V_L$(L46P), and version 6 contained $V_H$(R71V, N73K) and $V_L$(L46P, L47W).

Humanized and chimeric Fab versions of m2H7 antibody were expressed in E. coli and purified as follows. Plasmids were transformed into E. coli strain XL-1 Blue (Stratagene, San Diego, Calif.) for preparation of double- and single-stranded DNA. For each variant, both light and heavy chains were completely sequenced using the dideoxynucleotide method (Sequenase, U.S. Biochemical Corp.). Plasmids were transformed into E. coli strain 16C9, a derivative of MM294, plated onto LB plates containing 5 μg/ml carbenicillin, and a single colony selected for protein expression. The single colony was grown in 5 ml LB-100 μg/ml carbenicillin for 5-8 h at 37° C. The 5 ml culture was added to 500 ml AP5-100 μg/ml carbenicillin and allowed to grow for 16 h in a 4 L baffled shake flask at 37° C. AP5 media consists of: 1.5 g glucose, 11.0 Hycase SF, 0.6 g yeast extract (certified), 0.19 g anhydrous $MgSO_4$, 1.07 g $NH_4Cl$, 3.73 g KCl, 1.2 g NaCl, 120 ml 1 M triethanolamine, pH 7.4, to 1 L water and then sterile filtered through 0.1 μm Sealkeen filter.

Cells were harvested by centrifugation in a 1 L centrifuge bottle (Nalgene) at 3000×g and the supernatant removed. After freezing for 1 h, the pellet was resuspended in 25 ml cold 10 mM MES-10 mM EDTA, pH 5.0 (buffer A). 250 μl of 0.1M PMSF (Sigma) was added to inhibit proteolysis and 3.5 ml of stock 10 mg/ml hen egg white lysozyme (Sigma) was added to aid lysis of the bacterial cell wall. After gentle shaking on ice for 1 h, the sample was centrifuged at 40,000×g for 15 min. The supernatant was brought to 50 ml with buffer A and loaded onto a 2 ml DEAE column equilibrated with buffer A. The flow-through was then applied to a protein G-Sepharose CL-4B (Pharmacia) column (0.5 ml bed volume) equilibrated with buffer A. The column was washed with 10 ml buffer A and eluted with 3 ml 0.3 M glycine, pH 3.0, into 1.25 ml 1 M Tris, pH 8.0. The F(ab) was then buffer exchanged into PBS using a Centricon-30 (Amicon) and concentrated to a final volume of 0.5 ml. SDS-PAGE gels of all F(ab)s were run to ascertain purity and the molecular weight of each variant was verified by electrospray mass spectrometry.

In cell-based ELISA binding assays (described below), the binding of Fabs, including chimeric 2H7 Fab, to CD20 was difficult to detect. Therefore, the 2H7 Fab versions were reformatted as full-length IgG1 antibodies for assays and further mutagenesis.

Plasmids for expression of full-length IgG's were constructed by subcloning the $V_L$ and $V_H$ domains of chimeric 2H7 (v6.8) Fab as well as humanized Fab versions 2 to 6 into previously described pRK vectors for mammalian cell expression (Gorman et al., *DNA Prot. Eng. Tech.* 2:3-10 (1990)). Briefly, each Fab construct was digested with EcoRV and BlpI to excise a $V_L$ fragment, which was cloned into the EcoRV/BlpI sites of plasmid pDR1 (FIG. 4) for expression of the complete light chain ($V_L$-$C_L$ domains). Additionally, each Fab construct was digested with PvuII and ApaI to excise a $V_H$ fragment, which was cloned into the PvuII/ApaI sites of plasmid pDR2 (FIG. 5) for expression of the complete heavy chain (VH-$CH_1$-hinge-$CH_2$-$CH_3$ domains). For each IgG variant, transient transfections were performed by cotransfecting a light-chain expressing plasmid and a heavy-chain expressing plasmid into an adenovirus-transformed human embryonic kidney cell line, 293 (Graham et al., *J. Gen. Virol.*, 36:59-74, (1977)). Briefly, 293 cells were split on the day prior to transfection, and plated in serum-containing medium. On the following day, double-stranded DNA prepared as a calcium phosphate precipitate was added, followed by pAd-VAntage™ DNA (Promega, Madison, Wis.), and cells were incubated overnight at 37° C. Cells were cultured in serum-free medium and harvested after 4 days. Antibodies were purified from culture supernatants using protein A-Sepharose CL-4B, then buffer exchanged into 10 mM sodium succinate, 140 mM NaCl, pH 6.0, and concentrated using a Centricon-10 (Amicon). Protein concentrations were determined by quantitative amino acid analysis.

To measure relative binding affinities to the CD20 antigen, a cell-based ELISA assay was developed. Human B-lymphoblastoid WIL2-S cells (ATCC CRL 8885, American Type Culture Collection, Rockville, Md.) were grown in RPMI 1640 supplemented with 2 mM L-glutamine, 20 mM HEPES, pH 7.2 and 10% heat-inactivated fetal bovine serum in a humidified 5% $CO_2$ incubator. The cells were washed with PBS containing 1% FBS (assay buffer) and seeded at 250-300,000 cell/well in 96-well round bottom plates (Nunc, Roskilde, Denmark). Two-fold serially diluted standard (15.6-1000 ng/ml) of 2H7 v6.8 chimeric IgG) and threefold serially diluted samples (2.7-2000 ng/ml) in assay buffer were added to the plates. The plates were buried in ice and incubated for 45 min. To remove the unbound antibody, 0.1 mL assay buffer were added to the wells. Plates were centrifuged and supernatants were removed. Cells were washed two more times with 0.2 mL assay buffer. Antibody bound to the plates was detected by adding peroxidase conjugated goat anti-human Fc antibody (Jackson Immuno Research, West Grove, Pa.) to the plates. After a 45 min incubation, cells were washed as described before. TMB substrate (3,3'5,5'-tetramethyl benzidine; Kirkegaard & Perry Laboratories, Gaithersburg, Md.) was added to the plates. The reaction was stopped by adding 1 M phosphoric acid. Titration curves were fit with a four-parameter nonlinear regression curve-fitting program (KaleidaGraph, Synergy software, Reading, Pa.). The absorbance at the midpoint of the titration curve (mid-OD) and its corresponding concentration of the standard were determined. Then the concentration of each variant at this mid-OD was determined, and the concentration of the standard was divided by that of each variant. Hence the values are a ratio of the binding of each variant relative to the standard. Standard deviations in relative affinity (equivalent concentration) were generally +/−10% between experiments.

As shown in Table 2, binding of the CDR-swap variant (v.2) was extremely reduced compared to chimeric 2H7 (v.6.8). However, versions 3 to 6 showed improved binding. To determine the minimum number of mutations that might be required to restore binding affinity to that of chimeric 2H7, additional mutations and combinations of mutations were constructed by site-direct mutagenesis to produce variants 7 to 17 as indicated in Table 3. In particular, these included $V_H$ mutations A49G, F67A, I69L, N73K, and L78A; and $V_L$ mutations M4L, M33I, and F71Y. Versions 16 and 17 showed the best relative binding affinities, within 2-fold of that of the chimeric version, with no significant difference (s.d.=+/−10%) between the two. To minimize the number of mutations, version 16, having only 4 mutations of human framework residues to murine framework residues (Table 3), was therefore chosen as the humanized form for additional characterization.

TABLE 2

Relative binding affinity of humanized 2H7 IgG variants to CD20 compared to chimeric 2H7 using cell-based ELISA.

| 2H7 version | Heavy chain ($V_H$) substitutions | Light Chain ($V_L$) substitutions | Relative binding |
|---|---|---|---|
| 6.8 | (Chimera) | (Chimera) | -1- |
| 2 | (CDR swap) | (CDR swap) | 0.01 |
| 3 | R71V, N73K | (CDR swap) | 0.21 |
| 4 | R71V | (CDR swap) | 0.21 |
| 5 | R71V, N73K | L46P | 0.50 |
| 6 | R71V, N73K | L46P, L47W | 0.58 |
| 7 | R71V | L46P | 0.33 |
| 8 | R71V, L78A | L46P | 0.19 |
| 8 | R71V, F67A | L46P | 0.07 |
| 10 | R71V, F67A, I69L | L46P | 0.12 |
| 11 | R71V, F67A, L78A | L46P | 0.19 |
| 12 | R71V | L46P, M4L | 0.32 |
| 13 | R71V | L46P, M33I | 0.31 |
| 14 | R71V | L46P, F71Y | 0.25 |
| 15 | R71V | L46P, M4L, M33I | 0.26 |
| 16 | R71V, N73K, A49G | L46P | 0.65 |
| 17 | R71V, N73K, A49G | L46P, L47W | 0.67 |

The relative bidning is expressed as the concentration of the chimeric 2H7 over the concentration of the variant required for equivalent binding; hence a ratio <1 indicates weaker affinity for the variant. Standard deviation in relative affinity determination averaged +/−10%. Framework substitutions in the variable domains are relative to the CDR-swap version according to the numbering system to Kabat (Kabat et al., supra).

TABLE 3

Oligonucleotide sequences used for construction of mutations VH(A49G, R71V, N73K) and VL(L46P) in humanized 2H7 version 16 (2H7.v16).

| Substitution | Oligonucleotide sequence |
|---|---|
| $V_H$ (R71V, N73K) | GT TTC ACT ATA AGT GTC GAC AAG TCC AAA AAC ACA TT (SEQ ID NO. 34) |
| $V_H$ (A49G) | GCCAGGATAGATGGCGCCAACCCATTCCAGGCC (SEQ ID NO. 35) |
| $V_L$ (L46P) | AAGCTCCGAAACCACTGATTTACGCT (SEQ ID NO. 36) |

Underlined codons encode the indicated amino acid substitutions.
For $V_H$ (R71V, N73K) and $V_L$ (L46P), the oligos are shown as the sense strand since these were used for mutagenesis on the Fab template, while for $V_H$ (A49G), the oligo is shown as the anti-sense strand, since this was used with the pRK (IgG heavy chain) template.
The protein sequence of version 16 is shown in FIG. 6 and FIG. 7.

Example 2

Antigen-Binding Determinants (Paratope) of 2H7

Alanine substitutions (Cunningham & Wells, *Science* 244: 1081-1085 (1989) were made in 2H7.v16 or 2H7.v17 in order to test the contributions of individual side chains of the antibody in binding to CD20. IgG variants were expressed in 293 cells from pDR1 and pDR2 vectors, purified, and assayed for relative binding affinity as described above. Several alanine substitutions resulted in significant decreases in relative binding to CD20 on WIL-2S cells (Table 4).

TABLE 4

Effects of alanine substitutions in the CDR regions of humanized 2H7.v16 measured using cell-based ELISA (WIL2-S cells).

| 2H7 version | CDR location | Heavy chain substitutions | Light chain substitutions | Relative binding |
|---|---|---|---|---|
| 16 | — | — | — | -1- |
| 140 | H1 | G26A | — | 0.63 |
| 141 | H1 | Y27A | — | 0.47 |
| 34 | H1 | T28A | — | 0.86 |
| 35 | H1 | F29A | — | 0.07 |
| 36 | H1 | T30A | — | 0.81 |
| 37 | H1 | S31A | — | 0.97 |
| 142 | H1 | Y32A | — | 0.63 |
| 143 | H1 | N33A | — | NDB |
| 144 | H1 | M34A | — | 1.2 |
| 145 | H1 | H35A | — | <0.25 |
| 146 | H2 | A50G | — | 0.31 |
| 147 | H2 | I51A | — | 0.65 |
| 38 | H2 | Y52A | — | 0.01 |
| 148 | H2 | P52aA | — | 0.66 |
| 39 | H2 | G53A | — | 0.89 |
| 67 | H2 | N54A | — | 1.4 |
| 40 | H2 | G55A | — | 0.79 |
| 41 | H2 | D56A | — | 2.0 |
| 89 | H2 | T57A | — | 0.61 |
| 90 | H2 | S58A | — | 0.92 |
| 91 | H2 | Y59A | — | 0.74 |
| 92 | H2 | N60A | — | 0.80 |
| 93 | H2 | Q61A | — | 0.83 |
| 94 | H2 | K62A | — | 0.44 |
| 95 | H2 | F63A | — | 0.51 |
| 83 | H2 | V71A | — | 0.96 |
| 149 | H2 | K64A | — | 0.82 |
| 150 | H2 | G65A | — | 1.2 |
| 153 | H3 | V95A | — | 0.89 |
| 42 | H3 | V96A | — | 0.98 |
| 43 | H3 | Y97A | — | 0.63 |
| 44 | H3 | Y98A | — | 0.40 |
| 45 | H3 | S99A | — | 0.84; 0.92 |
| 46 | H3 | N100A | — | 0.81 |
| 47 | H3 | S100aA | — | 0.85 |
| 48 | H3 | Y100bA | — | 0.78 |
| 49 | H3 | W100cA | — | 0.02 |
| 59 | H3 | Y100dA | — | 0.98 |
| 60 | H3 | F100eA | — | NDB |
| 61 | H3 | D101A | — | 0.31 |
| 151 | H3 | V102A | — | 1.1 |
| 117 | L1 | — | R24A | 0.85 |
| 118 | L1 | — | A25G | 0.86 |
| 119 | L1 | — | S26A | 0.98 |
| 120 | L1 | — | S27A | 0.98 |
| 121 | L1 | — | S28A | 1.0 |
| 122 | L1 | — | V29A | 0.41 |
| 50 | L1 | — | S30A | 0.96 |
| 51 | L1 | — | Y32A | 1.0 |
| 123 | L1 | — | M33A | 1.0 |
| 124 | L1 | — | H34A | 0.21 |
| 125 | L2 | — | A50G | 0.92 |
| 126 | L2 | — | P51A | 0.88 |
| 52 | L2 | — | S52A | 0.80 |
| 53 | L2 | — | N53A | 0.76 |
| 54 | L2 | — | L54A | 0.60 |
| 127 | L2 | — | A55G | 1.1 |
| 128 | L2 | — | S56A | 1.1 |
| 129 | L3 | — | Q89A | 0.46 |
| 130 | L3 | — | Q90A | <0.22 |
| 55 | L2 | — | W91A | 0.88 |
| 56 | L3 | — | S92A | 1.1 |
| 57 | L3 | — | F93A | 0.36 |
| 58 | L3 | — | N94A | 0.61 |
| 131 | L3 | — | P95A | NDB |
| 132 | L3 | — | P96A | 0.18 |
| 133 | L3 | — | T97A | <0.22 |

The relative binding is expressed as the concentration of the 2H7.v16 parent over the concentration of the variant required for equivalent binding; hence a ratio <1 indicates weaker affinity for the variant; a ratio >1 indicates higher affinity for the variant. Standard deviation in relative affinity determination averaged +/−10%. Framework substitutions in the variable domains are relative to 2H7.v16 according to the numbering system of Kabat (Kabat et al., supra).
NBD means no detectable binding. The two numbers for version 45 are from separate experiments.

Example 3

Additional Mutations within 2H7 CDR Regions

Substitutions of additional residues and combinations of substitutions at CDR positions that were identified as important by Ala-scanning were also tested. Several combination variants, particularly v.96 appeared to bind more tightly than v.16.

TABLE 5

Effects of combinations of mutations and non-alanine substitutions in the CDR regions of humanized 2H7.v16 measured using cell-based ELISA (WIL2-S cells).

| 2H7 version | Heavy chain substitutions | Light chain substitutions | Relative binding |
|---|---|---|---|
| 16 | — | — | -1- |
| 96 | D56A, N100A | S92A | 3.5 |
| 97 | S99T, N100G, Y100bI | — | 0.99 |
| 98 | S99G, N100S, Y100bI | — | 1.6 |

TABLE 5-continued

Effects of combinations of mutations and non-alanine substitutions in the CDR regions of humanized 2H7.v16 measured using cell-based ELISA (WIL2-S cells).

| 2H7 version | Heavy chain substitutions | Light chain substitutions | Relative binding |
|---|---|---|---|
| 99 | N100G, Y100bI | — | 0.80 |
| 101 | N54S, D56A | — | 1.7 |
| 102 | N54K, D56A | — | 0.48 |
| 103 | D56A, N100A | — | 2.1 |
| 104 | S99T, N100G | — | 0.81 |
| 105 | S99G, N100S | — | 1.1 |
| 106 | N100G | — | ~1 |
| 167 | S100aG, Y100bS | — | |
| 136 | D56A, N100A | S56A, S92A | 2.6 |
| 137 | D56A, N100A | A55G, S92A | 2.1 |
| 156 | D56A, N100A | S26A, S56A, S92A | 2.1 |
| 107 | D56A, N100A, Y100bI | S92A | not expressed |
| 182 | Y27W | — | |
| 183 | Y27F | — | |
| 184 | F29Y | — | |
| 185 | F29W | — | |
| 186 | Y32F | — | |
| 187 | Y32W | — | |
| 188 | N33Q | — | |
| 189 | N33D | — | |
| 190 | N33Y | — | |
| 191 | N33S | — | |
| 208 | H35S | — | |
| 209 | A50S | — | |
| 210 | A50R | — | |
| 211 | A50V | — | |
| 212 | A50L | — | |
| 168 | Y52W | — | |
| 169 | Y52F | — | 0.75 |
| 170 | N54D | — | 0.25 |
| 171 | N54S | — | 1.2 |
| 172 | D56K | — | 1 |
| 173 | D56R | — | |
| 174 | D56H | — | 1.5 |
| 175 | D56E | — | 1.2 |
| 213 | D56S | — | |
| 214 | D56G | — | |
| 215 | D56N | — | |
| 216 | D56Y | — | |
| 176 | Y59W | — | |
| 177 | Y59F | — | |
| 180 | K62R | — | |
| 181 | K62D | — | |
| 178 | F63W | — | |
| 179 | F63Y | — | |
| 157 | Y97W | — | 0.64 |
| 158 | Y97F | — | 1.2 |
| 159 | Y98W | — | 0.64 |
| 160 | Y98F | — | 0.88 |
| 106 | N100G | — | |
| 161 | W100cY | — | 0.05 |
| 162 | W100cF | — | 0.27 |
| 163 | F100eY | — | 0.59 |
| 164 | F100eW | — | 0.71 |
| 165 | D101N | — | 0.64 |
| 166 | S99G, N100G, S100aD, Y100b deleted | — | 0.99 |
| 217 | V102Y | — | 1.0 |
| 207 | — | H34Y | |
| 192 | — | Q89E | |
| 193 | — | Q89N | |
| 194 | — | Q90E | |
| 195 | — | Q90N | |
| 196 | — | W91Y | |
| 197 | — | W91F | |
| 205 | — | S92N | |
| 206 | — | S92G | |
| 198 | — | F93Y | |
| 199 | — | F93W | |
| 204 | — | F93S, N94Y | |

TABLE 5-continued

Effects of combinations of mutations and non-alanine substitutions in the CDR regions of humanized 2H7.v16 measured using cell-based ELISA (WIL2-S cells).

| 2H7 version | Heavy chain substitutions | Light chain substitutions | Relative binding |
|---|---|---|---|
| 200 | — | P96L | |
| 201 | — | P96Y | |
| 202 | — | P96W | |
| 203 | — | P96R | |

The relative binding to CD20 is expressed as the concentration of the 2H7.v16 parent over the concentration of the variant required for equivalent binding; hence a ratio <1 indicates weaker affinity for the variant; a ratio >1 indicates higher affinity for the variant. Standard deviation in relative affinity determination averaged +/−10%. Framework substitutions in the variable domains are relative to 2H7.v16 according to the numbering system of Kabat (Kabat et al., supra).

Example 4

Mutations at Sites of Framework Humanization Substitutions

Substitutions of additional residues at framework positions that were changed during humanization were also tested in the 2H7.v16 background. In particular, alternative framework substitutions that were neither found in the murine 2H7 parent nor the human consensus framework were made at $V_L$(P46) and $V_H$(G49, V71, and K73).

These substitutions generally led to little change in relative binding (Table 6), indicating that there is some flexibility in framework residues at these positions.

TABLE 6

Relative binding in a cell-based (WIL2-S) assay of framework substitutions.

| 2H7 version | Heavy chain substitutions | Light chain substitutions | Relative binding |
|---|---|---|---|
| 6.8 | (chimera) | (chimera) | -1- |
| 16 | — | — | 0.64 |
| 78 | K73R | — | 0.72 |
| 79 | K73H | — | 0.49 |
| 80 | K73Q | — | 0.58 |
| 81 | V71I | — | 0.42 |
| 82 | V71T | — | 0.58 |
| 83 | V71A | — | |
| 84 | G49S | — | 0.32 |
| 85 | G49L | — | |
| 86 | — | P46E | 0.22 |
| 87 | — | P46V | 0.51 |
| 88 | — | P46T | |
| 108 | G49A, V71T, K73R | S92A, M32L, P46T | 0.026* |
| 109 | G49A, A49G, V71T, K73R | S92A, M32L, P46T | 0.026* |
| 110 | K73R, D56A, N100A | S92A, M32L | Not expressed |
| 111 | G49A, V71T, K73R | — | 0.46* |
| 112 | G49A, A50G, V71T, K73R | — | 0.12* |

IgG variants are shown with mutations with respect to the 2H7.v16 background. The relative binding is expressed as the concentration of the 2H7.v6.8 chimera over the concentration of the variant required for equivalent binding; hence a ratio <1 indicates weaker affinity for the variant; a ratio >1 indicates higher affinity for the variant. Standard deviation in relative affinity determination averaged +/−10%. Framework substitutions in the variable domains are relative to 2H7.v16 according to the numbering system of Kabat (Kabat et al., supra). (*) Variants that were assayed with 2H7.v16 as the standard comparator; relative values are normalized to that of the chimera.
*Variants that were assayed with 2H7.v16 as the standard comparator; relative values are normalized to that of the chimera.

Example 5

Humanized 2H7 Variants with Enhanced Effector Functions

Because 2H7 can mediate lysis of B-cells through both complement-dependent cytotoxicity (CDC) and antibody-dependent cellular cytotoxicity (ADCC), we sought to produce variants of humanized 2H7.v16 with improved CDC and ADCC activity. Mutations of certain residues within the Fc regions of other antibodies have been described (Idusogie et al., *J. Immunol.* 166:2571-2575 (2001)) for improving CDC through enhanced binding to the complement component C1q. Mutations have also been described (Shields et al., *J. Biol. Chem.* 276:6591-6604 (2001); Presta et al., *Biochem. Soc. Trans.* 30:487-490 (2002)) for improving ADCC through enhanced IgG binding to activating Fcγ receptors and reduced IgG binding to inhibitory Fcγ receptors. In particular, three mutations have been identified for improving CDC and ADCC activity: S298A/E333A/K334A (also referred to herein as a triple Ala mutant or variant; numbering in the Fc region is according to the EU numbering system; Kabat et al., supra) as described (Idusogie et al., supra (2001); Shields et al., supra).

In order to enhance CDC and ADCC activity of 2H7, a triple Ala mutant of the 2H7 Fc was constructed. A humanized variant of the anti-HER2 antibody 4d5 has been produced with mutations S298A/E333A/K334A and is known as 4D5Fc110 (i.e., anti-p$^{185}$HER2 IgG1 (S298A/E333A/K334A); Shields et al., supra). A plasmid, p4D5Fc110 encoding antibody 4D5Fc110 (Shields et al., supra) was digested with ApaI and HindIII, and the Fc-fragment (containing mutations S298A/E333A/K334A) was ligated into the ApaI/HindIII sites of the 2H7 heavy-chain vector pDR2-v16, to produce pDR2-v31. The amino acid sequence of the version 31 complete H chain is shown in FIG. 8. The L chain is the same as that of v16.

Although the constant domains of the Fc region of IgG1 antibodies are relatively conserved within a given species, allelic variations exist (reviewed by Lefranc and Lefranc, in *The human IgG subclasses: molecular analysis of structure, function, and regulation*, pp. 43-78, F. Shakib (ed.), Pergammon Press, Oxford (1990)).

TABLE 7

Effects of substitutions in the Fc region on CD20 binding.

| 2H7 version | Fc Substitutions* | Relative binding |
|---|---|---|
| 6.8 | — | -1- |
| 16 | — | 0.65 |
| 31 | S298A, E333A, K334A | 0.62 |

Relative binding to CD20 was measured in a cell-based (WIL2-S) assay of framework substitutions. Fc mutations (*) are indicated by EU numbering (Kabat, supra) and are relative to the 2H7.v16 parent. The combination of three Ala changes in the Fc region of v.31 is described as "Fc110." IgG variants are shown with mutations with respect to the 2H7.v16 background. The relative binding is expressed as the concentration of the 2H7.v6.8 chimera over the concentration of the variant required for equivalent binding; hence a ratio <1 indicates weaker affinity for the variant. Standard deviation in relative affinity determination averaged +/−10%.

Example 6

Humanized 2H7 Variants with Enhanced Stability

For development as therapeutic proteins, it is desirable to choose variants that remain stable with respect to oxidation, deamidation, or other processes that may affect product quality, in a suitable formulation buffer. In 2H7.v16, several residues were identified as possible sources of instability: VL (M32) and VH (M34, N100). Therefore, mutations were introduced at these sites for comparison with v16.

Table 8. Relative binding of 2H7 variants designed for enhanced stability and/or effector function, to CD20 in a cell-based (WIL2-S) assay. IgG variants are shown with mutations with respect to the 2H7.v16 background. The relative binding is expressed as the concentration of the 2H7.v6.8 chimera over the concentration of the variant required for equivalent binding; hence a ratio<1 indicates weaker affinity for the variant. Standard deviation in relative affinity determination averaged +/−10%. Framework substitutions in the variable domains are relative to 2H7.v16 according to the numbering system of Kabat and Fc mutations (*) are indicated by EU numbering (Kabat et al., supra). (**) Variants that were measured with 2H7.v16 as the standard comparator; relative values are normalized to that of the chimera.

Additional Fc mutations were combined with stability or affinity-enhancing mutations to alter or enhance effector functions based on previously reported mutations (Idusogie et al. (2000); Idusogie et al. (2001); Shields et al. (2001)). These changes include S298, E333A, K334A as described in Example 5; K322A to reduced CDC activity; D265A to reduce ADCC activity; K326A or K326W to enhance CDC activity; and E356D/M358L to test the effects of allotypic changes in the Fc region. None of these mutations caused significant differences in CD20 binding affinity.

| 2H7 version | Heavy chain ($V_H$) changes | Light chain ($V_L$) changes | Fc changes* | Relative binding |
|---|---|---|---|---|
| 6.8 | (chimera) | (chimera) | — | -1- |
| 16 | — | — | — | 0.65 |
| 62 | — | M32I | — | 0.46 |
| 63 | M34I | — | — | 0.49 |
| 64 | N100A | — | — | |
| 65 | N100A | L47W | — | 0.74 |
| 66 | S99A | L47W | — | 0.62 |
| 67 | N54A | — | — | |
| 68 | — | M32I | — | 0.48 |
| 69 | — | M32L | — | 0.52 |
| 70 | N100A | — | S298A, E333A, K334A | 0.80 |
| 71 | N100D | — | S298A, E333A, K334A | 0.44 |
| 72 | N100A | M32I | — | 0.58 |
| 73 | N100A | M32L | — | 0.53 |
| 74 | N100A | M32I | S298A, E333A, K334A | 0.61 |
| 75 | N100A | M32L | S298A, E333A, K334A | 0.60 |
| 113 | — | — | E356D, M358L | 0.60** |
| 114 | D56A, N100A | M32L, S92A | S298A, E333A, K334A | 1.2** |
| 115 | D56A, N100A | M32L, S92A | S298A, E333A, K334A, E356D, M358L | 1.4** |
| 116 | D56A, N100A | M32L, S92A | S298A, K334A, K322A | 1.2** |
| 134 | D56A, N100A | M32L, S92A | E356D, M358L, D265A | 1.5** |
| 135 | D56A, N100A | M32L, S92A | E356D, M358L, D265A, K326W | 0.95** |
| 138 | D56A, N100A | M32L, S92A | S298A, E333A, K334A, K326A | 1.2** |
| 139 | D56A, N100A | M32L, S92A | S298A, E333A, K334A, K326A, E356N, M358L | 1.1** |

-continued

| 2H7 version | Heavy chain (V$_H$) changes | Light chain (V$_L$) changes | Fc changes* | Relative binding |
|---|---|---|---|---|
| 154 | — | — | D265A | 0.70** |
| 155 | — | — | S298A, K322A, K334A | 0.70** |

**Variants that were measured with 2H7.v16 as comparator; relative binding values are normalized to that of the chimera.

To test the effects of stability mutations on the rate of protein degradation, 2H7.v16 and 2H7.v73 were formulated at 12-14 mg/mL in 10 mM histidine, 6% sucrose, 0.02% polysorbate 20, pH 5.8 and incubated at 40° C. for 16 days. The incubated samples were then assayed for changes in charge variants by ion exchange chromatography, aggregation and fragmentation by size exclusion chromatography, and relative binding by testing in a cell-based (WIL2-S) assay.

The results (FIG. 9) show that 2H7 v.73 has greater stability compared to 2H7 v.16 with respect to losses in the fraction of main peak by ion exchange chromatography under accelerated stability conditions. No significant differences were seen with respect to aggregation, fragmentation, or binding affinity.

Example 7

Scatchard Analysis of Antibody Binding to CD20 on WIL2-S Cells

Equilibrium dissociation constants ($K_d$) were determined for 2H7 IgG variants binding to WIL2-S cells using radiolabeled 2H7 IgG. IgG variants were produced in CHO cells. Rituxan® (source for all experiments is Genentech, S. San Francisco, Calif.) and murine 2H7 (BD PharMingen, San Diego, Calif.) were used for comparison with humanized variants. The murine 2H7 antibody is also available from other sources, e.g., eBioscience, and Calbiochem (both of San Diego, Calif.), Accurate Chemical & Scientific Corp., (Westbury, N.Y.), Ancell (Bayport, Minn.), and Vinci-Biochem (Vinci, Italy). All dilutions were performed in binding assay buffer (DMEM media containing 1% bovine serum albumin, 25 mM HEPES pH 7.2, and 0.01% sodium azide). Aliquots (0.025 mL) of $^{125}$I-2H7.v16 (iodinated with lactoperoxidase) at a concentration of 0.8 nM were dispensed into wells of a V-bottom 96-well microassay plate, and serial dilutions (0.05 mL) of cold antibody were added and mixed. WIL2-S cells (60,000 cells in 0.025 mL) were then added. The plate was sealed and incubated at room temperature for 24 h, then centrifuged for 15 min at 3,500 RPM. The supernatant was then aspirated and the cell pellet was washed and centrifuged. The supernatant was again aspirated, and the pellets were dissolved in 1N NaOH and transferred to tubes for gamma counting. The data were used for Scatchard analysis (Munson and Rodbard, *Anal. Biochem.* 107:220-239 (1980)) using the program Ligand (McPherson, *Comput. Programs Biomed.* 17: 107-114 (1983)). The results, shown in Table 9, indicate that humanized 2H7 variants had similar CD20 binding affinity as compared to murine 2H7, and similar binding affinity to Rituxan®. It is expected that 2H7.v31 will have very similar $K_d$ to v.16 on the basis of the binding shown in Table 7 above.

TABLE 9

Equilibrium binding affinity of 2H7 variants from Scatchard analysis

| Antibody variant | $K_d$ (nM) | n |
|---|---|---|
| Rituxan | 0.99 ± 0.49 | 3 |
| 2H7 (murine) | 1.23 ± 0.29 | 3 |
| 2H7.v16 | 0.84 ± 0.37 | 4 |
| 2H7.v73 | 1.22 ± 0.39 | 4 |
| 2H7.v75 | 1.09 ± 0.17 | 4 |

Example 8

Complement Dependent Cytotoxicity (CDC) Assays

2H7 IgG variants were assayed for their ability to mediate complement-dependent lysis of WIL2-S cells, a CD20 expressing lymphoblastoid B-cell line, essentially as described (Idusogie et al., *J. Immunol.* 164:4178-4184 (2000); Idusogie et al., *J. Immunol.* 166:2571-2575 (2001)). Antibodies were serially diluted 1:3 from a 0.1 mg/mL stock solution. A 0.05 mL aliquot of each dilution was added to a 96-well tissue culture plate that contained 0.05 mL of a solution of normal human complement (Quidel, San Diego, Calif.) To this mixture, 50,000 WIL2-S cells were added in a 0.05 mL volume. After incubation for 2 h at 37° C., 0.05 mL of a solution of Alamar blue (Accumed International, Westlake, Ohio) was added, and incubation was continued for an additional 18 h at 37° C. Covers were then removed from the plates, and they were shaken for 15 min at room temperature on an orbital shaker. Relative fluorescent units (RFU) were read using a 530 nm excitation filter and a 590 nm emission filter. An $EC_{50}$ was calculated by fitting RFU as a function of concentration for each antibody using KaleidaGraph software.

The results (Table 10) show surprising improvement in CDC by humanized 2H7 antibodies, with relative potency similar to Rituxan® for v.73, 3-fold more potent than Rituxan® for v.75, and 3-fold weaker than Rituxan® for v.16.

TABLE 10

CDC activity of 2H7 antibodies compared to Rituxan.

| Antibody variant | n | $EC_{50}$(variant)/$EC_{50}$(Rituxan) |
|---|---|---|
| Rituxan ® | 4 | -1- |
| 2H7.v16 | 4 | 3.72; 4.08 |
| 2H7.v31* | 4 | 2.21 |
| 2H7.v73 | 4 | 1.05 |
| 2H7.v75 | 4 | 0.33 |
| 2H7.v96* | 4 | 0.956 |
| 2H7.v114* | 4 | 0.378 |
| 2H7.v115* | 4 | 0.475 |
| 2H7.v116* | 1 | >100 |
| 2H7.v135* | 2 | 0.42 |

Numbers >1 indicate less potent CDC activity than Rituxan ® and numbers <1 indicate more potent activity than Rituxan ®. Antibodies were produced from stable CHO lines, except that those indicated by * were produced transiently.

Example 9

Antibody Dependent Cellular Cytotoxicity (ADCC) Assays

2H7 IgG variants were assayed for their ability to mediate Natural-Killer cell (NK cell) lysis of WIL2-S cells, a CD20 expressing lymphoblastoid B-cell line, essentially as described (Shields et al., *J. Biol. Chem.* 276:6591-6604 (2001)) using a lactate dehydrogenase (LDH) readout. NK cells were prepared from 100 mL of heparinized blood, diluted with 100 mL of PBS (phosphate buffered saline), obtained from normal human donors who had been isotyped for FcγRIII, also known as CD16 (Koene et al., *Blood* 90:1109-1114 (1997)). In this experiment, the NK cells were from human donors heterozygous for CD16 (F158/V158). The diluted blood was layered over 15 mL of lymphocyte separation medium (ICN Biochemical, Aurora, Ohio) and centrifuged for 20 min at 2000 RPM. White cells at the interface between layers were dispensed to 4 clean 50-mL tubes, which were filled with RPMI medium containing 15% fetal calf serum. Tubes were centrifuged for 5 min at 1400 RPM and the supernatant discarded. Pellets were resuspended in MACS buffer (0.5% BSA, 2 mM EDTA), and NK cells were purified using beads (NK Cell Isolation Kit, 130-046-502) according to the manufacturer's protocol (Miltenyi Biotech,). NK cells were diluted in MACS buffer to $2 \times 10^6$ cells/mL.

Serial dilutions of antibody (0.05 mL) in assay medium (F12/DMEM 50:50 without glycine, 1 mM HEPES buffer pH 7.2, Penicillin/Streptomycin (100 units/mL; Gibco), glutamine, and 1% heat-inactivated fetal bovine serum) were added to a 96-well round-bottom tissue culture plate. WIL2-S cells were diluted in assay buffer to a concentration of $4 \times 10^5$/mL. WIL2-S cells (0.05 mL per well) were mixed with diluted antibody in the 96-well plate and incubated for 30 min at room temperature to allow binding of antibody to CD20 (opsonization).

The ADCC reaction was initiated by adding 0.1 mL of NK cells to each well. In control wells, 2% Triton X-100 was added. The plate was then incubated for 4 h at 37° C. Levels of LDH released were measured using a cytotoxicity (LDH) detection kit (Kit#1644793, Roche Diagnostics, Indianapolis, Ind.) following the manufacturers instructions. 0.1 mL of LDH developer was added to each well, followed by mixing for 10 s. The plate was then covered with aluminum foil and incubated in the dark at room temperature for 15 min. Optical density at 490 nm was then read and use to calculate % lysis by dividing by the total LDH measured in control wells. Lysis was plotted as a function of antibody concentration, and a 4-parameter curve fit (KaleidaGraph) was used to determine $EC_{50}$ concentrations.

The results showed that humanized 2H7 antibodies were active in ADCC, with relative potency 20-fold higher than Rituxan® for v.31 and v.75, 5-fold more potent than Rituxan® for v.16, and almost 4-fold higher than Rituxan® for v.73.

TABLE 11

ADCC activity of 2H7 antibodies on WIL2-S cells compared to 2H7.v16, based on n experiments. (Values >1 indicate lower potency than 2H7.v16, and values <1 indicate greater potency.)

| Antibody variant | n | $EC_{50}$(variant)/$EC_{50}$(2H7.v16) |
|---|---|---|
| Rituxan ® | 4 | 5.3 |
| 2H7.v16 | 5 | 1 |
| 2H7.v31 | 1 | 0.24 |
| 2H7.v73 | 5 | 1.4 |
| 2H7.v75 | 4 | 0.25 |

Additional ADCC assays were carried out to compare combination-variants of 2H7 with Rituxan®. The results of these assays indicated that 2H7.v114 and 2H7.v115 have >10-fold improved ADCC potency as compared to Rituxan® (Table 12).

TABLE 12

ADCC activity of 2H7 antibodies on WIL2-S cells compared to Rituxan®, based on n experiments (Values >1 indicate lower potency than Rituxan ®, and values <1 indicate greater potency).

| Antibody variant | | $EC_{50}$(variant)/$EC_{50}$(Rituxan) |
|---|---|---|
| Rituxan ® | 2 | -1- |
| 2H7 v.16 | 2 | 0.52 |
| 2H7 v.96 | 2 | 0.58 |
| 2H7.v114 | 2 | 0.093 |
| 2H7.v115 | 2 | 0.083 |
| 2H7.v116 | 2 | 0.30 |

Example 10

In Vivo Effects of 2H7 Variants in a Pilot Study in Cynomolgus Monkeys

2H7 variants, produced by transient transfection of CHO cells, were tested in normal male cynomolgus (*Macaca fascicularis*) monkeys in order to evaluate their in vivo activities. Other anti-CD20 antibodies, such as C2B8 (Rituxan®) have demonstrated an ability to deplete B-cells in normal primates (Reff et al., *Blood* 83: 435-445 (1994)).

In one study, humanized 2H7 variants were compared. In a parallel study, Rituxan® was also tested in cynomolgus monkeys. Four monkeys were used in each of five dose groups: (1) vehicle, (2) 0.05 mg/kg hu2H7.v16, (3) 10 mg/kg hu2H7.v16, (4) 0.05 mg/kg hu2H7.v31, and (5) 10 mg/kg hu2H7.v31. Antibodies were administered intravenously at a concentration of 0, 0.2, or 20 mg/mL, for a total of two doses, one on day 1 of the study, and another on day 8. The first day of dosing is designated day 1 and the previous day is designated day -1; the first day of recovery (for 2 animals in each group) is designated as day 11. Blood samples were collected on days -19, -12, 1 (prior to dosing), and at 6 h, 24 h, and 72 h following the first dose. Additional samples were taken on day 8 (prior to dosing), day 10 (prior to sacrifice of 2 animals/group), and on days 36 and 67 (for recovery animals).

Peripheral B-cell concentrations were determined by a FACS method that counted CD3-/CD40+ cells. The percent of CD3-CD40+ B cells of total lymphocytes in monkey samples were obtained by the following gating strategy. The lymphocyte population was marked on the forward scatter/side scatter scattergram to define Region 1 (R1). Using events in R1, fluorescence intensity dot plots were displayed for CD40 and CD3 markers. Fluorescently labeled isotype controls were used to determine respective cutoff points for CD40 and CD3 positivity.

The results indicated that both 2H7.v16 and 2H7.v31 were capable of producing full peripheral B-cell depletion at the 10 mg/kg dose and partial peripheral B-cell depletion at the 0.05 mg/kg dose (FIG. 11). The time course and extent of B-cell depletion measured during the first 72 h of dosing were similar for the two antibodies. Subsequent analysis of the recovery animals indicated that animals treated with 2H7.v31 showed a prolonged depletion of B-cells as compared to those dosed with 2H7.v16. In particular, recovery animals treated with 10 mg/kg 2H7.v16, B-cells showed substantial B-cell recovery at some time between sampling on Day 10 and on Day 36. However, for recovery animals treated with 10 mg/kg 2H7.v31, B-cells did not show recovery until some time between Day 36 and Day 67 (FIG. 11). This suggests a greater duration of full depletion by about one month for 2H7.v31 compared to 2H7.v16.

No toxicity was observed in the monkey study at low or high dose and the gross pathology was normal. In other studies, v16 was well tolerated up to the highest dose evaluated of (10 mg/kg×2=1200 mg/m²×2) following i.v. administration of 2 doses given 2 weeks apart in these monkeys.

Data in Cynomolgus monkeys with 2H7.v16 versus Rituxan® suggests that a 5-fold reduction in CDC activity does not adversely affect potency. An antibody with potent ADCC activity but reduced CDC activity may have more favorable safety profile with regard to first infusion reactions than one with greater CDC activity.

Example 11

Fucose Deficient 2H7 Variant Antibodies with Enhanced Effector Function

Normal CHO and HEK293 cells add fucose to IgG oligosaccharide to a high degree (97-98%). IgG from sera are also highly fucosylated.

DP12, a dihydrofolate reductase minus (DHFR⁻) CHO cell line that is fucosylation competent, and Lec13, a cell line that is deficient in protein fucosylation were used to produce antibodies for this study. The CHO cell line Pro-Lec13.6a (Lec13), was obtained from Professor Pamela Stanley of Albert Einstein College of Medicine of Yeshiva University. Parental lines are Pro-(proline auxotroph) and Gat-(glycine, adenosine, thymidine auxotroph). The CHO-DP12 cell line is a derivative of the CHO-K1 cell line (ATCC #CCL-61), which is dihydrofolate reductase deficient, and has a reduced requirement for insulin. Cell lines were transfected with cDNA using the Superfect method (Qiagen, Valencia, Calif.). Selection of the Lec13 cells expressing transfected antibodies was performed using puromycin dihydrochloride (Calbiochem, San Diego, Calif.) at 10 µg/ml in growth medium containing: MEM Alpha Medium with L-glutamine, ribonucleosides and deoxyribonucleosides (GIBCO-BRL, Gaithersburg, Md.), supplemented with 10% inactivated FBS (GIBCO), 10 mM HEPES, and 1× penicillin/streptomycin (GIBCO). The CHO cells were similarly selected in growth medium containing Ham's F12 without GHT: Low Glucose DMEM without Glycine with NaHCO3 supplemented with 5% FBS (GIBCO), 10 mM HEPES, 2 mM L-glutamine, 1×GHT (glycine, hypoxanthine, thymidine), and 1× penicillin/streptomycin.

Colonies formed within two to three weeks and were pooled for expansion and protein expression. The cell pools were seeded initially at 3×10⁶ cells/10 cm plate for small batch protein expression. The cells were converted to serum-free media once they grew to 90-95% confluency and after 3-5 days cell supernatants were collected and tested in an Fc IgG- and intact IgG-ELISA to estimate protein expression levels. Lec13 and CHO cells were seeded at approximately 8×10⁶ cells/15 cm plate one day prior to converting to PS24 production medium, supplemented with 10 mg/L recombinant human insulin and 1 mg/L trace elements.

Lec13 cells and DP12 cells remained in serum-free production medium for 3-5 days. Supernatants were collected and clarified by centrifugation in 150 ml conical tubes to remove cells and debris. The protease inhibitors PMSF and aprotinin (Sigma, St. Louis, Mo.) were added and the supernatants were concentrated 5-fold on stirred cells using MWCO30 filters (Amicon, Beverly, Mass.) prior to immediate purification using protein G chromatography (Amersham Pharmacia Biotech, Piscataway, N.J.)). All proteins were buffer exchanged into phosphate-buffered saline (PBS) using Centripriep-30 concentrators (Amicon) and analyzed by SDS-polyacrylamide gel electrophoresis. Protein concentrations were determined using A280 and verified using amino acid composition analysis.

The CHO cells were transfected with vectors expressing humanized 2H7v16, 2H7v.31 and selected as described. The 2H7v.16 antibody retains the wild type Fc region while v.31 (see Example 5, Table 7 above) has an Fc region wherein 3 amino acid changes were made (S298A, E333A, K334A) which results in higher affinity for the FcγRIIIa receptor (Shields et al. J. Biol. Chem. 276 (9):6591-6604 (2001)). Following transfection and selection, individual colonies of cells were isolated and evaluated for protein expression level and the highest producers were subjected to methotrexate selection to select for cells that had amplified the plasmid copy number and which therefore produced higher levels of antibody. Cells were grown, transferred to serum free medium for a period of 7 days, then the medium was collected, loaded onto a protein A column and the antibody was eluted using standard techniques. The final concentration of the antibody was determined using an Elisa that measures intact antibody. All proteins were buffer exchanged into phosphate-buffered saline (PBS) using Centripriep-30 concentrators. (Amicon) and analyzed by SDS-polyacrylamide gel electrophoresis.

Matrix-Assisted Laser Desorption/Ionization Time-of-flight (MALDI-TOF) Mass Spectral Analysis of Asparagine-Linked Oligosaccharides: N-linked oligosaccharides were released from recombinant glycoproteins using the procedure of Papac et al., *Glycobiology* 8, 445-454 (1998). Briefly, the wells of a 96 well PVDF-lined microtitre plate (Millipore, Bedford, Mass.) were conditioned with 100 µl methanol that was drawn through the PDVF membranes by applying vacuum to the Millipore Multiscreen vacuum manifold. The conditioned PVDF membranes were washed with 3×250 µl water. Between all wash steps the wells were drained completely by applying gentle vacuum to the manifold. The membranes Were washed with reduction and carboxymethylation buffer (RCM) consisting of 6 M guanidine hydrochloride, 360 mM Tris, 2 mM EDTA, pH 8.6. Glycoprotein samples (50 µg) were applied to individual wells, again drawn through the PVDF membranes by gentle vacuum and the wells were washed with 2×50 µl of RCM buffer. The immobilized samples were reduced by adding 50 µl of a 0.1 M dithiothreitol (DTT) solution to each well and incubating the microtitre plate at 37° C. for 1 hr. DTT was removed by vacuum and the wells were washed 4×250 µl water. Cysteine residues were carboxylmethylated by the addition of 50 µl of a 0.1 M iodoacetic acid (IAA) solution which was freshly prepared in 1 M NaOH and diluted to 0.1 M with RCM buffer. Carboxymethylation was accomplished by incubation for 30 min in the dark at ambient temperature. Vacuum was applied to the plate to remove the IAA solution and the wells were washed with 4×250 µl purified water. The PVDF membranes were blocked by the addition of 100 µl of 1% PVP360 (polyvinylpyrrolidine 360,000 MW) (Sigma) solution and incubation for 1 hr at ambient temperature. The PVP-360 solution was removed by gentle vacuum and the wells were washed 4×250 µl water. The PNGase F (New England Biolabs, Beverly, Mass.) digest solution, 25 µl of a 25 Unit/ml solution in 10 mM Tris acetate, pH 8.4, was added to each well and the digest proceeded for 3 hr at 37° C. After digestion, the samples were transferred to 500 µl Eppendorf tubes and 2.5 µlL of a 1.5 M acetic acid solution was added to each sample. The acidified samples were incubated for 3 hr at ambient temperature to convert the oligosaccharides from glycosylamines to the hydroxyl form. Prior to MALDI-TOF mass spectral analysis, the released oligosaccharides were desalted using a 0.7-ml bed of cation exchange resin (AG50W-X8 resin in the hydrogen form) (Bio-Rad, Hercules, Calif.) slurried packed into compact reaction tubes (US Biochemical, Cleveland, Ohio).

For MALDI-TOF mass spectral analysis of the samples in the positive mode, the desalted oligosaccharides (0.5 µl aliquots) were applied to the stainless target with 0.5 µl of the 2,5 dihydroxybenzoic acid matrix (sDHB) that was prepared by dissolving 2 mg 2,5 dihydroxybenzoic acid with 0.1 mg of 5-methoxysilycylic acid in 1 ml of ethanol/O mM sodium chloride 1:1 (v/v). The sample/matrix mixture was dried by vacuum. For analysis in the negative mode, the desalted N-linked oligosaccharides (0.5 µl aliquots) were applied to the stainless target along with 0.5 µl 2',4',6'-trihydroxyacetophenone matrix (THAP) prepared in 1:3 (v/v) acetonitrile/13.3 mM ammonium citrate buffer. The sample/matrix mixture was vacuum dried and then allowed to absorb atmospheric moisture prior to analysis. Released oligosaccharides were analyzed by MALDI-TOF on a PerSeptive BioSystems Voyager-DE mass spectrometer. The mass spectrometer was operated at 20 kV either in the positive or negative mode with the linear configuration and utilizing delayed extraction. Data were acquired using a laser power of 1300 and in the data summation mode (240 scans) to improve the signal to noise. The instrument was calibrated with a mixture of standard oligosaccharides and the data was smoothed using a 19 point Savitsky-Golay algorithm before the masses were assigned. Integration of the mass spectral data was achieved using Caesar 7.0 data analysis software package (SciBridge Software).

Natural Killer (NK) Cell Antibody Dependent Cytoxicity Assays.

ADCC assays were performed as described in Example 9. NK to target cell (WIL2-S) ratio was 4 to 1, assays were run for 4 hours, and toxicity was measured as before using lactose dehydrogenase assay. Target cells were opsonized with the concentrations of antibody indicated for 30 min prior to addition of NK cells. The Rituxan® antibody used was from Genentech (S. San Francisco, Calif.). FIG. 12 shows the results of a representative ADCC assay.

The results show that underfucosylated antibodies mediate NK cell target cell killing more efficiently than do antibodies with a full complement of fucose. The underfucosylated antibody, 2H7v.31, is most efficient at mediating target cell killing. This antibody is effective at lower concentrations and is capable of mediating killing of a greater percentage of target cells at higher concentrations than are the other antibodies. The activity of the antibodies is as follows: Lec13-derived 2H7 v31>Lec 13 derived 2H7v16>Dp12 derived 2H7v31>Dp12 derived 2H7v16> or =to Rituxan. The protein and carbohydrate alterations are additive. Comparison of the carbohydrate found on native IgG from the Lec13-produced and CHO-produced IgG showed no appreciable differences in the extent of galactosylation and hence the results can be attributed solely to the presence/absence of fucose.

Example 12

Fucose-Deficient 2H7 Variant Antibodies with Enhanced ADCC in Vivo

This example describes ADCC activity in vivo of the fucose-deficient humanized 2H7 variants including v.16 and v.31 produced in Lec13 compared to normal fucosylated counterparts produced in DP12, in mice expressing human CD16 [FcRγIII] and human CD20.

Generation of huCD20Tg$^+$ huCD16Tg$^+$ mCD16$^{-/-}$ Mice

Human CD20 transgenic mice were generated from human CD20 BAC DNA (Invitrogen, Carlsbad, Calif.). Mice were screened based on the FACS analysis of human CD20 expression. HuCD20 Tg$^+$ mice were then crossed with huCD16Tg$^+$ mCD16$^{-/-}$ mice to generate huCD20 Tg$^+$huCD16Tg$^+$ mCD16$^{-/-}$ mice.

In Vivo Treatment

Ten to 100 µg of each of the 2H7 variants or Rituxan® is administrated to huCD20Tg$^+$huCD16Tg$^+$mCD16$^{-/-}$ mice via intraperitoneal injections. Equal amount of isotype-matched antibodies will be applied similarly to the negative control group of animals.

Mouse Lymphocytes Preparation

Mouse lymphocytes from whole blood, spleen, lymph nodes and bone marrow are prepared according to standard protocol described in "Current Protocols in Immunology, edited by John Coligan, Ada Kruisbeek, David Margulies, Ethan Shevach and Warren Strober, 1994".

FACS Analysis

Half million cells are washed and resuspended in 100 µl of FACS buffer, which is phosphate buffered saline with 1% BSA, containing 5 µl of staining or control antibody. All the staining antibodies, including isotype controls, are obtained from PharMingen, San Diego, Calif. Human CD20 expression is assessed by staining with Rituxan® along with FITC-conjugated anti-human IgG1 secondary antibody. FACS analysis is conducted using FACScan and Cell Quest (Becton Dickinson Immunocytometry Systems, San Jose, Calif.). All the lymphocytes are defined in the forward and side light scatterings, while all the B lymphocytes are defined with the expression of B220 on the cell surface.

B cell depletion and recovery are assessed by analyzing peripheral B cell counts and analysis of hCD20+ B cells by FACS in the spleen, lymph node and bone marrow on a daily basis for the first week after injection and thereafter on a weekly basis. Serum levels of the injected 2H7 variant antibody are monitored.

The results of this in vivo assay confirms the in vitro findings on the increased ADCC activity and greater B cell depletion of fucose-deficient 2H7 variants over wild-type (with respect to fucosylation) glycosylation counterparts.

Example 13

Apoptosis Activity

Anti-CD20 antibodies including Rituxan® have been shown to induce apoptosis in vitro when crosslinked by a secondary antibody or by chemical means (Shan et al., Blood 9:1644-1652 (1998); Byrd et al., Blood 99:1038-43 (2002); Pederson et al., Blood 99:1314-19 (2002)). When chemically crosslinked, murine 2H7 dimers induced apoptosis of Daudi cells (Ghetie et al., Proc Natl Acad Sci USA 94:7509-14 (1997)). Crosslinking with a secondary antibody also induced apoptosis with the murine 2H7 antibody (Shan et al., 1998). These activities are believed to be physiologically relevant because a variety of mechanisms could lead to crosslinking of anti-CD20 antibodies bound to cell-surface CD20 in vivo.

RhuMAb 2H7.v16 [humanized 2H7 v16; RhuMAb stands for recombinant human monoclonal antibody] and Rituxan® were compared in apoptosis assays in vitro using a secondary crosslinking antibody. Ramos cells (CRL-1596, ATCC, Manassas, Va.), a CD20-expressing, human B lymphocyte cell line, were used to measure the ability of the anti-CD20 monoclonal antibodies rhuMAb 2H7.v16 and Rituximab versus a negative-control antibody, Trastuzumab (Herceptin®, Genentech, South San Francisco, Calif.), to induce apoptosis as measured through Annexin V staining and propidium iodide dye exclusion (Vybrant® Apoptosis Assay Kit, Molecular Probes, Seattle, Wash.). The Ramos cells were cultured in RPMI-1640 medium (Gibco, Rockville, Md.) containing 10% fetal bovine serum (Biosource International, Camarillo, Calif.) and 2 mM L-glutamine (Gibco). Prior to being assayed, the cells were washed twice in fresh media and then adjusted to a cell concentration of $2 \times 10^6$ per mL. Cells (150 µL) were added to 96-well assay plates (Becton Dickinson, Palo Alto, Calif.) which contained 150 µL of a predetermined amount of control IgG1, rhuMAb 2H7.v16, or Rituximab, along with F(ab)'2 goat anti-human Fc (Pierce Biotechnology, Rockford, Ill.). The final IgG concentrations were 100, 10, 1.0, 0.1, 0.01 and 0.001 nM, and the F(ab)'2 goat anti-human Fc antibody concentration was set at twice the respective sample antibody concentration. Each dilution was set up in triplicate. After a 24-hour incubation at 37° C., the cells were washed twice with PBS and then stained with Annexin V and propidium iodide according to the manufacturer's recommendations. The staining patterns of the Ramos cells were analyzed by flow cytometry using a FACscan Flow Cytometer (Becton Dickinson, San Jose, Calif.), and data were collected for 10 s-periods. The data were reduced using the Cellquest Pro software (Becton Dickinson). Ramos cells that were positive for (1) Annexin V staining, (2) Annexin V and propiduim iodide double-staining, and (3) the number of unstained live cells, were counted and plotted using Kaleida-Graph software (Synergy Software, Reading, Pa.).

Both rhuMAb 2H7.v16 and Rituximab induced apoptosis of Ramos cells when crosslinked with anti-human Fc and as compared to an irrelevant IgG1 control antibody (FIGS. 13-15). The apoptotic activity of (rhuMAb 2H7) was slightly lower than that of Rituximab. At 10 nM concentrations of crosslinked rhuMAb 2H7, Rituximab, and control IgG1 antibody, fractions of Annexin V stained cells were 18.5, 16.5, 2.5%, respectively, fractions of doubly labeled cells were 29, 38, and 16%, and numbers of live cells counted per 10 s were 5200, 3100, and 8600.

These in vitro data demonstrate that apoptosis is one potential mechanism for in vivo B cell depletion. In vivo crosslinking of rhuMAb 2H7 or Rituximab bound to cell-surface CD20 may occur through FcγR on the surfaces of immune effector cells.

Example 14

In Vivo Suppression of Tumor Growth

The ability of rhuMAb 2H7.v16 to inhibit the growth of the Raji human B-cells, a lymphoma cell line (ATCC CCL 86), was evaluated in Balb/c nude (athymic) mice. The Raji cells express CD20 and have been reported to grow in nude mice, producing metastatic disease; tumor growth is inhibited by Rituxan® (Clynes et al., *Nature Medicine* 6, 443-446 (2000)). Fifty-six 8-10 week old, Balb/c nude mice were divided into 7 groups (A-G) with each group consisting of 8 mice. On day 0, each mouse received a subcutaneous injection of $5 \times 10^6$ Raji B-lymphoma cells in the flank. Beginning at day 0, each mouse received either 100 uL of the negative-control solution (PBS; phosphate-buffered saline), Rituxan® or 2H7.v16. Dosage was dependent on weight and drug delivery was intravenously via the tail vein. Group A mice received PBS. Groups B-D received Rituxan® at 5.0, mg/kg, 0.5 mg/kg, and 0.05 mg/kg respectively. Groups E-G mice received 2H7 v.16 at 5.0 mg/kg, 0.5 mg/kg, and 0.05 mg/kg respectively. The injections were repeated every week for 6 weeks. At weekly intervals during treatment, each mouse was inspected for the presence of palpable tumors at the site of injection, and the volume of the tumors if present were measured and recorded. A final inspection was made at week 8 (after a two-week interval of no treatments).

The results of this study showed that both rhuMAb 2H7.v16 and Rituxan® and were effective at inhibiting subcutaneous Raji-cell tumor growth in nude mice (FIGS. 16-18). Tumor growth was observed in the PBS control group beginning at 4 weeks. However, no tumor growth was observed in groups treated with Rituxan® or 2H7.v16 at 5 mg/kg or 0.5 mg/kg for the 8-week duration of the study. In the low-dose 0.05 mg/kg treatment groups, tumors were observed in one animal in the 2H7 group and in one animal in the Rituxan® group (FIG. 18).

Example 15

Cloning of Cynomolgus Monkey CD20 and Antibody Binding

The CD20 DNA sequence for cynomolgus monkey (*Macaca fascicularis*) was determined upon the isolation of cDNA encoding CD20 from a cynomolgus spleen cDNA library. A SUPERSCRIPT™ Plasmid System for cDNA Synthesis and Plasmid Cloning (Cat# 18248-013, Invitrogen, Carlsbad, Calif.) was used with slight modifications to construct the library. The cDNA library was ligated into a pRK5E vector using restriction sites Xho I- and Not I. mRNA was isolated from spleen tissue ((California Regional Research Primate Center, Davis, Calif.). Primers to amplify cDNA encoding CD20 were designed based on non-coding sequences of human CD20. N-terminal region primer 5'-AGTTTTGAGAGCAAAATG-3' (SEQ ID NO. 37) and C-terminal region primer 5'-AAGCTATGAACACTAATG-3' (SEQ ID NO. 38) were used to clone by polymerase chain reaction (PCR) the cDNA encoding cynomolgus monkey CD20. The PCR reaction was carried out using Platinum Taq DNA Polymerase High Fidelity according to the manufacturer's recommendation (Gibco, Rockville, Md.). The PCR product was subcloned into pCR® 2.1-TOPO® Vector (Invitrogen) and transformed into XL-1 blue *E. coli* (Stratagene. La Jolla, Calif.). Plasmid DNA containing ligated PCR products was isolated from individual clones and sequenced.

The amino acid sequence for cynomolgus monkey CD20 is shown in FIG. 19. FIG. 20 shows a comparison of cynomolgus and human CD20. The cynomolgus monkey CD20 is 97.3% similar to human CD20 with 8 differences. The extracellular domain contains one change at V157A, while the remaining 7 residues can be found in the cytoplasmic or transmembrane regions.

Antibodies directed against human CD20 were assayed for the ability to bind and displace FITC-conjugated murine 2H7 binding to cynomolgus monkey cells expressing CD20. Twenty milliliters of blood were drawn from 2 cynomolgus monkeys (California Regional Research Primate Center, Davis, Calif.) into sodium heparin and shipped directly to Genentech Inc. On the same day, the blood samples were pooled and diluted 1:1 by the addition of 40 ml of phosphate buffered saline (PBS). 20 ml of diluted blood was layered on 4×20 ml of Ficoll-Paque™ Plus (Amersham Biosciences, Uppsala, Sweden) in 50 ml conical tubes (Cat#352098, Falcon, Franklin Lakes, N.J.) and centrifuged at 1300 rpm for 30 minutes R.T. in a Sorval 7 centrifuge. (Dupont, Newtown, Conn.). The PBMC layer was isolated and washed in PBS. Red blood cells were lysed in a 0.2% NaCl solution, restored to isotonicity with an equivalent volume of a 1.6% NaCl solution, and centrifuged for 10 minutes at 1000 RPM. The PBMC pellet was resuspended in RPMI 1640 (Gibco, Rockville, Md.) containing 5% fetal bovine serum (FBS) and dispensed into a 10 cm tissue culture dish for 1 hour at 37° C. The non-adherent B and T cell populations were removed by aspiration, centrifuged and counted. A total of $2.4 \times 10^7$ cells were recovered. The resuspended PBMC were distributed into twenty 12×75 mm culture tubes (Cat#352053, Falcon), with each tube containing $1 \times 10^6$ cells in a volume of 0.25 ml. Tubes were divided into four sets of five tubes. To each set was added either media (RPMI1640, 5% FBS), titrated amounts of control human $IgG_1$ antibody, Rituxan®, 2H7.v16, or 2H7.v31, The final concentration of each antibody was 30, 10, 3.3 and 1.1 nM. In addition, each tube also received 20 ul of Fluorescein Isothiocyanate (FITC)-conjugated anti-human CD20 (Cat#555622, BD Biosciences, San Diego, Calif.). The cells were gently mixed, incubated for 1 hour on ice and then washed twice in cold PBS. The cell surface staining was analyzed on a Epic XL-MCL (Coulter, Miami, Fla.), the geometric means derived, plotted (Kaleida-Graph™, Synergy Software, Reading, Pa.) versus antibody concentrations.

Data in FIG. 21 showed that 2H7 v.16 and 2H7 v.31 competitively displaced FITC-murine 2H7 binding to cynomolgus monkey cells. Furthermore, Rituxan® also displaced FITC-murine 2H7 binding thus demonstrating that both 2H7 and Rituxan® bind to an overlapping epitope on CD20. In addition, the data show that the $IC_{50}$ value for 2H7 v.16, 2H7 v.31 and Rituxan are similar and fall in the 4-6 nM range.

Example 16

Phase I/II Study of rhuMAb 2H7 (2H7.v16) in Moderate to Severe Rheumatoid Arthritis Protocol Synopsis
A randomized, placebo-controlled, multicenter, blinded phase I/II study of the safety of escalating doses of PRO70769 (rhuMAb 2H7) in subjects with moderate to severe rheumatoid arthritis receiving stable doses of concomitant methotrexate.
Objectives
The primary objective of this study is to evaluate the safety and tolerability of escalating intravenous (IV) doses of PRO70769 (rhuMAb 2H7) in subjects with moderate to severe rheumatoid arthritis (RA).
Study Design
This is a randomized, placebo-controlled, multicenter, blinded Phase I/II, investigator- and subject-blinded study of the safety of escalating doses of PRO70769 in combination with MTX in subjects with moderate to severe RA. The study consists of a dose escalation phase and a second phase with enrollment of a larger number of subjects. The Sponsor will remain unblinded to treatment assignment.

Subjects with moderate to severe RA who have failed one to five disease-modifying antirheumatic drugs or biologics who currently have unsatisfactory clinical responses to treatment with MTX will be enrolled.

Subjects will be required to receive MTX in the range of 10-25 mg weekly for at least 12 weeks prior to study entry and to be on a stable dose for at least 4 weeks before receiving their initial dose of study drug (PRO70769 or placebo). Subjects may also receive stable doses of oral corticosteroids (up to 10 mg daily or prednisone equivalent) and stable doses of nonsteroidal anti-inflammatory drugs (NSAIDs). Subjects will receive two IV infusions of PRO70769 or placebo equivalent at the indicated dose on Days 1 and 15 according to the following dose escalation plan (see FIG. 22).

Dose escalation will occur according to specific criteria and after review of safety data by an internal safety data review committee and assessment of acute toxicity 72 hours following the second infusion in the last subject treated in each cohort. After the dose escalation phase, 40 additional subjects (32 active and 8 placebo) will be randomized to each of the following dose levels: 2×50 mg, 2×200 mg, 2×500 mg, and 2×1000 mg, if the dose levels have been demonstrated to be tolerable during the dose escalation phase. Approximately 205 subjects will be enrolled in the study.

B-cell counts will be obtained and recorded. B-cell counts will be evaluated using flow cytometry in a 48-week follow-up period beyond the 6-month efficacy evaluation. B-cell depletion will not be considered a dose-limiting toxicity (DLC), but rather the expected pharmacodynamic outcome of PRO70769 treatment.

In an optional substudy, blood for serum and RNA analyses, as well as urine samples will be obtained from subjects at various timepoints. These samples may be used to identify biomarkers that may be predictive of response to PRO70769 treatment in subjects with moderate to severe RA.
Outcome Measures
The primary outcome measure for this study is the safety and tolerability of PRO70769 in subjects with moderate to severe RA.
Study Treatment
Cohorts of subjects will receive two IV infusions of PRO70769 or placebo equivalent at the indicated dose on Days 1 and 15 according to the following escalation plan:
  10 mg PRO70769 or placebo equivalent: 4 subjects active drug, 1 control
  50 mg PRO70769 or placebo equivalent: 8 subjects active drug, 2 control
  200 mg PRO70769 or placebo equivalent: 8 subjects active drug, 2 control
  500 mg PRO70769 or placebo equivalent: 8 subjects active drug, 2 control
  1000 mg PRO70769 or placebo equivalent: 8 subjects active drug, 2 control
Efficacy
The efficacy of PRO70769 will be measured by ACR responses. The percentage of subjects who achieve an ACR20, ACR50, and ACR70 response will be summarized by treatment group and 95% confidence intervals will be generated for each group. The components of these response and their change from baseline will be summarized by treatment and visit.

CONCLUSION

The data above demonstrated the success in producing humanized CD20 binding antibodies, in particular humanized 2H7 antibody variants, that maintained and even enhanced their biological properties. The humanized 2H7 antibodies of the invention bound to CD20 at affinities similar to the murine donor and chimeric 2H7 antibodies and were effective at B cell killing in a primate, leading to B cell depletion. Certain variants showed enhanced ADCC over a chimeric anti-CD20 antibody currently used to treat NHL, favoring the use of lower doses of the therapeutic antibody in patients. Additional, whereas it may be necessary for a chimeric antibody that has murine FR residues to be administered at a dose effective to achieve complete B cell depletion to obviate an antibody response against it, the present humanized antibodies can be administered at dosages that achieve partial or complete B cell depletion, and for different durations of time, as desired for the particular disease and patient.

In addition, these antibodies demonstrated stability in solution. These properties of the humanized 2H7 antibodies make them ideal for use as immunotherapeutic agent in the treatment of CD20 positive cancers and autoimmune diseases; these antibodies are not expected to be immunogenic or will at least be less immunogenic than fully murine or chimeric anti-CD20 antibodies in human patients.

REFERENCES

References cited within this application, including patents, published applications and other publications, are hereby incorporated by reference.

The practice of the present invention will employ, unless otherwise indicated, conventional techniques of molecular biology and the like, which are within the skill of the art. Such techniques are explained fully in the literature. See e.g., *Molecular Cloning: A Laboratory Manual*, (J. Sambrook et al., Cold Spring Harbor Laboratory, Cold Spring Harbor, N.Y., 1989); *Current Protocols in Molecular Biology* (F. Ausubel et al., eds., 1987 updated); *Essential Molecular Biology* (T. Brown ed., IRL Press 1991); *Gene Expression Technology* (Goeddel ed., Academic Press 1991); *Methods for Cloning and Analysis of Eukaryotic Genes* (A. Bothwell et al. eds., Bartlett Publ. 1990); *Gene Transfer and Expression* (M. Kriegler, Stockton Press 1990); *Recombinant DNA Methodology II* (R. Wu et al. eds., Academic Press 1995); *PCR: A Practical Approach* (M. McPherson et al., IRL Press at Oxford University Press 1991); *Oligonucleotide Synthesis* (M. Gait ed., 1984); *Cell Culture for Biochemists* (R. Adams ed., Elsevier Science Publishers 1990); *Gene Transfer Vectors for Mammalian Cells* (J. Miller & M. Calos eds., 1987); *Mammalian Cell Biotechnology* (M. Butler ed., 1991); *Animal Cell Culture* (J. Pollard et al. eds., Humana Press 1990); *Culture of Animal Cells, 2$^{nd}$ Ed.* (R. Freshney et al. eds., Alan R. Liss 1987); *Flow Cytometry and Sorting* (M. Melamed et al. eds., Wiley-Liss 1990); the series *Methods in Enzymology* (Academic Press, Inc.); Wirth M. and Hauser H. (1993); *Immunochemistry in Practice,* 3rd edition, A. Johnstone & R. Thorpe, Blackwell Science, Cambridge, Mass., 1996; *Techniques in Immunocytochemistry*, (G. Bullock & P. Petrusz eds., Academic Press 1982, 1983, 1985, 1989); Handbook of Experimental Immunology, (D. Weir & C. Blackwell, eds.); *Current Protocols in Immunology* (J. Coligan et al. eds. 1991); *Immunoassay* (E. P. Diamandis & T. K. Christopoulos, eds., Academic Press, Inc., 1996); Goding (1986) *Monoclonal Antibodies: Principles and Practice* (2d ed) Academic Press, New York; Ed Harlow and David Lane, *Antibodies A laboratory Manual*, Cold Spring Harbor Laboratory, Cold Spring Harbor, N.Y., 1988; *Antibody Engineering, 2$^{nd}$* edition (C. Borrebaeck, ed., Oxford University Press, 1995); and the series Annual Review of Immunology; the series Advances in Immunology.

What is claimed is:

1. A method of treating multiple sclerosis, comprising administering to a patient suffering from multiple sclerosis, a therapeutically effective amount of a humanized antibody that binds human CD20 or an antigen-binding fragment thereof, wherein the antibody comprises the $V_H$ sequence of SEQ ID NO.8 and the $V_L$ sequence of SEQ ID NO.2.

2. The method of claim 1, wherein the antibody or the antigen-binding fragment is administered at a dosage selected from 2×10 mg, 2×50 mg, 2×200 mg and 2×500 mg.

3. The method of claim 1, wherein the antibody or the antigen-binding fragment is administered by intravenous infusion.

4. The method of claim 1, wherein the antibody comprises the heavy chain and light chain amino acid sequences of SEQ ID NO. 39 and 40, respectively.

5. The method of claim 1, wherein the antibody comprises the light chain and heavy chain amino acid sequences of SEQ ID NO. 40 and 41, respectively.

6. The method of claim 1, wherein the antibody or the antigen-binding fragment is administered subcutaneously.

* * * * *

UNITED STATES PATENT AND TRADEMARK OFFICE
CERTIFICATE OF CORRECTION

| | |
|---|---|
| PATENT NO. | : 8,562,992 B2 |
| APPLICATION NO. | : 12/256349 |
| DATED | : October 22, 2013 |
| INVENTOR(S) | : Adams et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 769 days.

Signed and Sealed this
First Day of September, 2015

Michelle K. Lee
*Director of the United States Patent and Trademark Office*

SEQUENCE LISTING

```
<160> NUMBER OF SEQ ID NOS: 55

<210> SEQ ID NO 1
<211> LENGTH: 107
<212> TYPE: PRT
<213> ORGANISM: Mus musculus

<400> SEQUENCE: 1

Gln Ile Val Leu Ser Gln Ser Pro Ala Ile Leu Ser Ala Ser Pro
 1               5                  10                  15

Gly Glu Lys Val Thr Met Thr Cys Arg Ala Ser Ser Ser Val Ser
                20                  25                  30

Tyr Met His Trp Tyr Gln Gln Lys Pro Gly Ser Ser Pro Lys Pro
                35                  40                  45

Trp Ile Tyr Ala Pro Ser Asn Leu Ala Ser Gly Val Pro Ala Arg
                50                  55                  60

Phe Ser Gly Ser Gly Ser Gly Thr Ser Tyr Ser Leu Thr Ile Ser
                65                  70                  75

Arg Val Glu Ala Glu Asp Ala Ala Thr Tyr Tyr Cys Gln Gln Trp
                80                  85                  90

Ser Phe Asn Pro Pro Thr Phe Gly Ala Gly Thr Lys Leu Glu Leu
                95                  100                 105

Lys Arg

<210> SEQ ID NO 2
<211> LENGTH: 107
<212> TYPE: PRT
<213> ORGANISM: Artificial sequence
<220> FEATURE:
<223> OTHER INFORMATION: Sequence is synthesized

<400> SEQUENCE: 2
```

```
Asp Ile Gln Met Thr Gln Ser Pro Ser Ser Leu Ser Ala Ser Val
1               5                  10                  15

Gly Asp Arg Val Thr Ile Thr Cys Arg Ala Ser Ser Ser Val Ser
                20                  25                  30

Tyr Met His Trp Tyr Gln Gln Lys Pro Gly Lys Ala Pro Lys Pro
            35                  40                  45

Leu Ile Tyr Ala Pro Ser Asn Leu Ala Ser Gly Val Pro Ser Arg
        50                  55                  60

Phe Ser Gly Ser Gly Ser Gly Thr Asp Phe Thr Leu Thr Ile Ser
65                  70                  75

Ser Leu Gln Pro Glu Asp Phe Ala Thr Tyr Tyr Cys Gln Gln Trp
        80                  85                  90

Ser Phe Asn Pro Pro Thr Phe Gly Gln Gly Thr Lys Val Glu Ile
        95                  100                 105

Lys Arg
```

```
<210> SEQ ID NO 3
<211> LENGTH: 108
<212> TYPE: PRT
<213> ORGANISM: Artificial Sequence
<220> FEATURE:
<223> OTHER INFORMATION: Sequence is synthesized

<400> SEQUENCE: 3

Asp Ile Gln Met Thr Gln Ser Pro Ser Ser Leu Ser Ala Ser Val
1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
        80                  85                  90

Tyr Asn Ser Leu Pro Trp Thr Phe Gly Gln Gly Thr Lys Val Glu
        95                  100                 105

Ile Lys Arg
```

```
<210> SEQ ID NO 4
<211> LENGTH: 10
<212> TYPE: PRT
<213> ORGANISM: Mus musculus

<400> SEQUENCE: 4

Arg Ala Ser Ser Ser Val Ser Tyr Met His
  5                  10
```

```
<210> SEQ ID NO 5
<211> LENGTH: 7
<212> TYPE: PRT
<213> ORGANISM: Mus musculus

<400> SEQUENCE: 5

Ala Pro Ser Asn Leu Ala Ser
  5
```

```
<210> SEQ ID NO 6
```

```
<211> LENGTH: 9
<212> TYPE: PRT
<213> ORGANISM: Mus musculus

<400> SEQUENCE: 6

Gln Gln Trp Ser Phe Asn Pro Pro Thr
  1               5

<210> SEQ ID NO 7
<211> LENGTH: 122
<212> TYPE: PRT
<213> ORGANISM: Mus musculus

<400> SEQUENCE: 7

Gln Ala Tyr Leu Gln Gln Ser Gly Ala Glu Leu Val Arg Pro Gly
  1               5                  10                  15

Ala Ser Val Lys Met Ser Cys Lys Ala Ser Gly Tyr Thr Phe Thr
                 20                  25                  30

Ser Tyr Asn Met His Trp Val Lys Gln Thr Pro Arg Gln Gly Leu
             35                  40                  45

Glu Trp Ile Gly Ala Ile Tyr Pro Gly Asn Gly Asp Thr Ser Tyr
         50                  55                  60

Asn Gln Lys Phe Lys Gly Lys Ala Thr Leu Thr Val Asp Lys Ser
             65                  70                  75

Ser Ser Thr Ala Tyr Met Gln Leu Ser Ser Leu Thr Ser Glu Asp
                 80                  85                  90

Ser Ala Val Tyr Phe Cys Ala Arg Val Val Tyr Tyr Ser Asn Ser
                 95                 100                 105

Tyr Trp Tyr Phe Asp Val Trp Gly Thr Gly Thr Thr Val Thr Val
                110                 115                 120

Ser Ser

<210> SEQ ID NO 8
<211> LENGTH: 122
<212> TYPE: PRT
<213> ORGANISM: Artificial sequence
<220> FEATURE:
<223> OTHER INFORMATION: Sequence is synthesized

<400> SEQUENCE: 8

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                 20                  25                  30

Ser Tyr Asn Met His Trp Val Arg Gln Ala Pro Gly Lys Gly Leu
             35                  40                  45

Glu Trp Val Gly Ala Ile Tyr Pro Gly Asn Gly Asp Thr Ser Tyr
         50                  55                  60

Asn Gln Lys Phe Lys Gly Arg Phe Thr Ile Ser Val Asp Lys Ser
             65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Val Val Tyr Tyr Ser Asn Ser
                 95                 100                 105

Tyr Trp Tyr Phe Asp Val Trp Gly Gln Gly Thr Leu Val Thr Val
                110                 115                 120

Ser Ser
```

```
<210> SEQ ID NO 9
<211> LENGTH: 119
<212> TYPE: PRT
<213> ORGANISM: Artificial Sequence
<220> FEATURE:
<223> OTHER INFORMATION: Sequence is synthesized

<400> SEQUENCE: 9

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
            35                  40                  45

Glu Trp Val Ala Val Ile Ser Gly Asp Gly Gly Ser Thr Tyr Tyr
        50                  55                  60

Ala Asp Ser Val Lys Gly Arg Phe Thr Ile Ser Arg Asp Asn Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Arg Val Gly Tyr Ser Leu
            95                  100                 105

Tyr Asp Tyr Trp Gly Gln Gly Thr Leu Val Thr Val Ser Ser
        110                 115

<210> SEQ ID NO 10
<211> LENGTH: 10
<212> TYPE: PRT
<213> ORGANISM: Mus musculus

<400> SEQUENCE: 10

Gly Tyr Thr Phe Thr Ser Tyr Asn Met His
 5                  10

<210> SEQ ID NO 11
<211> LENGTH: 17
<212> TYPE: PRT
<213> ORGANISM: Mus musculus

<400> SEQUENCE: 11

Ala Ile Tyr Pro Gly Asn Gly Asp Thr Ser Tyr Asn Gln Lys Phe
 1               5                  10                  15

Lys Gly

<210> SEQ ID NO 12
<211> LENGTH: 13
<212> TYPE: PRT
<213> ORGANISM: Mus musculus

<400> SEQUENCE: 12

Val Val Tyr Tyr Ser Asn Ser Tyr Trp Tyr Phe Asp Val
                5                  10

<210> SEQ ID NO 13
<211> LENGTH: 5679
<212> TYPE: DNA
<213> ORGANISM: Artificial Sequence
<220> FEATURE:
<223> OTHER INFORMATION: Sequence is synthesized

<400> SEQUENCE: 13
gaattcaact tctccatact ttggataagg aaatacagac atgaaaaatc          50
```

```
tcattgctga gttgttattt aagcttgccc aaaaagaaga agagtcgaat    100
gaactgtgtg cgcaggtaga agctttggag attatcgtca ctgcaatgct    150
tcgcaatatg gcgcaaaatg accaacagcg gttgattgat caggtagagg    200
gggcgctgta cgaggtaaag cccgatgcca gcattcctga cgacgatacg    250
gagctgctgc gcgattacgt aaagaagtta ttgaagcatc ctcgtcagta    300
aaaagttaat cttttcaaca gctgtcataa agttgtcacg gccgagactt    350
atagtcgctt tgttttattt ttttaatgta tttgtaacta gaattcgagc    400
tcggtacccg gggatcctct agaggttgag gtgattttat gaaaaagaat    450
atcgcatttc ttcttgcatc tatgttcgtt ttttctattg ctacaaacgc    500
gtacgctgat atccagatga cccagtcccc gagctccctg tccgcctctg    550
tgggcgatag ggtcaccatc acctgcagag ccagtcagag cgtgtcgact    600
agctcttata gctatatgca ctggtatcaa cagaaaccag gaaaagctcc    650
gaaactactg atttactatg ctagcaacct cgagtctgga gtcccttctc    700
gcttctctgg atccggttct gggacggatt tcactctgac catcagcagt    750
ctgcagccag aagacttcgc aacttattac tgtcaacact cttggggtat    800
tccgcgcaca tttggacagg gtaccaaggt ggagatcaaa cgaactgtgg    850
ctgcaccatc tgtcttcatc ttcccgccat ctgatgagca gttgaaatct    900
ggaactgctt ctgttgtgtg cctgctgaat aacttctatc ccagagaggc    950
caaagtacag tggaaggtgg ataacgccct ccaatcgggt aactcccagg    1000
agagtgtcac agagcaggac agcaaggaca gcacctacag cctcagcagc    1050
accctgacgc tgagcaaagc agactacgag aaacacaaag tctacgcctg    1100
cgaagtcacc catcagggcc tgagctcgcc cgtcacaaag agcttcaaca    1150
ggggagagtg ttaagctgat cctctacgcc ggacgcatcg tggccctagt    1200
acgcaagttc acgtaaaaag ggtatctaga ggttgaggtg attttatgaa    1250
aaagaatatc gcatttcttc ttgcatctat gttcgttttt tctattgcta    1300
caaacgcgta cgctgaggtt cagctggtgg agtctggcgg tggcctggtg    1350
cagccagggg gctcactccg tttgtcctgt gcagcttctg gctacacctt    1400
caccgaatat atcatccact gggtccgtca ggccccgggt aagggcctgg    1450
aatgggttgc atcgattaat cctgactacg acatcacgaa ctataaccag    1500
cgcttcaagg gccgtttcac tataagtcgc gacgattcca aaaacacatt    1550
atacctgcag atgaacagcc tgcgtgctga ggacactgcc gtctattatt    1600
gtgctcgatg gatcagcgat ttcttcgact actggggtca aggaaccctg    1650
gtcaccgtct cctcggcctc caccaagggc ccatcggtct tccccctggc    1700
accctcctcc aagagcacct ctgggggcac agcggccctg ggctgcctgg    1750
tcaaggacta cttccccgaa ccggtgacgg tgtcgtggaa ctcaggcgcc    1800
ctgaccagcg gcgtgcacac cttcccggct gtcctacagt cctcaggact    1850
ctactccctc agcagcgtgg tgaccgtgcc ctccagcagc ttgggcaccc    1900
agacctacat ctgcaacgtg aatcacaagc ccagcaacac caaggtggac    1950
aagaaagttg agcccaaatc ttgtgacaaa actcacacat gaccaccgca    2000
tgcaccagta tcgtccattc cgacagcatc gccagtcact atggcgtgct    2050
```

| | |
|---|---|
| gctagcgccg ccctatacct tgtctgcctc cccgcgttgc gtcgcggtgc | 2100 |
| atggagccgg gccacctcga cctgaatgga agccggcggc acctcgctaa | 2150 |
| cggattcacc actccaagaa ttggagccaa tcaattcttg cggagaactg | 2200 |
| tgaatgcgca aaccaaccct tggcagaaca tatccatcgc gtccgccatc | 2250 |
| tccagcagcc gcacgcggcg catctcgggc agcgttgggt cctggccacg | 2300 |
| ggtgcgcatg atcgtgctcc tgtcgttgag gacccggcta ggctggcggg | 2350 |
| gttgccttac tggttagcag aatgaatcac cgatacgcga gcgaacgtga | 2400 |
| agcgactgct gctgcaaaac gtctgcgacc tgagcaacaa catgaatggt | 2450 |
| cttcggtttc cgtgtttcgt aaagtctgga aacgcggaag tcagcgccct | 2500 |
| gcaccattat gttccggatc tgcatcgcag gatgctgctg gctaccctgt | 2550 |
| ggaacaccta catctgtatt aacgaagcgc tggcattgac cctgagtgat | 2600 |
| ttttctctgg tcccgccgca tccataccgc cagttgttta ccctcacaac | 2650 |
| gttccagtaa ccgggcatgt tcatcatcag taacccgtat cgtgagcatc | 2700 |
| ctctctcgtt tcatcggtat cattaccccc atgaacagaa attcccccct | 2750 |
| acacggaggc atcaagtgac caaacaggaa aaaaccgccc ttaacatggc | 2800 |
| ccgctttatc agaagccaga cattaacgct tctggagaaa ctcaacgagc | 2850 |
| tggacgcgga tgaacaggca gacatctgtg aatcgcttca cgaccacgct | 2900 |
| gatgagcttt accgcagcat ccggaaattg taaacgttaa tattttgtta | 2950 |
| aaattcgcgt taaatttttg ttaaatcagc tcattttttta accaataggc | 3000 |
| cgaaatcggc aaaatccctt ataaatcaaa agaatagacc gagatagggt | 3050 |
| tgagtgttgt tccagtttgg aacaagagtc cactattaaa gaacgtggac | 3100 |
| tccaacgtca aagggcgaaa aaccgtctat cagggctatg cccactacg | 3150 |
| tgaaccatca ccctaatcaa gttttttggg gtcgaggtgc cgtaaagcac | 3200 |
| taaatcggaa ccctaaaggg agcccccgat ttagagcttg acggggaaag | 3250 |
| ccggcgaacg tggcgagaaa ggaagggaag aaagcgaaag gagcgggcgc | 3300 |
| tagggcgctg gcaagtgtag cggtcacgct gcgcgtaacc accacacccg | 3350 |
| ccgcgcttaa tgcgccgcta cagggcgcgt ccgcatcctg cctcgcgcgt | 3400 |
| ttcggtgatg acggtgaaaa cctctgacac atgcagctcc cggagacggt | 3450 |
| cacagcttgt ctgtaagcgg atgccggag cagacaagcc cgtcagggcg | 3500 |
| cgtcagcggg tgttggcggg tgtcggggcg cagccatgac ccagtcacgt | 3550 |
| agcgatagcg gagtgtatac tggcttaact atgcggcatc agagcagatt | 3600 |
| gtactgagag tgcaccatat gcggtgtgaa ataccgcaca gatgcgtaag | 3650 |
| gagaaaatac cgcatcaggc gctcttccgc ttcctcgctc actgactcgc | 3700 |
| tgcgctcggt cgttcggctg cggcgagcgg tatcagctca ctcaaaggcg | 3750 |
| gtaatacggt tatccacaga atcagggat aacgcaggaa agaacatgtg | 3800 |
| agcaaaaggc cagcaaaagg ccaggaaccg taaaaaggcc gcgttgctgg | 3850 |
| cgttttccca taggctccgc ccccctgacg agcatcacaa aaatcgacgc | 3900 |
| tcaagtcaga ggtggcgaaa cccgacagga ctataaagat accaggcgtt | 3950 |
| tccccctgga agctccctcg tgcgctctcc tgttccgacc ctgccgctta | 4000 |
| ccggatacct gtccgccttt ctcccttcgg gaagcgtggc gctttctcat | 4050 |

| | |
|---|---|
| agctcacgct gtaggtatct cagttcggtg taggtcgttc gctccaagct | 4100 |
| gggctgtgtg cacgaacccc ccgttcagcc cgaccgctgc gccttatccg | 4150 |
| gtaactatcg tcttgagtcc aacccggtaa gacacgactt atcgccactg | 4200 |
| gcagcagcca ctggtaacag gattagcaga gcgaggtatg taggcggtgc | 4250 |
| tacagagttc ttgaagtggt ggcctaacta cggctacact agaaggacag | 4300 |
| tatttggtat ctgcgctctg ctgaagccag ttaccttcgg aaaaagagtt | 4350 |
| ggtagctctt gatccggcaa acaaaccacc gctggtagcg tggtttttt | 4400 |
| tgtttgcaag cagcagatta cgcgcagaaa aaaaggatct caagaagatc | 4450 |
| ctttgatctt ttctacgggg tctgacgctc agtggaacga aaactcacgt | 4500 |
| taagggattt tggtcatgag attatcaaaa aggatcttca cctagatcct | 4550 |
| tttaaattaa aaatgaagtt ttaaatcaat ctaaagtata tatgagtaaa | 4600 |
| cttggtctga cagttaccaa tgcttaatca gtgaggcacc tatctcagcg | 4650 |
| atctgtctat ttcgttcatc catagttgcc tgactccccg tcgtgtagat | 4700 |
| aactacgata cgggagggct taccatctgg ccccagtgct gcaatgatac | 4750 |
| cgcgagaccc acgctcaccg gctccagatt tatcagcaat aaaccagcca | 4800 |
| gccggaaggg ccgagcgcag aagtggtcct gcaactttat ccgcctccat | 4850 |
| ccagtctatt aattgttgcc gggaagctag agtaagtagt tcgccagtta | 4900 |
| atagtttgcg caacgttgtt gccattgctg caggcatcgt ggtgtcacgc | 4950 |
| tcgtcgtttg gtatggcttc attcagctcc ggttcccaac gatcaaggcg | 5000 |
| agttacatga tcccccatgt tgtgcaaaaa agcggttagc tccttcggtc | 5050 |
| ctccgatcgt tgtcagaagt aagttggccg cagtgttatc actcatggtt | 5100 |
| atggcagcac tgcataattc tcttactgtc atgccatccg taagatgctt | 5150 |
| ttctgtgact ggtgagtact caaccaagtc attctgagaa tagtgtatgc | 5200 |
| ggcgaccgag ttgctcttgc ccggcgtcaa cacgggataa taccgcgcca | 5250 |
| catagcagaa ctttaaaagt gctcatcatt ggaaaacgtt cttcggggcg | 5300 |
| aaaactctca aggatcttac cgctgttgag atccagttcg atgtaaccca | 5350 |
| ctcgtgcacc caactgatct tcagcatctt ttactttcac cagcgtttct | 5400 |
| gggtgagcaa aaacaggaag gcaaaatgcc gcaaaaaagg gaataagggc | 5450 |
| gacacggaaa tgttgaatac tcatactctt ccttttcaa tattattgaa | 5500 |
| gcatttatca gggttattgt ctcatgagcg gatacatatt tgaatgtatt | 5550 |
| tagaaaaata aacaaatagg ggttccgcgc acatttcccc gaaagtgcc | 5600 |
| acctgacgtc taagaaacca ttattatcat gacattaacc tataaaaata | 5650 |
| ggcgtatcac gaggcccttt cgtcttcaa | 5679 |

<210> SEQ ID NO 14
<211> LENGTH: 241
<212> TYPE: PRT
<213> ORGANISM: Artificial Sequence
<220> FEATURE:
<223> OTHER INFORMATION: Sequence is synthesized

<400> SEQUENCE: 14

Met Lys Lys Asn Ile Ala Phe Leu Leu Ala Ser Met Phe Val Phe
1               5                   10                  15

Ser Ile Ala Thr Asn Ala Tyr Ala Asp Ile Gln Met Thr Gln Ser

```
                    20                  25                  30
Pro Ser Ser Leu Ser Ala Ser Val Gly Asp Arg Val Thr Ile Thr
                35                  40                  45
Cys Arg Ala Ser Gln Ser Val Ser Thr Ser Ser Tyr Ser Tyr Met
                50                  55                  60
His Trp Tyr Gln Gln Lys Pro Gly Lys Ala Pro Lys Leu Leu Ile
                65                  70                  75
Tyr Tyr Ala Ser Asn Leu Glu Ser Gly Val Pro Ser Arg Phe Ser
                80                  85                  90
Gly Ser Gly Ser Gly Thr Asp Phe Thr Leu Thr Ile Ser Ser Leu
                95                 100                 105
Gln Pro Glu Asp Phe Ala Thr Tyr Tyr Cys Gln His Ser Trp Gly
               110                 115                 120
Ile Pro Arg Thr Phe Gly Gln Gly Thr Lys Val Glu Ile Lys Arg
               125                 130                 135
Thr Val Ala Ala Pro Ser Val Phe Ile Phe Pro Pro Ser Asp Glu
               140                 145                 150
Gln Leu Lys Ser Gly Thr Ala Ser Val Val Cys Leu Leu Asn Asn
               155                 160                 165
Phe Tyr Pro Arg Glu Ala Lys Val Gln Trp Lys Val Asp Asn Ala
               170                 175                 180
Leu Gln Ser Gly Asn Ser Gln Glu Ser Val Thr Glu Gln Asp Ser
               185                 190                 195
Lys Asp Ser Thr Tyr Ser Leu Ser Ser Thr Leu Thr Leu Ser Lys
               200                 205                 210
Ala Asp Tyr Glu Lys His Lys Val Tyr Ala Cys Glu Val Thr His
               215                 220                 225
Gln Gly Leu Ser Ser Pro Val Thr Lys Ser Phe Asn Arg Gly Glu
               230                 235                 240
Cys

<210> SEQ ID NO 15
<211> LENGTH: 248
<212> TYPE: PRT
<213> ORGANISM: Artificial Sequence
<220> FEATURE:
<223> OTHER INFORMATION: Sequence is synthesized

<400> SEQUENCE: 15

Met Lys Lys Asn Ile Ala Phe Leu Leu Ala Ser Met Phe Val Phe
  1                   5                  10                  15
Ser Ile Ala Thr Asn Ala Tyr Ala Glu Val Gln Leu Val Glu Ser
                 20                  25                  30
Gly Gly Gly Leu Val Gln Pro Gly Gly Ser Leu Arg Leu Ser Cys
                 35                  40                  45
Ala Ala Ser Gly Tyr Thr Phe Thr Glu Tyr Ile Ile His Trp Val
                 50                  55                  60
Arg Gln Ala Pro Gly Lys Gly Leu Glu Trp Val Ala Ser Ile Asn
                 65                  70                  75
Pro Asp Tyr Asp Ile Thr Asn Tyr Asn Gln Arg Phe Lys Gly Arg
                 80                  85                  90
Phe Thr Ile Ser Arg Asp Asp Ser Lys Asn Thr Leu Tyr Leu Gln
                 95                 100                 105
Met Asn Ser Leu Arg Ala Glu Asp Thr Ala Val Tyr Tyr Cys Ala
                110                 115                 120
```

```
Arg Trp Ile Ser Asp Phe Phe Asp Tyr Trp Gly Gln Gly Thr Leu
            125                 130                 135
Val Thr Val Ser Ser Ala Ser Thr Lys Gly Pro Ser Val Phe Pro
            140                 145                 150
Leu Ala Pro Ser Ser Lys Ser Thr Ser Gly Gly Thr Ala Ala Leu
            155                 160                 165
Gly Cys Leu Val Lys Asp Tyr Phe Pro Glu Pro Val Thr Val Ser
            170                 175                 180
Trp Asn Ser Gly Ala Leu Thr Ser Gly Val His Thr Phe Pro Ala
            185                 190                 195
Val Leu Gln Ser Ser Gly Leu Tyr Ser Leu Ser Ser Val Val Thr
            200                 205                 210
Val Pro Ser Ser Ser Leu Gly Thr Gln Thr Tyr Ile Cys Asn Val
            215                 220                 225
Asn His Lys Pro Ser Asn Thr Lys Val Asp Lys Lys Val Glu Pro
            230                 235                 240
Lys Ser Cys Asp Lys Thr His Thr
            245

<210> SEQ ID NO 16
<211> LENGTH: 5678
<212> TYPE: DNA
<213> ORGANISM: Artificial Sequence
<220> FEATURE:
<223> OTHER INFORMATION: Sequence is chimeric

<400> SEQUENCE: 16
gaattcaact tctccatact ttggataagg aaatacagac atgaaaaatc        50
tcattgctga gttgttattt aagcttgccc aaaaagaaga agagtcgaat        100
gaactgtgtg cgcaggtaga agctttggag attatcgtca ctgcaatgct        150
tcgcaatatg gcgcaaaatg accaacagcg gttgattgat caggtagagg        200
gggcgctgta cgaggtaaag cccgatgcca gcattcctga cgacgatacg        250
gagctgctgc gcgattacgt aaagaagtta ttgaagcatc ctcgtcagta        300
aaaagttaat cttttcaaca gctgtcataa agttgtcacg gccgagactt        350
atagtcgctt tgttttttatt ttttaatgta tttgtaacta gaattcgagc       400
tcggtacccg gggatcctct agaggttgag gtgatttatg aaaaagaata        450
tcgcatttct tcttgcatct atgttcgttt tttctattgc tacaaacgcg        500
tacgctcaga tagtactgtc ccagtccccg gctatcctgt ccgcctctcc        550
tggcgagaag gtcactatga cctgcagagc cagctcttct gtgagctata        600
tgcattggta tcaacagaaa ccaggaagct ctccgaaacc atggatttac        650
gctccatcga acctcgcgtc tggagtccct gcgcgcttct ctggatccgg        700
ttctgggact agttactctc tgaccatcag cagagtggag cagaagacg         750
ccgcaactta ttactgtcaa cagtggagct caatccgcc cacatttgga         800
gccggcacca agctggagct caaacgaact gtggctgcac catctgtctt        850
catcttcccg ccatctgatg agcagttgaa atctggaact gcttctgttg        900
tgtgcctgct gaataacttc tatcccagag aggccaaagt acagtggaag        950
gtggataacg ccctccaatc gggtaactcc caggagagtg tcacagagca       1000
ggacagcaag gacagcacct acagcctcag cagcaccctg acgctgagca       1050
aagcagacta cgagaaacac aaagtctacg cctgcgaagt cacccatcag       1100
```

```
ggcctgagct cgcccgtcac aaagagcttc aacagggag  agtgttaagc        1150 tgatcctcta cgccggacgc atcgtggccc tagtacgcaa gttcacgtaa        1200
aaagggtatc tagaggttga ggtgatttta tgaaaaagaa tatcgcattt        1250
cttcttgcat ctatgttcgt tttttctatt gctacaaacg cgtacgctca        1300
ggcttatctg cagcagtctg cgccgagct  ggtgcggcca ggagctagcg        1350
tcaagatgtc ctgtaaagct tctggctaca ccttcaccag ctataacatg        1400
cattgggtca agcagacacc gaggcaaggc ctggaatgga ttggagcgat        1450
ctatcctggc aacggcgaca cgagctataa ccagaagttc aagggcaagg        1500
ccactctgac tgtggacaag tccagcagta ctgcctacat gcaactgagc        1550
agcctgactt ctgaggacag cgctgtctac ttttgtgctc gcgtggtcta        1600
ctatagcaac agctactggt acttcgacgt ctggggtacc ggaaccacag        1650
tcaccgtctc ctcggcctcc accaagggcc catcggtctt ccccctggca        1700
ccctcctcca agagcacctc tgggggcaca gcggccctgg gctgcctggt        1750
caaggactac ttccccgaac cggtgacggt gtcgtggaac tcaggcgccc        1800
tgaccagcgg cgtgcacacc ttcccggctg tcctacagtc ctcaggactc        1850
tactccctca gcagcgtggt gaccgtgccc tccagcagct gggcaccca         1900 gacctacatc tgcaacgtga atcacaagcc cagcaacacc aaggtggaca        1950
agaaagttga gcccaaatct tgtgacaaaa ctcacacatg accaccgcat        2000
gcaccagtat cgtccattcc gacagcatcg ccagtcacta tggcgtgctg        2050
ctagcgccgc cctataccct gtctgcctcc ccgcgttgcg tcgcggtgca        2100
tggagccggg ccacctcgac ctgaatggaa gccggcggca cctcgctaac        2150
ggattcacca ctccaagaat tggagccaat caattcttgc ggagaactgt        2200
gaatgcgcaa accaacccct ggcagaacat atccatcgcg tccgccatct        2250
ccagcagccg cacgcggcgc atctcgggca gcgttgggtc ctggccacgg        2300
gtgcgcatga tcgtgctcct gtcgttgagg acccggctag gctggcgggg        2350
ttgccttact ggttagcaga atgaatcacc gatacgcgag cgaacgtgaa        2400
gcgactgctg ctgcaaaacg tctgcgacct gagcaacaac atgaatggtc        2450 ttcggttttcc gtgtttcgta aagtctggaa acgcggaagt cagcgccctg       2500
caccattatg ttccggatct gcatcgcagg atgctgctgg ctaccctgtg        2550
gaacacctac atctgtatta cgaagcgct ggcattgacc ctgagtgatt         2600
tttctctggt cccgccgcat ccataccgcc agttgtttac cctcacaacg        2650
ttccagtaac cgggcatgtt catcatcagt aacccgtatc gtgagcatcc        2700
tctctcgttt catcggtatc attaccccca tgaacagaaa ttcccccta         2750 cacggaggca tcaagtgacc aaacaggaaa aaaccgccct taacatggcc        2800
cgctttatca gaagccagac attaacgctt ctggagaaac tcaacgagct        2850
ggacgcggat gaacaggcag acatctgtga atcgcttcac gaccacgctg        2900
atgagcttta ccgcagcatc cggaaattgt aaacgttaat attttgttaa        2950
aattcgcgtt aaattttgt  aaatcagct  cattttttaa ccataggcc         3000 gaaatcggca aaatccctta taatcaaaa  gaatagaccg atatagggtt        3050
gagtgttgtt ccagtttgga acaagagtcc actattaaag aacgtggact        3100
```

-continued

| | |
|---|---|
| ccaacgtcaa agggcgaaaa accgtctatc agggctatgg cccactacgt | 3150 |
| gaaccatcac cctaatcaag ttttttgggg tcgaggtgcc gtaaagcact | 3200 |
| aaatcggaac cctaaaggga gcccccgatt tagagcttga cggggaaagc | 3250 |
| cggcgaacgt ggcgagaaag gaagggaaga aagcgaaagg agcgggcgct | 3300 |
| agggcgctgg caagtgtagc ggtcacgctg cgcgtaacca ccacacccgc | 3350 |
| cgcgcttaat gcgccgctac agggcgcgtc cgcatcctgc ctcgcgcgtt | 3400 |
| tcggtgatga cggtgaaaac ctctgacaca tgcagctccc ggagacggtc | 3450 |
| acagcttgtc tgtaagcgga tgccgggagc agacaagccc gtcagggcgc | 3500 |
| gtcagcgggt gttggcgggt gtcggggcgc agccatgacc cagtcacgta | 3550 |
| gcgatagcgg agtgtatact ggcttaacta tgcggcatca gagcagattg | 3600 |
| tactgagagt gcaccatatg cggtgtgaaa taccgcacag atgcgtaagg | 3650 |
| agaaaatacc gcatcaggcg ctcttccgct tcctcgctca ctgactcgct | 3700 |
| gcgctcggtc gttcggctgc ggcgagcggt atcagctcac tcaaaggcgg | 3750 |
| taatacggtt atccacagaa tcaggggata acgcaggaaa gaacatgtga | 3800 |
| gcaaaaggcc agcaaaaggc caggaaccgt aaaaaggccg cgttgctggc | 3850 |
| gttttccat aggctccgcc cccctgacga gcatcacaaa aatcgacgct | 3900 |
| caagtcagag gtggcgaaac ccgacaggac tataaagata ccaggcgttt | 3950 |
| cccccctggaa gctccctcgt gcgctctcct gttccgaccc tgccgcttac | 4000 |
| cggatacctg tccgcctttc tcccttcggg aagcgtggcg ctttctcata | 4050 |
| gctcacgctg taggtatctc agttcggtgt aggtcgttcg ctccaagctg | 4100 |
| ggctgtgtgc acgaaccccc cgttcagccc gaccgctgcg ccttatccgg | 4150 |
| taactatcgt cttgagtcca acccggtaag acacgactta tcgccactgg | 4200 |
| cagcagccac tggtaacagg attagcagag cgaggtatgt aggcggtgct | 4250 |
| acagagttct tgaagtggtg gcctaactac ggctacacta aaggacagt | 4300 |
| atttggtatc tgcgctctgc tgaagccagt taccttcgga aaaagagttg | 4350 |
| gtagctcttg atccggcaaa caaaccaccg ctggtagcgg tggtttttt | 4400 |
| gtttgcaagc agcagattac gcgcagaaaa aaaggatctc aagaagatcc | 4450 |
| tttgatcttt tctacggggt ctgacgctca gtggaacgaa aactcacgtt | 4500 |
| aagggatttt ggtcatgaga ttatcaaaaa ggatcttcac ctagatcctt | 4550 |
| ttaaattaaa aatgaagttt taaatcaatc taaagtatat atgagtaaac | 4600 |
| ttggtctgac agttaccaat gcttaatcag tgaggcacct atctcagcga | 4650 |
| tctgtctatt tcgttcatcc atagttgcct gactccccgt cgtgtagata | 4700 |
| actacgatac gggagggctt accatctggc cccagtgctg caatgatacc | 4750 |
| gcgagaccca cgctcaccgg ctccagattt atcagcaata aaccagccag | 4800 |
| ccggaagggc cgagcgcaga agtggtcctg caactttatc cgcctccatc | 4850 |
| cagtctatta attgttgccg ggaagctaga gtaagtagtt cgccagttaa | 4900 |
| tagtttcgc aacgttgttg ccattgctgc aggcatcgtg gtgtcacgct | 4950 |
| cgtcgtttgg tatggcttca ttcagctccg gttcccaacg atcaaggcga | 5000 |
| gttacatgat cccccatgtt gtgcaaaaaa gcggttagct ccttcggtcc | 5050 |
| tccgatcgtt gtcagaagta agttggccgc agtgttatca ctcatggtta | 5100 |

-continued

```
tggcagcact gcataattct cttactgtca tgccatccgt aagatgcttt      5150
tctgtgactg gtgagtactc aaccaagtca ttctgagaat agtgtatgcg      5200
gcgaccgagt tgctcttgcc cggcgtcaac acgggataat accgcgccac      5250
atagcagaac tttaaaagtg ctcatcattg gaaaacgttc ttcggggcga      5300
aaactctcaa ggatcttacc gctgttgaga tccagttcga tgtaacccac      5350
tcgtgcaccc aactgatctt cagcatcttt tactttcacc agcgtttctg      5400
ggtgagcaaa aacaggaagg caaaatgccg caaaaaaggg aataagggcg      5450
acacggaaat gttgaatact catactcttc ctttttcaat attattgaag      5500
catttatcag ggttattgtc tcatgagcgg atacatattt gaatgtattt      5550
agaaaaataa acaaataggg gttccgcgca catttccccg aaaagtgcca      5600
cctgacgtct aagaaaccat tattatcatg acattaacct ataaaaatag      5650
gcgtatcacg aggccctttc gtcttcaa                              5678
```

<210> SEQ ID NO 17
<211> LENGTH: 236
<212> TYPE: PRT
<213> ORGANISM: Artificial sequence
<220> FEATURE:
<223> OTHER INFORMATION: Sequence is chimeric

<400> SEQUENCE: 17

```
Met Lys Lys Asn Ile Ala Phe Leu Leu Ala Ser Met Phe Val Phe
 1               5                  10                  15

Ser Ile Ala Thr Asn Ala Tyr Ala Gln Ile Val Leu Ser Gln Ser
                20                  25                  30

Pro Ala Ile Leu Ser Ala Ser Pro Gly Glu Lys Val Thr Met Thr
                35                  40                  45

Cys Arg Ala Ser Ser Ser Val Ser Tyr Met His Trp Tyr Gln Gln
                50                  55                  60

Lys Pro Gly Ser Ser Pro Lys Pro Trp Ile Tyr Ala Pro Ser Asn
                65                  70                  75

Leu Ala Ser Gly Val Pro Ala Arg Phe Ser Gly Ser Gly Ser Gly
                80                  85                  90

Thr Ser Tyr Ser Leu Thr Ile Ser Arg Val Glu Ala Glu Asp Ala
                95                 100                 105

Ala Thr Tyr Tyr Cys Gln Gln Trp Ser Phe Asn Pro Pro Thr Phe
               110                 115                 120

Gly Ala Gly Thr Lys Leu Glu Leu Lys Arg Thr Val Ala Ala Pro
               125                 130                 135

Ser Val Phe Ile Phe Pro Pro Ser Asp Glu Gln Leu Lys Ser Gly
               140                 145                 150

Thr Ala Ser Val Val Cys Leu Leu Asn Asn Phe Tyr Pro Arg Glu
               155                 160                 165

Ala Lys Val Gln Trp Lys Val Asp Asn Ala Leu Gln Ser Gly Asn
               170                 175                 180

Ser Gln Glu Ser Val Thr Glu Gln Asp Ser Lys Asp Ser Thr Tyr
               185                 190                 195

Ser Leu Ser Ser Thr Leu Thr Leu Ser Lys Ala Asp Tyr Glu Lys
               200                 205                 210

His Lys Val Tyr Ala Cys Glu Val Thr His Gln Gly Leu Ser Ser
               215                 220                 225
```

```
Pro Val Thr Lys Ser Phe Asn Arg Gly Glu Cys
            230                 235

<210> SEQ ID NO 18
<211> LENGTH: 253
<212> TYPE: PRT
<213> ORGANISM: Artificial sequence
<220> FEATURE:
<223> OTHER INFORMATION: Sequence is chimeric

<400> SEQUENCE: 18

Met Lys Lys Asn Ile Ala Phe Leu Leu Ala Ser Met Phe Val Phe
 1               5                  10                  15

Ser Ile Ala Thr Asn Ala Tyr Ala Gln Ala Tyr Leu Gln Gln Ser
                20                  25                  30

Gly Ala Glu Leu Val Arg Pro Gly Ala Ser Val Lys Met Ser Cys
                35                  40                  45

Lys Ala Ser Gly Tyr Thr Phe Thr Ser Tyr Asn Met His Trp Val
                50                  55                  60

Lys Gln Thr Pro Arg Gln Gly Leu Glu Trp Ile Gly Ala Ile Tyr
                65                  70                  75

Pro Gly Asn Gly Asp Thr Ser Tyr Asn Gln Lys Phe Lys Gly Lys
                80                  85                  90

Ala Thr Leu Thr Val Asp Lys Ser Ser Ser Thr Ala Tyr Met Gln
                95                 100                 105

Leu Ser Ser Leu Thr Ser Glu Asp Ser Ala Val Tyr Phe Cys Ala
               110                 115                 120

Arg Val Val Tyr Tyr Ser Asn Ser Tyr Trp Tyr Phe Asp Val Trp
               125                 130                 135

Gly Thr Gly Thr Thr Val Thr Val Ser Ser Ala Ser Thr Lys Gly
               140                 145                 150

Pro Ser Val Phe Pro Leu Ala Pro Ser Ser Lys Ser Thr Ser Gly
               155                 160                 165

Gly Thr Ala Ala Leu Gly Cys Leu Val Lys Asp Tyr Phe Pro Glu
               170                 175                 180

Pro Val Thr Val Ser Trp Asn Ser Gly Ala Leu Thr Ser Gly Val
               185                 190                 195

His Thr Phe Pro Ala Val Leu Gln Ser Ser Gly Leu Tyr Ser Leu
               200                 205                 210

Ser Ser Val Val Thr Val Pro Ser Ser Ser Leu Gly Thr Gln Thr
               215                 220                 225

Tyr Ile Cys Asn Val Asn His Lys Pro Ser Asn Thr Lys Val Asp
               230                 235                 240

Lys Lys Val Glu Pro Lys Ser Cys Asp Lys Thr His Thr
               245                 250

<210> SEQ ID NO 19
<211> LENGTH: 5391
<212> TYPE: DNA
<213> ORGANISM: Artificial sequence
<220> FEATURE:
<223> OTHER INFORMATION: Sequence is synthesized

<400> SEQUENCE: 19
ttcgagctcg cccgacattg attattgact agttattaat agtaatcaat         50
tacggggtca ttagttcata gcccatatat ggagttccgc gttacataac        100
ttacggtaaa tggcccgcct ggctgaccgc ccaacgaccc ccgcccattg        150
```

```
acgtcaataa tgacgtatgt tcccatagta acgccaatag ggactttcca      200
ttgacgtcaa tgggtggagt atttacggta aactgcccac ttggcagtac      250
atcaagtgta tcatatgcca agtacgcccc ctattgacgt caatgacggt      300
aaatggcccg cctggcatta tgcccagtac atgaccttat gggactttcc      350
tacttggcag tacatctacg tattagtcat cgctattacc atggtgatgc      400
ggttttggca gtacatcaat gggcgtggat agcggtttga ctcacgggga      450
tttccaagtc tccaccccat tgacgtcaat gggagtttgt tttggcacca      500
aaatcaacgg gactttccaa aatgtcgtaa caactccgcc ccattgacgc      550
aaatgggcgg taggcgtgta cggtgggagg tctatataag cagagctcgt      600
ttagtgaacc gtcagatcgc ctggagacgc catccacgct gttttgacct      650
ccatagaaga caccgggacc gatccagcct ccgcggccgg gaacggtgca      700
ttggaacgcg gattcccgt gccaagagtg acgtaagtac cgcctataga      750
gtctataggc ccaccccctt ggcttcgtta aacgcggct acaattaata      800
cataaccta tgtatcatac acatacgatt taggtgacac tatagaataa      850
catccacttt gcctttctct ccacaggtgt ccactcccag gtccaactgc      900
acctcggttc tatcgattga attccaccat gggatggtca tgtatcatcc      950
tttttctagt agcaactgca actggagtac attcagatat ccagatgacc     1000
cagtccccga gctccctgtc cgcctctgtg ggcgataggg tcaccatcac     1050
ctgccgtgcc agtcaggaca tccgtaatta tttgaactgg tatcaacaga     1100
aaccaggaaa agctccgaaa ctactgattt actataccct ccgcctggag     1150
tctggagtcc cttctcgctt ctctggttct ggttctggga cggattacac     1200
tctgaccatc agtagtctgc aaccggagga cttcgcaact tattactgtc     1250
agcaaggtaa tactctgccg tggacgttcg gacagggcac caaggtggag     1300
atcaaacgaa ctgtggctgc accatctgtc ttcatcttcc cgccatctga     1350
tgagcagttg aaatctggaa ctgcctctgt tgtgtgcctg ctgaataact     1400
tctatcccag agaggccaaa gtacagtgga aggtggataa cgccctccaa     1450
tcgggtaact cccaggagag tgtcacagag caggacagca aggacagcac     1500
ctacagcctc agcagcaccc tgacgctgag caaagcagac tacgagaaac     1550
acaaagtcta cgcctgcgaa gtcacccatc agggcctgag ctcgcccgtc     1600
acaaagagct tcaacagggg agagtgttaa gcttggccgc catggcccaa     1650
cttgtttatt gcagcttata atggttacaa ataaagcaat agcatcacaa     1700
atttcacaaa taaagcattt ttttcactgc attctagttg tggtttgtcc     1750
aaactcatca atgtatctta tcatgtctgg atcgatcggg aattaattcg     1800
gcgcagcacc atggcctgaa ataacctctg aaagaggaac ttggttaggt     1850
accttctgag gcggaaagaa ccagctgtgg aatgtgtgtc agttagggtg     1900
tggaaagtcc ccaggctccc cagcaggcag aagtatgcaa agcatgcatc     1950
tcaattagtc agcaaccagg tgtggaaagt cccaggctc cccagcaggc     2000
agaagtatgc aaagcatgca tctcaattag tcagcaacca tagtcccgcc     2050
cctaactccg cccatcccgc cctaactccg cccagttccg cccattctc     2100
cgccccatgg ctgactaatt ttttttattt atgcagaggc cgaggccgcc     2150
```

| | |
|---|---|
| tcggcctctg agctattcca gaagtagtga ggaggctttt ttggaggcct | 2200 |
| aggcttttgc aaaaagctgt taacagcttg cactggccg tcgttttaca | 2250 |
| acgtcgtgac tgggaaaacc ctggcgttac ccaacttaat cgccttgcag | 2300 |
| cacatccccc cttcgccagc tggcgtaata gcgaagaggc ccgcaccgat | 2350 |
| cgcccttccc aacagttgcg tagcctgaat ggcgaatggc gcctgatgcg | 2400 |
| gtattttctc cttacgcatc tgtgcggtat ttcacaccgc atacgtcaaa | 2450 |
| gcaaccatag tacgcgccct gtagcggcgc attaagcgcg gcgggtgtgg | 2500 |
| tggttacgcg cagcgtgacc gctacacttg ccagcgccct agcgcccgct | 2550 |
| cctttcgctt tcttcccttc ctttctcgcc acgttcgccg gctttccccg | 2600 |
| tcaagctcta atcgggggc tccctttagg gttccgattt agtgctttac | 2650 |
| ggcacctcga ccccaaaaaa cttgatttgg gtgatggttc acgtagtggg | 2700 |
| ccatcgccct gatagacggt ttttcgccct ttgacgttgg agtccacgtt | 2750 |
| ctttaatagt ggactcttgt tccaaactgg aacaacactc aaccctatct | 2800 |
| cgggctattc ttttgattta tagggatttt gccgatttc ggcctattgg | 2850 |
| ttaaaaaatg agctgattta acaaaaattt aacgcgaatt ttaacaaaat | 2900 |
| attaacgttt acaattttat ggtgcactct cagtacaatc tgctctgatg | 2950 |
| ccgcatagtt aagccaactc cgctatcgct acgtgactgg gtcatggctg | 3000 |
| cgccccgaca cccgccaaca cccgctgacg cgccctgacg ggcttgtctg | 3050 |
| ctcccggcat ccgcttacag acaagctgtg accgtctccg ggagctgcat | 3100 |
| gtgtcagagg ttttcaccgt catcaccgaa acgcgcgagg cagtattctt | 3150 |
| gaagacgaaa gggcctcgtg atacgcctat ttttataggt taatgtcatg | 3200 |
| ataataatgg tttcttagac gtcaggtggc acttttcggg gaaatgtgcg | 3250 |
| cggaacccct atttgtttat ttttctaaat acattcaaat atgtatccgc | 3300 |
| tcatgagaca ataaccctga taatgcttc aataatattg aaaaaggaag | 3350 |
| agtatgagta ttcaacattt ccgtgtcgcc cttattccct ttttgcggc | 3400 |
| attttgcctt cctgttttg ctcacccaga aacgctggtg aaagtaaaag | 3450 |
| atgctgaaga tcagttgggt gcacgagtgg gttacatcga actggatctc | 3500 |
| aacagcggta agatccttga gagttttcgc cccgaagaac gttttccaat | 3550 |
| gatgagcact tttaaagttc tgctatgtgg cgcggtatta tcccgtgatg | 3600 |
| acgccgggca agagcaactc ggtcgccgca tacactattc tcagaatgac | 3650 |
| ttggttgagt actcaccagt cacagaaaag catcttacgg atggcatgac | 3700 |
| agtaagagaa ttatgcagtg ctgccataac catgagtgat aacactgcgg | 3750 |
| ccaacttact tctgacaacg atcggaggac cgaaggagct aaccgctttt | 3800 |
| ttgcacaaca tgggggatca tgtaactcgc cttgatcgtt gggaaccgga | 3850 |
| gctgaatgaa gccataccaa acgacgagcg tgacaccacg atgccagcag | 3900 |
| caatggcaac aacgttgcgc aaactattaa ctggcgaact acttactcta | 3950 |
| gcttcccggc aacaattaat agactggatg gaggcggata agttgcagg | 4000 |
| accacttctg cgctcggccc ttccggctgg ctggtttatt gctgataaat | 4050 |
| ctggagccgg tgagcgtggg tctcgcggta tcattgcagc actggggcca | 4100 |
| gatggtaagc cctcccgtat cgtagttatc tacacgacgg ggagtcaggc | 4150 |

| | |
|---|---|
| aactatggat gaacgaaata gacagatcgc tgagataggt gcctcactga | 4200 |
| ttaagcattg gtaactgtca gaccaagttt actcatatat actttagatt | 4250 |
| gatttaaaac ttcattttta atttaaaagg atctaggtga agatccttt | 4300 |
| tgataatctc atgaccaaaa tcccttaacg tgagttttcg ttccactgag | 4350 |
| cgtcagaccc cgtagaaaag atcaaaggat cttcttgaga tcctttttt | 4400 |
| ctgcgcgtaa tctgctgctt gcaaacaaaa aaaccaccgc taccagcggt | 4450 |
| ggtttgtttg ccggatcaag agctaccaac tcttttccg aaggtaactg | 4500 |
| gcttcagcag agcgcagata ccaaatactg tccttctagt gtagccgtag | 4550 |
| ttaggccacc acttcaagaa ctctgtagca ccgcctacat acctcgctct | 4600 |
| gctaatcctg ttaccagtgg ctgctgccag tggcgataag tcgtgtctta | 4650 |
| ccgggttgga ctcaagacga tagttaccgg ataaggcgca gcggtcgggc | 4700 |
| tgaacggggg gttcgtgcac acagcccagc ttggagcgaa cgacctacac | 4750 |
| cgaactgaga tacctacagc gtgagcattg agaaagcgcc acgcttcccg | 4800 |
| aagggagaaa ggcggacagg tatccggtaa gcggcagggt cggaacagga | 4850 |
| gagcgcacga gggagcttcc agggggaaac gcctggtatc tttatagtcc | 4900 |
| tgtcgggttt cgccacctct gacttgagcg tcgatttttg tgatgctcgt | 4950 |
| caggggggcg gagcctatgg aaaaacgcca gcaacgcggc cttttacgg | 5000 |
| ttcctggcct tttgctggcc ttttgctcac atgttctttc ctgcgttatc | 5050 |
| ccctgattct gtggataacc gtattaccgc ctttgagtga gctgataccg | 5100 |
| ctcgccgcag ccgaacgacc gagcgcagcg agtcagtgag cgaggaagcg | 5150 |
| gaagagcgcc caatacgcaa accgcctctc ccgcgcgtt ggccgattca | 5200 |
| ttaatccagc tggcacgaca ggtttcccga ctggaaagcg ggcagtgagc | 5250 |
| gcaacgcaat taatgtgagt tacctcactc attaggcacc ccaggcttta | 5300 |
| cactttatgc ttccggctcg tatgttgtgt ggaattgtga gcggataaca | 5350 |
| atttcacaca ggaaacagct atgaccatga ttacgaatta a | 5391 |

<210> SEQ ID NO 20
<211> LENGTH: 6135
<212> TYPE: DNA
<213> ORGANISM: Artificial sequence
<220> FEATURE:
<223> OTHER INFORMATION: Sequence is synthesized

<400> SEQUENCE: 20

| | |
|---|---|
| attcgagctc gcccgacatt gattattgac tagttattaa tagtaatcaa | 50 |
| ttacggggtc attagttcat agcccatata tggagttccg cgttacataa | 100 |
| cttacggtaa atggcccgcc tggctgaccg cccaacgacc cccgcccatt | 150 |
| gacgtcaata atgacgtatg ttcccatagt aacgccaata gggactttcc | 200 |
| attgacgtca atgggtggag tatttacggt aaactgccca cttggcagta | 250 |
| catcaagtgt atcatatgcc aagtacgccc cctattgacg tcaatgacgg | 300 |
| taaatggccc gcctggcatt atgcccagta catgacctta tgggactttc | 350 |
| ctacttggca gtacatctac gtattagtca tcgctattac catggtgatg | 400 |
| cggttttggc agtacatcaa tgggcgtgga tagcggtttg actcacgggg | 450 |
| atttccaagt ctccacccca ttgacgtcaa tgggagtttg ttttggcacc | 500 |

```
aaaatcaacg ggactttcca aaatgtcgta acaactccgc cccattgacg       550
caaatgggcg gtaggcgtgt acggtgggag gtctatataa gcagagctcg       600
tttagtgaac cgtcagatcg cctggagacg ccatccacgc tgttttgacc       650
tccatagaag acaccgggac cgatccagcc tccgcggccg ggaacggtgc       700
attggaacgc ggattccccg tgccaagagt gacgtaagta ccgcctatag       750
agtctatagg cccaccccct tggcttcgtt agaacgcggc tacaattaat       800
acataacctt atgtatcata cacatacgat ttaggtgaca ctatagaata       850
acatccactt tgcctttctc tccacaggtg tccactccca ggtccaactg       900
cacctcggtt ctatcgattg aattccacca tgggatggtc atgtatcatc       950
cttttcctag tagcaactgc aactggagta cattcagaag ttcagctggt      1000
ggagtctggc ggtggcctgg tgcagccagg gggctcactc cgtttgtcct      1050
gtgcagcttc tggctactcc tttaccggct acactatgaa ctgggtgcgt      1100
caggccccag gtaagggcct ggaatgggtt gcactgatta atccttataa      1150
aggtgttact acctatgccg atagcgtcaa gggccgtttc actataagcg      1200
tagataaatc caaaaacaca gcctacctgc aaatgaacag cctgcgtgct      1250
gaggacactg ccgtctatta ttgtgctaga agcggatact acggcgatag      1300
cgactggtat tttgacgtct ggggtcaagg aaccctggtc accgtctcct      1350
cggcctccac caagggccca tcggtcttcc cctggcacc  ctcctccaag      1400 agcacctctg ggggcacagc ggccctgggc tgcctggtca aggactactt      1450
ccccgaaccg gtgacggtgt cgtggaactc aggcgccctg accagcggcg      1500
tgcacacctt cccggctgtc ctacagtcct caggactcta ctccctcagc      1550
agcgtggtga ctgtgccctc tagcagcttg ggcacccaga cctacatctg      1600
caacgtgaat cacaagccca gcaacaccaa ggtggacaag aaagttgagc      1650
ccaaatcttg tgacaaaact cacacatgcc caccgtgccc agcacctgaa      1700
ctcctggggg gaccgtcagt cttcctcttc cccccaaaac ccaaggacac      1750
cctcatgatc tcccggaccc ctgaggtcac atgcgtggtg gtggacgtga      1800
gccacgaaga ccctgaggtc aagttcaact ggtacgtgga cggcgtggag      1850
gtgcataatg ccaagacaaa gccgcgggag gagcagtaca acagcacgta      1900
ccgtgtggtc agcgtcctca ccgtcctgca ccaggactgg ctgaatggca      1950
aggagtacaa gtgcaaggtc tccaacaaag ccctcccagc ccccatcgag      2000
aaaaccatct ccaaagccaa agggcagccc cgagaaccac aggtgtacac      2050
cctgccccca tcccgggaag agatgaccaa gaaccaggtc agcctgacct      2100
gcctggtcaa aggcttctat cccagcgaca tcgccgtgga gtgggagagc      2150
aatgggcagc cggagaacaa ctacaagacc acgcctcccg tgctggactc      2200
cgacggctcc ttcttcctct acagcaagct caccgtggac aagagcaggt      2250
ggcagcaggg gaacgtcttc tcatgctccg tgatgcatga ggctctgcac      2300
aaccactaca cgcagaagag cctctccctg tctccgggta aatgagtgcg      2350
acggccctag agtcgacctg cagaagcttg gccgccatgg cccaacttgt      2400
ttattgcagc ttataatggt tacaaataaa gcaatagcat cacaaatttc      2450
acaaataaag catttttttc actgcattct agttgtggtt tgtccaaact      2500
```

-continued

```
catcaatgta tcttatcatg tctggatcga tcgggaatta attcggcgca      2550
gcaccatggc ctgaaataac ctctgaaaga ggaacttggt taggtaccttc     2600
```


```
catcaatgta tcttatcatg tctggatcga tcgggaatta attcggcgca      2550
gcaccatggc ctgaaataac ctctgaaaga ggaacttggt taggtacctt      2600
ctgaggcgga aagaaccatc tgtggaatgt gtgtcagtta gggtgtggaa      2650
agtccccagg ctccccagca ggcagaagta tgcaaagcat gcatctcaat      2700
tagtcagcaa ccaggtgtgg aaagtcccca ggctccccag caggcagaag      2750
tatgcaaagc atgcatctca attagtcagc aaccatagtc ccgcccctaa      2800
ctccgcccat cccgccccta actccgccca gttccgccca ttctccgccc      2850
catggctgac taatttttt tatttatgca gaggccgagg ccgcctcggc       2900
ctctgagcta ttccagaagt agtgaggagg ctttttggag gcctaggct       2950
tttgcaaaaa gctgttaaca gcttggcact ggccgtcgtt ttacaacgtc      3000
gtgactggga aaaccctggc gttacccaac ttaatcgcct tgcagcacat      3050
cccccttcg ccagttggcg taatagcgaa gaggcccgca ccgatcgccc       3100
ttcccaacag ttgcgtagcc tgaatggcga atggcgcctg atgcggtatt      3150
ttctccttac gcatctgtgc ggtatttcac accgcatacg tcaaagcaac      3200
catagtacgc gccctgtagc ggcgcattaa gcgcggcggg tgtggtggtt      3250
acgcgcagcg tgaccgctac acttgccagc gccctagcgc ccgctccttt      3300
cgctttcttc ccttcctttc tcgccacgtt cgccggcttt ccccgtcaag      3350
ctctaaatcg ggggctccct ttagggttcc gatttagtgc tttacggcac      3400
ctcgacccca aaaaacttga tttgggtgat ggttcacgta gtgggccatc      3450
gccctgatag acggttttc gccctttgac gttggagtcc acgttcttta       3500
atagtggact cttgttccaa actggaacaa cactcaaccc tatctcgggc      3550
tattcttttg atttataagg gattttgccg atttcggcct attggttaaa      3600
aaatgagctg atttaacaaa aatttaacgc gaattttaac aaaatattaa      3650
cgtttacaat tttatggtgc actctcagta caatctgctc tgatgccgca      3700
tagttaagcc aactccgcta tcgctacgtg actgggtcat gctgcgccc      3750
cgacacccgc caacacccgc tgacgcgccc tgacgggctt gtctgctccc      3800
ggcatccgct tacagacaag ctgtgaccgt ctccgggagc tgcatgtgtc      3850
agaggttttc accgtcatca ccgaaacgcg cgaggcagta ttcttgaaga      3900
cgaaagggcc tcgtgatacg cctatttta taggttaatg tcatgataat       3950
aatggtttct tagacgtcag gtggcacttt tcggggaaat gtgcgcggaa      4000
cccctatttg tttattttc taaatacatt caaatatgta tccgctcatg       4050
agacaataac cctgataaat gcttcaataa tattgaaaaa ggaagagtat      4100
gagtattcaa catttccgtg tcgcccttat tccctttttt gcggcatttt      4150
gccttcctgt ttttgctcac ccagaaacgc tggtgaaagt aaaagatgct      4200
gaagatcagt tgggtgcacg agtgggttac atcgaactgg atctcaacag      4250
cggtaagatc cttgagagtt ttcgccccga agaacgtttt ccaatgatga      4300
gcacttttaa agttctgcta tgtggcgcgg tattatcccg tgatgacgcc      4350
gggcaagagc aactcggtcg ccgcatacac tattctcaga atgacttggt      4400
tgagtactca ccagtcacag aaaagcatct tacggatggc atgacagtaa      4450
gagaattatg cagtgctgcc ataaccatga gtgataacac tgcggccaac      4500
```

-continued

| | |
|---|---|
| ttacttctga caacgatcgg aggaccgaag gagctaaccg ctttttttgca | 4550 |
| caacatgggg gatcatgtaa ctcgccttga tcgttgggaa ccggagctga | 4600 |
| atgaagccat accaaacgac gagcgtgaca ccacgatgcc agcagcaatg | 4650 |
| gcaacaacgt tgcgcaaact attaactggc gaactactta ctctagcttc | 4700 |
| ccggcaacaa ttaatagact ggatggaggc ggataaagtt gcaggaccac | 4750 |
| ttctgcgctc ggcccttccg gctggctggt ttattgctga taaatctgga | 4800 |
| gccggtgagc gtgggtctcg cggtatcatt gcagcactgg ggccagatgg | 4850 |
| taagccctcc cgtatcgtag ttatctacac gacggggagt caggcaacta | 4900 |
| tggatgaacg aaatagacag atcgctgaga taggtgcctc actgattaag | 4950 |
| cattggtaac tgtcagacca gtttactca tatatacttt agattgattt | 5000 |
| aaaacttcat ttttaattta aaaggatcta ggtgaagatc cttttttgata | 5050 |
| atctcatgac caaaatccct taacgtgagt tttcgttcca ctgagcgtca | 5100 |
| gaccccgtag aaaagatcaa aggatcttct tgagatcctt ttttttctgcg | 5150 |
| cgtaatctgc tgcttgcaaa caaaaaaacc accgctacca gcggtggttt | 5200 |
| gtttgccgga tcaagagcta ccaactcttt ttccgaaggt aactggcttc | 5250 |
| agcagagcgc agataccaaa tactgtcctt ctagtgtagc cgtagttagg | 5300 |
| ccaccacttc aagaactctg tagcaccgcc tacatacctc gctctgctaa | 5350 |
| tcctgttacc agtggctgct gccagtggcg ataagtcgtg tcttaccggg | 5400 |
| ttggactcaa gacgatagtt accggataag gcgcagcggt cgggctgaac | 5450 |
| ggggggttcg tgcacacagc ccagcttgga gcgaacgacc tacaccgaac | 5500 |
| tgagatacct acagcgtgag cattgagaaa gcgccacgct tcccgaaggg | 5550 |
| agaaaggcgg acaggtatcc ggtaagcggc agggtcggaa caggagagcg | 5600 |
| cacgagggag cttccagggg gaaacgcctg gtatctttat agtcctgtcg | 5650 |
| ggtttcgcca cctctgactt gagcgtcgat ttttgtgatg ctcgtcaggg | 5700 |
| gggcggagcc tatggaaaaa cgccagcaac gcggcctttt tacggttcct | 5750 |
| ggccttttgc tggccttttg ctcacatgtt ctttcctgcg ttatcccctg | 5800 |
| attctgtgga taaccgtatt accgcctttg agtgagctga taccgctcgc | 5850 |
| cgcagccgaa cgaccgagcg cagcgagtca gtgagcgagg aagcggaaga | 5900 |
| gcgcccaata cgcaaaccgc ctctccccgc gcgttggccg attcattaat | 5950 |
| ccaactggca cgacaggttt cccgactgga aagcgggcag tgagcgcaac | 6000 |
| gcaattaatg tgagttacct cactcattag gcacccagg ctttacactt | 6050 |
| tatgcttccg gctcgtatgt tgtgtggaat tgtgagcgga taacaatttc | 6100 |
| acacaggaaa cagctatgac catgattacg aatta | 6135 |

<210> SEQ ID NO 21
<211> LENGTH: 232
<212> TYPE: PRT
<213> ORGANISM: Artificial sequence
<220> FEATURE:
<223> OTHER INFORMATION: Sequence is synthesized

<400> SEQUENCE: 21

Met Gly Trp Ser Cys Ile Ile Leu Phe Leu Val Ala Thr Ala Thr
1               5                   10                  15

Gly Val His Ser Asp Ile Gln Met Thr Gln Ser Pro Ser Ser Leu

```
                    20                  25                  30

Ser Ala Ser Val Gly Asp Arg Val Thr Ile Thr Cys Arg Ala Ser
             35                  40                  45

Ser Ser Val Ser Tyr Met His Trp Tyr Gln Gln Lys Pro Gly Lys
         50                  55                  60

Ala Pro Lys Pro Leu Ile Tyr Ala Pro Ser Asn Leu Ala Ser Gly
     65                  70                  75

Val Pro Ser Arg Phe Gly Ser Gly Ser Gly Thr Asp Phe Thr
                 80                  85                  90

Leu Thr Ile Ser Ser Leu Gln Pro Glu Asp Phe Ala Thr Tyr Tyr
             95                 100                 105

Cys Gln Gln Trp Ser Phe Asn Pro Pro Thr Phe Gly Gln Gly Thr
                110                 115                 120

Lys Val Glu Ile Lys Arg Thr Val Ala Ala Pro Ser Val Phe Ile
            125                 130                 135

Phe Pro Pro Ser Asp Glu Gln Leu Lys Ser Gly Thr Ala Ser Val
            140                 145                 150

Val Cys Leu Leu Asn Asn Phe Tyr Pro Arg Glu Ala Lys Val Gln
            155                 160                 165

Trp Lys Val Asp Asn Ala Leu Gln Ser Gly Asn Ser Gln Glu Ser
            170                 175                 180

Val Thr Glu Gln Asp Ser Lys Asp Ser Thr Tyr Ser Leu Ser Ser
            185                 190                 195

Thr Leu Thr Leu Ser Lys Ala Asp Tyr Glu Lys His Lys Val Tyr
            200                 205                 210

Ala Cys Glu Val Thr His Gln Gly Leu Ser Ser Pro Val Thr Lys
            215                 220                 225

Ser Phe Asn Arg Gly Glu Cys
            230

<210> SEQ ID NO 22
<211> LENGTH: 471
<212> TYPE: PRT
<213> ORGANISM: Artificial sequence
<220> FEATURE:
<223> OTHER INFORMATION: Sequence is synthesized

<400> SEQUENCE: 22

Met Gly Trp Ser Cys Ile Ile Leu Phe Leu Val Ala Thr Ala Thr
  1               5                  10                  15

Gly Val His Ser Glu Val Gln Leu Val Glu Ser Gly Gly Gly Leu
             20                  25                  30

Val Gln Pro Gly Gly Ser Leu Arg Leu Ser Cys Ala Ala Ser Gly
             35                  40                  45

Tyr Thr Phe Thr Ser Tyr Asn Met His Trp Val Arg Gln Ala Pro
         50                  55                  60

Gly Lys Gly Leu Glu Trp Val Gly Ala Ile Tyr Pro Gly Asn Gly
     65                  70                  75

Asp Thr Ser Tyr Asn Gln Lys Phe Lys Gly Arg Phe Thr Ile Ser
         80                  85                  90

Val Asp Lys Ser Lys Asn Thr Leu Tyr Leu Gln Met Asn Ser Leu
         95                 100                 105

Arg Ala Glu Asp Thr Ala Val Tyr Tyr Cys Ala Arg Val Val Tyr
            110                 115                 120

Tyr Ser Asn Ser Tyr Trp Tyr Phe Asp Val Trp Gly Gln Gly Thr
            125                 130                 135
```

Leu Val Thr Val Ser Ser Ala Ser Thr Lys Gly Pro Ser Val Phe
                140                 145                 150

Pro Leu Ala Pro Ser Ser Lys Ser Thr Ser Gly Gly Thr Ala Ala
                155                 160                 165

Leu Gly Cys Leu Val Lys Asp Tyr Phe Pro Glu Pro Val Thr Val
                170                 175                 180

Ser Trp Asn Ser Gly Ala Leu Thr Ser Gly Val His Thr Phe Pro
                185                 190                 195

Ala Val Leu Gln Ser Ser Gly Leu Tyr Ser Leu Ser Ser Val Val
                200                 205                 210

Thr Val Pro Ser Ser Ser Leu Gly Thr Gln Thr Tyr Ile Cys Asn
                215                 220                 225

Val Asn His Lys Pro Ser Asn Thr Lys Val Asp Lys Lys Val Glu
                230                 235                 240

Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn
                290                 295                 300

Trp Tyr Val Asp Gly Val Glu Val His Asn Ala Lys Thr Lys Pro
                305                 310                 315

Arg Glu Glu Gln Tyr Asn Ser Thr Tyr Arg Val Val Ser Val Leu
                320                 325                 330

Thr Val Leu His Gln Asp Trp Leu Asn Gly Lys Glu Tyr Lys Cys
                335                 340                 345

Lys Val Ser Asn Lys Ala Leu Pro Ala Pro Ile Glu Lys Thr Ile
                350                 355                 360

Ser Lys Ala Lys Gly Gln Pro Arg Glu Pro Gln Val Tyr Thr Leu
                365                 370                 375

Pro Pro Ser Arg Glu Glu Met Thr Lys Asn Gln Val Ser Leu Thr
                380                 385                 390

Cys Leu Val Lys Gly Phe Tyr Pro Ser Asp Ile Ala Val Glu Trp
                395                 400                 405

Glu Ser Asn Gly Gln Pro Glu Asn Asn Tyr Lys Thr Thr Pro Pro
                410                 415                 420

Val Leu Asp Ser Asp Gly Ser Phe Phe Leu Tyr Ser Lys Leu Thr
                425                 430                 435

Val Asp Lys Ser Arg Trp Gln Gln Gly Asn Val Phe Ser Cys Ser
                440                 445                 450

Val Met His Glu Ala Leu His Asn His Tyr Thr Gln Lys Ser Leu
                455                 460                 465

Ser Leu Ser Pro Gly Lys
                470

<210> SEQ ID NO 23
<211> LENGTH: 471
<212> TYPE: PRT
<213> ORGANISM: Artificial sequence
<220> FEATURE:
<223> OTHER INFORMATION: Sequence is synthesized

<400> SEQUENCE: 23

```
Met Gly Trp Ser Cys Ile Ile Leu Phe Leu Val Ala Thr Ala Thr
 1               5                  10                  15

Gly Val His Ser Glu Val Gln Leu Val Glu Ser Gly Gly Gly Leu
            20                  25                  30

Val Gln Pro Gly Gly Ser Leu Arg Leu Ser Cys Ala Ala Ser Gly
            35                  40                  45

Tyr Thr Phe Thr Ser Tyr Asn Met His Trp Val Arg Gln Ala Pro
            50                  55                  60

Gly Lys Gly Leu Glu Trp Val Gly Ala Ile Tyr Pro Gly Asn Gly
            65                  70                  75

Asp Thr Ser Tyr Asn Gln Lys Phe Lys Gly Arg Phe Thr Ile Ser
            80                  85                  90

Val Asp Lys Ser Lys Asn Thr Leu Tyr Leu Gln Met Asn Ser Leu
            95                 100                 105

Arg Ala Glu Asp Thr Ala Val Tyr Tyr Cys Ala Arg Val Val Tyr
           110                 115                 120

Tyr Ser Asn Ser Tyr Trp Tyr Phe Asp Val Trp Gly Gln Gly Thr
           125                 130                 135

Leu Val Thr Val Ser Ser Ala Ser Thr Lys Gly Pro Ser Val Phe
           140                 145                 150

Pro Leu Ala Pro Ser Ser Lys Ser Thr Ser Gly Gly Thr Ala Ala
           155                 160                 165

Leu Gly Cys Leu Val Lys Asp Tyr Phe Pro Glu Pro Val Thr Val
           170                 175                 180

Ser Trp Asn Ser Gly Ala Leu Thr Ser Gly Val His Thr Phe Pro
           185                 190                 195

Ala Val Leu Gln Ser Ser Gly Leu Tyr Ser Leu Ser Ser Val Val
           200                 205                 210

Thr Val Pro Ser Ser Ser Leu Gly Thr Gln Thr Tyr Ile Cys Asn
           215                 220                 225

Val Asn His Lys Pro Ser Asn Thr Lys Val Asp Lys Lys Val Glu
           230                 235                 240

Pro Lys Ser Cys Asp Lys Thr His Thr Cys Pro Pro Cys Pro Ala
           245                 250                 255

Pro Glu Leu Leu Gly Gly Pro Ser Val Phe Leu Phe Pro Pro Lys
           260                 265                 270

Pro Lys Asp Thr Leu Met Ile Ser Arg Thr Pro Glu Val Thr Cys
           275                 280                 285

Val Val Val Asp Val Ser His Glu Asp Pro Glu Val Lys Phe Asn
           290                 295                 300

Trp Tyr Val Asp Gly Val Glu Val His Asn Ala Lys Thr Lys Pro
           305                 310                 315

Arg Glu Glu Gln Tyr Asn Ala Thr Tyr Arg Val Val Ser Val Leu
           320                 325                 330

Thr Val Leu His Gln Asp Trp Leu Asn Gly Lys Glu Tyr Lys Cys
           335                 340                 345

Lys Val Ser Asn Lys Ala Leu Pro Ala Pro Ile Ala Ala Thr Ile
           350                 355                 360

Ser Lys Ala Lys Gly Gln Pro Arg Glu Pro Gln Val Tyr Thr Leu
           365                 370                 375

Pro Pro Ser Arg Glu Glu Met Thr Lys Asn Gln Val Ser Leu Thr
           380                 385                 390

Cys Leu Val Lys Gly Phe Tyr Pro Ser Asp Ile Ala Val Glu Trp
           395                 400                 405
```

```
Glu Ser Asn Gly Gln Pro Glu Asn Asn Tyr Lys Thr Thr Pro Pro
            410                 415                 420

Val Leu Asp Ser Asp Gly Ser Phe Phe Leu Tyr Ser Lys Leu Thr
            425                 430                 435

Val Asp Lys Ser Arg Trp Gln Gln Gly Asn Val Phe Ser Cys Ser
            440                 445                 450

Val Met His Glu Ala Leu His Asn His Tyr Thr Gln Lys Ser Leu
            455                 460                 465

Ser Leu Ser Pro Gly Lys
            470

<210> SEQ ID NO 24
<211> LENGTH: 891
<212> TYPE: DNA
<213> ORGANISM: Macaca fascicularis

<400> SEQUENCE: 24
atgacaacac ccagaaattc agtaaatggg actttcccag cagagccaat           50
gaaaggccct attgctatgc aacctggtcc aaaaccactc ctcaggagga          100
tgtcttcact ggtgggtccc acgcaaagct tcttcatgag ggaatctaag          150 gctttgggg  ctgtccagat tatgaatggg ctcttccaca ttgccctggg          200
gggtcttctg atgatcccag cagggatcta tgcacccatc tgtgtgactg          250
tgtggtaccc tctgtgggga ggcattatgt atattatttc cggatcactc          300
ctggcagcaa cggagaaaaa ctccaggaag tgtttggtca aggaaaaat           350 gataatgaat tcattgagcc tctttgctgc catttctgga atgattcttt          400
caatcatgga catacttaat attaaaattt cccattttt  aaaaatggag          450 agtctgaatt ttatcagagt tcacacacca tatattaaca tatacaactg          500
tgaaccagct aatccctctg agaaaaactc tccatctact caatactgtt          550
acagcataca atctctgttc ctgggcattt tgtcagtgat gctgatcttt          600
gccttcttcc aggaacttgt aatagctggc atcgttgaga tgaatggag            650 agaacatgc tccagaccca atctagcgt  agttctcctg tcagctgaag            700 aaaaaaaga caagtcatt  gaaataaaag aagaagtggt ggggctaact           750
gaaacatctt cccaaccaaa gaatgaagaa gccattgaaa ttattccaat          800
ccaagaagag gaagaagaag aaacagagac aaactttcca gaacctcccc          850
aagatcagga atcttcacca atagaaaatg acagctctcc t                   891

<210> SEQ ID NO 25
<211> LENGTH: 297
<212> TYPE: PRT
<213> ORGANISM: Macaca fascicularis

<400> SEQUENCE: 25

Met Thr Thr Pro Arg Asn Ser Val Asn Gly Thr Phe Pro Ala Glu
  1               5                  10                  15

Pro Met Lys Gly Pro Ile Ala Met Gln Pro Gly Pro Lys Pro Leu
             20                  25                  30

Leu Arg Arg Met Ser Ser Leu Val Gly Pro Thr Gln Ser Phe Phe
             35                  40                  45

Met Arg Glu Ser Lys Ala Leu Gly Ala Val Gln Ile Met Asn Gly
             50                  55                  60
```

```
Leu Phe His Ile Ala Leu Gly Gly Leu Leu Met Ile Pro Ala Gly
             65                  70                  75

Ile Tyr Ala Pro Ile Cys Val Thr Val Trp Tyr Pro Leu Trp Gly
                 80                  85                  90

Gly Ile Met Tyr Ile Ile Ser Gly Ser Leu Leu Ala Ala Thr Glu
                 95                 100                 105

Lys Asn Ser Arg Lys Cys Leu Val Lys Gly Lys Met Ile Met Asn
                110                 115                 120

Ser Leu Ser Leu Phe Ala Ala Ile Ser Gly Met Ile Leu Ser Ile
                125                 130                 135

Met Asp Ile Leu Asn Ile Lys Ile Ser His Phe Leu Lys Met Glu
                140                 145                 150

Ser Leu Asn Phe Ile Arg Val His Thr Pro Tyr Ile Asn Ile Tyr
                155                 160                 165

Asn Cys Glu Pro Ala Asn Pro Ser Glu Lys Asn Ser Pro Ser Thr
                170                 175                 180

Gln Tyr Cys Tyr Ser Ile Gln Ser Leu Phe Leu Gly Ile Leu Ser
                185                 190                 195

Val Met Leu Ile Phe Ala Phe Phe Gln Glu Leu Val Ile Ala Gly
                200                 205                 210

Ile Val Glu Asn Glu Trp Arg Arg Thr Cys Ser Arg Pro Lys Ser
                215                 220                 225

Ser Val Val Leu Leu Ser Ala Glu Lys Lys Glu Gln Val Ile
                230                 235                 240

Glu Ile Lys Glu Glu Val Val Gly Leu Thr Glu Thr Ser Ser Gln
                245                 250                 255

Pro Lys Asn Glu Glu Ala Ile Glu Ile Pro Ile Gln Glu Glu
                260                 265                 270

Glu Glu Glu Glu Thr Glu Thr Asn Phe Pro Glu Pro Pro Gln Asp
                275                 280                 285

Gln Glu Ser Ser Pro Ile Glu Asn Asp Ser Ser Pro
                290                 295

<210> SEQ ID NO 26
<211> LENGTH: 297
<212> TYPE: PRT
<213> ORGANISM: Homo sapiens

<400> SEQUENCE: 26

Met Thr Thr Pro Arg Asn Ser Val Asn Gly Thr Phe Pro Ala Glu
  1               5                  10                  15

Pro Met Lys Gly Pro Ile Ala Met Gln Ser Gly Pro Lys Pro Leu
                 20                  25                  30

Phe Arg Arg Met Ser Ser Leu Val Gly Pro Thr Gln Ser Phe Phe
                 35                  40                  45

Met Arg Glu Ser Lys Ala Leu Gly Ala Val Gln Ile Met Asn Gly
                 50                  55                  60

Leu Phe His Ile Ala Leu Gly Gly Leu Leu Met Ile Pro Ala Gly
                 65                  70                  75

Ile Tyr Ala Pro Ile Cys Val Thr Val Trp Tyr Pro Leu Trp Gly
                 80                  85                  90

Gly Ile Met Tyr Ile Ile Ser Gly Ser Leu Leu Ala Ala Thr Glu
                 95                 100                 105

Lys Asn Ser Arg Lys Cys Leu Val Lys Gly Lys Met Ile Met Asn
                110                 115                 120
```

```
Ser Leu Ser Leu Phe Ala Ala Ile Ser Gly Met Ile Leu Ser Ile
            125                 130                 135

Met Asp Ile Leu Asn Ile Lys Ile Ser His Phe Leu Lys Met Glu
            140                 145                 150

Ser Leu Asn Phe Ile Arg Ala His Thr Pro Tyr Ile Asn Ile Tyr
            155                 160                 165

Asn Cys Glu Pro Ala Asn Pro Ser Glu Lys Asn Ser Pro Ser Thr
            170                 175                 180

Gln Tyr Cys Tyr Ser Ile Gln Ser Leu Phe Leu Gly Ile Leu Ser
            185                 190                 195

Val Met Leu Ile Phe Ala Phe Phe Gln Glu Leu Val Ile Ala Gly
            200                 205                 210

Ile Val Glu Asn Glu Trp Lys Arg Thr Cys Ser Arg Pro Lys Ser
            215                 220                 225

Asn Ile Val Leu Leu Ser Ala Glu Glu Lys Lys Glu Gln Thr Ile
            230                 235                 240

Glu Ile Lys Glu Glu Val Val Gly Leu Thr Glu Thr Ser Ser Gln
            245                 250                 255

Pro Lys Asn Glu Glu Asp Ile Glu Ile Ile Pro Ile Gln Glu Glu
            260                 265                 270

Glu Glu Glu Glu Thr Glu Thr Asn Phe Pro Glu Pro Pro Gln Asp
            275                 280                 285

Gln Glu Ser Ser Pro Ile Glu Asn Asp Ser Ser Pro
            290                 295

<210> SEQ ID NO 27
<211> LENGTH: 36
<212> TYPE: DNA
<213> ORGANISM: Artificial sequence
<220> FEATURE:
<223> OTHER INFORMATION: Sequence is synthesized

<400> SEQUENCE: 27
ctacaccttc acgagctata acatgcactg ggtccg                              36

<210> SEQ ID NO 28
<211> LENGTH: 51
<212> TYPE: DNA
<213> ORGANISM: Artificial sequence
<220> FEATURE:
<223> OTHER INFORMATION: Sequence is synthesized

<400> SEQUENCE: 28
gattaatcct gacaacggcg acacgagcta taaccagaag ttcaagggcc               50
g                                                                    51

<210> SEQ ID NO 29
<211> LENGTH: 38
<212> TYPE: DNA
<213> ORGANISM: Artificial sequence
<220> FEATURE:
<223> OTHER INFORMATION: Sequence is synthesized

<400> SEQUENCE: 29
gaatgggttg cagcgatcta tcctggcaac ggcgacac                            38

<210> SEQ ID NO 30
<211> LENGTH: 65
<212> TYPE: DNA
<213> ORGANISM: Artificial sequence
<220> FEATURE:
```

-continued

<223> OTHER INFORMATION: Sequence is synthesized

<400> SEQUENCE: 30
attattgtgc tcgagtggtc tactatagca acagctactg gtacttcgac      50
gtctggggtc aagga      65

<210> SEQ ID NO 31
<211> LENGTH: 36
<212> TYPE: DNA
<213> ORGANISM: Artificial sequence
<220> FEATURE:
<223> OTHER INFORMATION: Sequence is synthesized

<400> SEQUENCE: 31
ctgcacagcc agctcttctg tcagctatat gcattg      36

<210> SEQ ID NO 32
<211> LENGTH: 42
<212> TYPE: DNA
<213> ORGANISM: Artificial sequence
<220> FEATURE:
<223> OTHER INFORMATION: Sequence is synthesized

<400> SEQUENCE: 32
aactactgat ttacgctcca tcgaacctcg cgtctggagt cc      42

<210> SEQ ID NO 33
<211> LENGTH: 45
<212> TYPE: DNA
<213> ORGANISM: Artificial sequence
<220> FEATURE:
<223> OTHER INFORMATION: Sequence is synthesized

<400> SEQUENCE: 33
tattactgtc aacagtggag cttcaatccg cccacatttg gacag      45

<210> SEQ ID NO 34
<211> LENGTH: 37
<212> TYPE: DNA
<213> ORGANISM: Artificial sequence
<220> FEATURE:
<223> OTHER INFORMATION: Sequence is synthesized

<400> SEQUENCE: 34
gtttcactat aagtgtcgac aagtccaaaa acacatt      37

<210> SEQ ID NO 35
<211> LENGTH: 33
<212> TYPE: DNA
<213> ORGANISM: Artificial sequence
<220> FEATURE:
<223> OTHER INFORMATION: Sequence is synthesized

<400> SEQUENCE: 35
gccaggatag atggcgccaa cccattccag gcc      33

<210> SEQ ID NO 36
<211> LENGTH: 26
<212> TYPE: DNA
<213> ORGANISM: Artificial sequence
<220> FEATURE:
<223> OTHER INFORMATION: Sequence is synthesized

<400> SEQUENCE: 36
aagctccgaa accactgatt tacgct      26

<210> SEQ ID NO 37
<211> LENGTH: 18
<212> TYPE: DNA
<213> ORGANISM: Artificial Sequence
<220> FEATURE:
<223> OTHER INFORMATION: Sequence is synthesized

<400> SEQUENCE: 37
agttttgaga gcaaaatg                                                 18

<210> SEQ ID NO 38
<211> LENGTH: 18
<212> TYPE: DNA
<213> ORGANISM: Artificial Sequence
<220> FEATURE:
<223> OTHER INFORMATION: Sequence is synthesized

<400> SEQUENCE: 38
aagctatgaa cactaatg                                                 18

<210> SEQ ID NO 39
<211> LENGTH: 452
<212> TYPE: PRT
<213> ORGANISM: Artificial sequence
<220> FEATURE:
<223> OTHER INFORMATION: sequence is synthesized

<400> SEQUENCE: 39

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
             20                  25                  30

Ser Tyr Asn Met His Trp Val Arg Gln Ala Pro Gly Lys Gly Leu
         35                  40                  45

Glu Trp Val Gly Ala Ile Tyr Pro Gly Asn Gly Asp Thr Ser Tyr
     50                  55                  60

Asn Gln Lys Phe Lys Gly Arg Phe Thr Ile Ser Val Asp Lys Ser
 65                  70                  75

Lys Asn Thr Leu Tyr Leu Gln Met Asn Ser Leu Arg Ala Glu Asp
             80                  85                  90

Thr Ala Val Tyr Tyr Cys Ala Arg Val Val Tyr Tyr Ser Asn Ser
         95                 100                 105

Tyr Trp Tyr Phe Asp Val Trp Gly Gln Gly Thr Leu Val Thr Val
                    110                 115                 120

Ser Ser Ala Ser Thr Lys Gly Pro Ser Val Phe Pro Leu Ala Pro
                    125                 130                 135

Ser Ser Lys Ser Thr Ser Gly Gly Thr Ala Ala Leu Gly Cys Leu
                    140                 145                 150

Val Lys Asp Tyr Phe Pro Glu Pro Val Thr Val Ser Trp Asn Ser
                    155                 160                 165

Gly Ala Leu Thr Ser Gly Val His Thr Phe Pro Ala Val Leu Gln
                    170                 175                 180

Ser Ser Gly Leu Tyr Ser Leu Ser Ser Val Val Thr Val Pro Ser
                    185                 190                 195

Ser Ser Leu Gly Thr Gln Thr Tyr Ile Cys Asn Val Asn His Lys
                    200                 205                 210

Pro Ser Asn Thr Lys Val Asp Lys Lys Val Glu Pro Lys Ser Cys
                    215                 220                 225

Asp Lys Thr His Thr Cys Pro Pro Cys Pro Ala Pro Glu Leu Leu

-continued

```
                    230                 235                 240
Gly Gly Pro Ser Val Phe Leu Phe Pro Lys Pro Lys Asp Thr
                245                 250                 255

Leu Met Ile Ser Arg Thr Pro Glu Val Thr Cys Val Val Asp
                260                 265                 270

Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln
                290                 295                 300

Tyr Asn Ser Thr Tyr Arg Val Val Ser Val Leu Thr Val Leu His
                305                 310                 315

Gln Asp Trp Leu Asn Gly Lys Glu Tyr Lys Cys Lys Val Ser Asn
                320                 325                 330

Lys Ala Leu Pro Ala Pro Ile Glu Lys Thr Ile Ser Lys Ala Lys
                335                 340                 345

Gly Gln Pro Arg Glu Pro Gln Val Tyr Thr Leu Pro Pro Ser Arg
                350                 355                 360

Glu Glu Met Thr Lys Asn Gln Val Ser Leu Thr Cys Leu Val Lys
                365                 370                 375

Gly Phe Tyr Pro Ser Asp Ile Ala Val Glu Trp Glu Ser Asn Gly
                380                 385                 390

Gln Pro Glu Asn Asn Tyr Lys Thr Thr Pro Pro Val Leu Asp Ser
                395                 400                 405

Asp Gly Ser Phe Phe Leu Tyr Ser Lys Leu Thr Val Asp Lys Ser
                410                 415                 420

Arg Trp Gln Gln Gly Asn Val Phe Ser Cys Ser Val Met His Glu
                425                 430                 435

Ala Leu His Asn His Tyr Thr Gln Lys Ser Leu Ser Leu Ser Pro
                440                 445                 450

Gly Lys

<210> SEQ ID NO 40
<211> LENGTH: 213
<212> TYPE: PRT
<213> ORGANISM: Artificial sequence
<220> FEATURE:
<223> OTHER INFORMATION: sequence is synthesized

<400> SEQUENCE: 40

Asp Ile Gln Met Thr Gln Ser Pro Ser Ser Leu Ser Ala Ser Val
  1                   5                  10                  15

Gly Asp Arg Val Thr Ile Thr Cys Arg Ala Ser Ser Ser Val Ser
                 20                  25                  30

Tyr Met His Trp Tyr Gln Gln Lys Pro Gly Lys Ala Pro Lys Pro
                 35                  40                  45

Leu Ile Tyr Ala Pro Ser Asn Leu Ala Ser Gly Val Pro Ser Arg
                 50                  55                  60

Phe Ser Gly Ser Gly Ser Gly Thr Asp Phe Thr Leu Thr Ile Ser
                 65                  70                  75

Ser Leu Gln Pro Glu Asp Phe Ala Thr Tyr Tyr Cys Gln Gln Trp
                 80                  85                  90

Ser Phe Asn Pro Pro Thr Phe Gly Gln Gly Thr Lys Val Glu Ile
                 95                 100                 105

Lys Arg Thr Val Ala Ala Pro Ser Val Phe Ile Phe Pro Pro Ser
                110                 115                 120
```

```
Asp Glu Gln Leu Lys Ser Gly Thr Ala Ser Val Val Cys Leu Leu
            125                 130                 135

Asn Asn Phe Tyr Pro Arg Glu Ala Lys Val Gln Trp Lys Val Asp
            140                 145                 150

Asn Ala Leu Gln Ser Gly Asn Ser Gln Glu Ser Val Thr Glu Gln
            155                 160                 165

Asp Ser Lys Asp Ser Thr Tyr Ser Leu Ser Ser Thr Leu Thr Leu
            170                 175                 180

Ser Lys Ala Asp Tyr Glu Lys His Lys Val Tyr Ala Cys Glu Val
            185                 190                 195

Thr His Gln Gly Leu Ser Ser Pro Val Thr Lys Ser Phe Asn Arg
            200                 205                 210

Gly Glu Cys

<210> SEQ ID NO 41
<211> LENGTH: 452
<212> TYPE: PRT
<213> ORGANISM: Artificial sequence
<220> FEATURE:
<223> OTHER INFORMATION: sequence is synthesized

<400> SEQUENCE: 41

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
            20                  25                  30

Ser Tyr Asn Met His Trp Val Arg Gln Ala Pro Gly Lys Gly Leu
            35                  40                  45

Glu Trp Val Gly Ala Ile Tyr Pro Gly Asn Gly Asp Thr Ser Tyr
            50                  55                  60

Asn Gln Lys Phe Lys Gly Arg Phe Thr Ile Ser Val Asp Lys Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Arg Val Val Tyr Tyr Ser Asn Ser
            95                  100                 105

Tyr Trp Tyr Phe Asp Val Trp Gly Gln Gly Thr Leu Val Thr Val
            110                 115                 120

Ser Ser Ala Ser Thr Lys Gly Pro Ser Val Phe Pro Leu Ala Pro
            125                 130                 135

Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
            155                 160                 165

Gly Ala Leu Thr Ser Gly Val His Thr Phe Pro Ala Val Leu Gln
            170                 175                 180

Ser Ser Gly Leu Tyr Ser Leu Ser Ser Val Val Thr Val Pro Ser
            185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
            215                 220                 225

Asp Lys Thr His Thr Cys Pro Pro Cys Pro Ala Pro Glu Leu Leu
            230                 235                 240

Gly Gly Pro Ser Val Phe Leu Phe Pro Pro Lys Pro Lys Asp Thr
            245                 250                 255
```

```
Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln
        290                 295                 300

Tyr Asn Ala Thr Tyr Arg Val Val Ser Val Leu Thr Val Leu His
    305                 310                 315

Gln Asp Trp Leu Asn Gly Lys Glu Tyr Lys Cys Lys Val Ser Asn
320                 325                 330

Lys Ala Leu Pro Ala Pro Ile Ala Ala Thr Ile Ser Lys Ala Lys
                335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
        365                 370                 375

Gly Phe Tyr Pro Ser Asp Ile Ala Val Glu Trp Glu Ser Asn Gly
    380                 385                 390

Gln Pro Glu Asn Asn Tyr Lys Thr Thr Pro Pro Val Leu Asp Ser
395                 400                 405

Asp Gly Ser Phe Phe Leu Tyr Ser Lys Leu Thr Val Asp Lys Ser
                410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
        440                 445                 450

Gly Lys

<210> SEQ ID NO 42
<211> LENGTH: 452
<212> TYPE: PRT
<213> ORGANISM: Artificial sequence
<220> FEATURE:
<223> OTHER INFORMATION: sequence is synthesized

<400> SEQUENCE: 42

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
            20                  25                  30

Ser Tyr Asn Met His Trp Val Arg Gln Ala Pro Gly Lys Gly Leu
        35                  40                  45

Glu Trp Val Gly Ala Ile Tyr Pro Gly Asn Gly Asp Thr Ser Tyr
    50                  55                  60

Asn Gln Lys Phe Lys Gly Arg Phe Thr Ile Ser Val Asp Lys Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Tyr Tyr Ser Ala Ser
            95                  100                 105

Tyr Trp Tyr Phe Asp Val Trp Gly Gln Gly Thr Leu Val Thr Val
        110                 115                 120

Ser Ser Ala Ser Thr Lys Gly Pro Ser Val Phe Pro Leu Ala Pro
    125                 130                 135

Ser Ser Lys Ser Thr Ser Gly Gly Thr Ala Ala Leu Gly Cys Leu
```

```
                140             145             150
Val Lys Asp Tyr Phe Pro Glu Pro Val Thr Val Ser Trp Asn Ser
            155                 160                 165
Gly Ala Leu Thr Ser Gly Val His Thr Phe Pro Ala Val Leu Gln
            170                 175                 180
Ser Ser Gly Leu Tyr Ser Leu Ser Ser Val Val Thr Val Pro Ser
            185                 190                 195
Ser Ser Leu Gly Thr Gln Thr Tyr Ile Cys Asn Val Asn His Lys
            200                 205                 210
Pro Ser Asn Thr Lys Val Asp Lys Lys Val Glu Pro Lys Ser Cys
            215                 220                 225
Asp Lys Thr His Thr Cys Pro Pro Cys Pro Ala Pro Glu Leu Leu
            230                 235                 240
Gly Gly Pro Ser Val Phe Leu Phe Pro Pro Lys Pro Lys Asp Thr
            245                 250                 255
Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln
            290                 295                 300
Tyr Asn Ala Thr Tyr Arg Val Val Ser Val Leu Thr Val Leu His
            305                 310                 315
Gln Asp Trp Leu Asn Gly Lys Glu Tyr Lys Cys Lys Val Ser Asn
            320                 325                 330
Lys Ala Leu Pro Ala Pro Ile Ala Ala Thr Ile Ser Lys Ala Lys
            335                 340                 345
Gly Gln Pro Arg Glu Pro Gln Val Tyr Thr Leu Pro Pro Ser Arg
            350                 355                 360
Glu Glu Met Thr Lys Asn Gln Val Ser Leu Thr Cys Leu Val Lys
            365                 370                 375
Gly Phe Tyr Pro Ser Asp Ile Ala Val Glu Trp Glu Ser Asn Gly
            380                 385                 390
Gln Pro Glu Asn Asn Tyr Lys Thr Thr Pro Pro Val Leu Asp Ser
            395                 400                 405
Asp Gly Ser Phe Phe Leu Tyr Ser Lys Leu Thr Val Asp Lys Ser
            410                 415                 420
Arg Trp Gln Gln Gly Asn Val Phe Ser Cys Ser Val Met His Glu
            425                 430                 435
Ala Leu His Asn His Tyr Thr Gln Lys Ser Leu Ser Leu Ser Pro
            440                 445                 450
Gly Lys

<210> SEQ ID NO 43
<211> LENGTH: 213
<212> TYPE: PRT
<213> ORGANISM: Artificial sequence
<220> FEATURE:
<223> OTHER INFORMATION: sequence is synthesized

<400> SEQUENCE: 43

Asp Ile Gln Met Thr Gln Ser Pro Ser Ser Leu Ser Ala Ser Val
 1               5                  10                  15
Gly Asp Arg Val Thr Ile Thr Cys Arg Ala Ser Ser Val Ser
                20                  25                  30
```

```
Tyr Leu His Trp Tyr Gln Gln Lys Pro Gly Lys Ala Pro Lys Pro
                 35                  40                  45

Leu Ile Tyr Ala Pro Ser Asn Leu Ala Ser Gly Val Pro Ser Arg
             50                  55                  60

Phe Ser Gly Ser Gly Ser Gly Thr Asp Phe Thr Leu Thr Ile Ser
         65                  70                  75

Ser Leu Gln Pro Glu Asp Phe Ala Thr Tyr Tyr Cys Gln Gln Trp
             80                  85                  90

Ser Phe Asn Pro Pro Thr Phe Gly Gln Gly Thr Lys Val Glu Ile
             95                 100                 105

Lys Arg Thr Val Ala Ala Pro Ser Val Phe Ile Phe Pro Pro Ser
            110                 115                 120

Asp Glu Gln Leu Lys Ser Gly Thr Ala Ser Val Val Cys Leu Leu
            125                 130                 135

Asn Asn Phe Tyr Pro Arg Glu Ala Lys Val Gln Trp Lys Val Asp
            140                 145                 150

Asn Ala Leu Gln Ser Gly Asn Ser Gln Glu Ser Val Thr Glu Gln
            155                 160                 165

Asp Ser Lys Asp Ser Thr Tyr Ser Leu Ser Ser Thr Leu Thr Leu
            170                 175                 180

Ser Lys Ala Asp Tyr Glu Lys His Lys Val Tyr Ala Cys Glu Val
            185                 190                 195

Thr His Gln Gly Leu Ser Ser Pro Val Thr Lys Ser Phe Asn Arg
            200                 205                 210

Gly Glu Cys

<210> SEQ ID NO 44
<211> LENGTH: 452
<212> TYPE: PRT
<213> ORGANISM: Artificial sequence
<220> FEATURE:
<223> OTHER INFORMATION: sequence is synthesized

<400> SEQUENCE: 44

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
             20                  25                  30

Ser Tyr Asn Met His Trp Val Arg Gln Ala Pro Gly Lys Gly Leu
             35                  40                  45

Glu Trp Val Gly Ala Ile Tyr Pro Gly Asn Gly Ala Thr Ser Tyr
             50                  55                  60

Asn Gln Lys Phe Lys Gly Arg Phe Thr Ile Ser Val Asp Lys Ser
             65                  70                  75

Lys Asn Thr Leu Tyr Leu Gln Met Asn Ser Leu Arg Ala Glu Asp
             80                  85                  90

Thr Ala Val Tyr Tyr Cys Ala Arg Val Tyr Tyr Ser Ala Ser
             95                 100                 105

Tyr Trp Tyr Phe Asp Val Trp Gly Gln Gly Thr Leu Val Thr Val
            110                 115                 120

Ser Ser Ala Ser Thr Lys Gly Pro Ser Val Phe Pro Leu Ala Pro
            125                 130                 135

Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
            155                 160                 165
```

```
Gly Ala Leu Thr Ser Gly Val His Thr Phe Pro Ala Val Leu Gln
                170                 175                 180

Ser Ser Gly Leu Tyr Ser Leu Ser Ser Val Thr Val Pro Ser
            185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
            215                 220                 225

Asp Lys Thr His Thr Cys Pro Pro Cys Pro Ala Pro Glu Leu Leu
            230                 235                 240

Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His
            305                 310                 315

Gln Asp Trp Leu Asn Gly Lys Glu Tyr Lys Cys Lys Val Ser Asn
            320                 325                 330

Lys Ala Leu Pro Ala Pro Ile Glu Lys Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Glu Ser Asn Gly
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly Lys

<210> SEQ ID NO 45
<211> LENGTH: 213
<212> TYPE: PRT
<213> ORGANISM: Artificial sequence
<220> FEATURE:
<223> OTHER INFORMATION: sequence is synthesized

<400> SEQUENCE: 45

Asp Ile Gln Met Thr Gln Ser Pro Ser Ser Leu Ser Ala Ser Val
 1               5                  10                  15

Gly Asp Arg Val Thr Ile Thr Cys Arg Ala Ser Ser Ser Val Ser
                20                  25                  30

Tyr Met His Trp Tyr Gln Gln Lys Pro Gly Lys Ala Pro Lys Pro
                35                  40                  45

Leu Ile Tyr Ala Pro Ser Asn Leu Ala Ser Gly Val Pro Ser Arg
```

-continued

```
                   50                  55                  60
Phe Ser Gly Ser Gly Ser Gly Thr Asp Phe Thr Leu Thr Ile Ser
                65                  70                  75
Ser Leu Gln Pro Glu Asp Phe Ala Thr Tyr Tyr Cys Gln Gln Trp
                80                  85                  90
Ala Phe Asn Pro Pro Thr Phe Gly Gln Gly Thr Lys Val Glu Ile
                95                 100                 105
Lys Arg Thr Val Ala Ala Pro Ser Val Phe Ile Phe Pro Pro Ser
               110                 115                 120
Asp Glu Gln Leu Lys Ser Gly Thr Ala Ser Val Val Cys Leu Leu
               125                 130                 135
Asn Asn Phe Tyr Pro Arg Glu Ala Lys Val Gln Trp Lys Val Asp
               140                 145                 150
Asn Ala Leu Gln Ser Gly Asn Ser Gln Glu Ser Val Thr Glu Gln
               155                 160                 165
Asp Ser Lys Asp Ser Thr Tyr Ser Leu Ser Ser Thr Leu Thr Leu
               170                 175                 180
Ser Lys Ala Asp Tyr Glu Lys His Lys Val Tyr Ala Cys Glu Val
               185                 190                 195
Thr His Gln Gly Leu Ser Ser Pro Val Thr Lys Ser Phe Asn Arg
               200                 205                 210
Gly Glu Cys
```

<210> SEQ ID NO 46
<211> LENGTH: 452
<212> TYPE: PRT
<213> ORGANISM: Artificial sequence
<220> FEATURE:
<223> OTHER INFORMATION: sequence is synthesized

<400> SEQUENCE: 46

```
Glu Val Gln Leu Val Glu Ser Gly Gly Gly Leu Val Gln Pro Gly
  1               5                  10                  15
Gly Ser Leu Arg Leu Ser Cys Ala Ala Ser Gly Tyr Thr Phe Thr
                 20                  25                  30
Ser Tyr Asn Met His Trp Val Arg Gln Ala Pro Gly Lys Gly Leu
                 35                  40                  45
Glu Trp Val Gly Ala Ile Tyr Pro Gly Asn Gly Ala Thr Ser Tyr
                 50                  55                  60
Asn Gln Lys Phe Lys Gly Arg Phe Thr Ile Ser Val Asp Lys Ser
                 65                  70                  75
Lys Asn Thr Leu Tyr Leu Gln Met Asn Ser Leu Arg Ala Glu Asp
                 80                  85                  90
Thr Ala Val Tyr Tyr Cys Ala Arg Val Val Tyr Tyr Ser Ala Ser
                 95                 100                 105
Tyr Trp Tyr Phe Asp Val Trp Gly Gln Gly Thr Leu Val Thr Val
                110                 115                 120
Ser Ser Ala Ser Thr Lys Gly Pro Ser Val Phe Pro Leu Ala Pro
                125                 130                 135
Ser Ser Lys Ser Thr Ser Gly Gly Thr Ala Ala Leu Gly Cys Leu
                140                 145                 150
Val Lys Asp Tyr Phe Pro Glu Pro Val Thr Val Ser Trp Asn Ser
                155                 160                 165
Gly Ala Leu Thr Ser Gly Val His Thr Phe Pro Ala Val Leu Gln
                170                 175                 180
```

```
Ser Ser Gly Leu Tyr Ser Leu Ser Ser Val Val Thr Val Pro Ser
            185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
            215                 220                 225

Asp Lys Thr His Thr Cys Pro Pro Cys Pro Ala Pro Glu Leu Leu
            230                 235                 240

Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln
            290                 295                 300

Tyr Asn Ala Thr Tyr Arg Val Val Ser Val Leu Thr Val Leu His
            305                 310                 315

Gln Asp Trp Leu Asn Gly Lys Glu Tyr Lys Cys Lys Val Ser Asn
            320                 325                 330

Lys Ala Leu Pro Ala Pro Ile Ala Ala Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Glu Ser Asn Gly
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly Lys

<210> SEQ ID NO 47
<211> LENGTH: 213
<212> TYPE: PRT
<213> ORGANISM: Artificial sequence
<220> FEATURE:
<223> OTHER INFORMATION: sequence is synthesized

<400> SEQUENCE: 47

Asp Ile Gln Met Thr Gln Ser Pro Ser Ser Leu Ser Ala Ser Val
 1               5                  10                  15

Gly Asp Arg Val Thr Ile Thr Cys Arg Ala Ser Ser Ser Val Ser
             20                  25                  30

Tyr Leu His Trp Tyr Gln Gln Lys Pro Gly Lys Ala Pro Lys Pro
             35                  40                  45

Leu Ile Tyr Ala Pro Ser Asn Leu Ala Ser Gly Val Pro Ser Arg
             50                  55                  60

Phe Ser Gly Ser Gly Ser Gly Thr Asp Phe Thr Leu Thr Ile Ser
             65                  70                  75
```

Ser Leu Gln Pro Glu Asp Phe Ala Thr Tyr Tyr Cys Gln Gln Trp
                80                  85                  90

Ala Phe Asn Pro Pro Thr Phe Gly Gln Gly Thr Lys Val Glu Ile
            95                 100                 105

Lys Arg Thr Val Ala Ala Pro Ser Val Phe Ile Phe Pro Pro Ser
        110                 115                 120

Asp Glu Gln Leu Lys Ser Gly Thr Ala Ser Val Val Cys Leu Leu
    125                 130                 135

Asn Asn Phe Tyr Pro Arg Glu Ala Lys Val Gln Trp Lys Val Asp
140                 145                 150

Asn Ala Leu Gln Ser Gly Asn Ser Gln Glu Ser Val Thr Glu Gln
            155                 160                 165

Asp Ser Lys Asp Ser Thr Tyr Ser Leu Ser Ser Thr Leu Thr Leu
        170                 175                 180

Ser Lys Ala Asp Tyr Glu Lys His Lys Val Tyr Ala Cys Glu Val
    185                 190                 195

Thr His Gln Gly Leu Ser Ser Pro Val Thr Lys Ser Phe Asn Arg
200                 205                 210

Gly Glu Cys

<210> SEQ ID NO 48
<211> LENGTH: 452
<212> TYPE: PRT
<213> ORGANISM: Artificial sequence
<220> FEATURE:
<223> OTHER INFORMATION: sequence is synthesized

<400> SEQUENCE: 48

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
             20                  25                  30

Ser Tyr Asn Met His Trp Val Arg Gln Ala Pro Gly Lys Gly Leu
         35                  40                  45

Glu Trp Val Gly Ala Ile Tyr Pro Gly Asn Gly Ala Thr Ser Tyr
     50                  55                  60

Asn Gln Lys Phe Lys Gly Arg Phe Thr Ile Ser Val Asp Lys Ser
 65                  70                  75

Lys Asn Thr Leu Tyr Leu Gln Met Asn Ser Leu Arg Ala Glu Asp
             80                  85                  90

Thr Ala Val Tyr Tyr Cys Ala Arg Val Val Tyr Tyr Ser Ala Ser
         95                 100                 105

Tyr Trp Tyr Phe Asp Val Trp Gly Gln Gly Thr Leu Val Thr Val
    110                 115                 120

Ser Ser Ala Ser Thr Lys Gly Pro Ser Val Phe Pro Leu Ala Pro
125                 130                 135

Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
        155                 160                 165

Gly Ala Leu Thr Ser Gly Val His Thr Phe Pro Ala Val Leu Gln
    170                 175                 180

Ser Ser Gly Leu Tyr Ser Leu Ser Ser Val Val Thr Val Pro Ser
185                 190                 195

Ser Ser Leu Gly Thr Gln Thr Tyr Ile Cys Asn Val Asn His Lys

```
                    200                 205                 210
Pro Ser Asn Thr Lys Val Asp Lys Lys Val Glu Pro Lys Ser Cys
                215                 220                 225
Asp Lys Thr His Thr Cys Pro Pro Cys Pro Ala Pro Glu Leu Leu
                230                 235                 240
Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp
                275                 280                 285
Gly Val Glu Val His Asn Ala Lys Thr Lys Pro Arg Glu Glu Gln
                290                 295                 300
Tyr Asn Ala Thr Tyr Arg Val Val Ser Val Leu Thr Val Leu His
                305                 310                 315
Gln Asp Trp Leu Asn Gly Lys Glu Tyr Lys Cys Lys Val Ser Asn
                320                 325                 330
Lys Ala Leu Pro Ala Pro Ile Ala Ala Thr Ile Ser Lys Ala Lys
                335                 340                 345
Gly Gln Pro Arg Glu Pro Gln Val Tyr Thr Leu Pro Pro Ser Arg
                350                 355                 360
Asp Glu Leu Thr Lys Asn Gln Val Ser Leu Thr Cys Leu Val Lys
                365                 370                 375
Gly Phe Tyr Pro Ser Asp Ile Ala Val Glu Trp Glu Ser Asn Gly
                380                 385                 390
Gln Pro Glu Asn Asn Tyr Lys Thr Thr Pro Pro Val Leu Asp Ser
                395                 400                 405
Asp Gly Ser Phe Phe Leu Tyr Ser Lys Leu Thr Val Asp Lys Ser
                410                 415                 420
Arg Trp Gln Gln Gly Asn Val Phe Ser Cys Ser Val Met His Glu
                425                 430                 435
Ala Leu His Asn His Tyr Thr Gln Lys Ser Leu Ser Leu Ser Pro
                440                 445                 450
Gly Lys

<210> SEQ ID NO 49
<211> LENGTH: 452
<212> TYPE: PRT
<213> ORGANISM: Artificial sequence
<220> FEATURE:
<223> OTHER INFORMATION: sequence is synthesized

<400> SEQUENCE: 49

Glu Val Gln Leu Val Glu Ser Gly Gly Gly Leu Val Gln Pro Gly
  1               5                  10                  15
Gly Ser Leu Arg Leu Ser Cys Ala Ala Ser Gly Tyr Thr Phe Thr
                 20                  25                  30
Ser Tyr Asn Met His Trp Val Arg Gln Ala Pro Gly Lys Gly Leu
                 35                  40                  45
Glu Trp Val Gly Ala Ile Tyr Pro Gly Asn Gly Ala Thr Ser Tyr
                 50                  55                  60
Asn Gln Lys Phe Lys Gly Arg Phe Thr Ile Ser Val Asp Lys Ser
                 65                  70                  75
Lys Asn Thr Leu Tyr Leu Gln Met Asn Ser Leu Arg Ala Glu Asp
                 80                  85                  90
```

```
Thr Ala Val Tyr Tyr Cys Ala Arg Val Val Tyr Tyr Ser Ala Ser
             95                 100                 105

Tyr Trp Tyr Phe Asp Val Trp Gly Gln Gly Thr Leu Val Thr Val
            110                 115                 120

Ser Ser Ala Ser Thr Lys Gly Pro Ser Val Phe Pro Leu Ala Pro
            125                 130                 135

Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
            155                 160                 165

Gly Ala Leu Thr Ser Gly Val His Thr Phe Pro Ala Val Leu Gln
            170                 175                 180

Ser Ser Gly Leu Tyr Ser Leu Ser Ser Val Val Thr Val Pro Ser
            185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
            215                 220                 225

Asp Lys Thr His Thr Cys Pro Pro Cys Pro Ala Pro Glu Leu Leu
            230                 235                 240

Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln
            290                 295                 300

Tyr Asn Ala Thr Tyr Arg Val Val Ser Val Leu Thr Val Leu His
            305                 310                 315

Gln Asp Trp Leu Asn Gly Lys Glu Tyr Lys Cys Ala Val Ser Asn
            320                 325                 330

Lys Ala Leu Pro Ala Pro Ile Glu Ala Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Glu Ser Asn Gly
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly Lys

<210> SEQ ID NO 50
<211> LENGTH: 452
<212> TYPE: PRT
<213> ORGANISM: Artificial sequence
<220> FEATURE:
```

<223> OTHER INFORMATION: sequence is synthesized

<400> SEQUENCE: 50

| | | | | | | | | | | | | | | |
|---|---|---|---|---|---|---|---|---|---|---|---|---|---|---|
|Glu|Val|Gln|Leu|Val|Glu|Ser|Gly|Gly|Gly|Leu|Val|Gln|Pro|Gly|
|1| | | |5| | | | |10| | | | |15|
|Gly|Ser|Leu|Arg|Leu|Ser|Cys|Ala|Ala|Ser|Gly|Tyr|Thr|Phe|Thr|
| | | | |20| | | | |25| | | | |30|
|Ser|Tyr|Asn|Met|His|Trp|Val|Arg|Gln|Ala|Pro|Gly|Lys|Gly|Leu|
| | | | |35| | | | |40| | | | |45|
|Glu|Trp|Val|Gly|Ala|Ile|Tyr|Pro|Gly|Asn|Gly|Ala|Thr|Ser|Tyr|
| | | | |50| | | | |55| | | | |60|
|Asn|Gln|Lys|Phe|Lys|Gly|Arg|Phe|Thr|Ile|Ser|Val|Asp|Lys|Ser|
| | | | |65| | | | |70| | | | |75|
|Lys|Asn|Thr|Leu|Tyr|Leu|Gln|Met|Asn|Ser|Leu|Arg|Ala|Glu|Asp|
| | | | |80| | | | |85| | | | |90|
|Thr|Ala|Val|Tyr|Tyr|Cys|Ala|Arg|Val|Val|Tyr|Tyr|Ser|Ala|Ser|
| | | | |95| | | | |100| | | | |105|
|Tyr|Trp|Tyr|Phe|Asp|Val|Trp|Gly|Gln|Gly|Thr|Leu|Val|Thr|Val|
| | | | |110| | | | |115| | | | |120|
|Ser|Ser|Ala|Ser|Thr|Lys|Gly|Pro|Ser|Val|Phe|Pro|Leu|Ala|Pro|
| | | | |125| | | | |130| | | | |135|
|Ser|Ser|Lys|Ser|Thr|Ser|Gly|Gly|Thr|Ala|Ala|Leu|Gly|Cys|Leu|
| | | | |140| | | | |145| | | | |150|
|Val|Lys|Asp|Tyr|Phe|Pro|Glu|Pro|Val|Thr|Val|Ser|Trp|Asn|Ser|
| | | | |155| | | | |160| | | | |165|
|Gly|Ala|Leu|Thr|Ser|Gly|Val|His|Thr|Phe|Pro|Ala|Val|Leu|Gln|
| | | | |170| | | | |175| | | | |180|
|Ser|Ser|Gly|Leu|Tyr|Ser|Leu|Ser|Ser|Val|Val|Thr|Val|Pro|Ser|
| | | | |185| | | | |190| | | | |195|
|Ser|Ser|Leu|Gly|Thr|Gln|Thr|Tyr|Ile|Cys|Asn|Val|Asn|His|Lys|
| | | | |200| | | | |205| | | | |210|
|Pro|Ser|Asn|Thr|Lys|Val|Asp|Lys|Lys|Val|Glu|Pro|Lys|Ser|Cys|
| | | | |215| | | | |220| | | | |225|
|Asp|Lys|Thr|His|Thr|Cys|Pro|Pro|Cys|Pro|Ala|Pro|Glu|Leu|Leu|
| | | | |230| | | | |235| | | | |240|
|Gly|Gly|Pro|Ser|Val|Phe|Leu|Phe|Pro|Pro|Lys|Pro|Lys|Asp|Thr|
| | | | |245| | | | |250| | | | |255|
|Leu|Met|Ile|Ser|Arg|Thr|Pro|Glu|Val|Thr|Cys|Val|Val|Val|Asp|
| | | | |260| | | | |265| | | | |270|
|Val|Ser|His|Glu|Asp|Pro|Glu|Val|Lys|Phe|Asn|Trp|Tyr|Val|Asp|
| | | | |275| | | | |280| | | | |285|
|Gly|Val|Glu|Val|His|Asn|Ala|Lys|Thr|Lys|Pro|Arg|Glu|Glu|Gln|
| | | | |290| | | | |295| | | | |300|
|Tyr|Asn|Ala|Thr|Tyr|Arg|Val|Val|Ser|Val|Leu|Thr|Val|Leu|His|
| | | | |305| | | | |310| | | | |315|
|Gln|Asp|Trp|Leu|Asn|Gly|Lys|Glu|Tyr|Lys|Cys|Lys|Val|Ser|Asn|
| | | | |320| | | | |325| | | | |330|
|Ala|Ala|Leu|Pro|Ala|Pro|Ile|Ala|Ala|Thr|Ile|Ser|Lys|Ala|Lys|
| | | | |335| | | | |340| | | | |345|
|Gly|Gln|Pro|Arg|Glu|Pro|Gln|Val|Tyr|Thr|Leu|Pro|Pro|Ser|Arg|
| | | | |350| | | | |355| | | | |360|
|Glu|Glu|Met|Thr|Lys|Asn|Gln|Val|Ser|Leu|Thr|Cys|Leu|Val|Lys|
| | | | |365| | | | |370| | | | |375|
|Gly|Phe|Tyr|Pro|Ser|Asp|Ile|Ala|Val|Glu|Trp|Glu|Ser|Asn|Gly|

```
                        380                 385                 390
Gln Pro Glu Asn Asn Tyr Lys Thr Thr Pro Pro Val Leu Asp Ser
                    395                 400                 405

Asp Gly Ser Phe Phe Leu Tyr Ser Lys Leu Thr Val Asp Lys Ser
                410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
        440                 445                 450

Gly Lys

<210> SEQ ID NO 51
<211> LENGTH: 122
<212> TYPE: PRT
<213> ORGANISM: Artificial sequence
<220> FEATURE:
<223> OTHER INFORMATION: sequence is synthesized

<400> SEQUENCE: 51

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
            35                  40                  45

Glu Trp Val Gly Ala Ile Tyr Pro Gly Asn Gly Ala Thr Ser Tyr
        50                  55                  60

Asn Gln Lys Phe Lys Gly Arg Phe Thr Ile Ser Val Asp Lys Ser
    65                  70                  75

Lys Asn Thr Leu Tyr Leu Gln Met Asn Ser Leu Arg Ala Glu Asp
            80                  85                  90

Thr Ala Val Tyr Tyr Cys Ala Arg Val Val Tyr Tyr Ser Ala Ser
                95                  100                 105

Tyr Trp Tyr Phe Asp Val Trp Gly Gln Gly Thr Leu Val Thr Val
                    110                 115                 120

Ser Ser

<210> SEQ ID NO 52
<211> LENGTH: 107
<212> TYPE: PRT
<213> ORGANISM: Artificial sequence
<220> FEATURE:
<223> OTHER INFORMATION: sequence is synthesized

<400> SEQUENCE: 52

Asp Ile Gln Met Thr Gln Ser Pro Ser Ser Leu Ser Ala Ser Val
 1               5                  10                  15

Gly Asp Arg Val Thr Ile Thr Cys Arg Ala Ser Ser Ser Val Ser
                20                  25                  30

Tyr Met His Trp Tyr Gln Gln Lys Pro Gly Lys Ala Pro Lys Pro
            35                  40                  45

Leu Ile Tyr Ala Pro Ser Asn Leu Ala Ser Gly Val Pro Ser Arg
        50                  55                  60

Phe Ser Gly Ser Gly Ser Gly Thr Asp Phe Thr Leu Thr Ile Ser
    65                  70                  75

Ser Leu Gln Pro Glu Asp Phe Ala Thr Tyr Tyr Cys Gln Gln Trp
            80                  85                  90
```

```
Ala Phe Asn Pro Pro Thr Phe Gly Gln Gly Thr Lys Val Glu Ile
             95                 100                 105

Lys Arg

<210> SEQ ID NO 53
<211> LENGTH: 107
<212> TYPE: PRT
<213> ORGANISM: Artificial sequence
<220> FEATURE:
<223> OTHER INFORMATION: sequence is synthesized

<400> SEQUENCE: 53

Asp Ile Gln Met Thr Gln Ser Pro Ser Ser Leu Ser Ala Ser Val
 1               5                  10                  15

Gly Asp Arg Val Thr Ile Thr Cys Arg Ala Ser Ser Ser Val Ser
             20                  25                  30

Tyr Leu His Trp Tyr Gln Gln Lys Pro Gly Lys Ala Pro Lys Pro
             35                  40                  45

Leu Ile Tyr Ala Pro Ser Asn Leu Ala Ser Gly Val Pro Ser Arg
             50                  55                  60

Phe Ser Gly Ser Gly Ser Gly Thr Asp Phe Thr Leu Thr Ile Ser
 65                  70                  75

Ser Leu Gln Pro Glu Asp Phe Ala Thr Tyr Tyr Cys Gln Gln Trp
             80                  85                  90

Ala Phe Asn Pro Pro Thr Phe Gly Gln Gly Thr Lys Val Glu Ile
             95                 100                 105

Lys Arg

<210> SEQ ID NO 54
<211> LENGTH: 5679
<212> TYPE: DNA
<213> ORGANISM: Artificial sequence
<220> FEATURE:
<223> OTHER INFORMATION: Sequence is synthesized

<400> SEQUENCE: 54
cttaagttga agaggtatga aacctattcc tttatgtctg tacttttag agtaacgact      60 caacaataaa ttcgaacggg ttttcttct tctcagctta cttgacacac gcgtccatct     120
tcgaaacctc taatagcagt gacgttacga agcgttatac cgcgttttac tggttgtcgc    180
caactaacta gtccatctcc cccgcgacat gctccatttc gggctacggt cgtaaggact    240
gctgctatgc ctcgacgacg cgctaatgca tttcttcaat aacttcgtag gagcagtcat    300
ttttcaatta gaaaagttgt cgacagtatt tcaacagtgc cggctctgaa tatcagcgaa    360
acaaaaataa aaattacat aaacattgat cttaagctcg agccatgggc cctaggaga     420 tctccaactc cactaaaata ctttttctta tagcgtaaag aagaacgtag atacaagcaa    480
aaaagataac gatgtttgcg catgcgacta taggtctact gggtcagggg ctcgaggac    540 aggcggagac acccgctatc ccagtggtag tggacgtctc ggtcagtctc gcacagctga    600
tcgagaatat cgatatacgt gaccatagtt gtctttggtc cttttcgagg ctttgatgac    660
taaatgatac gatcgttgga gctcagacct cagggaagag cgaagagacc taggccaaga    720
ccctgcctaa agtgagactg gtagtcgtca gacgtcggtc ttctgaagcg ttgaataatg    780
acagttgtga gaaccccata aggcgcgtgt aaacctgtcc catggttcca cctctagttt    840
gcttgacacc gacgtggtag acagaagtag aagggcggta gactactcgt caactttaga    900
ccttgacgaa gacaacacac ggacgactta ttgaagatag ggtctctccg gtttcatgtc    960
```

```
accttccacc tattgcggga ggttagccca ttgagggtcc tctcacagtg tctcgtcctg    1020
tcgttcctgt cgtggatgtc ggagtcgtcg tgggactgcg actcgtttcg tctgatgctc    1080
tttgtgtttc agatgcggac gcttcagtgg gtagtcccgg actcgagcgg gcagtgtttc    1140
tcgaagttgt cccctctcac aattcgacta ggagatgcgg cctgcgtagc accgggatca    1200
tgcgttcaag tgcattttc ccatagatct ccaactccac taaaatactt tttcttatag    1260
cgtaaagaag aacgtagata caagcaaaaa agataacgat gtttgcgcat gcgactccaa    1320
gtcgaccacc tcagaccgcc accggaccac gtcggtcccc cgagtgaggc aaacaggaca    1380
cgtcgaagac cgatgtggaa gtggcttata tagtaggtga cccaggcagt ccggggccca    1440
ttcccggacc ttacccaacg tagctaatta ggactgatgc tgtagtgctt gatattggtc    1500
gcgaagttcc cggcaaagtg atattcagcg ctgctaaggt ttttgtgtaa tatggacgtc    1560
tacttgtcgg acgcacgact cctgtgacgg cagataataa cacgagctac ctagtcgcta    1620
aagaagctga tgaccccagt tccttgggac cagtggcaga ggagccggag gtggttcccg    1680
ggtagccaga aggggaccg tgggaggagg ttctcgtgga dacccccgtg tcgccgggac    1740
ccgacggacc agttcctgat gaagggcgtt ggccactgcc acagcaccgtt gagtccgcgg    1800 gactggtcgc cgcacgtgtg gaagggccga caggatgtca ggagtcctga gatgagggag    1860
tcgtcgcacc actggcacgg gaggtcgtcg aacccgtggg tctggatgta gacgttgcac    1920
ttagtgttcg ggtcgttgtg gttccacctg ttctttcaac tcgggtttag aacactgttt    1980
tgagtgtgta ctggtggcgt acgtggtcat agcaggtaag gctgtcgtag cggtcagtga    2040
taccgcacga cgatcgcggc gggatatgga acagacggag gggcgcaacg cagcgccacg    2100
tacctcggcc cggtggagct ggacttacct tcggccgccg tggagcgatt gcctaagtgg    2160
tgaggttctt aacctcggtt agttaagaac gcctcttgac acttacgcgt ttggttggga    2220
accgtcttgt ataggtagcg caggcggtag aggtcgtcgg cgtgcgccgc gtagagcccg    2280
tcgcaaccca ggaccggtgc ccacgcgtac tagcacgagg acagcaactc ctgggccgat    2340
ccgaccgccc caacggaatg accaatcgtc ttacttagtg gctatgcgct cgcttgcact    2400
tcgctgacga cgacgttttg cagacgctgg actcgttgtt gtacttacca gaagccaaag    2460
gcacaaagca tttcagacct ttgcgccttc agtcgcggga cgtggtaata caaggcctag    2520
acgtagcgtc ctacgacgac cgatgggaca ccttgtggat gtagacataa ttgcttcgcg    2580
accgtaactg ggactcacta aaaagagacc agggcggcgt aggtatggcg gtcaacaaat    2640
gggagtgttg caaggtcatt ggcccgtaca agtagtagtc attgggcata gcactcgtag    2700
gagagagcaa agtagccata gtaatgggg tacttgtctt aagggggaa tgtgcctccg    2760 tagttcactg gtttgtcctt ttttggcggg aattgtaccg ggcgaaatag tcttcggtct    2820
gtaattgcga agacctcttt gagttgctcg acctgcgcct acttgtccgt ctgtagacac    2880
ttagcgaagt gctggtgcga ctactcgaaa tggcgtcgta ggcctttaac atttgcaatt    2940
ataaaacaat tttaagcgca atttaaaaac aatttagtcg agtaaaaaat tggttatccg    3000
gctttagccg ttttagggaa tatttagttt tcttatctgg ctctatccca actcacaaca    3060
aggtcaaacc ttgttctcag gtgataattt cttgcacctg aggttgcagt ttcccgcttt    3120
ttggcagata gtcccgatac cgggtgatgc acttggtagt gggattagtt caaaaaccc    3180 cagctccacg gcatttcgtg atttagcctt gggatttccc tcggggcta aatctcgaac    3240 tgccccttc ggccgcttgc accgctcttt ccttcccttc tttcgctttc ctcgcccgcg    3300
atcccgcgac cgttcacatc gccagtgcga cgcgcattgg tggtgtgggc ggcgcgaatt    3360
```

```
acgcggcgat gtcccgcgca ggcgtaggac ggagcgcgca aagccactac tgccacttt    3420
ggagactgtg tacgtcgagg gcctctgcca gtgtcgaaca gacattcgcc tacggccctc    3480
gtctgttcgg gcagtcccgc gcagtcgccc acaaccgccc acagcccgc gtcggtactg     3540
ggtcagtgca tcgctatcgc ctcacatatg accgaattga tacgccgtag tctcgtctaa    3600
catgactctc acgtggtata cgccacactt tatggcgtgt ctacgcattc ctcttttatg    3660
gcgtagtccg cgagaaggcg aaggagcgag tgactgagcg acgcgagcca gcaagccgac    3720
gccgctcgcc atagtcgagt gagtttccgc cattatgcca ataggtgtct tagtcccta    3780
ttgcgtcctt tcttgtacac tcgttttccg gtcgttttcc ggtccttggc attttccgg     3840
cgcaacgacc gcaaaaaggt atccgaggcg ggggactgc tcgtagtgtt tttagctgcg     3900
agttcagtct ccaccgcttt gggctgtcct gatatttcta tggtccgcaa agggggacct    3960
tcgagggagc acgcgagagg acaaggctgg gacggcgaat ggcctatgga caggcggaaa    4020
gagggaagcc cttcgcaccg cgaaagagta tcgagtgcga catccataga gtcaagccac    4080
atccagcaag cgaggttcga cccgacacac gtgcttgggg ggcaagtcgg gctggcgacg    4140
cggaataggc cattgatagc agaactcagg ttgggccatt ctgtgctgaa tagcggtgac    4200
cgtcgtcggt gaccattgtc ctaatcgtct cgctccatac atccgccacg atgtctcaag    4260
aacttcacca ccggattgat gccgatgtga tcttcctgtc ataaaccata dacgcgagac    4320
gacttcggtc aatggaagcc ttttctcaa ccatcgagaa ctaggccgtt tgtttggtgg     4380
cgaccatcgc caccaaaaaa acaaacgttc gtcgtctaat gcgcgtcttt ttttcctaga    4440
gttcttctag gaaactagaa aagatgcccc agactgcgag tcaccttgct tttgagtgca    4500
attccctaaa accagtactc taatagtttt tcctagaagt ggatctagga aaatttaatt    4560
tttacttcaa aatttagtta gatttcatat atactcattt gaaccagact gtcaatggtt    4620
acgaattagt cactccgtgg atagagtcgc tagacagata aagcaagtag gtatcaacgg    4680
actgaggggc agcacatcta ttgatgctat gccctcccga atggtagacc ggggtcacga    4740
cgttactatg gcgctctggg tgcgagtggc cgaggtctaa atagtcgtta tttggtcggt    4800
cggccttccc ggctcgcgtc ttcaccagga cgttgaaata ggcggaggta ggtcagataa    4860
ttaacaacgg cccttcgatc tcattcatca agcggtcaat tatcaaacgc gttgcaacaa    4920
cggtaacgac gtccgtagca ccacagtgcg agcagcaaac cataccgaag taagtcgagg    4980
ccaagggttg ctagttccgc tcaatgtact agggggtaca acacgttttt tcgccaatcg    5040
aggaagccag gaggctagca acagtcttca ttcaaccggc gtcacaatag tgagtaccaa    5100
taccgtcgtg acgtattaag agaatgacag tacggtaggc attctacgaa aagacactga    5160
ccactcatga gttggttcag taagactctt atcacatacg ccgctggctc aacgagaacg    5220
ggccgcagtt gtgccctatt atggcgcggt gtatcgtctt gaaattttca cgagtagtaa    5280
ccttttgcaa gaagccccgc ttttgagagt tcctagaatg gcgacaactc taggtcaagc    5340
tacattgggt gagcacgtgg gttgactaga agtcgtagaa aatgaaagtg gtcgcaaaga    5400
cccactcgtt tttgtccttc cgtttacgg cgttttttcc cttattcccg ctgtgccttt     5460
acaacttatg agtatgagaa ggaaaaagtt ataataactt cgtaaatagt cccaataaca    5520
gagtactcgc ctatgtataa acttacataa atctttttat ttgttatcc ccaaggcgcg     5580
tgtaaagggg cttttcacgg tggactgcag attctttggt aataatagta ctgtaattgg    5640
atatttttat ccgcatagtg ctccgggaaa gcagaagtt                           5679
```

<210> SEQ ID NO 55

<211> LENGTH: 5678
<212> TYPE: DNA
<213> ORGANISM: Artificial sequence
<220> FEATURE:
<223> OTHER INFORMATION: Sequence is synthesized

<400> SEQUENCE: 55

| | | | | | |
|---|---|---|---|---|---|
| cttaagttga | agaggtatga | aacctattcc | tttatgtctg | tacttttag | agtaacgact | 60 |
| caacaataaa | ttcgaacggg | tttttcttct | tctcagctta | cttgacacac | gcgtccatct | 120 |
| tcgaaacctc | taatagcagt | gacgttacga | agcgttatac | cgcgttttac | tggttgtcgc | 180 |
| caactaacta | gtccatctcc | cccgcgacat | gctccatttc | gggctacggt | cgtaaggact | 240 |
| gctgctatgc | ctcgacgacg | cgctaatgca | tttcttcaat | aacttcgtag | gagcagtcat | 300 |
| ttttcaatta | gaaaagttgt | cgacagtatt | tcaacagtgc | cggctctgaa | tatcagcgaa | 360 |
| acaaaataa | aaaattacat | aaacattgat | cttaagctcg | agccatgggc | cctaggaga | 420 |
| tctccaactc | cactaaatac | ttttctttat | agcgtaaaga | agaacgtaga | tacaagcaaa | 480 |
| aaagataacg | atgtttgcgc | atgcgagtct | atcatgacag | ggtcaggggc | cgataggaca | 540 |
| ggcggagagg | accgctcttc | cagtgatact | ggacgtctcg | gtcgagaaga | cactcgatat | 600 |
| acgtaaccat | agttgtcttt | ggtccttcga | gaggctttgg | tacctaaatg | cgaggtagct | 660 |
| tggagcgcag | acctcaggga | cgcgcgaaga | gacctaggcc | aagaccctga | tcaatgagag | 720 |
| actggtagtc | gtctcacctc | cgtcttctgc | ggcgttgaat | aatgacagtt | gtcacctcga | 780 |
| agttaggcgg | gtgtaaacct | cggccgtggt | tcgacctcga | gtttgcttga | caccgacgtg | 840 |
| gtagacagaa | gtagaagggc | ggtagactac | tcgtcaactt | tagaccttga | cgaagacaac | 900 |
| acacggacga | cttattgaag | atagggtctc | tccggtttca | tgtcaccttc | cacctattgc | 960 |
| gggaggttag | cccattgagg | gtcctctcac | agtgtctcgt | cctgtcgttc | ctgtcgtgga | 1020 |
| tgtcggagtc | gtcgtgggac | tgcgactcgt | ttcgtctgat | gctctttgtg | tttcagatgc | 1080 |
| ggacgcttca | gtgggtagtc | ccggactcga | gcgggcagtg | tttctcgaag | ttgtcccctc | 1140 |
| tcacaattcg | actaggagat | gcggcctgcg | tagcaccggg | atcatgcgtt | caagtgcatt | 1200 |
| tttcccatag | atctccaact | ccactaaaat | acttttctt | atagcgtaaa | gaagaacgta | 1260 |
| gatacaagca | aaaagataa | cgatgtttgc | gcatgcgagt | ccgaatagac | gtcgtcagac | 1320 |
| cgcggctcga | ccacgccggt | cctcgatcgc | agttctacag | gacatttcga | agaccgatgt | 1380 |
| ggaagtggtc | gatattgtac | gtaacccagt | tcgtctgtgg | ctccgttccg | gaccttacct | 1440 |
| aacctcgcta | gataggaccg | ttgccgctgt | gctcgatatt | ggtcttcaag | ttcccgttcc | 1500 |
| ggtgagactg | acacctgttc | aggtcgtcat | gacggatgta | cgttgactcg | tcggactgaa | 1560 |
| gactcctgtc | gcgacagatg | aaaacacgag | cgcaccagat | gatatcgttg | tcgatgacca | 1620 |
| tgaagctgca | gaccccatgg | ccttggtgtc | agtggcagag | gagccggagg | tggttcccgg | 1680 |
| gtagccagaa | gggggaccgt | gggaggaggt | tctcgtggag | accccgtgt | cgccgggacc | 1740 |
| cgacggacca | gttcctgatg | aagggcttg | gccactgcca | cagcaccttg | agtccgcggg | 1800 |
| actggtcgcc | gcacgtgtgg | aagggccgac | aggatgtcag | gagtcctgag | atgagggagt | 1860 |
| cgtcgcacca | ctggcacggg | aggtcgtcga | acccgtgggt | ctggatgtag | acgttgcact | 1920 |
| tagtgttcgg | gtcgttgtgg | ttccacctgt | tctttcaact | cgggtttaga | acactgtttt | 1980 |
| gagtgtgtac | tggtggcgta | cgtggtcata | gcaggtaagg | ctgtcgtagc | ggtcagtgat | 2040 |
| accgcacgac | gatcgcggcg | ggatatggaa | cagacggagg | ggcgcaacgc | agcgccacgt | 2100 |
| acctcggccc | ggtggagctg | gacttacctt | cggccgccgt | ggagcgattg | cctaagtggt | 2160 |

-continued

```
gaggttctta acctcggtta gttaagaacg cctcttgaca cttacgcgtt tggtttgggaa   2220 ccgtcttgta taggtagcgc aggcggtaga ggtcgtcggc gtgcgccgcg tagagcccgt   2280
cgcaacccag gaccggtgcc cacgcgtact agcacgagga cagcaactcc tgggccgatc   2340
cgaccgcccc aacggaatga ccaatcgtct tacttagtgg ctatgcgctc gcttgcactt   2400
cgctgacgac gacgttttgc agacgctgga ctcgttgttg tacttaccag aagccaaagg   2460
cacaaagcat ttcagacctt tgcgccttca gtcgcgggac gtggtaatac aaggcctaga   2520
cgtagcgtcc tacgacgacc gatgggacac cttgtggatg tagacataat tgcttcgcga   2580
ccgtaactgg gactcactaa aaagagacca gggcggcgta ggtatggcgg tcaacaaatg   2640
ggagtgttgc aaggtcattg gcccgtacaa gtagtagtca ttgggcatag cactcgtagg   2700
agagagcaaa gtagccatag taatgggggt acttgtcttt aagggggaat gtgcctccgt   2760
agttcactgg tttgtccttt tttggcggga attgtaccgg gcgaaatagt cttcggtctg   2820
taattgcgaa gacctctttg agttgctcga cctgcgccta cttgtccgtc tgtagacact   2880
tagcgaagtg ctggtgcgac tactcgaaat ggcgtcgtag gcctttaaca tttgcaatta   2940
taaaacaatt ttaagcgcaa tttaaaaaca atttagtcga gtaaaaaatt ggttatccgg   3000
ctttagccgt tttagggaat atttagtttt cttatctggc tctatcccaa ctcacaacaa   3060
ggtcaaacct tgttctcagg tgataaattc ttgcacctga ggttgcagtt tcccgctttt   3120
tggcagatag tcccgatacc gggtgatgca cttggtagtg ggattagttc aaaaaacccc   3180
agctccacgg catttcgtga tttagccttg ggatttccct cggggggctaa atctcgaact   3240 gcccctttcg gccgcttgca ccgctctttc cttcccttct ttcgctttcc tcgcccgcga   3300
tcccgcgacc gttcacatcg ccagtgcgac gcgcattggt ggtgtgggcg gcgcgaatta   3360
cgcggcgatg tcccgcgcag gcgtaggacg gagcgcgcaa agccactact gccacttttg   3420
gagactgtgt acgtcgaggg cctctgccag tgtcgaacag acattcgcct acggccctcg   3480
tctgttcggg cagtcccgcg cagtcgccca caaccgccca cagccccgcg tcggtactgg   3540
gtcagtgcat cgctatcgcc tcacatatga ccgaattgat acgccgtagt ctcgtctaac   3600
atgactctca cgtggtatac gccacacttt atggcgtgtc tacgcattcc tcttttatgg   3660
cgtagtccgc gagaaggcga aggagcgagt gactgagcga cgcgagccag caagccgacg   3720
ccgctcgcca tagtcgagtg agtttccgcc attatgccaa taggtgtctt agtccctat   3780 tgcgtccttt cttgtacact cgttttccgg tcgttttccg gtccttggca ttttccggc   3840 gcaacgaccg caaaaaggta tccgaggcgg ggggactgct cgtagtgttt ttagctgcga   3900
gttcagtctc caccgctttg ggctgtcctg atatttctat ggtccgcaaa gggggacctt   3960
cgagggagca cgcgagagga caaggctggg acggcgaatg gcctatggac aggcggaaag   4020
agggaagccc ttcgcaccgc gaaagagtat cgagtgcgac atccatagag tcaagccaca   4080
tccagcaagc gaggttcgac ccgacacacg tgcttggggg gcaagtcggg ctggcgacgc   4140
ggaataggcc attgatagca gaactcaggt tgggccattc tgtgctgaat agcggtgacc   4200
gtcgtcggtg accattgtcc taatcgtctc gctccataca tccgccacga tgtctcaaga   4260
acttcaccac cggattgatg ccgatgtgat cttcctgtca taaaccatag acgcgagacg   4320
acttcggtca atggaagcct ttttctcaac catcgagaac taggccgttt gtttggtggc   4380
gaccatcgcc accaaaaaaa caaacgttcg tcgtctaatg cgcgtctttt tttcctagag   4440
ttcttctagg aaactagaaa agatgcccca gactgcgagt caccttgctt ttgagtgcaa   4500
ttccctaaaa ccagtactct aatagttttt cctagaagtg gatctaggaa aatttaattt   4560
```

```
ttacttcaaa atttagttag atttcatata tactcatttg aaccagactg tcaatggtta      4620
cgaattagtc actccgtgga tagagtcgct agacagataa agcaagtagg tatcaacgga      4680
ctgaggggca gcacatctat tgatgctatg ccctcccgaa tggtagaccg gggtcacgac      4740
gttactatgg cgctctgggt gcgagtggcc gaggtctaaa tagtcgttat ttggtcggtc      4800
ggccttcccg gctcgcgtct tcaccaggac gttgaaatag gcggaggtag gtcagataat      4860
taacaacggc ccttcgatct cattcatcaa gcggtcaatt atcaaacgcg ttgcaacaac      4920
ggtaacgacg tccgtagcac cacagtgcga gcagcaaacc ataccgaagt aagtcgaggc      4980
caagggttgc tagttccgct caatgtacta gggggtacaa cacgtttttt cgccaatcga      5040
ggaagccagg aggctagcaa cagtcttcat tcaaccggcg tcacaatagt gagtaccaat      5100
accgtcgtga cgtattaaga gaatgacagt acggtaggca ttctacgaaa agacactgac      5160
cactcatgag ttggttcagt aagactctta tcacatacgc cgctggctca acgagaacgg      5220
gccgcagttg tgccctatta tggcgcggtg tatcgtcttg aaattttcac gagtagtaac      5280
cttttgcaag aagcccgct tttgagagtt cctagaatgg cgacaactct aggtcaagct       5340
acattgggtg agcacgtggg ttgactagaa gtcgtagaaa atgaaagtgg tcgcaaagac      5400
ccactcgttt ttgtccttcc gttttacggc gttttttccc ttattccgc tgtgccttta       5460 caacttatga gtatgagaag gaaaaagtta taataacttc gtaaatagtc ccaataacag      5520
agtactcgcc tatgtataaa cttacataaa tcttttatt tgtttatccc caaggcgcgt       5580 gtaaagggc ttttcacggt ggactgcaga ttctttggta ataatagtac tgtaattgga       5640
tatttttatc cgcatagtgc tccgggaaag cagaagtt                              5678
```